United States Patent
Xu et al.

(10) Patent No.: US 8,907,068 B2
(45) Date of Patent: *Dec. 9, 2014

(54) ANTI-IL-20 ANTIBODIES AND BINDING PARTNERS AND METHODS OF USING IN INFLAMMATION

(75) Inventors: Wenfeng Xu, Seattle, WA (US); Wayne R. Kindsvogel, Seattle, WA (US); Zhi Chen, Bellevue, WA (US); Steven D. Hughes, Kenmore, WA (US); Yasmin A. Chandrasekher, Saratoga, CA (US); Stacey R. Dillon, Seattle, WA (US); Joyce M. Lehner, Seattle, WA (US); Anthony W. Siadak, Seattle, WA (US); Pallavar V. Sivakumar, Seattle, WA (US); Margaret D. Moore, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 640 days.

This patent is subject to a terminal disclaimer.

(21) Appl. No.: 12/124,946

(22) Filed: May 21, 2008

(65) Prior Publication Data

US 2008/0247945 A1 Oct. 9, 2008

Related U.S. Application Data

(63) Continuation of application No. 10/994,116, filed on Nov. 19, 2004, now Pat. No. 7,393,684.

(60) Provisional application No. 60/524,131, filed on Nov. 21, 2003, provisional application No. 60/555,857, filed on Mar. 24, 2004.

(51) Int. Cl.
| | | |
|---|---|---|
| C07K 16/24 | (2006.01) | |
| A61K 38/17 | (2006.01) | |
| A61K 47/48 | (2006.01) | |
| C07K 16/28 | (2006.01) | |
| C07K 14/715 | (2006.01) | |
| C07K 14/54 | (2006.01) | |
| A61K 38/20 | (2006.01) | |
| A61K 39/00 | (2006.01) | |

(52) U.S. Cl.
CPC ........... *C07K 16/2866* (2013.01); *C07K 16/244* (2013.01); *A61K 38/1793* (2013.01); *C07K 2317/73* (2013.01); *A61K 47/48215* (2013.01); *A61K 2039/505* (2013.01); *C07K 2316/96* (2013.01); *C07K 2319/30* (2013.01); *C07K 14/7155* (2013.01); *C07K 14/54* (2013.01); *A61K 38/20* (2013.01)
USPC .................................................. 530/388.23

(58) Field of Classification Search
None
See application file for complete search history.

(56) References Cited

U.S. PATENT DOCUMENTS

| | | | | |
|---|---|---|---|---|
| 5,723,299 | A | 3/1998 | Bell et al. | 435/7.1 |
| 5,789,192 | A | 8/1998 | Moore et al. | 435/69.1 |
| 5,843,725 | A | 12/1998 | Sledziewski et al. | 435/69.7 |
| 5,945,511 | A | 8/1999 | Lok et al. | 530/350 |
| 5,985,614 | A | 11/1999 | Rosen et al. | 435/69.52 |
| 6,020,163 | A | 2/2000 | Conklin | 435/69.1 |
| 6,486,301 | B1 | 11/2002 | Ebner et al. | 530/351 |
| 6,576,743 | B1 | 6/2003 | Conklin et al. | 530/351 |
| 6,610,286 | B2 | 8/2003 | Thompson et al. | 424/85.2 |
| 2002/0042366 | A1 | 4/2002 | Thompson et al. | |
| 2002/0099179 | A1* | 7/2002 | Jolliffe et al. | 530/387.3 |
| 2003/0157096 | A1 | 8/2003 | Kindsvogel et al. | |
| 2004/0005320 | A1 | 1/2004 | Thompson et al. | |
| 2004/0152878 | A1 | 8/2004 | Conklin et al. | |
| 2004/0181040 | A1 | 9/2004 | Conklin et al. | |
| 2006/0068471 | A1 | 3/2006 | Kindsvogel et al. | |
| 2006/0134756 | A1 | 6/2006 | Xu et al. | |
| 2008/0171014 | A1* | 7/2008 | Wu et al. | 424/85.2 |
| 2008/0171041 | A1 | 7/2008 | Thompson et al. | |
| 2009/0226426 | A1 | 9/2009 | Thompson et al. | |

FOREIGN PATENT DOCUMENTS

| | | |
|---|---|---|
| JP | 2001-500369 | 1/2001 |
| WO | WO94/13801 | 6/1994 |
| WO | WO 98/08870 | 3/1998 |
| WO | WO 9848837 A1 * | 11/1998 |
| WO | WO99/03982 | 1/1999 |
| WO | WO99/07740 | 2/1999 |
| WO | WO99/07848 | 2/1999 |
| WO | WO99/27103 | 6/1999 |
| WO | WO99/37772 | 7/1999 |
| WO | WO99/46281 | 9/1999 |
| WO | WO99/46379 | 9/1999 |
| WO | WO99/61630 | 12/1999 |
| WO | WO00/12708 | 3/2000 |

(Continued)

OTHER PUBLICATIONS

Chang et al., Crystal structure of interleukin-19 defines a new subfamily of helical cytokines, J Biol Chem. Jan. 31, 2003;278(5):3308-13.*

(Continued)

*Primary Examiner* — Zachary Skelding

(74) *Attorney, Agent, or Firm* — Nelson Mullins Riley & Scarborough LLP; Jane E. Remillard, Esq.; Jeanne M. DiGiorgio

(57) ABSTRACT

The present invention relates to blocking the activity of IL-20 polypeptide molecules. IL-20 is a cytokine that is involved in inflammatory processes and human disease. IL-20RA/IL-20RB is a common receptor for IL-20. The present invention includes anti-IL-20 antibodies and binding partners, as well as methods for antagonizing IL-20 using such antibodies and binding partners.

9 Claims, No Drawings

(56) References Cited

FOREIGN PATENT DOCUMENTS

| WO | 00/31278 A1 | 6/2000 |
|---|---|---|
| WO | WO 00/31278 | 6/2000 |
| WO | WO00/39161 | 7/2000 |
| WO | WO00/42189 | 7/2000 |
| WO | WO00/73457 | 12/2000 |
| WO | WO00/78961 | 12/2000 |
| WO | WO01/12672 | 2/2001 |
| WO | 01/40467 A1 | 6/2001 |
| WO | WO 01/40467 | 6/2001 |
| WO | WO01/46261 | 6/2001 |
| WO | WO02/12345 | 2/2002 |
| WO | WO02/058724 | 8/2002 |
| WO | WO02/070001 | 9/2002 |
| WO | WO02/072607 | 9/2002 |
| WO | WO03/039444 | 5/2003 |
| WO | WO03/051384 | 6/2003 |
| WO | 03/083062 A2 | 10/2003 |
| WO | WO 03/083062 | 10/2003 |
| WO | 2004/085476 A2 | 10/2004 |
| WO | WO2004/085475 | 10/2004 |
| WO | 2006047249 A1 | 5/2006 |
| WO | WO 2010000721 A1 * | 1/2010 |

OTHER PUBLICATIONS

Pletnev et al., Characterization of the recombinant extracellular domains of human interleukin-20 receptors and their complexes with interleukin-19 and interleukin-20, Biochemistry. Nov. 4, 2003;42(43):12617-24.*
Gallagher et al., Interleukin-19: multiple roles in immune regulation and disease, Cytokine Growth Factor Rev. Oct. 2010;21(5):345-52.*
"Using Antibodies, a laboratory manual," Harlow et al., Cold Spring Harbor Laboratory Press, 1999, pp. 81-90.*
Carter et al., Current Protocols in Immunology (2004), John Wiley & Sons, Inc., pp. 9.4.1-9.4.23.*
Damschroder et al., Mol Immunol. Aug. 2004;41(10):985-1000.*
Albert et al., "Molecular Biology of the Cell," 3$^{rd}$ Ed., pp. 156-159, Garland Publishing, Inc., 1994.
Blumberg et al., *Cell* 104:9-19, 2001.
Harlow et al., "Antibodies a Laboratory Manual," p. 76, Ch. 5, Cold Springs Harbor Laboratory, 1988.
Kotenko, *Cytokine & Growth Factor Reviews* 13:223-240, 2002.
Parrish-Novak et al., *J. Biol. Chem.* 277(49):47517-47523, 2002.
EST from Incyte Pharmaceuticals Inc., INC1429789, 1996.
EST from Incyte Pharmaceuticals Inc., INC1922140, 1996.
EST from Incyte Pharmaceuticals Inc., INC1923851, 1996.
EST from Incyte Pharmaceuticals Inc., INC2119350, 1996.
EST from Incyte Pharmaceuticals Inc., INC2270605, 1996.
EST from Incyte Pharmaceuticals Inc., INC2699058, 1997.
EST from Incyte Pharmaceuticals Inc., INC2701079, 1997.
EST from Incyte Pharmaceuticals Inc., INC2720417, 1997.
EST from Incyte Pharmaceuticals Inc., INC2763478, 1997.
EST from Incyte Pharmaceuticals Inc., INC3256488, 1997.
EST from Incyte Pharmaceuticals Inc., INC3257185, 1997.
EST from Incyte Pharmaceuticals Inc., INC3316826, 1997.
EST from Incyte Pharmaceuticals Inc., INC3376533, 1997.
EST from Incyte Pharmaceuticals Inc., INC357666, 1995.
EST from Incyte Pharmaceuticals Inc., INC4304592, 1998.
EST from Incyte Pharmaceuticals Inc., INC758088, 1996.
EST from Incyte Pharmaceuticals Inc., INC819592, 1996.
EST from Incyte Pharmaceuticals Inc., INC904360, 1996.
EST from TIGR Tentative Human Consensus, THC174656, 1997.
EST from TIGR Tentative Human Consensus, THC197949, 1997.
EST from TIGR Tentative Human Consensus, THC215509, 1997.
GenBank Accession No. AA018585, 1995.
GenBank Accession No. AA018749, 1995.
GenBank Accession No. AA035594, 1995.
GenBank Accession No. AA132964, 1995.
GenBank Accession No. AA134881, 1995.
GenBank Accession No. AA135185, 1995.
GenBank Accession No. AA135300, 1995.
GenBank Accession No. AA299011, 1995.
GenBank Accession No. AA412292, 1997.
GenBank Accession No. AA470014, 1997.
GenBank Accession No. AA494556, 1997.
GenBank Accession No. AA514541, 1997.
GenBank Accession No. AA516435, 1997.
GenBank Accession No. AA528216, 1997.
GenBank Accession No. AA583432, 1997.
GenBank Accession No. AA632915, 1997.
GenBank Accession No. H17201, 1995.
GenBank Accession No. H17978, 1995.
GenBank Accession No. N62509, 1995.
GenBank Accession No. N79409, 1995.
GenBank Accession No. R14678, 1995.
GenBank Accession No. R42401, 1995.
GenBank Accession No. T70354, 1995.
GenBank Accession No. T70439, 1995.
U.S. Appl. No. 10/994,116, Nov. 19, 2004, Xu et al.
Wei et al., "IL-20: biological functions and clinical implications", Journal of Biomedical Science, Apr. 2006, 601-612.

* cited by examiner

```
                        SEQUENCE LISTING

<160> NUMBER OF SEQ ID NOS: 91

<210> SEQ ID NO 1
<211> LENGTH: 926
<212> TYPE: DNA
<213> ORGANISM: Homo sapiens
<220> FEATURE:
<221> NAME/KEY: CDS
<222> LOCATION: (45)...(575)

<400> SEQUENCE: 1
ctttgaattc ctagctcctg tggtctccag atttcaggcc taag atg aaa gcc tct        56
                                              Met Lys Ala Ser
                                                1 agt ctt gcc ttc agc ctt ctc tct gct gcg ttt tat ctc cta tgg act       104
Ser Leu Ala Phe Ser Leu Leu Ser Ala Ala Phe Tyr Leu Leu Trp Thr
  5                  10                  15                  20 cct tcc act gga ctg aag aca ctc aat ttg gga agc tgt gtg atc gcc       152
Pro Ser Thr Gly Leu Lys Thr Leu Asn Leu Gly Ser Cys Val Ile Ala
                 25                  30                  35 aca aac ctt cag gaa ata cga aat gga ttt tct gac ata cgg ggc agt       200
Thr Asn Leu Gln Glu Ile Arg Asn Gly Phe Ser Asp Ile Arg Gly Ser
             40                  45                  50 gtg caa gcc aaa gat gga aac att gac atc aga atc tta agg agg act       248
Val Gln Ala Lys Asp Gly Asn Ile Asp Ile Arg Ile Leu Arg Arg Thr
         55                  60                  65 gag tct ttg caa gac aca aag cct gcg aat cga tgc tgc ctc ctg cgc       296
Glu Ser Leu Gln Asp Thr Lys Pro Ala Asn Arg Cys Cys Leu Leu Arg
 70                  75                  80 cat ttg cta aga ctc tat ctg gac agg gta ttt aaa aac tac cag acc       344
His Leu Leu Arg Leu Tyr Leu Asp Arg Val Phe Lys Asn Tyr Gln Thr
 85                  90                  95                 100 cct gac cat tat act ctc cgg aag atc agc agc ctc gcc aat tcc ttt       392
Pro Asp His Tyr Thr Leu Arg Lys Ile Ser Ser Leu Ala Asn Ser Phe
                105                 110                 115 ctt acc atc aag aag gac ctc cgg ctc tgt cat gcc cac atg aca tgc       440
Leu Thr Ile Lys Lys Asp Leu Arg Leu Cys His Ala His Met Thr Cys
            120                 125                 130 cat tgt ggg gag gaa gca atg aag aaa tac agc cag att ctg agt cac       488
His Cys Gly Glu Glu Ala Met Lys Lys Tyr Ser Gln Ile Leu Ser His
        135                 140                 145 ttt gaa aag ctg gaa cct cag gca gca gtt gtg aag gct ttg ggg gaa       536
Phe Glu Lys Leu Glu Pro Gln Ala Ala Val Val Lys Ala Leu Gly Glu
    150                 155                 160 cta gac att ctt ctg caa tgg atg gag gag aca gaa tag gaggaaagtg        585
Leu Asp Ile Leu Leu Gln Trp Met Glu Glu Thr Glu  *
165                 170                 175 atgctgctgc taagaatatt cgaggtcaag agctccagtc ttcaatacct gcagaggagg     645 catgaccoca aaccaccatc tctttactgt actagtcttg tgctggtcac agtgtatctt     705
atttatgcat tacttgcttc cttgcatgat tgtctttatg catccccaat cttaattgag     765
accatacttg tataagattt ttgtaatatc tttctgctat tggatatatt tattagttaa     825
```

```
tatatttatt tatttttttgc tattaatgta tttaattttt tacttgggca tgaaacttta    885
aaaaaaattc acaagattat atttataacc tgactagagc a                         926
```

<210> SEQ ID NO 2
<211> LENGTH: 176
<212> TYPE: PRT
<213> ORGANISM: Homo sapiens

<400> SEQUENCE: 2

```
Met Lys Ala Ser Ser Leu Ala Phe Ser Leu Leu Ser Ala Ala Phe Tyr
 1               5                  10                  15

Leu Leu Trp Thr Pro Ser Thr Gly Leu Lys Thr Leu Asn Leu Gly Ser
             20                  25                  30

Cys Val Ile Ala Thr Asn Leu Gln Glu Ile Arg Asn Gly Phe Ser Asp
         35                  40                  45

Ile Arg Gly Ser Val Gln Ala Lys Asp Gly Asn Ile Asp Ile Arg Ile
     50                  55                  60

Leu Arg Arg Thr Glu Ser Leu Gln Asp Thr Lys Pro Ala Asn Arg Cys
 65                  70                  75                  80

Cys Leu Leu Arg His Leu Leu Arg Leu Tyr Leu Asp Arg Val Phe Lys
                 85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175
```

<210> SEQ ID NO 3
<211> LENGTH: 152
<212> TYPE: PRT
<213> ORGANISM: Homo sapiens

<400> SEQUENCE: 3

```
Leu Lys Thr Leu Asn Leu Gly Ser Cys Val Ile Ala Thr Asn Leu Gln
 1               5                  10                  15

Glu Ile Arg Asn Gly Phe Ser Asp Ile Arg Gly Ser Val Gln Ala Lys
             20                  25                  30

Asp Gly Asn Ile Asp Ile Arg Ile Leu Arg Arg Thr Glu Ser Leu Gln
         35                  40                  45

Asp Thr Lys Pro Ala Asn Arg Cys Cys Leu Leu Arg His Leu Leu Arg
     50                  55                  60

Leu Tyr Leu Asp Arg Val Phe Lys Asn Tyr Gln Thr Pro Asp His Tyr
 65                  70                  75                  80

Thr Leu Arg Lys Ile Ser Ser Leu Ala Asn Ser Phe Leu Thr Ile Lys
                 85                  90                  95

Lys Asp Leu Arg Leu Cys His Ala His Met Thr Cys His Cys Gly Glu
            100                 105                 110

Glu Ala Met Lys Lys Tyr Ser Gln Ile Leu Ser His Phe Glu Lys Leu
        115                 120                 125

Glu Pro Gln Ala Ala Val Val Lys Ala Leu Gly Glu Leu Asp Ile Leu
```

```
                    130                 135                 140
Leu Gln Trp Met Glu Glu Thr Glu
145                 150

<210> SEQ ID NO 4
<211> LENGTH: 793
<212> TYPE: DNA
<213> ORGANISM: Homo sapiens
<220> FEATURE:
<221> NAME/KEY: CDS
<222> LOCATION: (45)...(500)

<400> SEQUENCE: 4
ctttgaattc ctagctcctg tggtctccag atttcaggcc taag atg aaa gcc tct      56
                                              Met Lys Ala Ser
                                              1 agt ctt gcc ttc agc ctt ctc tct gct gcg ttt tat ctc cta tgg act     104
Ser Leu Ala Phe Ser Leu Leu Ser Ala Ala Phe Tyr Leu Leu Trp Thr
 5               10                  15                  20 cct tcc act gga ctg aag aca ctc aat ttg gga agc tgt gtg atc gcc     152
Pro Ser Thr Gly Leu Lys Thr Leu Asn Leu Gly Ser Cys Val Ile Ala
             25                  30                  35 aca aac ctt cag gaa ata cga aat gga ttt tct gac ata cgg ggc agt     200
Thr Asn Leu Gln Glu Ile Arg Asn Gly Phe Ser Asp Ile Arg Gly Ser
         40                  45                  50 gtg caa gcc aaa gat gga aac att gac atc aga atc tta agg agg act     248
Val Gln Ala Lys Asp Gly Asn Ile Asp Ile Arg Ile Leu Arg Arg Thr
     55                  60                  65 gag tct ttg caa gac aca aag cct gcg aat cga tgc tgc ctc ctg cgc     296
Glu Ser Leu Gln Asp Thr Lys Pro Ala Asn Arg Cys Cys Leu Leu Arg
 70                  75                  80 cat ttg cta aga ctc tat ctg gac agg gta ttt aaa aac tac cag acc     344
His Leu Leu Arg Leu Tyr Leu Asp Arg Val Phe Lys Asn Tyr Gln Thr
 85                  90                  95                 100 cct gac cat tat act ctc cgg aag atc agc agc ctc gcc aat tcc ttt     392
Pro Asp His Tyr Thr Leu Arg Lys Ile Ser Ser Leu Ala Asn Ser Phe
             105                 110                 115 ctt acc atc aag aag gac ctc cgg ctc tgt ctg gaa cct cag gca gca     440
Leu Thr Ile Lys Lys Asp Leu Arg Leu Cys Leu Glu Pro Gln Ala Ala
         120                 125                 130 gtt gtg aag gct ttg ggg gaa cta gac att ctt ctg caa tgg atg gag     488
Val Val Lys Ala Leu Gly Glu Leu Asp Ile Leu Leu Gln Trp Met Glu
     135                 140                 145 gag aca gaa tag gaggaaagtg atgctgctgc taagaatatt cgaggtcaag         540
Glu Thr Glu  *
     150 agctccagtc ttcaatacct gcagaggagg catgacccca aaccaccatc tctttactgt    600 actagtcttg tgctggtcac agtgtatctt atttatgcat tacttgcttc cttgcatgat    660 tgtctttatg catccccaat cttaattgag accatacttg tataagattt ttgtaatatc    720 tttctgctat tggatatatt tattagttaa tatatttatt tatttttgc tattaatgta     780 tttaattttt tac                                                       793

<210> SEQ ID NO 5
<211> LENGTH: 151
<212> TYPE: PRT
<213> ORGANISM: Homo sapiens

<400> SEQUENCE: 5

Met Lys Ala Ser Ser Leu Ala Phe Ser Leu Leu Ser Ala Ala Phe Tyr
```

```
                1               5                   10                  15
Leu Leu Trp Thr Pro Ser Thr Gly Leu Lys Thr Leu Asn Leu Gly Ser
                20                  25                  30

Cys Val Ile Ala Thr Asn Leu Gln Glu Ile Arg Asn Gly Phe Ser Asp
                35                  40                  45

Ile Arg Gly Ser Val Gln Ala Lys Asp Gly Asn Ile Asp Ile Arg Ile
                50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                    85                  90                  95

Asn Tyr Gln Thr Pro Asp His Tyr Thr Leu Arg Lys Ile Ser Ser Leu
                100                 105                 110

Ala Asn Ser Phe Leu Thr Ile Lys Lys Asp Leu Arg Leu Cys Leu Glu
                115                 120                 125

Pro Gln Ala Ala Val Val Lys Ala Leu Gly Glu Leu Asp Ile Leu Leu
                130                 135                 140

Gln Trp Met Glu Glu Thr Glu
145                 150
```

<210> SEQ ID NO 6
<211> LENGTH: 127
<212> TYPE: PRT
<213> ORGANISM: Homo sapiens

<400> SEQUENCE: 6

```
Leu Lys Thr Leu Asn Leu Gly Ser Cys Val Ile Ala Thr Asn Leu Gln
1               5                   10                  15

Glu Ile Arg Asn Gly Phe Ser Asp Ile Arg Gly Ser Val Gln Ala Lys
                20                  25                  30

Asp Gly Asn Ile Asp Ile Arg Ile Leu Arg Arg Thr Glu Ser Leu Gln
                35                  40                  45

Asp Thr Lys Pro Ala Asn Arg Cys Cys Leu Leu Arg His Leu Leu Arg
                50                  55                  60

Leu Tyr Leu Asp Arg Val Phe Lys Asn Tyr Gln Thr Pro Asp His Tyr
65                  70                  75                  80

Thr Leu Arg Lys Ile Ser Ser Leu Ala Asn Ser Phe Leu Thr Ile Lys
                    85                  90                  95

Lys Asp Leu Arg Leu Cys Leu Glu Pro Gln Ala Ala Val Val Lys Ala
                100                 105                 110

Leu Gly Glu Leu Asp Ile Leu Leu Gln Trp Met Glu Glu Thr Glu
                115                 120                 125
```

<210> SEQ ID NO 7
<211> LENGTH: 144
<212> TYPE: PRT
<213> ORGANISM: Homo sapiens

<400> SEQUENCE: 7

```
Cys Val Ile Ala Thr Asn Leu Gln Glu Ile Arg Asn Gly Phe Ser Asp
1               5                   10                  15

Ile Arg Gly Ser Val Gln Ala Lys Asp Gly Asn Ile Asp Ile Arg Ile
                20                  25                  30

Leu Arg Arg Thr Glu Ser Leu Gln Asp Thr Lys Pro Ala Asn Arg Cys
                35                  40                  45

Cys Leu Leu Arg His Leu Leu Arg Leu Tyr Leu Asp Arg Val Phe Lys
```

```
            50                  55                  60
Asn Tyr Gln Thr Pro Asp His Tyr Thr Leu Arg Lys Ile Ser Ser Leu
 65                  70                  75                  80

Ala Asn Ser Phe Leu Thr Ile Lys Lys Asp Leu Arg Leu Cys His Ala
                 85                  90                  95

His Met Thr Cys His Cys Gly Glu Glu Ala Met Lys Lys Tyr Ser Gln
            100                 105                 110

Ile Leu Ser His Phe Glu Lys Leu Glu Pro Gln Ala Ala Val Val Lys
        115                 120                 125

Ala Leu Gly Glu Leu Asp Ile Leu Leu Gln Trp Met Glu Glu Thr Glu
    130                 135                 140

<210> SEQ ID NO 8
<211> LENGTH: 253
<212> TYPE: DNA
<213> ORGANISM: Mus musculus

<400> SEQUENCE: 8
ctttgaattc ctagctcctg tggtctccag atttcaggcc taagatgaaa gcctctagtc    60
ttgccttcag ccttctctct gctgcgtttt atctcctatg gactccttcc actggactga   120
agacactcaa tttgggaagc tgtgtgatcg ccacaaacct tcaggaaata cgaaatggat   180
tttctgagat acggggcagt gtgcaagcca aagatggaaa cattgacatc agaatcttaa   240
ggaggactga gtc                                                      253

<210> SEQ ID NO 9
<211> LENGTH: 24
<212> TYPE: DNA
<213> ORGANISM: Mus musculus

<400> SEQUENCE: 9
attcctagct cctgtggtct ccag                                           24

<210> SEQ ID NO 10
<211> LENGTH: 25
<212> TYPE: DNA
<213> ORGANISM: Mus musculus

<400> SEQUENCE: 10
ctctgctgcg ttttatctcc tatgg                                          25

<210> SEQ ID NO 11
<211> LENGTH: 22
<212> TYPE: DNA
<213> ORGANISM: Mus musculus

<400> SEQUENCE: 11
tcccaaattg agtgtcttca gt                                             22

<210> SEQ ID NO 12
<211> LENGTH: 45
<212> TYPE: DNA
<213> ORGANISM: Mus musculus

<400> SEQUENCE: 12
cacagcttcc caaattgagt gtcttcagtc cagtggaagg agtcc                    45

<210> SEQ ID NO 13
<211> LENGTH: 3516
<212> TYPE: DNA
```

```
<213> ORGANISM: Homo sapiens
<220> FEATURE:
<221> NAME/KEY: CDS
<222> LOCATION: (237)...(1898)

<400> SEQUENCE: 13
tccagctggg tagccggggg agcgcgcgtg ggggctccgc gagtcgctcg cccttggttt      60
ctggggaagc ctgggggacg cggctgtggc ggaggcgccc tgggactcag gtcgcctgga    120
gcgtggcacg cagagcccca ggcgcggagc tgaggccgcg cggccgcgct tggccccagc    180
gggcgtggga ctgagcagtc tgctgccccc cgacatgtga cccagccccg ccgccc atg    239
                                                                Met
                                                                  1 cgg gct ccc ggc cgc ccg gcc ctg cgg ccg ctg ccg ctg ccg ccg ctg       287
Arg Ala Pro Gly Arg Pro Ala Leu Arg Pro Leu Pro Leu Pro Pro Leu
              5                  10                  15 ctg ctg ttg ctc ctg gcg gcg cct tgg gga cgg gca gtt ccc tgt gtc       335
Leu Leu Leu Leu Leu Ala Ala Pro Trp Gly Arg Ala Val Pro Cys Val
          20                  25                  30 tct ggt ggt ttg cct aaa cct gca aac atc acc ttc tta tcc atc aac       383
Ser Gly Gly Leu Pro Lys Pro Ala Asn Ile Thr Phe Leu Ser Ile Asn
 35                  40                  45 atg aag aat gtc cta caa tgg act cca cca gag ggt ctt caa gga gtt       431
Met Lys Asn Val Leu Gln Trp Thr Pro Pro Glu Gly Leu Gln Gly Val
 50                  55                  60                  65 aaa gtt act tac act gtg cag tat ttc ata tat ggg caa aag aaa tgg       479
Lys Val Thr Tyr Thr Val Gln Tyr Phe Ile Tyr Gly Gln Lys Lys Trp
              70                  75                  80 ctg aat aaa tca gaa tgc aga aat atc aat aga acc tac tgt gat ctt       527
Leu Asn Lys Ser Glu Cys Arg Asn Ile Asn Arg Thr Tyr Cys Asp Leu
          85                  90                  95 tct gct gaa act tct gac tac gaa cac cag tat tat gcc aaa gtt aag       575
Ser Ala Glu Thr Ser Asp Tyr Glu His Gln Tyr Tyr Ala Lys Val Lys
        100                 105                 110 gcc att tgg gga aca aag tgt tcc aaa tgg gct gaa agt gga cgg ttc       623
Ala Ile Trp Gly Thr Lys Cys Ser Lys Trp Ala Glu Ser Gly Arg Phe
115                 120                 125 tat cct ttt tta gaa aca caa att ggc cca cca gag gtg gca ctg act       671
Tyr Pro Phe Leu Glu Thr Gln Ile Gly Pro Pro Glu Val Ala Leu Thr
130                 135                 140                 145 aca gat gag aag tcc att tct gtt gtc ctg aca gct cca gag aag tgg       719
Thr Asp Glu Lys Ser Ile Ser Val Val Leu Thr Ala Pro Glu Lys Trp
                150                 155                 160 aag aga aat cca gaa gac ctt cct gtt tcc atg caa caa ata tac tcc       767
Lys Arg Asn Pro Glu Asp Leu Pro Val Ser Met Gln Gln Ile Tyr Ser
            165                 170                 175 aat ctg aag tat aac gtg tct gtg ttg aat act aaa tca aac aga acg       815
Asn Leu Lys Tyr Asn Val Ser Val Leu Asn Thr Lys Ser Asn Arg Thr
        180                 185                 190 tgg tcc cag tgt gtg acc aac cac acg ctg gtg ctc acc tgg ctg gag       863
Trp Ser Gln Cys Val Thr Asn His Thr Leu Val Leu Thr Trp Leu Glu
    195                 200                 205 ccg aac act ctt tac tgc gta cac gtg gag tcc ttc gtc cca ggg ccc       911
Pro Asn Thr Leu Tyr Cys Val His Val Glu Ser Phe Val Pro Gly Pro
210                 215                 220                 225 cct cgc cgt gct cag cct tct gag aag cag tgt gcc agg act ttg aaa       959
Pro Arg Arg Ala Gln Pro Ser Glu Lys Gln Cys Ala Arg Thr Leu Lys
                230                 235                 240 gat caa tca tca gag ttc aag gct aaa atc atc ttc tgg tat gtt ttg      1007
Asp Gln Ser Ser Glu Phe Lys Ala Lys Ile Ile Phe Trp Tyr Val Leu
```

```
                     245                 250                 255
ccc ata tct att acc gtg ttt ctt ttt tct gtg atg ggc tat tcc atc    1055
Pro Ile Ser Ile Thr Val Phe Leu Phe Ser Val Met Gly Tyr Ser Ile
            260                 265                 270 tac cga tat atc cac gtt ggc aaa gag aaa cac cca gca aat ttg att    1103
Tyr Arg Tyr Ile His Val Gly Lys Glu Lys His Pro Ala Asn Leu Ile
    275                 280                 285 ttg att tat gga aat gaa ttt gac aaa aga ttc ttt gtg cct gct gaa    1151
Leu Ile Tyr Gly Asn Glu Phe Asp Lys Arg Phe Phe Val Pro Ala Glu
290                 295                 300                 305 aaa atc gtg att aac ttt atc acc ctc aat atc tcg gat gat tct aaa    1199
Lys Ile Val Ile Asn Phe Ile Thr Leu Asn Ile Ser Asp Asp Ser Lys
                310                 315                 320 att tct cat cag gat atg agt tta ctg gga aaa agc agt gat gta tcc    1247
Ile Ser His Gln Asp Met Ser Leu Leu Gly Lys Ser Ser Asp Val Ser
            325                 330                 335 agc ctt aat gat cct cag ccc agc ggg aac ctg agg ccc cct cag gag    1295
Ser Leu Asn Asp Pro Gln Pro Ser Gly Asn Leu Arg Pro Pro Gln Glu
        340                 345                 350 gaa gag gag gtg aaa cat tta ggg tat gct tcg cat ttg atg gaa att    1343
Glu Glu Glu Val Lys His Leu Gly Tyr Ala Ser His Leu Met Glu Ile
355                 360                 365 ttt tgt gac tct gaa gaa aac acg gaa ggt act tct ttc acc cag caa    1391
Phe Cys Asp Ser Glu Glu Asn Thr Glu Gly Thr Ser Phe Thr Gln Gln
370                 375                 380                 385 gag tcc ctc agc aga aca ata ccc ccg gat aaa aca gtc att gaa tat    1439
Glu Ser Leu Ser Arg Thr Ile Pro Pro Asp Lys Thr Val Ile Glu Tyr
                390                 395                 400 gaa tat gat gtc aga acc act gac att tgt gcg ggg cct gaa gag cag    1487
Glu Tyr Asp Val Arg Thr Thr Asp Ile Cys Ala Gly Pro Glu Glu Gln
            405                 410                 415 gag ctc agt ttg cag gag gag gtg tcc aca caa gga aca tta ttg gag    1535
Glu Leu Ser Leu Gln Glu Glu Val Ser Thr Gln Gly Thr Leu Leu Glu
        420                 425                 430 tcg cag gca gcg ttg gca gtc ttg ggc ccg caa acg tta cag tac tca    1583
Ser Gln Ala Ala Leu Ala Val Leu Gly Pro Gln Thr Leu Gln Tyr Ser
435                 440                 445 tac acc cct cag ctc caa gac tta gac ccc ctg gcg cag gag cac aca    1631
Tyr Thr Pro Gln Leu Gln Asp Leu Asp Pro Leu Ala Gln Glu His Thr
450                 455                 460                 465 gac tcg gag gag ggg ccg gag gaa gag cca tcg acg acc ctg gtc gac    1679
Asp Ser Glu Glu Gly Pro Glu Glu Glu Pro Ser Thr Thr Leu Val Asp
                470                 475                 480 tgg gat ccc caa act ggc agg ctg tgt att cct tcg ctg tcc agc ttc    1727
Trp Asp Pro Gln Thr Gly Arg Leu Cys Ile Pro Ser Leu Ser Ser Phe
            485                 490                 495 gac cag gat tca gag ggc tgc gag cct tct gag ggg gat ggg ctc gga    1775
Asp Gln Asp Ser Glu Gly Cys Glu Pro Ser Glu Gly Asp Gly Leu Gly
        500                 505                 510 gag gag ggt ctt cta tct aga ctc tat gag gag ccg gct cca gac agg    1823
Glu Glu Gly Leu Leu Ser Arg Leu Tyr Glu Glu Pro Ala Pro Asp Arg
515                 520                 525 cca cca gga gaa aat gaa acc tat ctc atg caa ttc atg gag gaa tgg    1871
Pro Pro Gly Glu Asn Glu Thr Tyr Leu Met Gln Phe Met Glu Glu Trp
530                 535                 540                 545 ggg tta tat gtg cag atg gaa aac tga tgccaacact tcctttgcc          1918
Gly Leu Tyr Val Gln Met Glu Asn  *
                550 ttttgtttcc tgtgcaaaca agtgagtcac ccctttgatc ccagccataa agtacctggg  1978
```

```
atgaaagaag ttttttccag tttgtcagtg tctgtgagaa ttacttattt ctttctctca   2038
ttctcatagc acgtgtgtga ttggttcatg catgtaggtc tcttaacaat gatggtgggc   2098
ctctggagtc caggggctgg ccggttgttc tatgcagaga aagcagtcaa taaatgtttg   2158
ccagactggg tgcagaattt attcaggtgg gtgtactctg gcctcttggt tcattatttt   2218
caaacaagca cacttgtaca attattttct gggtacttcc catatgcaca tagcactgta   2278
aaaaatattt cccaaagatc actcatttta taaataccac ttttcagaa ttgggtttat    2338
tgcgagcagg aggagatact taaaacatgc acatatacca ggttggtggt aagttggtca   2398
catgtgaaaa cctcaactat ttaatcatca tgattcatat tttgagtgaa tacatcaggc   2458
acagaccttc atgatatcac acactcttgg ctactttaag aggccatctt taatacttta   2518
tgagtagttc tggagtgtaa acataaacga gtattctttt gtagtcagaa aagtgtcctc   2578
tcaataattt agtaggggct tattgtctct caaaactaac ctaaagaaaa atgacacatt   2638
ttataatgaa atattacatt tatttctgga agtgtgtttt caaaaagata tttacatagt   2698
ctgtaaacta gaaagtgtta ggtaaagctc taggttactg tgttactatt ataatattaa   2758
acattcgaat aggcagtcgt tcaaagactc tttggaatat ctatgaatga atatcctcta   2818
ttcttataat attaaaaccc ataagtaaat ataggacata caagagaaat gagttaaatg   2878
actatgtaag ggagagttta ttaaaatttg atgaaattta ctgtaggaac taaactatgc   2938
cataaaacaa tagctttcta gttcatttcc agtaactgtt cccatctcct ttaccacttg   2998
ttaagaaaat taaattcttc agtcacgctg ctttaaaatg ggacaaaatc tattaagttg   3058
aaccatatat aattgtggat atttggctgt ttttaatctg acaagcagta acttcatatg   3118
gtttgcctta atatatattt gttttagtca tgaactcata atccattgat gctctttcat   3178
gagaagagat atgacccata tttccttatt gatattattg gtacaggcag acaaccctgg   3238
taggagagat ggattctggg gtcatgacct ttcgtgatta ccgcaaatg caaacagttt    3298
cagatctaat ggtttaattt agggagtaat tatattaatc agagtgttct gttattctca   3358
atctttatag aaacgattct gctggttttg aagaacagat gtattacact aactgtaaaa   3418
gtagttcaag agtgagaaag aataaattgt tattaagagc aaaagaaaaa taagtgatt    3478
gatgataaaa aaaaaaaaaa aaaagcggcc gcctcgag                          3516
```

<210> SEQ ID NO 14
<211> LENGTH: 553
<212> TYPE: PRT
<213> ORGANISM: Homo sapiens

<400> SEQUENCE: 14

Met Arg Ala Pro Gly Arg Pro Ala Leu Arg Pro Leu Pro Leu Pro Pro
1               5                   10                  15

Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
        35                  40                  45

Asn Met Lys Asn Val Leu Gln Trp Thr Pro Pro Glu Gly Leu Gln Gly
    50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

-continued

```
Leu Ser Ala Glu Thr Ser Asp Tyr Glu His Gln Tyr Ala Lys Val
            100                 105                 110
Lys Ala Ile Trp Gly Thr Lys Cys Ser Lys Trp Ala Glu Ser Gly Arg
        115                 120                 125
Phe Tyr Pro Phe Leu Glu Thr Gln Ile Gly Pro Pro Glu Val Ala Leu
    130                 135                 140
Thr Thr Asp Glu Lys Ser Ile Ser Val Val Leu Thr Ala Pro Glu Lys
145                 150                 155                 160
Trp Lys Arg Asn Pro Glu Asp Leu Pro Val Ser Met Gln Gln Ile Tyr
                165                 170                 175
Ser Asn Leu Lys Tyr Asn Val Ser Val Leu Asn Thr Lys Ser Asn Arg
            180                 185                 190
Thr Trp Ser Gln Cys Val Thr Asn His Thr Leu Val Leu Thr Trp Leu
        195                 200                 205
Glu Pro Asn Thr Leu Tyr Cys Val His Val Glu Ser Phe Val Pro Gly
    210                 215                 220
Pro Pro Arg Arg Ala Gln Pro Ser Glu Lys Gln Cys Ala Arg Thr Leu
225                 230                 235                 240
Lys Asp Gln Ser Ser Glu Phe Lys Ala Lys Ile Ile Phe Trp Tyr Val
                245                 250                 255
Leu Pro Ile Ser Ile Thr Val Phe Leu Phe Ser Val Met Gly Tyr Ser
            260                 265                 270
Ile Tyr Arg Tyr Ile His Val Gly Lys Glu Lys His Pro Ala Asn Leu
        275                 280                 285
Ile Leu Ile Tyr Gly Asn Glu Phe Asp Lys Arg Phe Phe Val Pro Ala
    290                 295                 300
Glu Lys Ile Val Ile Asn Phe Ile Thr Leu Asn Ile Ser Asp Asp Ser
305                 310                 315                 320
Lys Ile Ser His Gln Asp Met Ser Leu Leu Gly Lys Ser Ser Asp Val
                325                 330                 335
Ser Ser Leu Asn Asp Pro Gln Pro Ser Gly Asn Leu Arg Pro Pro Gln
            340                 345                 350
Glu Glu Glu Glu Val Lys His Leu Gly Tyr Ala Ser His Leu Met Glu
        355                 360                 365
Ile Phe Cys Asp Ser Glu Glu Asn Thr Glu Gly Thr Ser Phe Thr Gln
    370                 375                 380
Gln Glu Ser Leu Ser Arg Thr Ile Pro Pro Asp Lys Thr Val Ile Glu
385                 390                 395                 400
Tyr Glu Tyr Asp Val Arg Thr Thr Asp Ile Cys Ala Gly Pro Glu Glu
                405                 410                 415
Gln Glu Leu Ser Leu Gln Glu Glu Val Ser Thr Gln Gly Thr Leu Leu
            420                 425                 430
Glu Ser Gln Ala Ala Leu Ala Val Leu Gly Pro Gln Thr Leu Gln Tyr
        435                 440                 445
Ser Tyr Thr Pro Gln Leu Gln Asp Leu Asp Pro Leu Ala Gln Glu His
    450                 455                 460
Thr Asp Ser Glu Glu Gly Pro Glu Glu Pro Ser Thr Thr Leu Val
465                 470                 475                 480
Asp Trp Asp Pro Gln Thr Gly Arg Leu Cys Ile Pro Ser Leu Ser Ser
                485                 490                 495
Phe Asp Gln Asp Ser Glu Gly Cys Glu Pro Ser Glu Gly Asp Gly Leu
            500                 505                 510
Gly Glu Glu Gly Leu Leu Ser Arg Leu Tyr Glu Glu Pro Ala Pro Asp
```

```
              515                 520                 525
Arg Pro Pro Gly Glu Asn Glu Thr Tyr Leu Met Gln Phe Met Glu Glu
    530                 535                 540

Trp Gly Leu Tyr Val Gln Met Glu Asn
545                 550

<210> SEQ ID NO 15
<211> LENGTH: 221
<212> TYPE: PRT
<213> ORGANISM: Homo sapiens

<400> SEQUENCE: 15

Asp Glu Val Ala Ile Leu Pro Ala Pro Gln Asn Leu Ser Val Leu Ser
  1               5                  10                  15

Thr Asn Met Lys His Leu Leu Met Trp Ser Pro Val Ile Ala Pro Gly
             20                  25                  30

Glu Thr Val Tyr Tyr Ser Val Glu Tyr Gln Gly Glu Tyr Glu Ser Leu
         35                  40                  45

Tyr Thr Ser His Ile Trp Ile Pro Ser Ser Trp Cys Ser Leu Thr Glu
     50                  55                  60

Gly Pro Glu Cys Asp Val Thr Asp Asp Ile Thr Ala Thr Val Pro Tyr
 65                  70                  75                  80

Asn Leu Arg Val Arg Ala Thr Leu Gly Ser Gln Thr Ser Ala Trp Ser
                 85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala Ile Pro Leu Val Leu Ala Leu
        195                 200                 205

Phe Ala Phe Val Gly Phe Met Leu Ile Leu Val Val Val
    210                 215                 220

<210> SEQ ID NO 16
<211> LENGTH: 221
<212> TYPE: PRT
<213> ORGANISM: Homo sapiens

<400> SEQUENCE: 16

Val Pro Cys Val Ser Gly Gly Leu Pro Lys Pro Ala Asn Ile Thr Phe
  1               5                  10                  15

Leu Ser Ile Asn Met Lys Asn Val Leu Gln Trp Thr Pro Pro Glu Gly
             20                  25                  30

Leu Gln Gly Val Lys Val Thr Tyr Thr Val Gln Tyr Phe Ile Tyr Gly
         35                  40                  45

Gln Lys Lys Trp Leu Asn Lys Ser Glu Cys Arg Asn Ile Asn Arg Thr
     50                  55                  60

Tyr Cys Asp Leu Ser Ala Glu Thr Ser Asp Tyr Glu His Gln Tyr Tyr
```

Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
                100                 105                 110

Val Ala Leu Thr Thr Asp Glu Lys Ser Ile Ser Val Val Leu Thr Ala
                115                 120                 125

Pro Glu Lys Trp Lys Arg Asn Pro Glu Asp Leu Pro Val Ser Met Gln
        130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
                180                 185                 190

Val Pro Gly Pro Pro Arg Arg Ala Gln Pro Ser Glu Lys Gln Cys Ala
                195                 200                 205

Arg Thr Leu Lys Asp Gln Ser Ser Glu Phe Lys Ala Lys
        210                 215                 220

<210> SEQ ID NO 17
<211> LENGTH: 217
<212> TYPE: PRT
<213> ORGANISM: Homo sapiens

<400> SEQUENCE: 17

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Pro Glu Gly
                20                  25                  30

Leu Gln Gly Val Lys Val Thr Tyr Thr Val Gln Tyr Phe Ile Tyr Gly
                35                  40                  45

Gln Lys Lys Trp Leu Asn Lys Ser Glu Cys Arg Asn Ile Asn Arg Thr
        50                  55                  60

Tyr Cys Asp Leu Ser Ala Glu Thr Ser Asp Tyr Glu His Gln Tyr Tyr
65                  70                  75                  80

Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
                100                 105                 110

Val Ala Leu Thr Thr Asp Glu Lys Ser Ile Ser Val Val Leu Thr Ala
                115                 120                 125

Pro Glu Lys Trp Lys Arg Asn Pro Glu Asp Leu Pro Val Ser Met Gln
        130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
                180                 185                 190

Val Pro Gly Pro Pro Arg Arg Ala Gln Pro Ser Glu Lys Gln Cys Ala
                195                 200                 205

Arg Thr Leu Lys Asp Gln Ser Ser Glu
        210                 215

```
<210> SEQ ID NO 18
<211> LENGTH: 214
<212> TYPE: PRT
<213> ORGANISM: Homo sapiens

<400> SEQUENCE: 18

Val Pro Cys Val Ser Gly Gly Leu Pro Lys Pro Ala Asn Ile Thr Phe
  1               5                  10                  15

Leu Ser Ile Asn Met Lys Asn Val Leu Gln Trp Thr Pro Pro Glu Gly
             20                  25                  30

Leu Gln Gly Val Lys Val Thr Tyr Thr Val Gln Tyr Phe Ile Tyr Gly
         35                  40                  45

Gln Lys Lys Trp Leu Asn Lys Ser Glu Cys Arg Asn Ile Asn Arg Thr
 50                  55                  60

Tyr Cys Asp Leu Ser Ala Glu Thr Ser Asp Tyr Glu His Gln Tyr Tyr
 65                  70                  75                  80

Ala Lys Val Lys Ala Ile Trp Gly Thr Lys Cys Ser Lys Trp Ala Glu
                 85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
        115                 120                 125

Pro Glu Lys Trp Lys Arg Asn Pro Glu Asp Leu Pro Val Ser Met Gln
130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln
    210

<210> SEQ ID NO 19
<211> LENGTH: 207
<212> TYPE: PRT
<213> ORGANISM: Homo sapiens

<400> SEQUENCE: 19

Leu Pro Lys Pro Ala Asn Ile Thr Phe Leu Ser Ile Asn Met Lys Asn
  1               5                  10                  15

Val Leu Gln Trp Thr Pro Pro Glu Gly Leu Gln Gly Val Lys Val Thr
             20                  25                  30

Tyr Thr Val Gln Tyr Phe Ile Tyr Gly Gln Lys Lys Trp Leu Asn Lys
         35                  40                  45

Ser Glu Cys Arg Asn Ile Asn Arg Thr Tyr Cys Asp Leu Ser Ala Glu
 50                  55                  60

Thr Ser Asp Tyr Glu His Gln Tyr Tyr Ala Lys Val Lys Ala Ile Trp
 65                  70                  75                  80

Gly Thr Lys Cys Ser Lys Trp Ala Glu Ser Gly Arg Phe Tyr Pro Phe
                 85                  90                  95

Leu Glu Thr Gln Ile Gly Pro Pro Glu Val Ala Leu Thr Thr Asp Glu
            100                 105                 110
```

-continued

```
Lys Ser Ile Ser Val Val Leu Thr Ala Pro Glu Lys Trp Lys Arg Asn
            115                 120                 125

Pro Glu Asp Leu Pro Val Ser Met Gln Gln Ile Tyr Ser Asn Leu Lys
        130                 135                 140

Tyr Asn Val Ser Val Leu Asn Thr Lys Ser Asn Arg Thr Trp Ser Gln
145                 150                 155                 160

Cys Val Thr Asn His Thr Leu Val Leu Thr Trp Leu Pro Asn Thr
                165                 170                 175

Leu Tyr Cys Val His Val Glu Ser Phe Val Pro Gly Pro Arg Arg
        180                 185                 190

Ala Gln Pro Ser Glu Lys Gln Cys Ala Arg Thr Leu Lys Asp Gln
        195                 200                 205
```

<210> SEQ ID NO 20
<211> LENGTH: 971
<212> TYPE: DNA
<213> ORGANISM: Homo sapiens
<220> FEATURE:
<221> NAME/KEY: CDS
<222> LOCATION: (18)...(950)

<400> SEQUENCE: 20

```
gaattcgagt ctaccaa atg cag act ttc aca atg gtt cta gaa gaa atc         50
                   Met Gln Thr Phe Thr Met Val Leu Glu Glu Ile
                     1               5                  10 tgg aca agt ctt ttc atg tgg ttt ttc tac gca ttg att cca tgt ttg        98
Trp Thr Ser Leu Phe Met Trp Phe Phe Tyr Ala Leu Ile Pro Cys Leu
             15                  20                  25 ctc aca gat gaa gtg gcc att ctg cct gcc cct cag aac ctc tct gta       146
Leu Thr Asp Glu Val Ala Ile Leu Pro Ala Pro Gln Asn Leu Ser Val
         30                  35                  40 ctc tca acc aac atg aag cat ctc ttg atg tgg agc cca gtg atc gcg       194
Leu Ser Thr Asn Met Lys His Leu Leu Met Trp Ser Pro Val Ile Ala
     45                  50                  55 cct gga gaa aca gtg tac tat tct gtc gaa tac cag ggg gag tac gag       242
Pro Gly Glu Thr Val Tyr Tyr Ser Val Glu Tyr Gln Gly Glu Tyr Glu
 60                  65                  70                  75 agc ctg tac acg agc cac atc tgg atc ccc agc agc tgg tgc tca ctc       290
Ser Leu Tyr Thr Ser His Ile Trp Ile Pro Ser Ser Trp Cys Ser Leu
                 80                  85                  90 act gaa ggt cct gag tgt gat gtc act gat gac atc acg gcc act gtg       338
Thr Glu Gly Pro Glu Cys Asp Val Thr Asp Asp Ile Thr Ala Thr Val
             95                 100                 105 cca tac aac ctt cgt gtc agg gcc aca ttg ggc tca cag acc tca gcc       386
Pro Tyr Asn Leu Arg Val Arg Ala Thr Leu Gly Ser Gln Thr Ser Ala
         110                 115                 120 tgg agc atc ctg aag cat ccc ttt aat aga aac tca acc atc ctt acc       434
Trp Ser Ile Leu Lys His Pro Phe Asn Arg Asn Ser Thr Ile Leu Thr
     125                 130                 135 cga cct ggg atg gag atc acc aaa gat ggc ttc cac ctg gtt att gag       482
Arg Pro Gly Met Glu Ile Thr Lys Asp Gly Phe His Leu Val Ile Glu
140                 145                 150                 155 ctg gag gac ctg ggg ccc cag ttt gag ttc ctt gtg gcc tac tgg agg       530
Leu Glu Asp Leu Gly Pro Gln Phe Glu Phe Leu Val Ala Tyr Trp Arg
                160                 165                 170 agg gag cct ggt gcc gag gaa cat gtc aaa atg gtg agg agt ggg ggt       578
Arg Glu Pro Gly Ala Glu Glu His Val Lys Met Val Arg Ser Gly Gly
            175                 180                 185 att cca gtg cac cta gaa acc atg gag cca ggg gct gca tac tgt gtg       626
Ile Pro Val His Leu Glu Thr Met Glu Pro Gly Ala Ala Tyr Cys Val
```

```
aag gcc cag aca ttc gtg aag gcc att ggg agg tac agc gcc ttc agc      674
Lys Ala Gln Thr Phe Val Lys Ala Ile Gly Arg Tyr Ser Ala Phe Ser
    205                 210                 215 cag aca gaa tgt gtg gag gtg caa gga gag gcc att ccc ctg gta ctg      722
Gln Thr Glu Cys Val Glu Val Gln Gly Glu Ala Ile Pro Leu Val Leu
220                 225                 230                 235 gcc ctg ttt gcc ttt gtt ggc ttc atg ctg atc ctt gtg gtc gtg cca      770
Ala Leu Phe Ala Phe Val Gly Phe Met Leu Ile Leu Val Val Val Pro
                240                 245                 250 ctg ttc gtc tgg aaa atg ggc cgg ctg ctc cag tac tcc tgt tgc ccc      818
Leu Phe Val Trp Lys Met Gly Arg Leu Leu Gln Tyr Ser Cys Cys Pro
        255                 260                 265 gtg gtg gtc ctc cca gac acc ttg aaa ata acc aat tca ccc cag aag      866
Val Val Val Leu Pro Asp Thr Leu Lys Ile Thr Asn Ser Pro Gln Lys
    270                 275                 280 tta atc agc tgc aga agg gag gag gtg gat gcc tgt gcc acg gct gtg      914
Leu Ile Ser Cys Arg Arg Glu Glu Val Asp Ala Cys Ala Thr Ala Val
285                 290                 295 atg tct cct gag gaa ctc ctc agg gcc tgg atc tca taggtttgcg           960
Met Ser Pro Glu Glu Leu Leu Arg Ala Trp Ile Ser
300                 305                 310 gaaggctcga g                                                         971
```

<210> SEQ ID NO 21
<211> LENGTH: 311
<212> TYPE: PRT
<213> ORGANISM: Homo sapiens

<400> SEQUENCE: 21

```
Met Gln Thr Phe Thr Met Val Leu Glu Glu Ile Trp Thr Ser Leu Phe
 1               5                  10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205
```

```
Val Lys Ala Ile Gly Arg Tyr Ser Ala Phe Ser Gln Thr Glu Cys Val
    210                 215                 220

Glu Val Gln Gly Glu Ala Ile Pro Leu Val Leu Ala Leu Phe Ala Phe
225                 230                 235                 240

Val Gly Phe Met Leu Ile Leu Val Val Pro Leu Phe Val Trp Lys
                245                 250                 255

Met Gly Arg Leu Leu Gln Tyr Ser Cys Cys Pro Val Val Leu Pro
            260                 265                 270

Asp Thr Leu Lys Ile Thr Asn Ser Pro Gln Lys Leu Ile Ser Cys Arg
        275                 280                 285

Arg Glu Glu Val Asp Ala Cys Ala Thr Ala Val Met Ser Pro Glu Glu
290                 295                 300

Leu Leu Arg Ala Trp Ile Ser
305                 310

<210> SEQ ID NO 22
<211> LENGTH: 33
<212> TYPE: DNA
<213> ORGANISM: Homo sapiens

<400> SEQUENCE: 22
gcgaattcga gtctaccaaa tgcagacttt cac                                   33

<210> SEQ ID NO 23
<211> LENGTH: 32
<212> TYPE: DNA
<213> ORGANISM: Homo sapiens

<400> SEQUENCE: 23
cgctcgagcc ttccgcaaac ctatgagatc ca                                    32

<210> SEQ ID NO 24
<211> LENGTH: 203
<212> TYPE: PRT
<213> ORGANISM: Homo sapiens

<400> SEQUENCE: 24

Asp Glu Val Ala Ile Leu Pro Ala Pro Gln Asn Leu Ser Val Leu Ser
  1               5                  10                  15

Thr Asn Met Lys His Leu Leu Met Trp Ser Pro Val Ile Ala Pro Gly
             20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160
```

Val His Leu Glu Thr Met Glu Pro Gly Ala Ala Tyr Cys Val Lys Ala
            165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala Ile Pro
        195                 200

<210> SEQ ID NO 25
<211> LENGTH: 201
<212> TYPE: PRT
<213> ORGANISM: Homo sapiens

<400> SEQUENCE: 25

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
            35                  40                  45

Tyr Thr Ser His Ile Trp Ile Pro Ser Ser Trp Cys Ser Leu Thr Glu
        50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
            85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
            165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala
        195                 200

<210> SEQ ID NO 26
<211> LENGTH: 201
<212> TYPE: PRT
<213> ORGANISM: Homo sapiens

<400> SEQUENCE: 26

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
            35                  40                  45

Tyr Thr Ser His Ile Trp Ile Pro Ser Ser Trp Cys Ser Leu Thr Glu
        50                  55                  60

Gly Pro Glu Cys Asp Val Thr Asp Asp Ile Thr Ala Thr Val Pro Tyr
65                  70                  75                  80

```
Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
            100                 105                 110

Gly Met Glu Ile Pro Lys His Gly Phe His Leu Val Ile Glu Leu Glu
        115                 120                 125

Asp Leu Gly Pro Gln Phe Glu Phe Leu Val Ala Tyr Trp Thr Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala
        195                 200
```

<210> SEQ ID NO 27
<211> LENGTH: 196
<212> TYPE: PRT
<213> ORGANISM: Homo sapiens

<400> SEQUENCE: 27

```
Leu Pro Ala Pro Gln Asn Leu Ser Val Leu Ser Thr Asn Met Lys His
  1               5                  10                  15

Leu Leu Met Trp Ser Pro Val Ile Ala Pro Gly Glu Thr Val Tyr Tyr
            20                  25                  30

Ser Val Glu Tyr Gln Gly Glu Tyr Glu Ser Leu Tyr Thr Ser His Ile
        35                  40                  45

Trp Ile Pro Ser Ser Trp Cys Ser Leu Thr Glu Gly Pro Glu Cys Asp
    50                  55                  60

Val Thr Asp Asp Ile Thr Ala Thr Val Pro Tyr Asn Leu Arg Val Arg
 65                  70                  75                  80

Ala Thr Leu Gly Ser Gln Thr Ser Ala Trp Ser Ile Leu Lys His Pro
                85                  90                  95

Phe Asn Arg Asn Ser Thr Ile Leu Thr Arg Pro Gly Met Glu Ile Thr
            100                 105                 110

Lys Asp Gly Phe His Leu Val Ile Glu Leu Glu Asp Leu Gly Pro Gln
        115                 120                 125

Phe Glu Phe Leu Val Ala Tyr Trp Arg Arg Glu Pro Gly Ala Glu Glu
    130                 135                 140

His Val Lys Met Val Arg Ser Gly Gly Ile Pro Val His Leu Glu Thr
145                 150                 155                 160

Met Glu Pro Gly Ala Ala Tyr Cys Val Lys Ala Gln Thr Phe Val Lys
                165                 170                 175

Ala Ile Gly Arg Tyr Ser Ala Phe Ser Gln Thr Glu Cys Val Glu Val
            180                 185                 190

Gln Gly Glu Ala
        195
```

<210> SEQ ID NO 28
<211> LENGTH: 203
<212> TYPE: PRT
<213> ORGANISM: Homo sapiens

<400> SEQUENCE: 28

```
Asp Glu Val Ala Ile Leu Pro Ala Pro Gln Asn Leu Ser Val Leu Ser
 1               5                  10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
        35                  40                  45

Tyr Thr Ser His Ile Trp Ile Pro Ser Ser Trp Cys Ser Leu Thr Glu
    50                  55                  60

Gly Pro Glu Cys Asp Val Thr Asp Asp Ile Thr Ala Thr Val Pro Tyr
65                  70                  75                  80

Asn Leu Arg Val Arg Ala Thr Leu Gly Ser Gln Thr Ser Ala Trp Ser
                85                  90                  95

Ile Leu Lys His Pro Phe Asn Arg Asn Ser Thr Ile Leu Thr Arg Pro
            100                 105                 110

Gly Met Glu Ile Pro Lys His Gly Phe His Leu Val Ile Glu Leu Glu
        115                 120                 125

Asp Leu Gly Pro Gln Phe Glu Phe Leu Val Ala Tyr Trp Thr Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala Ile Pro
            195                 200

<210> SEQ ID NO 29
<211> LENGTH: 196
<212> TYPE: PRT
<213> ORGANISM: Homo sapiens

<400> SEQUENCE: 29

Leu Pro Ala Pro Gln Asn Leu Ser Val Leu Ser Thr Asn Met Lys His
 1               5                  10                  15

Leu Leu Met Trp Ser Pro Val Ile Ala Pro Gly Glu Thr Val Tyr Tyr
            20                  25                  30

Ser Val Glu Tyr Gln Gly Glu Tyr Glu Ser Leu Tyr Thr Ser His Ile
        35                  40                  45

Trp Ile Pro Ser Ser Trp Cys Ser Leu Thr Glu Gly Pro Glu Cys Asp
    50                  55                  60

Val Thr Asp Asp Ile Thr Ala Thr Val Pro Tyr Asn Leu Arg Val Arg
65                  70                  75                  80

Ala Thr Leu Gly Ser Gln Thr Ser Ala Trp Ser Ile Leu Lys His Pro
                85                  90                  95

Phe Asn Arg Asn Ser Thr Ile Leu Thr Arg Pro Gly Met Glu Ile Pro
            100                 105                 110

Lys His Gly Phe His Leu Val Ile Glu Leu Glu Asp Leu Gly Pro Gln
        115                 120                 125

Phe Glu Phe Leu Val Ala Tyr Trp Thr Arg Glu Pro Gly Ala Glu Glu
    130                 135                 140

His Val Lys Met Val Arg Ser Gly Gly Ile Pro Val His Leu Glu Thr
145                 150                 155                 160

Met Glu Pro Gly Ala Ala Tyr Cys Val Lys Ala Gln Thr Phe Val Lys
                165                 170                 175
```

Ala Ile Gly Arg Tyr Ser Ala Phe Ser Gln Thr Glu Cys Val Glu Val
            180                 185                 190

Gln Gly Glu Ala
        195

<210> SEQ ID NO 30
<211> LENGTH: 747
<212> TYPE: DNA
<213> ORGANISM: Homo sapiens

<400> SEQUENCE: 30

| | | | | | |
|---|---|---|---|---|---|
| ttttctgaca | tacggggcag | tgtgcaagcc | aaagatggaa | acattgacat | cagaatctta | 60 |
| aggaggactg | agtctttgca | agacacaaag | cctgcgaatc | gatgctgcct | cctgcgccat | 120 |
| ttgctaagac | tctatctgga | cagggtattt | aaaaactacc | agacccctga | ccattatact | 180 |
| ctccggaaga | tcagcagcct | cgccaattcc | tttcttacca | tcaagaagga | cctccggctc | 240 |
| tgtcatgccc | acatgacatg | ccattgtggg | aggaagcaa | tgaagaaata | cagccagatt | 300 |
| ctgagtcact | ttgaaaagct | ggaacctcag | gcagcagttg | tgaaggcttt | ggggaacta | 360 |
| gacattcttc | tgcaatggat | ggaggagaca | gaataggagg | aaagtgatgc | tgctgctaag | 420 |
| aatattcgag | gtcaagagct | ccagtcttca | atacctgcag | aggaggcatg | accccaaacc | 480 |
| accatctctt | tactgtacta | gtcttgtgct | ggtcacagtg | tatcttattt | atgcattact | 540 |
| tgcttccttg | catgattgtc | tttatgcatc | cccaatctta | attgagacca | tacttgtata | 600 |
| agattttttgt | aatatctttc | tgctattgga | tatatttatt | agttaatata | tttatttatt | 660 |
| ttttgctatt | aatgtattta | attttttact | tgggcatgaa | actttaaaaa | aaattcacaa | 720 |
| gattatatttt | ataacctgac | tagagca | | | | 747 |

<210> SEQ ID NO 31
<211> LENGTH: 614
<212> TYPE: DNA
<213> ORGANISM: Homo sapiens

<400> SEQUENCE: 31

| | | | | | |
|---|---|---|---|---|---|
| ttttctgaca | tacggggcag | tgtgcaagcc | aaagatggaa | acattgacat | cagaatctta | 60 |
| aggaggactg | agtctttgca | agacacaaag | cctgcgaatc | gatgctgcct | cctgcgccat | 120 |
| ttgctaagac | tctatctgga | cagggtattt | aaaaactacc | agacccctga | ccattatact | 180 |
| ctccggaaga | tcagcagcct | cgccaattcc | tttcttacca | tcaagaagga | cctccggctc | 240 |
| tgtctggaac | ctcaggcagc | agttgtgaag | gctttggggg | aactagacat | tcttctgcaa | 300 |
| tggatggagg | agacagaata | ggaggaaagt | gatgctgctg | ctaagaatat | tcgaggtcaa | 360 |
| gagctccagt | cttcaatacc | tgcagaggag | gcatgacccc | aaaccaccat | ctctttactg | 420 |
| tactagtcctt | gtgctggtca | cagtgtatct | tatttatgca | ttacttgctt | ccttgcatga | 480 |
| ttgtctttat | gcatccccaa | tcttaattga | gaccatactt | gtataagatt | tttgtaatat | 540 |
| ctttctgcta | ttggatatat | ttattagtta | atatatttat | ttattttttg | ctattaatgt | 600 |
| atttaatttt | ttac | | | | | 614 |

<210> SEQ ID NO 32
<211> LENGTH: 253
<212> TYPE: DNA
<213> ORGANISM: Homo sapiens

<400> SEQUENCE: 32

```
ctttgaattc ctagctcctg tggtctccag atttcaggcc taagatgaaa gcctctagtc    60
ttgccttcag ccttctctct gctgcgtttt atctcctatg gactccttcc actggactga   120
agacactcaa tttgggaagc tgtgtgatcg ccacaaacct tcaggaaata cgaaatggat   180
tttctgagat acggggcagt gtgcaagcca aagatggaaa cattgacatc agaatcttaa   240
ggaggactga gtc                                                     253
```

```
<210> SEQ ID NO 33
<211> LENGTH: 24
<212> TYPE: DNA
<213> ORGANISM: Homo sapiens

<400> SEQUENCE: 33
attcctagct cctgtggtct ccag                                          24

<210> SEQ ID NO 34
<211> LENGTH: 25
<212> TYPE: DNA
<213> ORGANISM: Homo sapiens

<400> SEQUENCE: 34
ctctgctgcg ttttatctcc tatgg                                         25

<210> SEQ ID NO 35
<211> LENGTH: 25
<212> TYPE: DNA
<213> ORGANISM: Mus musculus

<400> SEQUENCE: 35
tggcgaggct gctgatcttt ctcag                                         25

<210> SEQ ID NO 36
<211> LENGTH: 25
<212> TYPE: DNA
<213> ORGANISM: Mus musculus

<400> SEQUENCE: 36
ctttatgtct ttcaaagact cagtc                                         25

<210> SEQ ID NO 37
<211> LENGTH: 26
<212> TYPE: DNA
<213> ORGANISM: Mus musculus

<400> SEQUENCE: 37
catcagaatt ttaaggacga ctgagt                                        26

<210> SEQ ID NO 38
<211> LENGTH: 25
<212> TYPE: DNA
<213> ORGANISM: Mus musculus

<400> SEQUENCE: 38
ggtggtcagg ggtctggtag acttt                                         25

<210> SEQ ID NO 39
<211> LENGTH: 824
<212> TYPE: DNA
<213> ORGANISM: Mus musculus
<220> FEATURE:
<221> NAME/KEY: CDS
<222> LOCATION: (71)...(598)
```

```
<400> SEQUENCE: 39
tgggagacat cgatagccct gattgatctc tttgaatttt cgcttctggt ctccaggatc        60
taggtgtaag atg aaa ggc ttt ggt ctt gcc ttt gga ctg ttc tcc gct         109
         Met Lys Gly Phe Gly Leu Ala Phe Gly Leu Phe Ser Ala
         1               5                   10 gtg ggt ttt ctt ctc tgg act cct tta act ggg ctc aag acc ctc cat        157
Val Gly Phe Leu Leu Trp Thr Pro Leu Thr Gly Leu Lys Thr Leu His
 15              20                  25 ttg gga agc tgt gtg att act gca aac cta cag gca ata caa aag gaa        205
Leu Gly Ser Cys Val Ile Thr Ala Asn Leu Gln Ala Ile Gln Lys Glu
 30              35                  40                  45 ttt tct gag att cgg gat agt gtg caa gct gaa gat aca aat att gac        253
Phe Ser Glu Ile Arg Asp Ser Val Gln Ala Glu Asp Thr Asn Ile Asp
                 50                  55                  60 atc aga att tta agg acg act gag tct ttg aaa gac ata aag tct ttg        301
Ile Arg Ile Leu Arg Thr Thr Glu Ser Leu Lys Asp Ile Lys Ser Leu
                 65                  70                  75 gat agg tgc tgc ttc ctt cgt cat cta gtg aga ttc tat ctg gac agg        349
Asp Arg Cys Cys Phe Leu Arg His Leu Val Arg Phe Tyr Leu Asp Arg
         80                  85                  90 gta ttc aaa gtc tac cag acc cct gac cac cat acc ctg aga aag atc        397
Val Phe Lys Val Tyr Gln Thr Pro Asp His His Thr Leu Arg Lys Ile
     95                  100                 105 agc agc ctc gcc aac tcc ttt ctt atc atc aag aag gac ctc tca gtc        445
Ser Ser Leu Ala Asn Ser Phe Leu Ile Ile Lys Lys Asp Leu Ser Val
110                 115                 120                 125 tgt cat tct cac atg gca tgt cat tgt ggg gaa gaa gca atg gag aaa        493
Cys His Ser His Met Ala Cys His Cys Gly Glu Glu Ala Met Glu Lys
                 130                 135                 140 tac aac caa att ctg agt cac ttc ata gag ttg gaa ctt cag gca gcg        541
Tyr Asn Gln Ile Leu Ser His Phe Ile Glu Leu Glu Leu Gln Ala Ala
                 145                 150                 155 gtg gta aag gct ttg gga gaa cta ggc att ctt ctg aga tgg atg gag        589
Val Val Lys Ala Leu Gly Glu Leu Gly Ile Leu Leu Arg Trp Met Glu
160                 165                 170 gag atg cta tagatgaaag tggagaggct gctgagaaca ctcctgtcca               638
Glu Met Leu
        175 agaatctcag acctcagcac catgaagaca tggccccagg tgctggcatt tctactcaag      698 agttccagtc ctcagcacca cgaagatggc ctcaaaccac cacccctttg tgatataact      758 tagtgctagc tatgtgtata ttatttctac attattggct cccttatgtg aatgccttca      818 tgtgtc                                                                824

<210> SEQ ID NO 40
<211> LENGTH: 176
<212> TYPE: PRT
<213> ORGANISM: Mus musculus

<400> SEQUENCE: 40

Met Lys Gly Phe Gly Leu Ala Phe Gly Leu Phe Ser Ala Val Gly Phe
 1               5                   10                  15

Leu Leu Trp Thr Pro Leu Thr Gly Leu Lys Thr Leu His Leu Gly Ser
             20                  25                  30

Cys Val Ile Thr Ala Asn Leu Gln Ala Ile Gln Lys Glu Phe Ser Glu
         35                  40                  45

Ile Arg Asp Ser Val Gln Ala Glu Asp Thr Asn Ile Asp Ile Arg Ile
     50                  55                  60
```

```
Leu Arg Thr Thr Glu Ser Leu Lys Asp Ile Lys Ser Leu Asp Arg Cys
 65                  70                  75                  80

Cys Phe Leu Arg His Leu Val Arg Phe Tyr Leu Asp Arg Val Phe Lys
                 85                  90                  95

Val Tyr Gln Thr Pro Asp His His Thr Leu Arg Lys Ile Ser Ser Leu
            100                 105                 110

Ala Asn Ser Phe Leu Ile Ile Lys Lys Asp Leu Ser Val Cys His Ser
        115                 120                 125

His Met Ala Cys His Cys Gly Glu Glu Ala Met Glu Lys Tyr Asn Gln
    130                 135                 140

Ile Leu Ser His Phe Ile Glu Leu Glu Leu Gln Ala Ala Val Val Lys
145                 150                 155                 160

Ala Leu Gly Glu Leu Gly Ile Leu Leu Arg Trp Met Glu Glu Met Leu
                165                 170                 175

<210> SEQ ID NO 41
<211> LENGTH: 756
<212> TYPE: DNA
<213> ORGANISM: Mus musculus
<220> FEATURE:
<221> NAME/KEY: CDS
<222> LOCATION: (71)...(532)

<400> SEQUENCE: 41
tgggagacat cgatagccct gattgatctc tttgaatttt cgcttctggt ctccaggatc      60
taggtgtaag atg aaa ggc ttt ggt ctt gcc ttt gga ctg ttc tcc gct         109
        Met Lys Gly Phe Gly Leu Ala Phe Gly Leu Phe Ser Ala
          1               5                  10 gtg ggt ttt ctt ctc tgg act cct tta act ggg ctc aag acc ctc cat        157
Val Gly Phe Leu Leu Trp Thr Pro Leu Thr Gly Leu Lys Thr Leu His
 15                  20                  25 ttg gga agc tgt gtg att act gca aac cta cag gca ata caa aag gaa        205
Leu Gly Ser Cys Val Ile Thr Ala Asn Leu Gln Ala Ile Gln Lys Glu
 30                  35                  40                  45 ttt tct gag att cgg gat agt gtg tct ttg gat agg tgc tgc ttc ctt        253
Phe Ser Glu Ile Arg Asp Ser Val Ser Leu Asp Arg Cys Cys Phe Leu
                 50                  55                  60 cgt cat cta gtg aga ttc tat ctg gac agg gta ttc aaa gtc tac cag        301
Arg His Leu Val Arg Phe Tyr Leu Asp Arg Val Phe Lys Val Tyr Gln
             65                  70                  75 acc cct gac cac cat acc ctg aga aag atc agc agc ctc gcc aac tcc        349
Thr Pro Asp His His Thr Leu Arg Lys Ile Ser Ser Leu Ala Asn Ser
         80                  85                  90 ttt ctt atc atc aag aag gac ctc tca gtc tgt cat tct cac atg gca        397
Phe Leu Ile Ile Lys Lys Asp Leu Ser Val Cys His Ser His Met Ala
     95                 100                 105 tgt cat tgt ggg gaa gaa gca atg gag aaa tac aac caa att ctg agt        445
Cys His Cys Gly Glu Glu Ala Met Glu Lys Tyr Asn Gln Ile Leu Ser
110                 115                 120                 125 cac ttc ata gag ttg gaa ctt cag gca gcg gtg gta aag gct ttg gga        493
His Phe Ile Glu Leu Glu Leu Gln Ala Ala Val Val Lys Ala Leu Gly
                130                 135                 140 gaa cta ggc att ctt ctg aga tgg atg gag gag atg cta tagatgaaag        542
Glu Leu Gly Ile Leu Leu Arg Trp Met Glu Glu Met Leu
            145                 150 tggataggct gctgagaaca ctcctgtcca agaatctcag acctcagcac catgaagaca      602
tggccccagg tgctggcatt tctactcaag agttccagtc ctcagcacca cgaagatggc      662
```
ctcaaaccac cacccctttg tgatataact tagtgctagc tatgtgtata ttatttctac    722
attattggct cccttatgtg aatgccttca tgtg                                756

<210> SEQ ID NO 42
<211> LENGTH: 154
<212> TYPE: PRT
<213> ORGANISM: Mus musculus

<400> SEQUENCE: 42

Met Lys Gly Phe Gly Leu Ala Phe Gly Leu Phe Ser Ala Val Gly Phe
1               5                   10                  15

Leu Leu Trp Thr Pro Leu Thr Gly Leu Lys Thr Leu His Leu Gly Ser
            20                  25                  30

Cys Val Ile Thr Ala Asn Leu Gln Ala Ile Gln Lys Glu Phe Ser Glu
        35                  40                  45

Ile Arg Asp Ser Val Ser Leu Asp Arg Cys Cys Phe Leu Arg His Leu
    50                  55                  60

Val Arg Phe Tyr Leu Asp Arg Val Phe Lys Val Tyr Gln Thr Pro Asp
65                  70                  75                  80

His His Thr Leu Arg Lys Ile Ser Ser Leu Ala Asn Ser Phe Leu Ile
                85                  90                  95

Ile Lys Lys Asp Leu Ser Val Cys His Ser His Met Ala Cys His Cys
            100                 105                 110

Gly Glu Glu Ala Met Glu Lys Tyr Asn Gln Ile Leu Ser His Phe Ile
        115                 120                 125

Glu Leu Glu Leu Gln Ala Ala Val Val Lys Ala Leu Gly Leu Gly Leu Gly
    130                 135                 140

Ile Leu Leu Arg Trp Met Glu Glu Met Leu
145                 150

<210> SEQ ID NO 43
<211> LENGTH: 23
<212> TYPE: DNA
<213> ORGANISM: Mus musculus

<400> SEQUENCE: 43
ggtgcatatt cctggtggct aga                                             23

<210> SEQ ID NO 44
<211> LENGTH: 25
<212> TYPE: DNA
<213> ORGANISM: Mus musculus

<400> SEQUENCE: 44
attgcagtgt aagggaatac agaga                                           25

<210> SEQ ID NO 45
<211> LENGTH: 451
<212> TYPE: DNA
<213> ORGANISM: Artificial Sequence
<220> FEATURE:
<223> OTHER INFORMATION: EST 277139
<220> FEATURE:
<221> NAME/KEY: misc_feature
<222> LOCATION: (1)...(451)
<223> OTHER INFORMATION: n = A,T,C or G

<400> SEQUENCE: 45
agtgtgtgac caaccacacg ctggtgctca cctgggctgg agccgaacac tctttactgc    60
gtacacgtgg agtccttcgt cccagggccc cctcgccgtg ctcagccttc tgagaagcag   120

-continued

```
tgtgccagga ctttgaaaga tcaatcatca gagttcaagg ctaaaatcat cttctggtat      180
gttttgccca tatctattac cgtgtttctt ttttctgtga tgggctattc catctaccga      240
tatatccacg ttgggcaaag agaaacaccc aggcaaattt gattttgatt tatgggaaat      300
gaatttgaca aaagattctt tgtgcctgct ggaaaaaatc gtggattaac tttattcacc      360
ctcaatatct cgggtggatt ctaaaatttt ctccatccag gggtatggag gtttactggg      420
ggtaaangcg ggtgttgttt nccaggcctt a                                     451
```

<210> SEQ ID NO 46
<211> LENGTH: 18
<212> TYPE: DNA
<213> ORGANISM: Homo sapiens

<400> SEQUENCE: 46

```
gctgggtgtt tctctttg                                                     18
```

<210> SEQ ID NO 47
<211> LENGTH: 27
<212> TYPE: DNA
<213> ORGANISM: Homo sapiens

<400> SEQUENCE: 47

```
ccatcctaat acgactcact atagggc                                           27
```

<210> SEQ ID NO 48
<211> LENGTH: 20
<212> TYPE: DNA
<213> ORGANISM: Homo sapiens

<400> SEQUENCE: 48

```
ggaatagccc atcacagaaa                                                   20
```

<210> SEQ ID NO 49
<211> LENGTH: 23
<212> TYPE: DNA
<213> ORGANISM: Homo sapiens

<400> SEQUENCE: 49

```
actcactata gggctcgagc ggc                                               23
```

<210> SEQ ID NO 50
<211> LENGTH: 22
<212> TYPE: DNA
<213> ORGANISM: Homo sapiens

<400> SEQUENCE: 50

```
caccagaggg tcttcaagga gt                                                22
```

<210> SEQ ID NO 51
<211> LENGTH: 49
<212> TYPE: DNA
<213> ORGANISM: Homo sapiens

<400> SEQUENCE: 51

```
gagcacagaa ttcactactc gaggcggccg ctttttttttt tttttttt                   49
```

<210> SEQ ID NO 52
<211> LENGTH: 553
<212> TYPE: PRT
<213> ORGANISM: Artificial Sequence
<220> FEATURE:

<223> OTHER INFORMATION: PCR Primer

<400> SEQUENCE: 52

```
Met Arg Ala Pro Gly Arg Pro Ala Leu Arg Pro Leu Pro Leu Pro Pro
 1               5                  10                  15
Leu Leu Leu Leu Leu Leu Ala Ala Pro Trp Gly Arg Ala Val Pro Cys
            20                  25                  30
Val Ser Gly Gly Leu Pro Lys Pro Ala Asn Ile Thr Phe Leu Ser Ile
        35                  40                  45
Asn Met Lys Asn Val Leu Gln Trp Thr Pro Pro Glu Gly Leu Gln Gly
    50                  55                  60
Val Lys Val Thr Tyr Thr Val Gln Tyr Phe Ile Tyr Gly Gln Lys Lys
 65                  70                  75                  80
Trp Leu Asn Lys Ser Glu Cys Arg Asn Ile Asn Arg Thr Tyr Cys Asp
                85                  90                  95
Leu Ser Ala Glu Thr Ser Asp Tyr Glu His Gln Tyr Tyr Ala Lys Val
            100                 105                 110
Lys Ala Ile Trp Gly Thr Lys Cys Ser Lys Trp Ala Glu Ser Gly Arg
        115                 120                 125
Phe Tyr Pro Phe Leu Glu Thr Gln Ile Gly Pro Pro Glu Val Ala Leu
130                 135                 140
Thr Thr Asp Glu Lys Ser Ile Ser Val Val Leu Thr Ala Pro Glu Lys
145                 150                 155                 160
Trp Lys Arg Asn Pro Glu Asp Leu Pro Val Ser Met Gln Gln Ile Tyr
                165                 170                 175
Ser Asn Leu Lys Tyr Asn Val Ser Val Leu Asn Thr Lys Ser Asn Arg
            180                 185                 190
Thr Trp Ser Gln Cys Val Thr Asn His Thr Leu Val Leu Thr Trp Leu
        195                 200                 205
Glu Pro Asn Thr Leu Tyr Cys Val His Val Glu Ser Phe Val Pro Gly
210                 215                 220
Pro Pro Arg Arg Ala Gln Pro Ser Glu Lys Gln Cys Ala Arg Thr Leu
225                 230                 235                 240
Lys Asp Gln Ser Ser Glu Phe Lys Ala Lys Ile Ile Phe Trp Tyr Val
                245                 250                 255
Leu Pro Ile Ser Ile Thr Val Phe Leu Phe Ser Val Met Gly Tyr Ser
            260                 265                 270
Ile Tyr Arg Tyr Ile His Val Gly Lys Glu Lys His Pro Ala Asn Leu
        275                 280                 285
Ile Leu Ile Tyr Gly Asn Glu Phe Asp Lys Arg Phe Phe Val Pro Ala
    290                 295                 300
Glu Lys Ile Val Ile Asn Phe Ile Thr Leu Asn Ile Ser Asp Asp Ser
305                 310                 315                 320
Lys Ile Ser His Gln Asp Met Ser Leu Leu Gly Lys Ser Ser Asp Val
                325                 330                 335
Ser Ser Leu Asn Asp Pro Gln Pro Ser Gly Asn Leu Arg Pro Pro Gln
            340                 345                 350
Glu Glu Glu Glu Val Lys His Leu Gly Tyr Ala Ser His Leu Met Glu
        355                 360                 365
Ile Phe Cys Asp Ser Glu Glu Asn Thr Glu Gly Thr Ser Phe Thr Gln
    370                 375                 380
Gln Glu Ser Leu Ser Arg Thr Ile Pro Pro Asp Lys Thr Val Ile Glu
385                 390                 395                 400
```

```
Tyr Glu Tyr Asp Val Arg Thr Thr Asp Ile Cys Ala Gly Pro Glu
                405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
            435                 440                 445

Ser Tyr Thr Pro Gln Leu Gln Asp Leu Asp Pro Leu Ala Gln Glu His
    450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
            515                 520                 525

Arg Pro Pro Gly Glu Asn Glu Thr Tyr Leu Met Gln Phe Met Glu Glu
    530                 535                 540

Trp Gly Leu Tyr Val Gln Met Glu Asn
545                 550

<210> SEQ ID NO 53
<211> LENGTH: 1659
<212> TYPE: DNA
<213> ORGANISM: Artificial Sequence
<220> FEATURE:
<221> NAME/KEY: CDS
<222> LOCATION: (1)...(1659)
<220> FEATURE:
<223> OTHER INFORMATION: PCR Primer

<400> SEQUENCE: 53 atg cgg gct ccc ggc cgc ccg gcc ctg cgg ccg ctg ccg ctg ccg ccg      48
Met Arg Ala Pro Gly Arg Pro Ala Leu Arg Pro Leu Pro Leu Pro Pro
 1               5                  10                  15 ctg ctg ctg ttg ctc ctg gcg gcg cct tgg gga cgg gca gtt ccc tgt      96
Leu Leu Leu Leu Leu Leu Ala Ala Pro Trp Gly Arg Ala Val Pro Cys
                20                  25                  30 gtc tct ggt ggt ttg cct aaa cct gca aac atc acc ttc tta tcc atc     144
Val Ser Gly Gly Leu Pro Lys Pro Ala Asn Ile Thr Phe Leu Ser Ile
         35                  40                  45 aac atg aag aat gtc cta caa tgg act cca cca gag ggt ctt caa gga     192
Asn Met Lys Asn Val Leu Gln Trp Thr Pro Pro Glu Gly Leu Gln Gly
     50                  55                  60 gtt aaa gtt act tac act gtg cag tat ttc ata tat ggg caa aag aaa     240
Val Lys Val Thr Tyr Thr Val Gln Tyr Phe Ile Tyr Gly Gln Lys Lys
 65                  70                  75                  80 tgg ctg aat aaa tca gaa tgc aga aat atc aat aga acc tac tgt gat     288
Trp Leu Asn Lys Ser Glu Cys Arg Asn Ile Asn Arg Thr Tyr Cys Asp
                 85                  90                  95 ctt tct gct gaa act tct gac tac gaa cac cag tat tat gcc aaa gtt     336
Leu Ser Ala Glu Thr Ser Asp Tyr Glu His Gln Tyr Tyr Ala Lys Val
            100                 105                 110 aag gcc att tgg gga acc aag tgt tcc aaa tgg gct gaa agt gga cgg     384
Lys Ala Ile Trp Gly Thr Lys Cys Ser Lys Trp Ala Glu Ser Gly Arg
        115                 120                 125 ttc tat cct ttt tta gaa acc caa att ggc cca cca gag gtg gca ctg     432
Phe Tyr Pro Phe Leu Glu Thr Gln Ile Gly Pro Pro Glu Val Ala Leu
    130                 135                 140
```

```
act acc gat gag aag tcc att tct gtt gtc ctg acc gct cca gag aag        480
Thr Thr Asp Glu Lys Ser Ile Ser Val Val Leu Thr Ala Pro Glu Lys
145                 150                 155                 160 tgg aag aga aat cca gaa gac ctt cct gtt tcc atg caa caa ata tac        528
Trp Lys Arg Asn Pro Glu Asp Leu Pro Val Ser Met Gln Gln Ile Tyr
                165                 170                 175 tcc aat ctg aag tat aac gtg tct gtg ttg aat act aaa tca aac aga        576
Ser Asn Leu Lys Tyr Asn Val Ser Val Leu Asn Thr Lys Ser Asn Arg
            180                 185                 190 acg tgg tcc cag tgt gtg acc aac cac acg ctg gtg ctc acc tgg ctg        624
Thr Trp Ser Gln Cys Val Thr Asn His Thr Leu Val Leu Thr Trp Leu
        195                 200                 205 gag ccg aac act ctt tac tgc gta cac gtg gag tcc ttc gtc cca ggg        672
Glu Pro Asn Thr Leu Tyr Cys Val His Val Glu Ser Phe Val Pro Gly
    210                 215                 220 ccc cct cgc cgt gct cag cct tct gag aag cag tgt gcc agg act ttg        720
Pro Pro Arg Arg Ala Gln Pro Ser Glu Lys Gln Cys Ala Arg Thr Leu
225                 230                 235                 240 aaa gat caa tca tca gag ttc aag gct aaa atc atc ttc tgg tat gtt        768
Lys Asp Gln Ser Ser Glu Phe Lys Ala Lys Ile Ile Phe Trp Tyr Val
                245                 250                 255 ttg ccc ata tct att acc gtg ttt ctt ttt tct gtg atg ggc tat tcc        816
Leu Pro Ile Ser Ile Thr Val Phe Leu Phe Ser Val Met Gly Tyr Ser
            260                 265                 270 atc tac cga tat atc cac gtt ggc aaa gag aaa cac cca gca aat ttg        864
Ile Tyr Arg Tyr Ile His Val Gly Lys Glu Lys His Pro Ala Asn Leu
        275                 280                 285 att ttg att tat gga aat gaa ttt gac aaa aga ttc ttt gtg cct gct        912
Ile Leu Ile Tyr Gly Asn Glu Phe Asp Lys Arg Phe Phe Val Pro Ala
    290                 295                 300 gaa aaa atc gtg att aac ttt atc acc ctc aat atc tcg gat gat tct        960
Glu Lys Ile Val Ile Asn Phe Ile Thr Leu Asn Ile Ser Asp Asp Ser
305                 310                 315                 320 aaa att tct cat cag gat atg agt tta ctg gga aaa agt agt gat gta       1008
Lys Ile Ser His Gln Asp Met Ser Leu Leu Gly Lys Ser Ser Asp Val
                325                 330                 335 tcc agt ctt aat gat cct cag ccc agt ggg aac ctg agg ccc cct cag       1056
Ser Ser Leu Asn Asp Pro Gln Pro Ser Gly Asn Leu Arg Pro Pro Gln
            340                 345                 350 gag gaa gag gag gtg aaa cat tta ggg tat gct tcg cat ttg atg gaa       1104
Glu Glu Glu Glu Val Lys His Leu Gly Tyr Ala Ser His Leu Met Glu
        355                 360                 365 att ttt tgt gac tct gaa gaa aac acg gaa ggt act tct ttc acc cag       1152
Ile Phe Cys Asp Ser Glu Glu Asn Thr Glu Gly Thr Ser Phe Thr Gln
    370                 375                 380 caa gag tcc ctc agt aga acc ata ccc ccg gat aaa acc gtc att gaa       1200
Gln Glu Ser Leu Ser Arg Thr Ile Pro Pro Asp Lys Thr Val Ile Glu
385                 390                 395                 400 tat gaa tat gat gtc aga acc act gac att tgt gcg ggg cct gaa gag       1248
Tyr Glu Tyr Asp Val Arg Thr Thr Asp Ile Cys Ala Gly Pro Glu Glu
                405                 410                 415 cag gag ctc agt ttg cag gag gag gtg tcc acc caa gga acc tta ttg       1296
Gln Glu Leu Ser Leu Gln Glu Glu Val Ser Thr Gln Gly Thr Leu Leu
            420                 425                 430 gag tcg cag gca gcg ttg gca gtc ttg ggc ccg caa acg tta cag tac       1344
Glu Ser Gln Ala Ala Leu Ala Val Leu Gly Pro Gln Thr Leu Gln Tyr
        435                 440                 445 tca tac acc cct cag ctc caa gac tta gac ccc ctg gcg cag gag cac       1392
Ser Tyr Thr Pro Gln Leu Gln Asp Leu Asp Pro Leu Ala Gln Glu His
    450                 455                 460
```

| | | | | | | | | | | | | | | | |
|---|---|---|---|---|---|---|---|---|---|---|---|---|---|---|---|
| acc | gac | tcg | gag | gag | ggg | ccg | gag | gaa | gag | cca | tcg | acg | acc | ctg | gtc | 1440 |
| Thr | Asp | Ser | Glu | Glu | Gly | Pro | Glu | Glu | Glu | Pro | Ser | Thr | Thr | Leu | Val |
| 465 | | | | 470 | | | | | 475 | | | | | 480 |

```
acc gac tcg gag gag ggg ccg gag gaa gag cca tcg acg acc ctg gtc    1440
Thr Asp Ser Glu Glu Gly Pro Glu Glu Glu Pro Ser Thr Thr Leu Val
465                 470                 475                 480 gac tgg gat ccc caa act ggc agg ctg tgt att cct tcg ctg tcc agt    1488
Asp Trp Asp Pro Gln Thr Gly Arg Leu Cys Ile Pro Ser Leu Ser Ser
                485                 490                 495 ttc gac cag gat tca gag ggc tgc gag cct tct gag ggg gat ggg ctc    1536
Phe Asp Gln Asp Ser Glu Gly Cys Glu Pro Ser Glu Gly Asp Gly Leu
            500                 505                 510 gga gag gag ggt ctt cta tct aga ctc tat gag gag ccg gct cca gac    1584
Gly Glu Glu Gly Leu Leu Ser Arg Leu Tyr Glu Glu Pro Ala Pro Asp
        515                 520                 525 agg cca cca gga gaa aat gaa acc tat ctc atg caa ttc atg gag gaa    1632
Arg Pro Pro Gly Glu Asn Glu Thr Tyr Leu Met Gln Phe Met Glu Glu
    530                 535                 540 tgg ggg tta tat gtg cag atg gaa aac                                1659
Trp Gly Leu Tyr Val Gln Met Glu Asn
545                 550

<210> SEQ ID NO 54
<211> LENGTH: 553
<212> TYPE: PRT
<213> ORGANISM: Mus musculus

<400> SEQUENCE: 54

Met Arg Ala Pro Gly Arg Pro Ala Leu Arg Pro Leu Pro Leu Pro Pro
  1               5                  10                  15

Leu Leu Leu Leu Leu Leu Ala Ala Pro Trp Gly Arg Ala Val Pro Cys
             20                  25                  30

Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
     50                  55                  60

Val Lys Val Thr Tyr Thr Val Gln Tyr Phe Ile Tyr Gly Gln Lys Lys
 65                  70                  75                  80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
        115                 120                 125

Phe Tyr Pro Phe Leu Glu Thr Gln Ile Gly Pro Pro Glu Val Ala Leu
    130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
    210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
```

```
                    245                 250                 255
Leu Pro Ile Ser Ile Thr Val Phe Leu Phe Ser Val Met Gly Tyr Ser
                260                 265                 270

Ile Tyr Arg Tyr Ile His Val Gly Lys Glu Lys His Pro Ala Asn Leu
            275                 280                 285

Ile Leu Ile Tyr Gly Asn Glu Phe Asp Lys Arg Phe Val Pro Ala
        290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
                340                 345                 350

Glu Glu Glu Val Lys His Leu Gly Tyr Ala Ser His Leu Met Glu
                355                 360                 365

Ile Phe Cys Asp Ser Glu Glu Asn Thr Glu Gly Thr Ser Phe Thr Gln
        370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
        435                 440                 445

Ser Tyr Thr Pro Gln Leu Gln Asp Leu Asp Pro Leu Ala Gln Glu His
    450                 455                 460

Thr Asp Ser Glu Glu Gly Pro Glu Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
        515                 520                 525

Arg Pro Pro Gly Glu Asn Glu Thr Tyr Leu Met Gln Phe Met Glu Glu
    530                 535                 540

Trp Gly Leu Tyr Val Gln Met Glu Asn
545                 550

<210> SEQ ID NO 55
<211> LENGTH: 1659
<212> TYPE: DNA
<213> ORGANISM: Mus musculus
<220> FEATURE:
<221> NAME/KEY: CDS
<222> LOCATION: (1)...(1659)

<400> SEQUENCE: 55 atg cgg gct ccc ggc cgc ccg gcc ctg cgg ccg ctg ccg ctg ccg ccg         48
Met Arg Ala Pro Gly Arg Pro Ala Leu Arg Pro Leu Pro Leu Pro Pro
 1               5                  10                  15 ctg ctg ctg ttg ctc ctg gcg gcg cct tgg gga cgg gca gtt ccc tgt         96
Leu Leu Leu Leu Leu Leu Ala Ala Pro Trp Gly Arg Ala Val Pro Cys
                20                  25                  30 gtc tct ggt ggt ttg cct aaa cct gca aac atc acc ttc tta tcc atc        144
```

|     |     |     |     |     |     |     |     |     |     |     |     |     |
|-----|-----|-----|-----|-----|-----|-----|-----|-----|-----|-----|-----|-----|
| Val | Ser | Gly | Gly | Leu | Pro | Lys | Pro | Ala | Asn | Ile | Thr | Phe | Leu | Ser | Ile |
|     |     | 35  |     |     |     | 40  |     |     |     |     | 45  |     |

```
aac atg aag aat gtc cta cag tgg act cca cca gag ggt ctt cag gga      192
Asn Met Lys Asn Val Leu Gln Trp Thr Pro Pro Glu Gly Leu Gln Gly
 50                  55                  60 gtt aaa gtt act tac act gtg cag tat ttc ata tat ggg cag aag aaa      240
Val Lys Val Thr Tyr Thr Val Gln Tyr Phe Ile Tyr Gly Gln Lys Lys
 65                  70                  75                  80 tgg ctg aat aaa tca gaa tgc agg aat atc aat agg acc tac tgt gat      288
Trp Leu Asn Lys Ser Glu Cys Arg Asn Ile Asn Arg Thr Tyr Cys Asp
                 85                  90                  95 ctt tct gct gaa act tct gac tac gaa cac cag tat tat gcc aaa gtt      336
Leu Ser Ala Glu Thr Ser Asp Tyr Glu His Gln Tyr Tyr Ala Lys Val
            100                 105                 110 aag gcc att tgg gga aca aag tgt tcc aaa tgg gct gaa agt gga cgg      384
Lys Ala Ile Trp Gly Thr Lys Cys Ser Lys Trp Ala Glu Ser Gly Arg
        115                 120                 125 ttc tat cct ttt tta gaa aca cag att ggc cca cca gag gtg gca ctg      432
Phe Tyr Pro Phe Leu Glu Thr Gln Ile Gly Pro Pro Glu Val Ala Leu
    130                 135                 140 act aca gat gag aag tcc att tct gtt gtc ctg aca gct cca gag aag      480
Thr Thr Asp Glu Lys Ser Ile Ser Val Val Leu Thr Ala Pro Glu Lys
145                 150                 155                 160 tgg aag agg aat cca gaa gac ctt cct gtt tcc atg cag cag ata tac      528
Trp Lys Arg Asn Pro Glu Asp Leu Pro Val Ser Met Gln Gln Ile Tyr
                165                 170                 175 tcc aat ctg aag tat aac gtg tct gtt ttg aat act aaa tca aac agg      576
Ser Asn Leu Lys Tyr Asn Val Ser Val Leu Asn Thr Lys Ser Asn Arg
            180                 185                 190 acg tgg tcc cag tgt gtg acc aac cac acg ctg gtg ctc acc tgg ctg      624
Thr Trp Ser Gln Cys Val Thr Asn His Thr Leu Val Leu Thr Trp Leu
        195                 200                 205 gag ccg aac act ctt tac tgc gta cac gtg gag tcc ttc gtc cca ggg      672
Glu Pro Asn Thr Leu Tyr Cys Val His Val Glu Ser Phe Val Pro Gly
    210                 215                 220 ccc cct cgc cgt gct cag cct tct gag aag cag tgt gcc agg act ttg      720
Pro Pro Arg Arg Ala Gln Pro Ser Glu Lys Gln Cys Ala Arg Thr Leu
225                 230                 235                 240 aaa gat cag tca tca gag ttc aag gct aaa atc atc ttc tgg tat gtt      768
Lys Asp Gln Ser Ser Glu Phe Lys Ala Lys Ile Ile Phe Trp Tyr Val
                245                 250                 255 ttg ccc ata tct att acc gtg ttt ctt ttt tct gtg atg ggc tat tcc      816
Leu Pro Ile Ser Ile Thr Val Phe Leu Phe Ser Val Met Gly Tyr Ser
            260                 265                 270 atc tac cga tat atc cac gtt ggc aaa gag aaa cac cca gca aat ttg      864
Ile Tyr Arg Tyr Ile His Val Gly Lys Glu Lys His Pro Ala Asn Leu
        275                 280                 285 att ttg att tat gga aat gaa ttt gac aaa agg ttc ttt gtg cct gct      912
Ile Leu Ile Tyr Gly Asn Glu Phe Asp Lys Arg Phe Phe Val Pro Ala
    290                 295                 300 gaa aaa atc gtg att aac ttt atc acc ctc aat atc tcg gat gat tct      960
Glu Lys Ile Val Ile Asn Phe Ile Thr Leu Asn Ile Ser Asp Asp Ser
305                 310                 315                 320 aaa att tct cat cag gat atg agt tta ctg gga aaa agc agt gat gta     1008
Lys Ile Ser His Gln Asp Met Ser Leu Leu Gly Lys Ser Ser Asp Val
                325                 330                 335 tcc agc ctt aat gat cct cag ccc agc ggg aac ctg agg ccc cct cag     1056
Ser Ser Leu Asn Asp Pro Gln Pro Ser Gly Asn Leu Arg Pro Pro Gln
            340                 345                 350
```

```
gag gaa gag gag gtg aaa cat tta ggg tat gct tcg cat ttg atg gaa      1104
Glu Glu Glu Glu Val Lys His Leu Gly Tyr Ala Ser His Leu Met Glu
            355                 360                 365 att ttt tgt gac tct gaa gaa aac acg gaa ggt act tct ttc acc cag      1152
Ile Phe Cys Asp Ser Glu Glu Asn Thr Glu Gly Thr Ser Phe Thr Gln
370                 375                 380 cag gag tcc ctc agc agg aca ata ccc ccg gat aaa aca gtc att gaa      1200
Gln Glu Ser Leu Ser Arg Thr Ile Pro Pro Asp Lys Thr Val Ile Glu
385                 390                 395                 400 tat gaa tat gat gtc agg acc act gac att tgt gcg ggg cct gaa gag      1248
Tyr Glu Tyr Asp Val Arg Thr Thr Asp Ile Cys Ala Gly Pro Glu Glu
                405                 410                 415 cag gag ctc agt ttg cag gag gag gtg tcc aca cag gga aca tta ttg      1296
Gln Glu Leu Ser Leu Gln Glu Glu Val Ser Thr Gln Gly Thr Leu Leu
            420                 425                 430 gag tcg cag gca gcg ttg gca gtc ttg ggc ccg cag acg tta cag tac      1344
Glu Ser Gln Ala Ala Leu Ala Val Leu Gly Pro Gln Thr Leu Gln Tyr
        435                 440                 445 tca tac acc cct cag ctc cag gac tta gac ccc ctg gcg cag gag cac      1392
Ser Tyr Thr Pro Gln Leu Gln Asp Leu Asp Pro Leu Ala Gln Glu His
450                 455                 460 aca gac tcg gag gag ggg ccg gag gaa gag cca tcg acg acc ctg gtc      1440
Thr Asp Ser Glu Glu Gly Pro Glu Glu Glu Pro Ser Thr Thr Leu Val
465                 470                 475                 480 gac tgg gat ccc cag act ggc agg ctg tgt att cct tcg ctg tcc agc      1488
Asp Trp Asp Pro Gln Thr Gly Arg Leu Cys Ile Pro Ser Leu Ser Ser
                485                 490                 495 ttc gac cag gat tca gag ggc tgc gag cct tct gag ggg gat ggg ctc      1536
Phe Asp Gln Asp Ser Glu Gly Cys Glu Pro Ser Glu Gly Asp Gly Leu
            500                 505                 510 gga gag gag ggt ctt cta tct agg ctc tat gag gag ccg gct cca gac      1584
Gly Glu Glu Gly Leu Leu Ser Arg Leu Tyr Glu Glu Pro Ala Pro Asp
        515                 520                 525 agg cca cca gga gaa aat gaa acc tat ctc atg caa ttc atg gag gaa      1632
Arg Pro Pro Gly Glu Asn Glu Thr Tyr Leu Met Gln Phe Met Glu Glu
530                 535                 540 tgg ggg tta tat gtg cag atg gaa aac                                  1659
Trp Gly Leu Tyr Val Gln Met Glu Asn
545                 550

<210> SEQ ID NO 56
<211> LENGTH: 553
<212> TYPE: PRT
<213> ORGANISM: Mus musculus

<400> SEQUENCE: 56

Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
        35                  40                  45

Asn Met Lys Asn Val Leu Gln Trp Thr Pro Pro Glu Gly Leu Gln Gly
    50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
```

```
                100                 105                 110
Lys Ala Ile Trp Gly Thr Lys Cys Ser Lys Trp Ala Glu Ser Gly Arg
            115                 120                 125
Phe Tyr Pro Phe Leu Glu Thr Gln Ile Gly Pro Pro Glu Val Ala Leu
            130                 135                 140
Thr Thr Asp Glu Lys Ser Ile Ser Val Val Leu Thr Ala Pro Glu Lys
145                 150                 155                 160
Trp Lys Arg Asn Pro Glu Asp Leu Pro Val Ser Met Gln Gln Ile Tyr
                165                 170                 175
Ser Asn Leu Lys Tyr Asn Val Ser Val Leu Asn Thr Lys Ser Asn Arg
            180                 185                 190
Thr Trp Ser Gln Cys Val Thr Asn His Thr Leu Val Leu Thr Trp Leu
            195                 200                 205
Glu Pro Asn Thr Leu Tyr Cys Val His Val Glu Ser Phe Val Pro Gly
            210                 215                 220
Pro Pro Arg Arg Ala Gln Pro Ser Glu Lys Gln Cys Ala Arg Thr Leu
225                 230                 235                 240
Lys Asp Gln Ser Ser Glu Phe Lys Ala Lys Ile Ile Phe Trp Tyr Val
                245                 250                 255
Leu Pro Ile Ser Ile Thr Val Phe Leu Phe Ser Val Met Gly Tyr Ser
            260                 265                 270
Ile Tyr Arg Tyr Ile His Val Gly Lys Glu Lys His Pro Ala Asn Leu
            275                 280                 285
Ile Leu Ile Tyr Gly Asn Glu Phe Asp Lys Arg Phe Phe Val Pro Ala
            290                 295                 300
Glu Lys Ile Val Ile Asn Phe Ile Thr Leu Asn Ile Ser Asp Asp Ser
305                 310                 315                 320
Lys Ile Ser His Gln Asp Met Ser Leu Leu Gly Lys Ser Ser Asp Val
                325                 330                 335
Ser Ser Leu Asn Asp Pro Gln Pro Ser Gly Asn Leu Arg Pro Pro Gln
            340                 345                 350
Glu Glu Glu Glu Val Lys His Leu Gly Tyr Ala Ser His Leu Met Glu
            355                 360                 365
Ile Phe Cys Asp Ser Glu Glu Asn Thr Glu Gly Thr Ser Phe Thr Gln
            370                 375                 380
Gln Glu Ser Leu Ser Arg Thr Ile Pro Pro Asp Lys Thr Val Ile Glu
385                 390                 395                 400
Tyr Glu Tyr Asp Val Arg Thr Thr Asp Ile Cys Ala Gly Pro Glu Glu
                405                 410                 415
Gln Glu Leu Ser Leu Gln Glu Glu Val Ser Thr Gln Gly Thr Leu Leu
            420                 425                 430
Glu Ser Gln Ala Ala Leu Ala Val Leu Gly Pro Gln Thr Leu Gln Tyr
            435                 440                 445
Ser Tyr Thr Pro Gln Leu Gln Asp Leu Asp Pro Leu Ala Gln Glu His
            450                 455                 460
Thr Asp Ser Glu Glu Gly Pro Glu Glu Glu Pro Ser Thr Thr Leu Val
465                 470                 475                 480
Asp Trp Asp Pro Gln Thr Gly Arg Leu Cys Ile Pro Ser Leu Ser Ser
                485                 490                 495
Phe Asp Gln Asp Ser Glu Gly Cys Glu Pro Ser Glu Gly Asp Gly Leu
            500                 505                 510
Gly Glu Glu Gly Leu Leu Ser Arg Leu Tyr Glu Glu Pro Ala Pro Asp
            515                 520                 525
```

Arg Pro Pro Gly Glu Asn Glu Thr Tyr Leu Met Gln Phe Met Glu Glu
            530                 535                 540

Trp Gly Leu Tyr Val Gln Met Glu Asn
545                 550

<210> SEQ ID NO 57
<211> LENGTH: 33
<212> TYPE: DNA
<213> ORGANISM: Homo sapiens

<400> SEQUENCE: 57
gcgaattcga gtctaccaaa tgcagacttt cac         33

<210> SEQ ID NO 58
<211> LENGTH: 32
<212> TYPE: DNA
<213> ORGANISM: Homo sapiens

<400> SEQUENCE: 58
cgctcgagcc ttccgcaaac ctatgagatc ca         32

<210> SEQ ID NO 59
<211> LENGTH: 203
<212> TYPE: PRT
<213> ORGANISM: Homo sapiens

<400> SEQUENCE: 59

Asp Glu Val Ala Ile Leu Pro Ala Pro Gln Asn Leu Ser Val Leu Ser
  1               5                  10                  15

Thr Asn Met Lys His Leu Leu Met Trp Ser Pro Val Ile Ala Pro Gly
             20                  25                  30

Glu Thr Val Tyr Tyr Ser Val Glu Tyr Gln Gly Glu Tyr Glu Ser Leu
         35                  40                  45

Tyr Thr Ser His Ile Trp Ile Pro Ser Ser Trp Cys Ser Leu Thr Glu
     50                  55                  60

Gly Pro Glu Cys Asp Val Thr Asp Asp Ile Thr Ala Thr Val Pro Tyr
 65                  70                  75                  80

Asn Leu Arg Val Arg Ala Thr Leu Gly Ser Gln Thr Ser Ala Trp Ser
                 85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala Ile Pro
        195                 200

<210> SEQ ID NO 60
<211> LENGTH: 29
<212> TYPE: DNA
<213> ORGANISM: Homo sapiens

```
<400> SEQUENCE: 60
ggccggccat gcagactttc acaatggtt                                          29

<210> SEQ ID NO 61
<211> LENGTH: 52
<212> TYPE: DNA
<213> ORGANISM: Homo sapiens

<400> SEQUENCE: 61
tccgctaccg ccgcctccac tgccaccacc tccggcctct ccttgcacct cc                52

<210> SEQ ID NO 62
<211> LENGTH: 53
<212> TYPE: DNA
<213> ORGANISM: Homo sapiens

<400> SEQUENCE: 62
gtggaggcgg cggtagcgga ggcggtggca gtcgaactgt ggctgcacca tct               53

<210> SEQ ID NO 63
<211> LENGTH: 38
<212> TYPE: DNA
<213> ORGANISM: Homo sapiens

<400> SEQUENCE: 63
ggcgcgcctc tagattaaca ctctcccctg ttgaagct                                38

<210> SEQ ID NO 64
<211> LENGTH: 15
<212> TYPE: PRT
<213> ORGANISM: Homo sapiens

<400> SEQUENCE: 64

Gly Gly Gly Gly Ser Gly Gly Gly Gly Ser Gly Gly Gly Gly Ser
 1               5                  10                  15

<210> SEQ ID NO 65
<211> LENGTH: 1081
<212> TYPE: DNA
<213> ORGANISM: Homo sapiens
<220> FEATURE:
<221> NAME/KEY: CDS
<222> LOCATION: (9)...(1067)

<400> SEQUENCE: 65 ggccggcc atg cag act ttc aca atg gtt cta gaa gaa atc tgg aca agt         50
         Met Gln Thr Phe Thr Met Val Leu Glu Glu Ile Trp Thr Ser
          1               5                  10 ctt ttc atg tgg ttt ttc tac gca ttg att cca tgt ttg ctc aca gat          98
Leu Phe Met Trp Phe Phe Tyr Ala Leu Ile Pro Cys Leu Leu Thr Asp
 15                  20                  25                  30 gaa gtg gcc att ctg cct gcc cct cag aac ctc tct gta ctc tca acc          146
Glu Val Ala Ile Leu Pro Ala Pro Gln Asn Leu Ser Val Leu Ser Thr
                 35                  40                  45 aac atg aag cat ctc ttg atg tgg agc cca gtg atc gcg cct gga gaa          194
Asn Met Lys His Leu Leu Met Trp Ser Pro Val Ile Ala Pro Gly Glu
             50                  55                  60 aca gtg tac tat tct gtc gaa tac cag ggg gag tac gag agc ctg tac          242
Thr Val Tyr Tyr Ser Val Glu Tyr Gln Gly Glu Tyr Glu Ser Leu Tyr
         65                  70                  75 acg agc cac atc tgg atc ccc agc agc tgg tgc tca ctc act gaa ggt          290
Thr Ser His Ile Trp Ile Pro Ser Ser Trp Cys Ser Leu Thr Glu Gly
```

```
cct gag tgt gat gtc act gat gac atc acg gcc act gtg cca tac aac       338
Pro Glu Cys Asp Val Thr Asp Asp Ile Thr Ala Thr Val Pro Tyr Asn
 95             100                 105                 110 ctt cgt gtc agg gcc aca ttg ggc tca cag acc tca gcc tgg agc atc       386
Leu Arg Val Arg Ala Thr Leu Gly Ser Gln Thr Ser Ala Trp Ser Ile
                115                 120                 125 ctg aag cat ccc ttt aat aga aac tca acc atc ctt acc cga cct ggg       434
Leu Lys His Pro Phe Asn Arg Asn Ser Thr Ile Leu Thr Arg Pro Gly
            130                 135                 140 atg gag atc ccc aaa cat ggc ttc cac ctg gtt att gag ctg gag gac       482
Met Glu Ile Pro Lys His Gly Phe His Leu Val Ile Glu Leu Glu Asp
        145                 150                 155 ctg ggg ccc cag ttt gag ttc ctt gtg gcc tac tgg acg agg gag cct       530
Leu Gly Pro Gln Phe Glu Phe Leu Val Ala Tyr Trp Thr Arg Glu Pro
160                 165                 170 ggt gcc gag gaa cat gtc aaa atg gtg agg agt ggg ggt att cca gtg       578
Gly Ala Glu Glu His Val Lys Met Val Arg Ser Gly Gly Ile Pro Val
175                 180                 185                 190 cac cta gaa acc atg gag cca ggg gct gca tac tgt gtg aag gcc cag       626
His Leu Glu Thr Met Glu Pro Gly Ala Ala Tyr Cys Val Lys Ala Gln
                195                 200                 205 aca ttc gtg aag gcc att ggg agg tac agc gcc ttc agc cag aca gaa       674
Thr Phe Val Lys Ala Ile Gly Arg Tyr Ser Ala Phe Ser Gln Thr Glu
            210                 215                 220 tgt gtg gag gtg caa gga gag gcc gga ggt ggt ggc agt gga ggc ggc       722
Cys Val Glu Val Gln Gly Glu Ala Gly Gly Gly Gly Ser Gly Gly Gly
        225                 230                 235 ggt agc gga ggc ggt ggc agt cga act gtg gct gca cca tct gtc ttc       770
Gly Ser Gly Gly Gly Gly Ser Arg Thr Val Ala Ala Pro Ser Val Phe
240                 245                 250 atc ttc ccg cca tct gat gag cag ttg aaa tct gga act gcc tct gtt       818
Ile Phe Pro Pro Ser Asp Glu Gln Leu Lys Ser Gly Thr Ala Ser Val
255                 260                 265                 270 gtg tgc ctg ctg aat aac ttc tat ccc aga gag gcc aaa gta cag tgg       866
Val Cys Leu Leu Asn Asn Phe Tyr Pro Arg Glu Ala Lys Val Gln Trp
                275                 280                 285 aag gtg gat aac gcc ctc caa tcg ggt aac tcc cag gag agt gtc aca       914
Lys Val Asp Asn Ala Leu Gln Ser Gly Asn Ser Gln Glu Ser Val Thr
            290                 295                 300 gag cag gac agc aag gac agc acc tac agc ctc agc agc acc ctg acg       962
Glu Gln Asp Ser Lys Asp Ser Thr Tyr Ser Leu Ser Ser Thr Leu Thr
        305                 310                 315 ctg agc aaa gca gac tac gag aaa cac aaa gtc tac gcc tgc gaa gtc       1010
Leu Ser Lys Ala Asp Tyr Glu Lys His Lys Val Tyr Ala Cys Glu Val
320                 325                 330 acc cat cag ggc ctg agc tcg ccc gtc aca aag agc ttc aac agg gga       1058
Thr His Gln Gly Leu Ser Ser Pro Val Thr Lys Ser Phe Asn Arg Gly
335                 340                 345                 350 gag tgt taa tctagaggcg cgcc                                           1081
Glu Cys *

<210> SEQ ID NO 66
<211> LENGTH: 352
<212> TYPE: PRT
<213> ORGANISM: Homo sapiens

<400> SEQUENCE: 66

Met Gln Thr Phe Thr Met Val Leu Glu Glu Ile Trp Thr Ser Leu Phe
 1               5                  10                  15
```

```
Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Pro Lys His Gly Phe His Leu Val Ile Glu Leu Glu Asp Leu Gly
145                 150                 155                 160

Pro Gln Phe Glu Phe Leu Val Ala Tyr Trp Thr Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Gly Gly Gly Ser Gly Gly Gly Ser
225                 230                 235                 240

Gly Gly Gly Gly Ser Arg Thr Val Ala Ala Pro Ser Val Phe Ile Phe
                245                 250                 255

Pro Pro Ser Asp Glu Gln Leu Lys Ser Gly Thr Ala Ser Val Val Cys
            260                 265                 270

Leu Leu Asn Asn Phe Tyr Pro Arg Glu Ala Lys Val Gln Trp Lys Val
        275                 280                 285

Asp Asn Ala Leu Gln Ser Gly Asn Ser Gln Glu Ser Val Thr Glu Gln
    290                 295                 300

Asp Ser Lys Asp Ser Thr Tyr Ser Leu Ser Ser Thr Leu Thr Leu Ser
305                 310                 315                 320

Lys Ala Asp Tyr Glu Lys His Lys Val Tyr Ala Cys Glu Val Thr His
                325                 330                 335

Gln Gly Leu Ser Ser Pro Val Thr Lys Ser Phe Asn Arg Gly Glu Cys
            340                 345                 350

<210> SEQ ID NO 67
<211> LENGTH: 323
<212> TYPE: PRT
<213> ORGANISM: Homo sapiens

<400> SEQUENCE: 67

Asp Glu Val Ala Ile Leu Pro Ala Pro Gln Asn Leu Ser Val Leu Ser
1               5                   10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
```

```
                    35                  40                  45
Tyr Thr Ser His Ile Trp Ile Pro Ser Ser Trp Cys Ser Leu Thr Glu
 50                  55                  60

Gly Pro Glu Cys Asp Val Thr Asp Asp Ile Thr Ala Thr Val Pro Tyr
 65                  70                  75                  80

Asn Leu Arg Val Arg Ala Thr Leu Gly Ser Gln Thr Ser Ala Trp Ser
                 85                  90                  95

Ile Leu Lys His Pro Phe Asn Arg Asn Ser Thr Ile Leu Thr Arg Pro
            100                 105                 110

Gly Met Glu Ile Pro Lys His Gly Phe His Leu Val Ile Glu Leu Glu
        115                 120                 125

Asp Leu Gly Pro Gln Phe Glu Phe Leu Val Ala Tyr Trp Thr Arg Glu
130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala Gly Gly Gly Ser Gly Gly
        195                 200                 205

Gly Gly Ser Gly Gly Gly Ser Arg Thr Val Ala Ala Pro Ser Val
210                 215                 220

Phe Ile Phe Pro Pro Ser Asp Glu Gln Leu Lys Ser Gly Thr Ala Ser
225                 230                 235                 240

Val Val Cys Leu Leu Asn Asn Phe Tyr Pro Arg Glu Ala Lys Val Gln
                245                 250                 255

Trp Lys Val Asp Asn Ala Leu Gln Ser Gly Asn Ser Gln Glu Ser Val
            260                 265                 270

Thr Glu Gln Asp Ser Lys Asp Ser Thr Tyr Ser Leu Ser Ser Thr Leu
        275                 280                 285

Thr Leu Ser Lys Ala Asp Tyr Glu Lys His Lys Val Tyr Ala Cys Glu
290                 295                 300

Val Thr His Gln Gly Leu Ser Ser Pro Val Thr Lys Ser Phe Asn Arg
305                 310                 315                 320

Gly Glu Cys

<210> SEQ ID NO 68
<211> LENGTH: 30
<212> TYPE: DNA
<213> ORGANISM: Homo sapiens

<400> SEQUENCE: 68
gtcgaccatg gatgcaatga agagagggct                                      30

<210> SEQ ID NO 69
<211> LENGTH: 30
<212> TYPE: DNA
<213> ORGANISM: Homo sapiens

<400> SEQUENCE: 69
cacagggaac tctacggaag cgtctcaact                                      30

<210> SEQ ID NO 70
<211> LENGTH: 33
<212> TYPE: DNA
```

```
<213> ORGANISM: Homo sapiens

<400> SEQUENCE: 70
cttccgtaga gttccctgtg tctctggtgg ttt                                33

<210> SEQ ID NO 71
<211> LENGTH: 53
<212> TYPE: DNA
<213> ORGANISM: Homo sapiens

<400> SEQUENCE: 71
gccagagcca cctccgcctg aaccgcctcc accttgatct ttcaaagtcc tgg          53

<210> SEQ ID NO 72
<211> LENGTH: 51
<212> TYPE: DNA
<213> ORGANISM: Homo sapiens

<400> SEQUENCE: 72
caggcggagg tggctctggc ggtggcggat cggcctccac caagggccca t            51

<210> SEQ ID NO 73
<211> LENGTH: 20
<212> TYPE: DNA
<213> ORGANISM: Homo sapiens

<400> SEQUENCE: 73
ctgggcacgg tgggcatgtg                                               20

<210> SEQ ID NO 74
<211> LENGTH: 20
<212> TYPE: DNA
<213> ORGANISM: Homo sapiens

<400> SEQUENCE: 74
cacatgccca ccgtgcccag                                               20

<210> SEQ ID NO 75
<211> LENGTH: 31
<212> TYPE: DNA
<213> ORGANISM: Homo sapiens

<400> SEQUENCE: 75
agatctagat tatttacccg gagacaggga g                                  31

<210> SEQ ID NO 76
<211> LENGTH: 1801
<212> TYPE: DNA
<213> ORGANISM: Homo sapiens
<220> FEATURE:
<221> NAME/KEY: CDS
<222> LOCATION: (8)...(1789)

<400> SEQUENCE: 76 gtcgacc atg gat gca atg aag aga ggg ctc tgc tgt gtg ctg ctg ctg     49
        Met Asp Ala Met Lys Arg Gly Leu Cys Cys Val Leu Leu Leu
        1               5                   10 tgt ggc gcc gtc ttc gtt tcg ctc agc cag gaa atc cat gcc gag ttg     97
Cys Gly Ala Val Phe Val Ser Leu Ser Gln Glu Ile His Ala Glu Leu
 15                  20                  25                  30 aga cgc ttc cgt aga gtt ccc tgt gtc tct ggt ggt ttg cct aaa cct    145
Arg Arg Phe Arg Arg Val Pro Cys Val Ser Gly Gly Leu Pro Lys Pro
                 35                  40                  45
```

| | | |
|---|---|---|
| gca aac atc acc ttc tta tcc atc aac atg aag aat gtc cta caa tgg<br>Ala Asn Ile Thr Phe Leu Ser Ile Asn Met Lys Asn Val Leu Gln Trp<br>50 55 60 | | 193 |
| act cca cca gag ggt ctt caa gga gtt aaa gtt act tac act gtg cag<br>Thr Pro Pro Glu Gly Leu Gln Gly Val Lys Val Thr Tyr Thr Val Gln<br>65 70 75 | | 241 |
| tat ttc ata tat ggg caa aag aaa tgg ctg aat aaa tca gaa tgc aga<br>Tyr Phe Ile Tyr Gly Gln Lys Lys Trp Leu Asn Lys Ser Glu Cys Arg<br>80 85 90 | | 289 |
| aat atc aat aga acc tac tgt gat ctt tct gct gaa act tct gac tac<br>Asn Ile Asn Arg Thr Tyr Cys Asp Leu Ser Ala Glu Thr Ser Asp Tyr<br>95 100 105 110 | | 337 |
| gaa cac cag tat tat gcc aaa gtt aag gcc att tgg gga aca aag tgt<br>Glu His Gln Tyr Tyr Ala Lys Val Lys Ala Ile Trp Gly Thr Lys Cys<br>115 120 125 | | 385 |
| tcc aaa tgg gct gaa agt gga cgg ttc tat cct ttt tta gaa aca caa<br>Ser Lys Trp Ala Glu Ser Gly Arg Phe Tyr Pro Phe Leu Glu Thr Gln<br>130 135 140 | | 433 |
| att ggc cca cca gag gtg gca ctg act aca gat gag aag tcc att tct<br>Ile Gly Pro Pro Glu Val Ala Leu Thr Thr Asp Glu Lys Ser Ile Ser<br>145 150 155 | | 481 |
| gtt gtc ctg aca gct cca gag aag tgg aag aga aat cca gaa gac ctt<br>Val Val Leu Thr Ala Pro Glu Lys Trp Lys Arg Asn Pro Glu Asp Leu<br>160 165 170 | | 529 |
| cct gtt tcc atg caa caa ata tac tcc aat ctg aag tat aac gtg tct<br>Pro Val Ser Met Gln Gln Ile Tyr Ser Asn Leu Lys Tyr Asn Val Ser<br>175 180 185 190 | | 577 |
| gtg ttg aat act aaa tca aac aga acg tgg tcc cag tgt gtg acc aac<br>Val Leu Asn Thr Lys Ser Asn Arg Thr Trp Ser Gln Cys Val Thr Asn<br>195 200 205 | | 625 |
| cac acg ctg gtg ctc acc tgg ctg gag ccg aac act ctt tac tgc gta<br>His Thr Leu Val Leu Thr Trp Leu Glu Pro Asn Thr Leu Tyr Cys Val<br>210 215 220 | | 673 |
| cac gtg gag tcc ttc gtc cca ggg ccc cct cgc cgt gct cag cct tct<br>His Val Glu Ser Phe Val Pro Gly Pro Pro Arg Arg Ala Gln Pro Ser<br>225 230 235 | | 721 |
| gag aag cag tgt gcc agg act ttg aaa gat caa ggt gga ggc ggt tca<br>Glu Lys Gln Cys Ala Arg Thr Leu Lys Asp Gln Gly Gly Gly Gly Ser<br>240 245 250 | | 769 |
| ggc gga ggt ggc tct ggc ggt ggc gga tcg gcc tcc acc aag ggc cca<br>Gly Gly Gly Gly Ser Gly Gly Gly Ser Ala Ser Thr Lys Gly Pro<br>255 260 265 270 | | 817 |
| tcg gtc ttc ccc ctg gca ccc tcc tcc aag agc acc tct ggg ggc aca<br>Ser Val Phe Pro Leu Ala Pro Ser Ser Lys Ser Thr Ser Gly Gly Thr<br>275 280 285 | | 865 |
| gcg gcc ctg ggc tgc ctg gtc aag gac tac ttc ccc gaa ccg gtg acg<br>Ala Ala Leu Gly Cys Leu Val Lys Asp Tyr Phe Pro Glu Pro Val Thr<br>290 295 300 | | 913 |
| gtg tcg tgg aac tca ggc gcc ctg acc agc ggc gtg cac acc ttc ccg<br>Val Ser Trp Asn Ser Gly Ala Leu Thr Ser Gly Val His Thr Phe Pro<br>305 310 315 | | 961 |
| gct gtc cta cag tcc tca gga ctc tac tcc ctc agc agc gtg gtg acc<br>Ala Val Leu Gln Ser Ser Gly Leu Tyr Ser Leu Ser Ser Val Val Thr<br>320 325 330 | | 1009 |
| gtg ccc tcc agc agc ttg ggc acc cag acc tac atc tgc aac gtg aat<br>Val Pro Ser Ser Ser Leu Gly Thr Gln Thr Tyr Ile Cys Asn Val Asn<br>335 340 345 350 | | 1057 |
| cac aag ccc agc aac acc aag gtg gac aag aaa gtt gag ccc aaa tct<br>His Lys Pro Ser Asn Thr Lys Val Asp Lys Lys Val Glu Pro Lys Ser<br>355 360 365 | | 1105 |

```
tgt gac aaa act cac aca tgc cca ccg tgc cca gca cct gaa gcc gag    1153
Cys Asp Lys Thr His Thr Cys Pro Pro Cys Pro Ala Pro Glu Ala Glu
            370                 375                 380 ggg gca ccg tca gtc ttc ctc ttc ccc cca aaa ccc aag gac acc ctc    1201
Gly Ala Pro Ser Val Phe Leu Phe Pro Pro Lys Pro Lys Asp Thr Leu
        385                 390                 395 atg atc tcc cgg acc cct gag gtc aca tgc gtg gtg gtg gac gtg agc    1249
Met Ile Ser Arg Thr Pro Glu Val Thr Cys Val Val Val Asp Val Ser
400                 405                 410 cac gaa gac cct gag gtc aag ttc aac tgg tac gtg gac ggc gtg gag    1297
His Glu Asp Pro Glu Val Lys Phe Asn Trp Tyr Val Asp Gly Val Glu
415                 420                 425                 430 gtg cat aat gcc aag aca aag ccg cgg gag gag cag tac aac agc acg    1345
Val His Asn Ala Lys Thr Lys Pro Arg Glu Glu Gln Tyr Asn Ser Thr
            435                 440                 445 tac cgt gtg gtc agc gtc ctc acc gtc ctg cac cag gac tgg ctg aat    1393
Tyr Arg Val Val Ser Val Leu Thr Val Leu His Gln Asp Trp Leu Asn
        450                 455                 460 ggc aag gag tac aag tgc aag gtc tcc aac aaa gcc ctc cca tcc tcc    1441
Gly Lys Glu Tyr Lys Cys Lys Val Ser Asn Lys Ala Leu Pro Ser Ser
465                 470                 475 atc gag aaa acc atc tcc aaa gcc aaa ggg cag ccc cga gaa cca cag    1489
Ile Glu Lys Thr Ile Ser Lys Ala Lys Gly Gln Pro Arg Glu Pro Gln
480                 485                 490 gtg tac acc ctg ccc cca tcc cgg gat gag ctg acc aag aac cag gtc    1537
Val Tyr Thr Leu Pro Pro Ser Arg Asp Glu Leu Thr Lys Asn Gln Val
495                 500                 505                 510 agc ctg acc tgc ctg gtc aaa ggc ttc tat ccc agc gac atc gcc gtg    1585
Ser Leu Thr Cys Leu Val Lys Gly Phe Tyr Pro Ser Asp Ile Ala Val
            515                 520                 525 gag tgg gag agc aat ggg cag ccg gag aac aac tac aag acc acg cct    1633
Glu Trp Glu Ser Asn Gly Gln Pro Glu Asn Asn Tyr Lys Thr Thr Pro
        530                 535                 540 ccc gtg ctg gac tcc gac ggc tcc ttc ttc ctc tac agc aag ctc acc    1681
Pro Val Leu Asp Ser Asp Gly Ser Phe Phe Leu Tyr Ser Lys Leu Thr
545                 550                 555 gtg gac aag agc agg tgg cag cag ggg aac gtc ttc tca tgc tcc gtg    1729
Val Asp Lys Ser Arg Trp Gln Gln Gly Asn Val Phe Ser Cys Ser Val
560                 565                 570 atg cat gag gct ctg cac aac cac tac acg cag aag agc ctc tcc ctg    1777
Met His Glu Ala Leu His Asn His Tyr Thr Gln Lys Ser Leu Ser Leu
575                 580                 585                 590 tct ccg ggt aaa taatctagat ct                                      1801
Ser Pro Gly Lys <210> SEQ ID NO 77
<211> LENGTH: 594
<212> TYPE: PRT
<213> ORGANISM: Homo sapiens

<400> SEQUENCE: 77

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Val Pro Cys Val Ser Gly Gly Leu Pro Lys Pro Ala Asn
        35                  40                  45

Ile Thr Phe Leu Ser Ile Asn Met Lys Asn Val Leu Gln Trp Thr Pro
    50                  55                  60
```

```
Pro Glu Gly Leu Gln Gly Val Lys Val Thr Tyr Thr Val Gln Tyr Phe
65                  70                  75                  80

Ile Tyr Gly Gln Lys Lys Trp Leu Asn Lys Ser Glu Cys Arg Asn Ile
                85                  90                  95

Asn Arg Thr Tyr Cys Asp Leu Ser Ala Glu Thr Ser Asp Tyr Glu His
                100                 105                 110

Gln Tyr Tyr Ala Lys Val Lys Ala Ile Trp Gly Thr Lys Cys Ser Lys
                115                 120                 125

Trp Ala Glu Ser Gly Arg Phe Tyr Pro Phe Leu Glu Thr Gln Ile Gly
130                 135                 140

Pro Pro Glu Val Ala Leu Thr Thr Asp Glu Lys Ser Ile Ser Val Val
145                 150                 155                 160

Leu Thr Ala Pro Glu Lys Trp Lys Arg Asn Pro Glu Asp Leu Pro Val
                165                 170                 175

Ser Met Gln Gln Ile Tyr Ser Asn Leu Lys Tyr Asn Val Ser Val Leu
                180                 185                 190

Asn Thr Lys Ser Asn Arg Thr Trp Ser Gln Cys Val Thr Asn His Thr
                195                 200                 205

Leu Val Leu Thr Trp Leu Glu Pro Asn Thr Leu Tyr Cys Val His Val
                210                 215                 220

Glu Ser Phe Val Pro Gly Pro Pro Arg Arg Ala Gln Pro Ser Glu Lys
225                 230                 235                 240

Gln Cys Ala Arg Thr Leu Lys Asp Gln Gly Gly Gly Ser Gly Gly
                245                 250                 255

Gly Gly Ser Gly Gly Gly Gly Ser Ala Ser Thr Lys Gly Pro Ser Val
                260                 265                 270

Phe Pro Leu Ala Pro Ser Ser Lys Ser Thr Ser Gly Gly Thr Ala Ala
                275                 280                 285

Leu Gly Cys Leu Val Lys Asp Tyr Phe Pro Glu Pro Val Thr Val Ser
                290                 295                 300

Trp Asn Ser Gly Ala Leu Thr Ser Gly Val His Thr Phe Pro Ala Val
305                 310                 315                 320

Leu Gln Ser Ser Gly Leu Tyr Ser Leu Ser Ser Val Val Thr Val Pro
                325                 330                 335

Ser Ser Ser Leu Gly Thr Gln Thr Tyr Ile Cys Asn Val Asn His Lys
                340                 345                 350

Pro Ser Asn Thr Lys Val Asp Lys Lys Val Glu Pro Lys Ser Cys Asp
                355                 360                 365

Lys Thr His Thr Cys Pro Pro Cys Pro Ala Pro Glu Ala Glu Gly Ala
                370                 375                 380

Pro Ser Val Phe Leu Phe Pro Pro Lys Pro Lys Asp Thr Leu Met Ile
385                 390                 395                 400

Ser Arg Thr Pro Glu Val Thr Cys Val Val Val Asp Val Ser His Glu
                405                 410                 415

Asp Pro Glu Val Lys Phe Asn Trp Tyr Val Asp Gly Val Glu Val His
                420                 425                 430

Asn Ala Lys Thr Lys Pro Arg Glu Glu Gln Tyr Asn Ser Thr Tyr Arg
                435                 440                 445

Val Val Ser Val Leu Thr Val Leu His Gln Asp Trp Leu Asn Gly Lys
                450                 455                 460

Glu Tyr Lys Cys Lys Val Ser Asn Lys Ala Leu Pro Ser Ser Ile Glu
465                 470                 475                 480
```

-continued

```
Lys Thr Ile Ser Lys Ala Lys Gly Gln Pro Arg Glu Pro Gln Val Tyr
                485                 490                 495

Thr Leu Pro Pro Ser Arg Asp Glu Leu Thr Lys Asn Gln Val Ser Leu
            500                 505                 510

Thr Cys Leu Val Lys Gly Phe Tyr Pro Ser Asp Ile Ala Val Glu Trp
            515                 520                 525

Glu Ser Asn Gly Gln Pro Glu Asn Asn Tyr Lys Thr Thr Pro Pro Val
            530                 535                 540

Leu Asp Ser Asp Gly Ser Phe Phe Leu Tyr Ser Lys Leu Thr Val Asp
545                 550                 555                 560

Lys Ser Arg Trp Gln Gln Gly Asn Val Phe Ser Cys Ser Val Met His
                565                 570                 575

Glu Ala Leu His Asn His Tyr Thr Gln Lys Ser Leu Ser Leu Ser Pro
            580                 585                 590

Gly Lys

<210> SEQ ID NO 78
<211> LENGTH: 559
<212> TYPE: PRT
<213> ORGANISM: Homo sapiens

<400> SEQUENCE: 78

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Glu Gly
            20                  25                  30

Leu Gln Gly Val Lys Val Thr Tyr Thr Val Gln Tyr Phe Ile Tyr Gly
            35                  40                  45

Gln Lys Lys Trp Leu Asn Lys Ser Glu Cys Arg Asn Ile Asn Arg Thr
50                  55                  60

Tyr Cys Asp Leu Ser Ala Glu Thr Ser Asp Tyr Glu His Gln Tyr Tyr
65                  70                  75                  80

Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
            115                 120                 125

Pro Glu Lys Trp Lys Arg Asn Pro Glu Asp Leu Pro Val Ser Met Gln
130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
            195                 200                 205

Arg Thr Leu Lys Asp Gln Gly Gly Gly Ser Gly Gly Gly Ser
210                 215                 220

Gly Gly Gly Gly Ser Ala Ser Thr Lys Gly Pro Ser Val Phe Pro Leu
225                 230                 235                 240

Ala Pro Ser Ser Lys Ser Thr Ser Gly Gly Thr Ala Ala Leu Gly Cys
                245                 250                 255
```

-continued

```
Leu Val Lys Asp Tyr Phe Pro Glu Pro Val Thr Val Ser Trp Asn Ser
            260                 265                 270

Gly Ala Leu Thr Ser Gly Val His Thr Phe Pro Ala Val Leu Gln Ser
        275                 280                 285

Ser Gly Leu Tyr Ser Leu Ser Ser Val Val Thr Val Pro Ser Ser Ser
290                 295                 300

Leu Gly Thr Gln Thr Tyr Ile Cys Asn Val Asn His Lys Pro Ser Asn
305                 310                 315                 320

Thr Lys Val Asp Lys Lys Val Glu Pro Lys Ser Cys Asp Lys Thr His
                325                 330                 335

Thr Cys Pro Pro Cys Pro Ala Pro Glu Ala Glu Gly Ala Pro Ser Val
            340                 345                 350

Phe Leu Phe Pro Pro Lys Pro Lys Asp Thr Leu Met Ile Ser Arg Thr
        355                 360                 365

Pro Glu Val Thr Cys Val Val Val Asp Val Ser His Glu Asp Pro Glu
370                 375                 380

Val Lys Phe Asn Trp Tyr Val Asp Gly Val Glu Val His Asn Ala Lys
385                 390                 395                 400

Thr Lys Pro Arg Glu Glu Gln Tyr Asn Ser Thr Tyr Arg Val Val Ser
                405                 410                 415

Val Leu Thr Val Leu His Gln Asp Trp Leu Asn Gly Lys Glu Tyr Lys
            420                 425                 430

Cys Lys Val Ser Asn Lys Ala Leu Pro Ser Ser Ile Glu Lys Thr Ile
        435                 440                 445

Ser Lys Ala Lys Gly Gln Pro Arg Glu Pro Gln Val Tyr Thr Leu Pro
450                 455                 460

Pro Ser Arg Asp Glu Leu Thr Lys Asn Gln Val Ser Leu Thr Cys Leu
465                 470                 475                 480

Val Lys Gly Phe Tyr Pro Ser Asp Ile Ala Val Glu Trp Glu Ser Asn
                485                 490                 495

Gly Gln Pro Glu Asn Asn Tyr Lys Thr Thr Pro Pro Val Leu Asp Ser
            500                 505                 510

Asp Gly Ser Phe Phe Leu Tyr Ser Lys Leu Thr Val Asp Lys Ser Arg
        515                 520                 525

Trp Gln Gln Gly Asn Val Phe Ser Cys Ser Val Met His Glu Ala Leu
530                 535                 540

His Asn His Tyr Thr Gln Lys Ser Leu Ser Leu Ser Pro Gly Lys
545                 550                 555

<210> SEQ ID NO 79
<211> LENGTH: 214
<212> TYPE: PRT
<213> ORGANISM: Homo sapiens

<400> SEQUENCE: 79

Val Pro Cys Val Ser Gly Gly Leu Pro Lys Pro Ala Asn Ile Thr Phe
1               5                   10                  15

Leu Ser Ile Asn Met Lys Asn Val Leu Gln Trp Thr Pro Pro Glu Gly
            20                  25                  30

Leu Gln Gly Val Lys Val Thr Tyr Thr Val Gln Tyr Phe Ile Tyr Gly
        35                  40                  45

Gln Lys Lys Trp Leu Asn Lys Ser Glu Cys Arg Asn Ile Asn Arg Thr
    50                  55                  60

Tyr Cys Asp Leu Ser Ala Glu Thr Ser Asp Tyr Glu His Gln Tyr Tyr
65                  70                  75                  80
```

```
Ala Lys Val Lys Ala Ile Trp Gly Thr Lys Cys Ser Lys Trp Ala Glu
                85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
        115                 120                 125

Pro Glu Lys Trp Lys Arg Asn Pro Glu Asp Leu Pro Val Ser Met Gln
    130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln
    210

<210> SEQ ID NO 80
<211> LENGTH: 19
<212> TYPE: PRT
<213> ORGANISM: Homo sapiens

<400> SEQUENCE: 80

Glu Glu Ile His Ala Glu Leu Arg Arg Phe Arg Val Pro Cys Val
1               5                   10                  15

Ser Gly Gly

<210> SEQ ID NO 81
<211> LENGTH: 18
<212> TYPE: DNA
<213> ORGANISM: Mus musculus

<400> SEQUENCE: 81
cgccgcgttc ccgagatg                                                      18

<210> SEQ ID NO 82
<211> LENGTH: 36
<212> TYPE: DNA
<213> ORGANISM: Homo sapiens

<400> SEQUENCE: 82
acttgtggaa ttcgctagca ccaagggccc atcggt                                  36

<210> SEQ ID NO 83
<211> LENGTH: 1806
<212> TYPE: DNA
<213> ORGANISM: Mus musculus
<220> FEATURE:
<221> NAME/KEY: CDS
<222> LOCATION: (38)...(1675)

<400> SEQUENCE: 83
cgccgcgttc ccgagatgtg acccgaactg acagccc atg cac act ccc ggg acc        55
                                        Met His Thr Pro Gly Thr
                                            1               5 ccg gcg ccg ggc cac ccg gac ccg ccg cca ctg ttg ctg ctc acg ctg        103
Pro Ala Pro Gly His Pro Asp Pro Pro Pro Leu Leu Leu Leu Thr Leu
            10                  15                  20
```

| | | | | | | | | | | | | | | | |
|---|---|---|---|---|---|---|---|---|---|---|---|---|---|---|---|
| ctt | ctg | ctg | ctg | gcc | gct | tcg | gga | cgc | gca | gtt | cct | tgt | gtc | ttc | tgt | 151 |
| Leu | Leu | Leu | Leu | Ala | Ala | Ser | Gly | Arg | Ala | Val | Pro | Cys | Val | Phe | Cys | |
| | | 25 | | | | 30 | | | | | 35 | | | | | |

| ggt | ttg | cct | aaa | cct | aca | aat | atc | acc | ttc | tta | tcc | atc | aac | atg | aag | 199 |
|---|---|---|---|---|---|---|---|---|---|---|---|---|---|---|---|---|
| Gly | Leu | Pro | Lys | Pro | Thr | Asn | Ile | Thr | Phe | Leu | Ser | Ile | Asn | Met | Lys | |
| 40 | | | | | 45 | | | | | 50 | | | | | | |

| aat | gtc | ctg | cat | tgg | aat | cca | cca | gag | agt | cta | cac | gga | gtt | gaa | gtc | 247 |
|---|---|---|---|---|---|---|---|---|---|---|---|---|---|---|---|---|
| Asn | Val | Leu | His | Trp | Asn | Pro | Pro | Glu | Ser | Leu | His | Gly | Val | Glu | Val | |
| 55 | | | | | 60 | | | | | 65 | | | | | 70 | |

| aca | tac | act | gtg | caa | tat | ttc | ata | tat | ggg | cag | aag | aaa | tgg | ctg | aat | 295 |
|---|---|---|---|---|---|---|---|---|---|---|---|---|---|---|---|---|
| Thr | Tyr | Thr | Val | Gln | Tyr | Phe | Ile | Tyr | Gly | Gln | Lys | Lys | Trp | Leu | Asn | |
| | | | 75 | | | | | 80 | | | | | 85 | | | |

| gcc | tct | aaa | tgc | ggg | agt | atc | aac | agg | acc | tac | tgt | gac | ctt | tct | gtt | 343 |
|---|---|---|---|---|---|---|---|---|---|---|---|---|---|---|---|---|
| Ala | Ser | Lys | Cys | Gly | Ser | Ile | Asn | Arg | Thr | Tyr | Cys | Asp | Leu | Ser | Val | |
| | | | 90 | | | | | 95 | | | | | 100 | | | |

| gag | acc | tca | gac | tat | gaa | cac | cag | ttc | tat | gcc | aaa | gtg | aag | gcc | att | 391 |
|---|---|---|---|---|---|---|---|---|---|---|---|---|---|---|---|---|
| Glu | Thr | Ser | Asp | Tyr | Glu | His | Gln | Phe | Tyr | Ala | Lys | Val | Lys | Ala | Ile | |
| | | 105 | | | | | 110 | | | | | 115 | | | | |

| tgg | gaa | gcc | agg | tgc | tcc | gaa | tgg | gcc | gag | acg | gaa | cgc | ttc | tat | cct | 439 |
|---|---|---|---|---|---|---|---|---|---|---|---|---|---|---|---|---|
| Trp | Glu | Ala | Arg | Cys | Ser | Glu | Trp | Ala | Glu | Thr | Glu | Arg | Phe | Tyr | Pro | |
| | 120 | | | | | 125 | | | | | 130 | | | | | |

| ttc | ttg | gaa | act | caa | gtc | agc | cca | cca | gag | att | gcc | ctg | aca | act | ggc | 487 |
|---|---|---|---|---|---|---|---|---|---|---|---|---|---|---|---|---|
| Phe | Leu | Glu | Thr | Gln | Val | Ser | Pro | Pro | Glu | Ile | Ala | Leu | Thr | Thr | Gly | |
| 135 | | | | | 140 | | | | | 145 | | | | | 150 | |

| gag | aag | tcc | atc | tct | att | gcc | ctg | aca | gca | cca | gag | aag | tgg | aaa | aga | 535 |
|---|---|---|---|---|---|---|---|---|---|---|---|---|---|---|---|---|
| Glu | Lys | Ser | Ile | Ser | Ile | Ala | Leu | Thr | Ala | Pro | Glu | Lys | Trp | Lys | Arg | |
| | | | 155 | | | | | 160 | | | | | 165 | | | |

| aat | cca | caa | gac | cac | act | gtt | tct | atg | caa | cag | ata | tac | ccc | aat | ttg | 583 |
|---|---|---|---|---|---|---|---|---|---|---|---|---|---|---|---|---|
| Asn | Pro | Gln | Asp | His | Thr | Val | Ser | Met | Gln | Gln | Ile | Tyr | Pro | Asn | Leu | |
| | | 170 | | | | | 175 | | | | | 180 | | | | |

| aag | tac | aat | gtg | tct | gtg | tat | aac | act | aag | tcg | aga | aga | acg | tgg | tcc | 631 |
|---|---|---|---|---|---|---|---|---|---|---|---|---|---|---|---|---|
| Lys | Tyr | Asn | Val | Ser | Val | Tyr | Asn | Thr | Lys | Ser | Arg | Arg | Thr | Trp | Ser | |
| | | 185 | | | | | 190 | | | | | 195 | | | | |

| cag | tgt | gtc | acc | aac | agc | aca | ctg | gtc | ctc | agc | tgg | ctg | gag | ccc | aac | 679 |
|---|---|---|---|---|---|---|---|---|---|---|---|---|---|---|---|---|
| Gln | Cys | Val | Thr | Asn | Ser | Thr | Leu | Val | Leu | Ser | Trp | Leu | Glu | Pro | Asn | |
| 200 | | | | | 205 | | | | | 210 | | | | | | |

| act | ctg | tat | tgt | gtc | cac | gtg | gag | tcc | ctt | gtc | cca | ggg | ccc | cct | cgc | 727 |
|---|---|---|---|---|---|---|---|---|---|---|---|---|---|---|---|---|
| Thr | Leu | Tyr | Cys | Val | His | Val | Glu | Ser | Leu | Val | Pro | Gly | Pro | Pro | Arg | |
| 215 | | | | | 220 | | | | | 225 | | | | | 230 | |

| ctc | ccg | atg | cct | tct | cag | aag | cag | tgc | atc | agt | act | ttg | gaa | gtt | caa | 775 |
|---|---|---|---|---|---|---|---|---|---|---|---|---|---|---|---|---|
| Leu | Pro | Met | Pro | Ser | Gln | Lys | Gln | Cys | Ile | Ser | Thr | Leu | Glu | Val | Gln | |
| | | | | 235 | | | | | 240 | | | | | 245 | | |

| aca | tca | gca | tgg | aag | gct | aaa | gtc | atc | ttc | tgg | tat | gtc | ttc | ctc | aca | 823 |
|---|---|---|---|---|---|---|---|---|---|---|---|---|---|---|---|---|
| Thr | Ser | Ala | Trp | Lys | Ala | Lys | Val | Ile | Phe | Trp | Tyr | Val | Phe | Leu | Thr | |
| | | | 250 | | | | | 255 | | | | | 260 | | | |

| tct | gtt | atc | gtg | ttt | ctt | ttc | tcc | gca | att | ggc | tac | ttg | gtt | tac | cgt | 871 |
|---|---|---|---|---|---|---|---|---|---|---|---|---|---|---|---|---|
| Ser | Val | Ile | Val | Phe | Leu | Phe | Ser | Ala | Ile | Gly | Tyr | Leu | Val | Tyr | Arg | |
| | | 265 | | | | | 270 | | | | | 275 | | | | |

| tac | atc | cat | gtt | ggc | aag | gaa | aaa | cac | cca | gca | aat | ttg | gta | ctg | att | 919 |
|---|---|---|---|---|---|---|---|---|---|---|---|---|---|---|---|---|
| Tyr | Ile | His | Val | Gly | Lys | Glu | Lys | His | Pro | Ala | Asn | Leu | Val | Leu | Ile | |
| | 280 | | | | | 285 | | | | | 290 | | | | | |

| tat | aga | aat | gaa | att | ggc | aca | aga | gtc | ttt | gaa | cct | act | gaa | aca | atc | 967 |
|---|---|---|---|---|---|---|---|---|---|---|---|---|---|---|---|---|
| Tyr | Arg | Asn | Glu | Ile | Gly | Thr | Arg | Val | Phe | Glu | Pro | Thr | Glu | Thr | Ile | |
| 295 | | | | | 300 | | | | | 305 | | | | | 310 | |

| aca | ctt | aat | ttt | atc | acc | ttc | agt | atg | ttg | gat | gat | act | aaa | att | tct | 1015 |
|---|---|---|---|---|---|---|---|---|---|---|---|---|---|---|---|---|
| Thr | Leu | Asn | Phe | Ile | Thr | Phe | Ser | Met | Leu | Asp | Asp | Thr | Lys | Ile | Ser | |
| | | | | 315 | | | | | 320 | | | | | 325 | | |

| cca | aag | gat | atg | aat | tta | ctg | gac | aaa | agc | agt | gat | gac | atc | agt | gtt | 1063 |
|---|---|---|---|---|---|---|---|---|---|---|---|---|---|---|---|---|
| Pro | Lys | Asp | Met | Asn | Leu | Leu | Asp | Lys | Ser | Ser | Asp | Asp | Ile | Ser | Val | |

```
aat gac cct gag cac aat gag gcc tgg gag ccg cac tgg gag gag gtg    1111
Asn Asp Pro Glu His Asn Glu Ala Trp Glu Pro His Trp Glu Glu Val
            345                 350                 355 gag ggg caa cat tta gga tgc tct tcg cat ttg atg gac gct gtc tgt    1159
Glu Gly Gln His Leu Gly Cys Ser Ser His Leu Met Asp Ala Val Cys
        360                 365                 370 ggt gct gag caa aga gac gga gac acc tcc cta acc cag cat ggg tgg    1207
Gly Ala Glu Gln Arg Asp Gly Asp Thr Ser Leu Thr Gln His Gly Trp
375                 380                 385                 390 ctt aac agc acc atc ccc aca gga gag aca gac act gag cct caa tac    1255
Leu Asn Ser Thr Ile Pro Thr Gly Glu Thr Asp Thr Glu Pro Gln Tyr
                395                 400                 405 aaa gtc cta agt gac ttc tac ggg gag ggt gaa atc caa ctg tcc tgt    1303
Lys Val Leu Ser Asp Phe Tyr Gly Glu Gly Glu Ile Gln Leu Ser Cys
            410                 415                 420 gag ccg gaa gag gcg gcc aga aca gag aaa ata tct gag cca ctg gtg    1351
Glu Pro Glu Glu Ala Ala Arg Thr Glu Lys Ile Ser Glu Pro Leu Val
        425                 430                 435 act tca gca aac ttg gac cca cag ctt gaa gac cta cat cac ctg ggt    1399
Thr Ser Ala Asn Leu Asp Pro Gln Leu Glu Asp Leu His His Leu Gly
440                 445                 450 cag gag cat act gtc tcc gag gat ggg cca gag gaa gag aca tct ata    1447
Gln Glu His Thr Val Ser Glu Asp Gly Pro Glu Glu Glu Thr Ser Ile
455                 460                 465                 470 aca gta gtg gat tgg gac cct caa act ggc agg ctg tgt atc cct tcc    1495
Thr Val Val Asp Trp Asp Pro Gln Thr Gly Arg Leu Cys Ile Pro Ser
                475                 480                 485 tta cct atc ttt ggc cgt gat cct gag aac tat ggt cat tat gag aga    1543
Leu Pro Ile Phe Gly Arg Asp Pro Glu Asn Tyr Gly His Tyr Glu Arg
            490                 495                 500 gac cag ctc tta gag ggt ggc ctt ttg tct aga ctc tat gag aac cag    1591
Asp Gln Leu Leu Glu Gly Gly Leu Leu Ser Arg Leu Tyr Glu Asn Gln
        505                 510                 515 gca cct gac aag cca gag aaa gaa aat gaa aac tgt ctc aca cgg ttt    1639
Ala Pro Asp Lys Pro Glu Lys Glu Asn Glu Asn Cys Leu Thr Arg Phe
520                 525                 530 atg gag gaa tgg ggg tta cat gta caa atg gaa agc tagtgccagg         1685
Met Glu Glu Trp Gly Leu His Val Gln Met Glu Ser
535                 540                 545 ctttctgttg actgccaaca aatgaaggaa ccatcccagg gggtgaacag tgttcaggtt  1745
atcagtgtca gcaatgagac tgttctctct gttcatgaac tttgtcagcc ctgcctcatc  1805
c                                                                  1806

<210> SEQ ID NO 84
<211> LENGTH: 546
<212> TYPE: PRT
<213> ORGANISM: Mus musculus

<400> SEQUENCE: 84

Met His Thr Pro Gly Thr Pro Ala Pro Gly His Pro Asp Pro Pro
 1               5                  10                  15

Leu Leu Leu Leu Thr Leu Leu Leu Leu Ala Ala Ser Gly Arg Ala
            20                  25                  30

Val Pro Cys Val Phe Cys Gly Leu Pro Lys Pro Thr Asn Ile Thr Phe
            35                  40                  45

Leu Ser Ile Asn Met Lys Asn Val Leu His Trp Asn Pro Pro Glu Ser
        50                  55                  60
```

```
Leu His Gly Val Glu Val Thr Tyr Thr Val Gln Tyr Phe Ile Tyr Gly
 65                  70                  75                  80

Gln Lys Lys Trp Leu Asn Ala Ser Lys Cys Gly Ser Ile Asn Arg Thr
                 85                  90                  95

Tyr Cys Asp Leu Ser Val Glu Thr Ser Asp Tyr Glu His Gln Phe Tyr
            100                 105                 110

Ala Lys Val Lys Ala Ile Trp Glu Ala Arg Cys Ser Glu Trp Ala Glu
            115                 120                 125

Thr Glu Arg Phe Tyr Pro Phe Leu Glu Thr Gln Val Ser Pro Pro Glu
            130                 135                 140

Ile Ala Leu Thr Thr Gly Glu Lys Ser Ile Ser Ile Ala Leu Thr Ala
145                 150                 155                 160

Pro Glu Lys Trp Lys Arg Asn Pro Gln Asp His Thr Val Ser Met Gln
                165                 170                 175

Gln Ile Tyr Pro Asn Leu Lys Tyr Asn Val Ser Val Tyr Asn Thr Lys
            180                 185                 190

Ser Arg Arg Thr Trp Ser Gln Cys Val Thr Asn Ser Thr Leu Val Leu
            195                 200                 205

Ser Trp Leu Glu Pro Asn Thr Leu Tyr Cys Val His Val Glu Ser Leu
210                 215                 220

Val Pro Gly Pro Pro Arg Leu Pro Met Pro Ser Gln Lys Gln Cys Ile
225                 230                 235                 240

Ser Thr Leu Glu Val Gln Thr Ser Ala Trp Lys Ala Lys Val Ile Phe
            245                 250                 255

Trp Tyr Val Phe Leu Thr Ser Val Ile Val Phe Leu Phe Ser Ala Ile
            260                 265                 270

Gly Tyr Leu Val Tyr Arg Tyr Ile His Val Gly Lys Glu Lys His Pro
            275                 280                 285

Ala Asn Leu Val Leu Ile Tyr Arg Asn Glu Ile Gly Thr Arg Val Phe
290                 295                 300

Glu Pro Thr Glu Thr Ile Thr Leu Asn Phe Ile Thr Phe Ser Met Leu
305                 310                 315                 320

Asp Asp Thr Lys Ile Ser Pro Lys Asp Met Asn Leu Leu Asp Lys Ser
            325                 330                 335

Ser Asp Asp Ile Ser Val Asn Asp Pro Glu His Asn Glu Ala Trp Glu
            340                 345                 350

Pro His Trp Glu Glu Val Glu Gly Gln His Leu Gly Cys Ser Ser His
            355                 360                 365

Leu Met Asp Ala Val Cys Gly Ala Glu Gln Arg Asp Gly Asp Thr Ser
            370                 375                 380

Leu Thr Gln His Gly Trp Leu Asn Ser Thr Ile Pro Thr Gly Glu Thr
385                 390                 395                 400

Asp Thr Glu Pro Gln Tyr Lys Val Leu Ser Asp Phe Tyr Gly Glu Gly
                405                 410                 415

Glu Ile Gln Leu Ser Cys Glu Pro Glu Ala Ala Arg Thr Glu Lys
            420                 425                 430

Ile Ser Glu Pro Leu Val Thr Ser Ala Asn Leu Asp Pro Gln Leu Glu
            435                 440                 445

Asp Leu His His Leu Gly Gln Glu His Thr Val Ser Glu Asp Gly Pro
            450                 455                 460

Glu Glu Glu Thr Ser Ile Thr Val Val Asp Trp Asp Pro Gln Thr Gly
465                 470                 475                 480
```

-continued

Arg Leu Cys Ile Pro Ser Leu Pro Ile Phe Gly Arg Asp Pro Glu Asn
            485                 490                 495

Tyr Gly His Tyr Glu Arg Asp Gln Leu Leu Glu Gly Gly Leu Leu Ser
        500                 505                 510

Arg Leu Tyr Glu Asn Gln Ala Pro Asp Lys Pro Glu Lys Glu Asn Glu
        515                 520                 525

Asn Cys Leu Thr Arg Phe Met Glu Glu Trp Gly Leu His Val Gln Met
        530                 535                 540

Glu Ser
545

<210> SEQ ID NO 85
<211> LENGTH: 217
<212> TYPE: PRT
<213> ORGANISM: Mus musculus

<400> SEQUENCE: 85

Val Pro Cys Val Phe Cys Gly Leu Pro Lys Pro Thr Asn Ile Thr Phe
 1               5                  10                  15

Leu Ser Ile Asn Met Lys Asn Val Leu His Trp Asn Pro Pro Glu Ser
            20                  25                  30

Leu His Gly Val Glu Val Thr Tyr Thr Val Gln Tyr Phe Ile Tyr Gly
        35                  40                  45

Gln Lys Lys Trp Leu Asn Ala Ser Lys Cys Gly Ser Ile Asn Arg Thr
    50                  55                  60

Tyr Cys Asp Leu Ser Val Glu Thr Ser Asp Tyr Glu His Gln Phe Tyr
65                  70                  75                  80

Ala Lys Val Lys Ala Ile Trp Glu Ala Arg Cys Ser Glu Trp Ala Glu
                85                  90                  95

Thr Glu Arg Phe Tyr Pro Phe Leu Glu Thr Gln Val Ser Pro Pro Glu
            100                 105                 110

Ile Ala Leu Thr Thr Gly Glu Lys Ser Ile Ser Ile Ala Leu Thr Ala
        115                 120                 125

Pro Glu Lys Trp Lys Arg Asn Pro Gln Asp His Thr Val Ser Met Gln
    130                 135                 140

Gln Ile Tyr Pro Asn Leu Lys Tyr Asn Val Ser Val Tyr Asn Thr Lys
145                 150                 155                 160

Ser Arg Arg Thr Trp Ser Gln Cys Val Thr Asn Ser Thr Leu Val Leu
                165                 170                 175

Ser Trp Leu Glu Pro Asn Thr Leu Tyr Cys Val His Val Glu Ser Leu
            180                 185                 190

Val Pro Gly Pro Pro Arg Leu Pro Met Pro Ser Gln Lys Gln Cys Ile
        195                 200                 205

Ser Thr Leu Glu Val Gln Thr Ser Ala
    210                 215

<210> SEQ ID NO 86
<211> LENGTH: 201
<212> TYPE: PRT
<213> ORGANISM: Homo sapiens

<400> SEQUENCE: 86

Asp Glu Val Ala Ile Leu Pro Ala Pro Gln Asn Leu Ser Val Leu Ser
 1               5                  10                  15

Thr Asn Met Lys His Leu Leu Met Trp Ser Pro Val Ile Ala Pro Gly
            20                  25                  30

Glu Thr Val Tyr Tyr Ser Val Glu Tyr Gln Gly Glu Tyr Glu Ser Leu
                35                  40                  45

Tyr Thr Ser His Ile Trp Ile Pro Ser Ser Trp Cys Ser Leu Thr Glu
 50                  55                  60

Gly Pro Glu Cys Asp Val Thr Asp Asp Ile Thr Ala Thr Val Pro Tyr
 65                  70                  75                  80

Asn Leu Arg Val Arg Ala Thr Leu Gly Ser Gln Thr Ser Ala Trp Ser
                 85                  90                  95

Ile Leu Lys His Pro Phe Asn Arg Asn Ser Thr Ile Leu Thr Arg Pro
                100                 105                 110

Gly Met Glu Ile Pro Lys His Gly Phe His Leu Val Ile Glu Leu Glu
                115                 120                 125

Asp Leu Gly Pro Gln Phe Glu Phe Leu Val Ala Tyr Trp Thr Arg Glu
            130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
                180                 185                 190

Glu Cys Val Glu Val Gln Gly Glu Ala
        195                 200

<210> SEQ ID NO 87
<211> LENGTH: 21
<212> TYPE: DNA
<213> ORGANISM: Artificial Sequence
<220> FEATURE:
<223> OTHER INFORMATION: forward primer, ZC40541

<400> SEQUENCE: 87
tcgccaattc ctttcttacc a                                        21

<210> SEQ ID NO 88
<211> LENGTH: 20
<212> TYPE: DNA
<213> ORGANISM: Artificial Sequence
<220> FEATURE:
<223> OTHER INFORMATION: reverse primer, ZC40542

<400> SEQUENCE: 88
cccacaatgg catgtcatgt                                          20

<210> SEQ ID NO 89
<211> LENGTH: 25
<212> TYPE: DNA
<213> ORGANISM: Artificial Sequence
<220> FEATURE:
<223> OTHER INFORMATION: IL-20 TaqMan(r) probe ZC40544

<400> SEQUENCE: 89
agaaggacct ccggctctgt catgc                                    25

<210> SEQ ID NO 90
<211> LENGTH: 38
<212> TYPE: PRT
<213> ORGANISM: Homo sapiens

<400> SEQUENCE: 90

Cys Gly Glu Glu Ala Met Lys Lys Tyr Glu Gln Ile Leu Ser His Phe
  1               5                  10                  15

-continued

```
Glu Lys Leu Glu Pro Gln Ala Ala Val Val Lys Ala Leu Gly Glu Leu
             20                  25                  30

Asp Ile Leu Leu Gln Trp
         35

<210> SEQ ID NO 91
<211> LENGTH: 16
<212> TYPE: PRT
<213> ORGANISM: Artificial Sequence
<220> FEATURE:
<223> OTHER INFORMATION: Peptide Linker

<400> SEQUENCE: 91

Gly Gly Ser Gly Gly Ser Gly Gly Gly Gly Ser Gly Gly Gly Gly Ser
1               5                   10                  15
```

ANTI-IL-20 ANTIBODIES AND BINDING PARTNERS AND METHODS OF USING IN INFLAMMATION

CROSS-REFERENCE TO RELATED APPLICATIONS

This application is a continuation of U.S. application Ser. No. 10/994,116, filed Nov. 19, 2004, which claims the benefit of U.S. Provisional Application Ser. No. 60/524,131, filed Nov. 21, 2003, and U.S. Provisional Application Ser. No. 60/555,857, filed Mar. 24, 2004, all of which are herein incorporated by reference.

BACKGROUND OF THE INVENTION

Cytokines are soluble, small proteins that mediate a variety of biological effects, including the regulation of the growth and differentiation of many cell types (see, for example, Arai et al., *Annu. Rev. Biochem.* 59:783 (1990); Mosmann, *Curr. Opin. Immunol* 3:311 (1991); Paul and Seder, *Cell* 76:241 (1994)). Proteins that constitute the cytokine group include interleukins, interferons, colony stimulating factors, tumor necrosis factors, and other regulatory molecules. For example, human interleukin-17 is a cytokine which stimulates the expression of interleukin-6, intracellular adhesion molecule 1, interleukin-8, granulocyte macrophage colony-stimulating factor, and prostaglandin E2 expression, and plays a role in the preferential maturation of CD34+ hematopoietic precursors into neutrophils (Yao et al., *J. Immunol.* 155:5483 (1995); Fossiez et al., *J. Exp. Med.* 183:2593 (1996)).

Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons are members of the class II cytokine receptor family, based upon a characteristic 200 residue extracellular domain.

The demonstrated in vivo activities of cytokines and their receptors illustrate the clinical potential of, and need for, other cytokines, cytokine receptors, cytokine agonists, and cytokine antagonists. For example, demonstrated in vivo activities of the pro-inflammatory cytokine family illustrates the enormous clinical potential of, and need for antagonists of pro-inflammatory molecules.

The present invention addresses these needs by providing antibodies to a pro-inflammatory cytokines, and particularly IL-20, including soluble IL-20RA, IL-20RB and IL-20RA/IL-20RB receptors and neutralizing anti-IL-20, IL-20RA and IL-20RB antibodies, as well as providing uses therefore in inflammatory disease, as well as related compositions and methods.

DESCRIPTION OF THE INVENTION

1. Overview

The present invention addresses these needs by providing antibodies to pro-inflammatory cytokines and cytokine receptors. In particular, the present invention is directed to antibodies to IL-20 (referred to interchangeably as Zcyto10) and one of its receptors, IL-20RA/IL-20RB (referred to interchangeably as ZcytoR7/pDIRS1), including neutralizing anti-IL-20 antibodies, anti-IL-20RA antibodies, anti-IL-20RB antibodies, and anti-IL-20RA/IL-20RB antibodies, as well as providing uses therefore in inflammatory disease, as well as related compositions and methods.

Amongst other inventions, the present invention provides novel uses for neutralizing antibodies to IL-20, and its receptor subunits IL-20RA and IL-20RB, as well as the receptor heterodimer, IL-20RA/IL-20RB. Specifically, these antibodies are useful in the treatment of human inflammatory and autoimmune diseases. The present invention also provides antibody fragments thereof, also for use in human inflammatory and autoimmune diseases. The neutralizing anti-IL-20 antibodies, anti-IL-20RA antibodies, anti-IL-20RB antibodies, and anti-IL-20RA/IL-20RB heterodimer antibodies of the present invention, can be used to antagonize the activity of IL-20 in the treatment of specific human diseases such as psoriasis, psoriatic arthritis, arthritis, endotoxemia, inflammatory bowel disease (IBD), colitis, and other inflammatory conditions disclosed herein.

An illustrative nucleotide sequence that encodes human IL-20 is provided by SEQ ID NO:1. The corresponding encoded polypeptides are shown in SEQ ID NO:2. Analysis of a human cDNA clone encoding IL-20 (SEQ ID NO:1) revealed an open reading frame encoding 176 amino acids (SEQ ID NO:2), with the initial Met as shown in SEQ ID NO:1 and SEQ ID NO:2. It is believed that amino residues 1-24 are signal sequence, and the mature IL-20 polypeptide is represented by the amino acid sequence comprised of residues 25, a leucine through reside 176, a glutamic acid, also defined by SEQ ID NO:3. Another embodiment of the present invention is defined by the sequences of SEQ ID NO: 4 and SEQ ID NO: 5. The polypeptide of SEQ ID NO: 5 is comprised of 151 amino acid residues wherein amino acids 1-24 comprise a signal sequence and the mature sequence is comprised of amino acid residues 25, a leucine, through amino acid 151 a glutamic acid, also defined by SEQ ID NO:6. Another active variant is comprised of amino acid residues 33, a cysteine, through amino acid residue 176 of SEQ ID NO:2. This variant is also defined by SEQ ID NO:7. Murine IL-20 is encoded by SEQ ID NOs: 8-12. IL-20 is disclosed in commonly owned U.S. Pat. No. 6,576,743, and commonly owned WIPO publication WO 98/25228, both of which are incorporated herein by reference.

One receptor for IL-20 is comprised of two chains, an alpha chain and a beta chain. The alpha chain, hereinafter referred to as IL-20RA, was formally called ZcytoR7. The beta chain, hereinafter referred to as IL-20RB, was formally called DIRS1. An illustrative nucleotide sequence for IL-20RA is SEQ ID NO:13. The encoded polypeptide is shown in SEQ ID NO:14. Analysis of a human cDNA clone encoding IL-20RA (SEQ ID NO:13) revealed an open reading frame encoding 553 amino acids (SEQ ID NO:14) comprising an extracellular ligand-binding domain of approximately 221 amino acid residues (residues 30-250 of SEQ ID NO:14 and SEQ ID NO:15), a transmembrane domain of approximately 24 amino acid residues (residues 251-274 of SEQ ID NO:14), and an intracellular domain of approximately 279 amino acid residues (residues 275-553 of SEQ ID NO:14). Thus, the extracellular domain of the human IL-20RA is comprised of a polypeptide selected from the group consisting of SEQ ID NOs: 16, 17, 18 and 19, the full-length receptor subunit being comprised of SEQ ID NO:14. IL-20RA is disclosed in commonly owned U.S. Pat. No. 5,945,511, and commonly owned WIPO publication WO 98/03029, both of which are incorporated herein by reference.

An illustrative nucleotide sequence that encodes human IL-20RB (pDIRS1) is provided by SEQ ID NO:20. The encoded polypeptide is shown in SEQ ID NO:21. A variant IL-20RB is provided by SEQ ID NOs:22 and 23. The extracellular domain of IL-20RB is comprised of a polypeptide selected from the group consisting of SEQ ID NOs: 24, 25, 26, 27, 28, 29 and 30. IL-20RB is disclosed in U.S. Pat. No. 6,586,228, which is incorporated herein by reference.

As described below, the present invention provides isolated polypeptides comprising an amino acid sequence that is at least 70%, at least 80%, or at least 90%, or greater than 95%, such as 96%, 97%, 98%, or greater than 99% or more identical to SEQ ID NOS:2, 3, 14, 15, 21 or 23, wherein the isolated polypeptide specifically binds with an antibody that specifically binds with a polypeptide consisting of the amino acid sequence of SEQ ID NOS:2, 3, 14, 15, 21 or 23. Moreover, the present invention also provides isolated polypeptides as disclosed above that bind IL-20 (e.g., human IL-20 polypeptide sequence as shown in SEQ ID NO:2 or 3), IL-20RA (e.g., human IL-20RA polypeptide sequence as shown in SEQ ID NO:14 or 15), and IL-20RB (e.g., human IL-20RB polypeptide sequence as shown in SEQ ID NO:21 or 23). The human IL-20 polynucleotide sequence is shown in SEQ ID NO:1.

The present invention also provides isolated polypeptides and epitopes comprising at least 15 contiguous amino acid residues of an amino acid sequence of SEQ ID NOS:2, 3, 14, 15, 21 or 23. Illustrative polypeptides include polypeptides that either comprise, or consist of SEQ ID NOS:2, 3, 14, 15, 21 or 23, an antigenic epitope thereof, or a functional IL-20 binding fragment thereof. Moreover, the present invention also provides isolated polypeptides as disclosed above that bind, antagonize or neutralize the activity of IL-20.

The present invention also includes variant IL-20, IL-20RA and IL-20RB polypeptides, wherein the amino acid sequence of the variant polypeptide shares an identity with the amino acid residues of SEQ ID NOS:2 or 3 for IL-20, SEQ ID NOS:14 or 15 for IL-20RA, or SEQ ID NOS:21 or 23 for IL-20RB, selected from the group consisting of at least 70% identity, at least 80% identity, at least 90% identity, at least 95% identity, or greater than 95% identity, such as 96%, 97%, 98%, or greater than 99% or more identity, and wherein any difference between the amino acid sequence of the variant polypeptide and the corresponding amino acid sequence is due to one or more conservative amino acid substitutions. Such conservative amino acid substitutions are described herein. Moreover, the present invention also provides isolated polypeptides as disclosed above that bind, antagonize or neutralize the activity of IL-20.

The present invention further provides antibodies and antibody fragments that specifically bind with such polypeptides. Exemplary antibodies include neutralizing antibodies, polyclonal antibodies, murine monoclonal antibodies, humanized antibodies derived from murine monoclonal antibodies, and human monoclonal antibodies. Illustrative antibody fragments include $F(ab')_2$, $F(ab)_2$, Fab', Fab, Fv, scFv, and minimal recognition units. Neutralizing antibodies preferably bind either IL-20, IL-20RA or IL-20RB such that the interaction of IL-20 with its receptor is neutralized. The present invention further includes compositions comprising a carrier and a peptide, polypeptide, or antibody described herein.

In addition, the present invention provides pharmaceutical compositions comprising a pharmaceutically acceptable carrier and at least one of such an expression vector or recombinant virus comprising such expression vectors. The present invention further includes pharmaceutical compositions, comprising a pharmaceutically acceptable carrier and a polypeptide or antibody described herein.

The present invention also contemplates anti-idiotype antibodies, or anti-idiotype antibody fragments, that specifically bind an antibody or antibody fragment that specifically binds a polypeptide comprising the amino acid sequence of SEQ ID NOs:2, 3, 5, 6, 7, 14-19, 21, 23-30 or a fragment thereof. An exemplary anti-idiotype antibody binds with an antibody that specifically binds a polypeptide consisting of SEQ ID NO:3.

The present invention also provides fusion proteins, comprising either an IL-20, IL-20RA or IL-20RB polypeptide and an immunoglobulin moiety. In such fusion proteins, the immunoglobulin moiety may be an immunoglobulin heavy chain constant region, such as a human $F_c$ fragment. The present invention further includes isolated nucleic acid molecules that encode such fusion proteins.

The present invention also provides polyclonal and monoclonal antibodies comprising either an IL-20 polypeptide fragment, or an IL-20RA or IL-20RB extracellular domain such as monomeric, homodimeric, heterodimeric and multimeric receptors, including soluble receptors. Moreover, such antibodies can be used antagonize the binding of IL-20 to its receptor.

Moreover, over expression of IL-20 was shown in human psoriatic lesions, suggesting that IL-20 is also involved in human psoriasis. Moreover, as described herein, over expression of IL-20 in transgenic mice showed epidermal thickening and immune cell involvement indicative of a psoriatic phenotype. As such, antagonists to IL-20 activity, such as IL-20RA soluble receptors and antibodies thereto including either anti-human-IL-20, anti-human-IL-20RA, or anti-human-IL-20RB monoclonal and neutralizing antibodies of the present invention, are useful in therapeutic treatment of inflammatory diseases, particularly as antagonists to IL-20 in the treatment of psoriasis. Moreover, antagonists to IL-20 activity, such as IL-20RA soluble receptors and antibodies thereto including the anti-human-IL-20RA monoclonal and neutralizing antibodies of the present invention, are useful in therapeutic treatment of other inflammatory diseases for example as antagonists to IL-20 in the treatment of atopic dermatitis, IBD, colitis, Endotoxemia, arthritis, rheumatoid arthritis, and psoriatic arthritis adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1.47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces IL-20, IL-20RA or IL-20RB from an expression vector. In contrast, IL-20, IL-20RA or IL-20RB can be produced by a cell that is a "natural source" of IL-20, IL-20RA or IL-20RB, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of either an IL-20, IL-20RA or IL-20RB polypeptide fused with a polypeptide that binds an affinity matrix. Such a fusion protein provides a means to isolate large quantities of these polypeptides using affinity chromatography.

As used herein, the term "antibody fusion protein" refers to a recombinant molecule that comprises an antibody component and a therapeutic agent. Examples of therapeutic agents suitable for such fusion proteins include immunomodulators ("antibody-immunomodulator fusion protein") and toxins ("antibody-toxin fusion protein").

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

A "soluble receptor" is a receptor polypeptide that is not bound to a cell membrane. Soluble receptors are most commonly ligand-binding receptor polypeptides that lack transmembrane and cytoplasmic domains, and other linkage to the cell membrane such as via glycophosphoinositol (gpi). Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Soluble receptors can be monomeric, homodimeric, heterodimeric, or multimeric, with multimeric receptors generally not comprising more than 9 subunits, preferably not comprising more than 6 subunits, and most preferably not comprising more than 3 subunits. Receptor polypeptides are said to be substantially free of transmembrane and intracellular polypeptide segments when they lack sufficient portions of these segments to provide membrane anchoring or signal transduction, respectively. Soluble receptors of class I and class II cytokine receptors generally comprise the extracellular cytokine binding domain free of a transmembrane domain and intracellular domain. It is well within the level of one of skill in the art to delineate what sequences of a known class I or class II cytokine sequence comprise the extracellular cytokine binding domain free of a transmembrane domain and intracellular domain. Moreover, one of skill in the art using the genetic code can readily determine polynucleotides that encode such soluble receptor polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and the like, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-IL-20 antibody, and thus, an anti-idiotype antibody mimics an epitope of IL-20. As a further example, an anti-idiotype antibody binds with the variable region of an anti-IL-20RA antibody, and thus, an anti-idiotype antibody mimics an epitope of IL-20RA. As yet another example, an anti-idiotype antibody binds with the variable region of an anti-IL-20RB antibody, and thus, an anti-idiotype antibody mimics an epitope of IL-20RB.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-IL-20 monoclonal antibody fragment binds with an epitope of IL-20. As a further example, an anti-IL-20RA monoclonal antibody fragment binds with an epitope of IL-20RA. As yet another example, an anti-IL-20RB monoclonal antibody fragment binds with an epitope of IL-20RB.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain. Construction of humanized antibodies for therapeutic use in humans that are derived from murine antibodies, such as those that bind to or neutralize a human protein, is within the skill of one in the art.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and either an IL-20, IL-20RA or IL-20RB polypeptide component. Examples of an antibody fusion protein include a protein that comprises a polypeptide domain of IL-20 or an extracellular domain of either IL-20RA or IL-20RB, and either an Fc domain or an antigen-binding region.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for IL-20" or a "IL-20 anti-sense oligonucleotide" is an oligonucleotide having a sequence (a) capable of forming a stable triplex with a portion of the IL-20 gene, or (b) capable of forming a stable duplex with a portion of an mRNA transcript of the IL-20 gene. An "anti-sense oligonucleotide specific for IL-20RA" or a "IL-20RA anti-sense oligonucleotide" is an oligonucleotide having a sequence (a) capable of forming a stable triplex with a portion of the IL-20RA gene, or (b) capable of forming a stable duplex with a portion of an mRNA transcript of the IL-20RA gene. An "anti-sense oligonucleotide specific for IL-20RB" or a "IL-20RB anti-sense oligonucleotide" is an oligonucleotide having a sequence (a) capable of forming a stable triplex with a portion of the IL-20RB gene, or (b) capable of forming a stable duplex with a portion of an mRNA transcript of the IL-20RB gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant IL-20 gene" refers to nucleic acid molecules that encode a polypeptide having an amino acid sequence that is a modification of SEQ ID NO:2. Such variants include naturally-occurring polymorphisms of IL-20 genes, as well as synthetic genes that contain conservative amino acid substitutions of the amino acid sequence of SEQ ID NO:2. Additional variant forms of IL-20 genes are nucleic acid molecules that contain insertions or deletions of the nucleotide sequences described herein. A variant IL-20 gene can be identified, for example, by determining whether the gene hybridizes with a nucleic acid molecule having the nucleotide sequence of SEQ ID NO:1, or its complement, under stringent conditions.

The term "variant IL-20RA gene" refers to nucleic acid molecules that encode a polypeptide having an amino acid sequence that is a modification of SEQ ID NO:14. Such variants include naturally-occurring polymorphisms of IL-20RA genes, as well as synthetic genes that contain conservative amino acid substitutions of the amino acid sequence of SEQ ID NO:14. Additional variant forms of IL-20RA genes are nucleic acid molecules that contain insertions or deletions of the nucleotide sequences described herein. A variant IL-20RA gene can be identified, for example, by determining whether the gene hybridizes with a nucleic acid molecule having the nucleotide sequence of SEQ ID NO:13, or its complement, under stringent conditions.

The term "variant IL-20RB gene" refers to nucleic acid molecules that encode a polypeptide having an amino acid sequence that is a modification of SEQ ID NO:21. Such variants include naturally-occurring polymorphisms of IL-20RB genes, as well as synthetic genes that contain conservative amino acid substitutions of the amino acid sequence of SEQ ID NO:21. Additional variant forms of IL-20RB genes are nucleic acid molecules that contain insertions or deletions of the nucleotide sequences described herein. A variant IL-20RB gene can be identified, for example, by determining whether the gene hybridizes with a nucleic acid molecule having the nucleotide sequence of SEQ ID NO:20, or its complement, under stringent conditions.

Alternatively, variant IL-20, IL-20RA or IL-20RB genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123-151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify any of the variant genes or variant polypeptides described above, a variant gene or polypeptide encoded by a variant gene may be functionally characterized by its ability to bind specifically to an anti-IL-20, anti-IL-20RA or anti-IL-20RB antibody. A variant IL-20RA or IL-20RB gene or variant polypeptide may also be functionally characterized the ability to bind to its ligand, IL-20, using a biological or biochemical assay described herein.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The present invention includes functional fragments of any of the IL-20, IL-20RA or IL-20RB genes. For example, within the context of this invention, a "functional fragment" of a IL-20RA gene refers to a nucleic acid molecule that encodes a portion of a IL-20RA polypeptide which is a domain described herein or at least specifically binds with an anti-IL-20RA antibody.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of IL-20, IL-20RA and IL-20RB Polynucleotides or Genes

Nucleic acid molecules encoding a human IL-20, IL-20RA or IL-20RB gene can be obtained by screening a human cDNA or genomic library using polynucleotide probes based upon SEQ ID NO:1, SEQ ID NO:13 or SEQ ID NO:20, respectively. These techniques are standard and well-established, and may be accomplished using cloning kits available by commercial suppliers. See, for example, Ausubel et al. (eds.), *Short Protocols in Molecular Biology, 3$^{rd}$ Edition*, John Wiley & Sons 1995; Wu et al., *Methods in Gene Biotechnology*, CRC Press, Inc. 1997; Aviv and Leder, *Proc. Nat'l Acad. Sci. USA* 69:1408 (1972); Huynh et al., "Constructing and Screening cDNA Libraries in λgt10 and λgt11," in *DNA Cloning: A Practical Approach Vol I*, Glover (ed.), page 49 (IRL Press, 1985); Wu (1997) at pages 47-52.

Nucleic acid molecules that encode a human IL-20, IL-20RA or IL-20RB gene can also be obtained using the polymerase chain reaction (PCR) with oligonucleotide primers having nucleotide sequences that are based upon the nucleotide sequences of any of the genes or cDNA. General methods for screening libraries with PCR are provided by, for example, Yu et al., "Use of the Polymerase Chain Reaction to Screen Phage Libraries," in *Methods in Molecular Biology*, Vol. 15. *PCR Protocols: Current Methods and Applications*, White (ed.), Humana Press, Inc., 1993. Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology*, Vol. 15: *PCR Protocols: Current Methods and Applications*, White (ed.), Humana Press, Inc. 1993. As an alternative, a IL-20RA gene can be obtained by synthesizing nucleic acid molecules using mutually priming long oligonucleotides and the nucleotide sequences described herein (see, for example, Ausubel (1995)). Established techniques using the polymerase chain reaction provide the ability to synthesize DNA molecules at least two kilobases in length (Adang et al., *Plant Molec. Biol* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology*, Vol 15: *PCR Protocols: Current Methods and Applications*, White (ed.), pages 263-268, (Humana Press, Inc. 1993), and Holowachuk et al., *PCR Methods Appl.* 4:299 (1995)). For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

4. Production of IL-20, IL-20RA or IL-20RB Gene Variants

The present invention provides a variety of nucleic acid molecules, including DNA and RNA molecules, that encode the IL-20, IL-20RA or IL-20RB polypeptides disclosed herein. Those skilled in the art will readily recognize that, in view of the degeneracy of the genetic code, considerable sequence variation is possible among these polynucleotide molecules. Moreover, the present invention also provides isolated soluble monomeric, homodimeric, heterodimeric and multimeric receptor polypeptides that comprise at least one IL-20RA or IL-20RB receptor subunit that is substantially homologous to the receptor polypeptide of SEQ ID NO:14 or SEQ ID NO:21, respectively.

Table 1 sets forth the one-letter codes to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |

TABLE 2-continued

| Amino Acid | One Letter Code | Codons | Degenerate Codon |
|---|---|---|---|
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of IL-20 (SEQ ID NO:2), IL-20RA (SEQ ID NO:14) and IL-20RB (SEQ ID NO:21). Variant sequences can be readily tested for functionality as described herein.

Different species can exhibit "preferential codon usage." In general, see, Grantham et al., *Nucl. Acids Res.* 8:1893 (1980), Haas et al. *Curr. Biol* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

Any of the IL-20, IL-20RA or IL-20RB-encoding cDNA can be isolated by a variety of methods, such as by probing with a complete or partial human cDNA or with one or more sets of degenerate probes based on the disclosed sequences. A cDNA can also be cloned using the polymerase chain reaction with primers designed from the representative human sequences disclosed herein. In addition, a cDNA library can be used to transform or transfect host cells, and expression of the cDNA of interest can be detected with an antibody to any of the IL-20, IL-20RA or IL-20RB polypeptides.

Those skilled in the art will recognize that the sequences disclosed in SEQ ID NOS:1, 10 and 12 represent a single allele of human IL-20, IL-20RA or IL-20RB, and that allelic variation and alternative splicing are expected to occur. Allelic variants of any of these sequences can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins which are allelic variants of the amino acid sequences disclosed herein. cDNA molecules generated from alternatively spliced mRNAs, which retain the properties of any of the polypeptides referenced above are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Using the methods discussed above, one of ordinary skill in the art can prepare a variety of polypeptides that comprise IL-20 or a fragment thereof that is substantially homologous to SEQ ID NO:1. One of ordinary skill in the art could also prepare a variety of polypeptides that comprise either a soluble IL-20RA receptor subunit that is substantially homologous to SEQ ID NO:13, or that encodes amino acids of SEQ ID NO:14, or a soluble IL-20RB receptor subunit that is substantially homologous to SEQ ID NO:20, or that encodes amino acids of SEQ ID NO:21, or allelic variants thereof, and all of which retain the ligand-binding properties of the wild-type IL-20RA or IL-20RB receptor subunit. Such polypeptides may also include additional polypeptide segments as generally disclosed herein.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of any of SEQ ID NO:1, SEQ ID NO:13 or SEQ ID NO:20 or to nucleic acid molecules comprising a nucleotide sequence complementary these sequences, or fragments thereof.

In general, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Following hybridization, the nucleic acid molecules can be washed to remove non-hybridized nucleic acid molecules under stringent conditions, or under highly stringent conditions. See, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol Biol* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating Tm based on user-defined criteria. It is well within the abilities of one skilled in the art to adapt hybridization and wash conditions for use with a particular polynucleotide hybrid.

The present invention also provides isolated IL-20, IL-20RA and IL-20RB polypeptides that have a substantially similar sequence identity to the polypeptides of SEQ ID NO:2, SEQ ID NO:14 and SEQ ID NO:21, or their orthologs. The term "substantially similar sequence identity" is used herein to denote polypeptides having at least 70%, at least 80%, at least 90%, at least 95%, such as 96%, 97%, 98%, or greater than 95% sequence identity to the sequences shown in SEQ ID NO:2, SEQ ID NO:14 and SEQ ID NO:21, or their orthologs. For example, variant and orthologous IL-20RA receptors can be used to generate an immune response and raise cross-reactive antibodies to human IL-20RA. Such antibodies can be humanized, and modified as described herein, and used therapeutically to treat psoriasis, psoriatic arthritis, IBD, colitis, endotoxemia as well as in other therapeutic applications described herein.

The present invention also contemplates IL-20, IL-20RA and IL-20RB variant nucleic acid molecules that can be identified using two criteria: a determination of the similarity between the encoded polypeptide with the amino acid sequence of SEQ ID NO:2, SEQ ID NO:14 and SEQ ID NO:21, and a hybridization assay. Such variants include nucleic acid molecules (1) that remain hybridized with a nucleic acid molecule having the nucleotide sequence of SEQ ID NO:1, SEQ ID NO:13 and SEQ ID NO:20 (or their complements) under stringent washing conditions, in which the wash stringency is equivalent to 0.5×-2×SSC with 0.1% SDS at 55-65° C., and (2) that encode a polypeptide having at least 70%, at least 80%, at least 90%, at least 95%, or greater than 95% such as 96%, 97%, 98%, or 99%, sequence identity to the amino acid sequence of SEQ ID NO:3. Alternatively, these variants can be characterized as nucleic acid molecules (1) that remain hybridized with a nucleic acid molecule having the nucleotide sequence of SEQ ID NO:1, SEQ ID NO:13 and SEQ ID NO:20 (or their complement) under highly stringent washing conditions, in which the wash stringency is equivalent to 0.1×-0.2×SSC with 0.1% SDS at 50-65° C., and (2) that encode a polypeptide having at least 70%, at least 80%, at least 90%, at least 95% or greater than 95%, such as 96%, 97%, 98%, or 99% or greater, sequence identity to the amino acid sequence of any of SEQ ID NO:2, SEQ ID NO:14 and SEQ ID NO:21.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "blosum62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative IL-20, IL-20RA or IL-20RB variant. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid change, compared with an amino acid sequence disclosed herein. For example, variants can be obtained that contain one or more amino acid substitutions of any of the sequences disclosed herein, in which an alkyl amino acid is substituted for an alkyl amino acid, an aromatic amino acid is substituted for an aromatic amino acid, a sulfur-containing amino acid is substituted for a sulfur-containing amino acid, a hydroxy-containing amino acid is substituted for a hydroxy-containing amino acid, an acidic amino acid is substituted for an acidic amino acid, a basic amino acid is substituted for a basic amino acid, or a dibasic monocarboxylic amino acid is substituted for a dibasic monocarboxylic amino acid. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Particular variants of any of IL-20, IL-20RA or IL-20RB are characterized by having at least 70%, at least 80%, at least 90%, at least 95% or greater than 95% such as 96%, 97%, 98%, or 99% or greater sequence identity to the corresponding amino acid sequences (e.g., SEQ ID NO:2, SEQ ID NO:14 and SEQ ID NO:21), wherein the variation in amino acid sequence is due to one or more conservative amino acid substitutions.

Conservative amino acid changes in any of the IL-20, IL-20RA or IL-20RB genes can be introduced, for example, by substituting nucleotides for the nucleotides recited in any of SEQ ID NO:1, SEQ ID NO:13 and SEQ ID NO:20. Such "conservative amino acid" variants can be obtained by oligonucleotide-directed mutagenesis, linker-scanning mutagenesis, mutagenesis using the polymerase chain reaction, and the like (see Ausubel (1995); and McPherson (ed.), *Directed Mutagenesis: A Practical Approach* (IRL Press 1991)). A variant IL-20, IL-20RA or IL-20RB polypeptide can be identified by the ability to specifically bind to its respective antibody.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for any of the IL-20, IL-20RA or IL-20RB amino acid residues.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., *J. Biol. Chem.* 271:4699 (1996).

Although sequence analysis can be used to further define the IL-20 binding domain or the IL-20RA or IL-20RB ligand binding region, amino acids that play a role in IL-20, IL-20RA and IL-20RB binding activity (such as binding to ligand IL-20, or to an anti-IL-20RA or IL-20RB antibody) can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992).

Multiple amino acid substitutions can be made and tested using known methods of mutagenesis and screening, such as those disclosed by Reidhaar-Olson and Sauer (*Science* 241: 53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)). Moreover, IL-20RA labeled with biotin or FITC can be used for expression cloning of IL-20RA ligands.

Variants of the disclosed IL-20, IL-20RA and IL-20RB nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-IL-20, anti-IL-20RA or anti-IL-20RB antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of IL-20, IL-20RA and IL-20RB polypeptides and nucleic acid molecules encoding such functional fragments. Routine deletion analyses of nucleic acid molecules can be performed to obtain functional fragments of a nucleic acid molecule that encodes an IL-20, IL-20RA or IL-20RB polypeptide. As an illustration, DNA molecules having the nucleotide sequence of SEQ ID NO:1 (IL-20) can be digested with Bal31 nuclease to obtain a series of nested deletions. The fragments are then inserted into expression vectors in proper reading frame, and the expressed polypeptides are isolated and tested for the ability to bind anti-IL-20 antibodies. One alternative to exonuclease digestion is to use oligonucleotide-directed mutagenesis to introduce deletions or stop codons to specify production of a desired fragment. Alternatively, particular fragments of an IL-20 gene can be synthesized using the polymerase chain reaction.

This general approach is exemplified by studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987), Herschman, "The EGF Receptor," in *Control of Animal Cell Proliferation, Vol 1*, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol* 50:1295 (1995), and Meisel et al., *Plant Molec. Biol.* 30:1 (1996).

The present invention also contemplates functional fragments of an IL-20, IL-20RA or IL-20RB gene that have amino acid changes, compared with an amino acid sequence disclosed herein. Such a variant gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant IL-20, IL-20RA or IL-20RB gene can hybridize to a nucleic acid molecule comprising a nucleotide sequence, such as SEQ ID NO:1, SEQ ID NO:13 or SEQ ID NO:20, respectively.

The present invention also includes using functional fragments of IL-20, IL-20RA or IL-20RB polypeptides, antigenic epitopes, epitope-bearing portions of IL-20, IL-20RA or IL-20RB polypeptides, and nucleic acid molecules that encode such functional fragments, antigenic epitopes, and epitope-bearing portions of IL-20, IL-20RA or IL-20RB polypeptides. Such fragments are used to generate polypeptides for use in generating antibodies and binding partners that bind, block, reduce, antagonize or neutralize activity of IL-20. A "functional" IL-20 polypeptide or fragment thereof as defined herein is characterized by its ability to antagonize IL-20 inflammatory, proliferative or differentiating activity, by its ability to induce or inhibit specialized cell functions, or by its ability to bind specifically to an anti-IL-20 antibody, cell, or IL-20 receptor. A "functional" IL-20RA polypeptide or fragment thereof as defined herein is characterized by its ability to antagonize IL-20 inflammatory, proliferative or differentiating activity, by its ability to induce or inhibit specialized cell functions, or by its ability to bind specifically to an anti-IL-20RA antibody, cell, or IL-20. A "functional" IL-20RB polypeptide or fragment thereof as defined herein is characterized by its ability to antagonize IL-20 inflammatory, proliferative or differentiating activity, by its ability to induce or inhibit specialized cell functions, or by its ability to bind specifically to an anti-IL-20RB antibody, cell, or IL-20. As previously described herein, IL-20 is a class II cytokine and IL-20RA and IL-20RB are characterized by class II cytokine receptor structure and domains as described herein. Thus, the present invention further contemplates using fusion proteins encompassing: (a) polypeptide molecules comprising one or more of the domains described above; and (b) functional fragments comprising one or more of these domains. The other polypeptide portion of the fusion protein may be contributed by another class II cytokine receptor, such as IL-10R, IL-13R, IL-20RA, Crf2-4, IL-20RA2, or by a non-native and/or an unrelated secretory signal peptide that facilitates secretion of the fusion protein.

The present invention also provides polypeptide fragments or peptides comprising an epitope-bearing portion of an IL-20, IL-20RA or IL-20RB polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein. Hopp/Woods hydrophilicity profiles can be used to determine regions that have the most antigenic potential within any of SEQ ID NO:2, SEQ ID NO:14 and SEQ ID NO:21 (Hopp et al., Proc. Natl. Acad. Sci. 78:3824-3828, 1981; Hopp, J. Immun. Meth. 88:1-18, 1986 and Triquier et al., Protein Engineering 11:153-169, 1998). The profile is based on a sliding six-residue window. Buried G, S, and T residues and exposed H, Y, and W residues were ignored. In any of IL-20, IL-20RA or IL-20RB, these regions can be determined by one of skill in the art.

Moreover, IL-20 antigenic epitopes within SEQ ID NO:2 as predicted by a Jameson-Wolf plot, e.g., using DNASTAR Protean program (DNASTAR, Inc., Madison, Wis.) serve as preferred antigenic epitopes, and can be determined by one of skill in the art. Such antigenic epitopes include: amino acid residues 42 (Ile) to 102 (Asp) of SEQ ID NO:2; amino acid residues 42 (Ile) to 60 (Ile) of SEQ ID NO:2; amino acid residues 42 (Ile) to 69 (Glu) of SEQ ID NO:2; amino acid residues 42 (Ile) to 81 (Cys) of SEQ ID NO:2; amino acid residues 42 (Ile) to 96 (Lys) of SEQ ID NO:2; amino acid residues 42 (Ile) to 102 (Asp) of SEQ ID NO:2; amino acid residues 60 (Ile) to 69 (Glu) of SEQ ID NO:2; amino acid residues 60 (Ile) to 81 (Cys) of SEQ ID NO:2; amino acid residues 60 (Ile) to 96 (Lys) of SEQ ID NO:2; amino acid residues 60 (Ile) to 102 (Asp) of SEQ ID NO:2; amino acid residues 69 (Glu) to 81 (Cys) of SEQ ID NO:2; amino acid residues 69 (Glu) to 96 (Lys) of SEQ ID NO:2; amino acid residues 69 (Glu) to 102 (Asp) of SEQ ID NO:2; amino acid residues 81 (Cys) to 96 (Lys) of SEQ ID NO:2; amino acid residues 81 (Cys) to 102 (Asp) of SEQ ID NO:2; amino acid residues 96 (Lys) to 102 (Asp) of SEQ ID NO:2.

IL-20RA antigenic epitopes include: amino acid residues 1 (Met) to 9 (Leu) of SEQ ID NO:14; amino acid residues 1 (Met) to 36 (Gly) of SEQ ID NO:14; amino acid residues 1 (Met) to 41 (Ala) of SEQ ID NO:14; amino acid residues 1 (Met) to 58 (Pro) of SEQ ID NO:14; amino acid residues 1 (Met) to 63 (Gln) of SEQ ID NO:14; amino acid residues 1 (Met) to 80 (Lys) of SEQ ID NO:14; amino acid residues 1 (Met) to 94 (Tyr) of SEQ ID NO:14; amino acid residues 1 (Met) to 104 (Tyr) of SEQ ID NO:14; amino acid residues 1 (Met) to 120 (Cys) of SEQ ID NO:14; amino acid residues 1 (Met) to 128 (Arg) of SEQ ID NO:14; amino acid residues 1 (Met) to 161 (Trp) of SEQ ID NO:14; amino acid residues 1 (Met) to 169 (Pro) of SEQ ID NO:14; amino acid residues 1 (Met) to 187 (Asn) of SEQ ID NO:14; amino acid residues 1 (Met) to 194 (Trp) of SEQ ID NO:14; amino acid residues 1 (Met) to 224 (Gly) of SEQ ID NO:14; amino acid residues 1 (Met) to 233 (Glu) of SEQ ID NO:14; amino acid residues 1 (Met) to 316 (Ile) of SEQ ID NO:14; amino acid residues 1 (Met) to 323 (Ile) of SEQ ID NO:14; amino acid residues 1 (Met) to 335 (Asp) of SEQ ID NO:14; amino acid residues 1 (Met) to 340 (Asn) of SEQ ID NO:14; amino acid residues 1 (Met) to 354 (Glu) of SEQ ID NO:14; amino acid residues 1 (Met) to 371 (Cys) of SEQ ID NO:14; amino acid residues 1 (Met) to 381 (Ser) of SEQ ID NO:14; amino acid residues 1 (Met) to 384 (Gln) of SEQ ID NO:14; amino acid residues 1 (Met) to 397 (Thr) of SEQ ID NO:14; amino acid residues 1 (Met) to 412 (Ala) of SEQ ID NO:14; amino acid residues 1 (Met) to 418 (Glu) of SEQ ID NO:14; amino acid residues 1 (Met) to 462 (Gln) of SEQ ID NO:14; amino acid residues 1 (Met) to 476 (Ser) of SEQ ID NO:14; amino acid residues 1 (Met) to 483 (Asp) of SEQ ID NO:14; amino acid residues 1 (Met) to 486 (Thr) of SEQ ID NO:14; amino acid residues 1 (Met) to 496 (Ser) of SEQ ID NO:14; amino acid residues 1 (Met) to 511 (Gly) of SEQ ID NO:14; amino acid residues 1 (Met) to 523 (Glu) of SEQ ID NO:14; amino acid residues 1 (Met) to 536 (Thr) of SEQ ID NO:14; amino acid residues 36 (Gly) to 63 (Gln) of SEQ ID NO:14; amino acid residues 36 (Gly) to 94 (tyr) of SEQ ID NO:14; amino acid residues 36 (Gly) to 128 (Arg) of SEQ ID NO:14; amino acid residues 36 (Gly) to 169 (Pro) of SEQ ID NO:14; amino acid residues 36 (Gly) to 194 (Trp) of SEQ ID NO:14; amino acid residues 36 (Gly) to 233 (Glu) of SEQ ID NO:14; amino acid residues 36 (Gly) to 323 (Ser) of SEQ ID NO:14; amino acid residues 36 (Gly) to 340 (Asn) of SEQ ID NO:14; amino acid residues 36 (Gly) to 354 (Glu) of SEQ ID NO:14; amino acid residues 36 (Gly) to 381 (Ser) of SEQ ID NO:14; amino acid residues 36 (Gly) to 397 (Thr) of SEQ ID NO:14; amino acid residues 36 (Gly) to 418 (Glu) of SEQ ID NO:14; amino acid residues 36 (Gly) to 476 (Ser) of SEQ ID NO:14; amino acid residues 36 (Gly) to 486 (Thr) of SEQ ID NO:14; amino acid residues 36 (Gly) to 511 (Gly) of SEQ ID NO:14; amino acid residues 36 (Gly) to 536 (Thr) of SEQ ID NO:14; amino acid residues 58 (Pro) to 63 (Gln) of SEQ ID NO:14; amino acid residues 58 (Pro) to 94 (tyr) of SEQ ID NO:14; amino acid residues 58 (Pro) to 128 (Arg) of SEQ ID NO:14; amino acid residues 58 (Pro) to 169 (Pro) of SEQ ID NO:14; amino acid residues 58 (Pro) to 194 (Trp) of SEQ ID NO:14; amino acid residues 58 (Pro) to 233 (Glu) of SEQ ID NO:14; amino acid residues 58 (Pro) to 323 (Ser) of SEQ ID NO:14; amino acid residues 58 (Pro) to 340 (Asn) of SEQ ID NO:14; amino acid residues 58 (Pro) to 354 (Glu) of SEQ ID NO:14; amino acid residues 58 (Pro) to 381 (Ser) of SEQ ID NO:14; amino acid residues 58 (Pro) to 397 (Thr) of SEQ ID NO:14; amino acid residues 58 (Pro) to 418 (Glu) of SEQ ID NO:14; amino acid residues 58 (Pro) to 476 (Ser) of SEQ ID NO:14; amino acid residues 58 (Pro) to 486 (Thr) of SEQ ID NO:14; amino acid residues 58 (Pro) to 511 (Gly) of SEQ ID NO:14; amino acid residues 58 (Pro) to 536 (Thr) of SEQ ID NO:14; amino acid residues 80 (Lys) to 94 (tyr) of SEQ ID NO:14; amino acid residues 80 (Lys) to 128 (Arg) of SEQ ID NO:14; amino acid residues 80 (Lys) to 169 (Pro) of SEQ ID NO:14; amino acid residues 80 (Lys) to 194 (Trp) of SEQ ID NO:14; amino acid residues 80 (Lys) to 233 (Glu) of SEQ ID NO:14; amino acid residues 80 (Lys) to 323 (Ser) of SEQ ID NO:14; amino acid residues 80 (Lys) to 340 (Asn) of SEQ ID NO:14; amino acid residues 80 (Lys) to 354 (Glu) of SEQ ID NO:14; amino acid residues 80 (Lys) to 381 (Ser) of SEQ ID NO:14; amino acid residues 80 (Lys) to 397 (Thr) of SEQ ID NO:14; amino acid residues 80 (Lys) to 418 (Glu) of SEQ ID NO:14; amino acid residues 80 (Lys) to 476 (Ser) of SEQ ID NO:14; amino acid residues 80

(Lys) to 486 (Thr) of SEQ ID NO:14; amino acid residues 80 (Lys) to 511 (Gly) of SEQ ID NO:14; amino acid residues 80 (Lys) to 536 (Thr) of SEQ ID NO:14; amino acid residues 120 (Cys) to 128 (Arg) of SEQ ID NO:14; amino acid residues 120 (Cys) to 169 (Pro) of SEQ ID NO:14; amino acid residues 120 (Cys) to 194 (Trp) of SEQ ID NO:14; amino acid residues 120 (Cys) to 233 (Glu) of SEQ ID NO:14; amino acid residues 120 (Cys) to 323 (Ser) of SEQ ID NO:14; amino acid residues 120 (Cys) to 340 (Asn) of SEQ ID NO:14; amino acid residues 120 (Cys) to 354 (Glu) of SEQ ID NO:14; amino acid residues 120 (Cys) to 381 (Ser) of SEQ ID NO:14; amino acid residues 120 (Cys) to 397 (Thr) of SEQ ID NO:14; amino acid residues 120 (Cys) to 418 (Glu) of SEQ ID NO:14; amino acid residues 120 (Cys) to 476 (Ser) of SEQ ID NO:14; amino acid residues 120 (Cys) to 486 (Thr) of SEQ ID NO:14; amino acid residues 120 (Cys) to 511 (Gly) of SEQ ID NO:14; amino acid residues 120 (Cys) to 536 (Thr) of SEQ ID NO:14; amino acid residues 161 (Trp) to 169 (Pro) of SEQ ID NO:14; amino acid residues 161 (Trp) to 194 (Trp) of SEQ ID NO:14; amino acid residues 161 (Trp) to 233 (Glu) of SEQ ID NO:14; amino acid residues 161 (Trp) to 323 (Ser) of SEQ ID NO:14; amino acid residues 161 (Trp) to 340 (Asn) of SEQ ID NO:14; amino acid residues 161 (Trp) to 354 (Glu) of SEQ ID NO:14; amino acid residues 161 (Trp) to 381 (Ser) of SEQ ID NO:14; amino acid residues 161 (Trp) to 397 (Thr) of SEQ ID NO:14; amino acid residues 161 (Trp) to 418 (Glu) of SEQ ID NO:14; amino acid residues 161 (Trp) to 476 (Ser) of SEQ ID NO:14; amino acid residues 161 (Trp) to 486 (Thr) of SEQ ID NO:14; amino acid residues 161 (Trp) to 511 (Gly) of SEQ ID NO:14; amino acid residues 161 (Trp) to 536 (Thr) of SEQ ID NO:14; amino acid residues 187 (Asn) to 194 (Trp) of SEQ ID NO:14; amino acid residues 187 (Asn) to 233 (Glu) of SEQ ID NO:14; amino acid residues 187 (Asn) to 323 (Ser) of SEQ ID NO:14; amino acid residues 187 (Asn) to 340 (Asn) of SEQ ID NO:14; amino acid residues 187 (Asn) to 354 (Glu) of SEQ ID NO:14; amino acid residues 187 (Asn) to 381 (Ser) of SEQ ID NO:14; amino acid residues 187 (Asn) to 397 (Thr) of SEQ ID NO:14; amino acid residues 187 (Asn) to 418 (Glu) of SEQ ID NO:14; amino acid residues 187 (Asn) to 476 (Ser) of SEQ ID NO:14; amino acid residues 187 (Asn) to 486 (Thr) of SEQ ID NO:14; amino acid residues 187 (Asn) to 511 (Gly) of SEQ ID NO:14; amino acid residues 187 (Asn) to 536 (Thr) of SEQ ID NO:14; amino acid residues 224 (Gly) to 233 (Glu) of SEQ ID NO:14; amino acid residues 224 (Gly) to 323 (Ser) of SEQ ID NO:14; amino acid residues 224 (Gly) to 340 (Asn) of SEQ ID NO:14; amino acid residues 224 (Gly) to 354 (Glu) of SEQ ID NO:14; amino acid residues 224 (Gly) to 381 (Ser) of SEQ ID NO:14; amino acid residues 224 (Gly) to 397 (Thr) of SEQ ID NO:14; amino acid residues 224 (Gly) to 418 (Glu) of SEQ ID NO:14; amino acid residues 224 (Gly) to 476 (Ser) of SEQ ID NO:14; amino acid residues 224 (Gly) to 486 (Thr) of SEQ ID NO:14; amino acid residues 224 (Gly) to 511 (Gly) of SEQ ID NO:14; amino acid residues 224 (Gly) to 536 (Thr) of SEQ ID NO:14; amino acid residues 316 (Ile) to 323 (Ser) of SEQ ID NO:14; amino acid residues 316 (Ile) to 340 (Asn) of SEQ ID NO:14; amino acid residues 316 (Ile) to 354 (Glu) of SEQ ID NO:14; amino acid residues 316 (Ile) to 381 (Ser) of SEQ ID NO:14; amino acid residues 316 (Ile) to 397 (Thr) of SEQ ID NO:14; amino acid residues 316 (Ile) to 418 (Glu) of SEQ ID NO:14; amino acid residues 316 (Ile) to 476 (Ser) of SEQ ID NO:14; amino acid residues 316 (Ile) to 486 (Thr) of SEQ ID NO:14; amino acid residues 316 (Ile) to 511 (Gly) of SEQ ID NO:14; amino acid residues 316 (Ile) to 536 (Thr) of SEQ ID NO:14; amino acid residues 335 (Asp) to 340 (Asn) of SEQ ID NO:14; amino acid residues 335 (Asp) to 354 (Glu) of SEQ ID NO:14; amino acid residues 335 (Asp) to 381 (Ser) of SEQ ID NO:14; amino acid residues 335 (Asp) to 397 (Thr) of SEQ ID NO:14; amino acid residues 335 (Asp) to 418 (Glu) of SEQ ID NO:14; amino acid residues 335 (Asp) to 476 (Ser) of SEQ ID NO:14; amino acid residues 335 (Asp) to 486 (Thr) of SEQ ID NO:14; amino acid residues 335 (Asp) to 511 (Gly) of SEQ ID NO:14; amino acid residues 335 (Asp) to 536 (Thr) of SEQ ID NO:14; amino acid residues 371 (Cys) to 381 (Ser) of SEQ ID NO:14; amino acid residues 371 (Cys) to 397 (Thr) of SEQ ID NO:14; amino acid residues 371 (Cys) to 418 (Glu) of SEQ ID NO:14; amino acid residues 371 (Cys) to 476 (Ser) of SEQ ID NO:14; amino acid residues 371 (Cys) to 486 (Thr) of SEQ ID NO:14; amino acid residues 371 (Cys) to 511 (Gly) of SEQ ID NO:14; amino acid residues 371 (Cys) to 536 (Thr) of SEQ ID NO:14; amino acid residues 384 (Gln) to 397 (Thr) of SEQ ID NO:14; amino acid residues 384 (Gln) to 418 (Glu) of SEQ ID NO:14; amino acid residues 384 (Gln) to 476 (Ser) of SEQ ID NO:14; amino acid residues 384 (Gln) to 486 (Thr) of SEQ ID NO:14; amino acid residues 384 (Gln) to 511 (Gly) of SEQ ID NO:14; amino acid residues 384 (Gln) to 536 (Thr) of SEQ ID NO:14; amino acid residues 412 (Ala) to 418 (Glu) of SEQ ID NO:14; amino acid residues 412 (Ala) to 476 (Ser) of SEQ ID NO:14; amino acid residues 412 (Ala) to 486 (Thr) of SEQ ID NO:14; amino acid residues 412 (Ala) to 511 (Gly) of SEQ ID NO:14; amino acid residues 412 (Ala) to 536 (Thr) of SEQ ID NO:14; amino acid residues 462 (Gln) to 476 (Ser) of SEQ ID NO:14; amino acid residues 462 (Gln) to 486 (Thr) of SEQ ID NO:14; amino acid residues 462 (Gln) to 511 (Gly) of SEQ ID NO:14; amino acid residues 462 (Gln) to 536 (Thr) of SEQ ID NO:14; amino acid residues 483 (Asp) to 486 (Thr) of SEQ ID NO:14; amino acid residues 483 (Asp) to 511 (Gly) of SEQ ID NO:14; amino acid residues 483 (Asp) to 536 (Thr) of SEQ ID NO:14; amino acid residues 496 (Ser) to 511 (Gly) of SEQ ID NO:14; amino acid residues 496 (Ser) to 536 (Thr) of SEQ ID NO:14; amino acid residues 523 (Glu) to 536 (Thr) of SEQ ID NO:14.

IL-20RB antigenic epitopes within SEQ ID NO:21 include: amino acid residues 70 (Tyr) to 74 (Tyr) of SEQ ID NO:21; amino acid residues 70 (Tyr) to 101 (Asp) of SEQ ID NO:21; amino acid residues 70 (Tyr) to 135 (Ser) of SEQ ID NO:21; amino acid residues 70 (Tyr) to 178 (Glu) of SEQ ID NO:21; amino acid residues 70 (Tyr) to 283 (Lys) of SEQ ID NO:21; amino acid residues 92 (Thr) to 101 (Asp) of SEQ ID NO:21; amino acid residues 92 (Thr) to 135 (Ser) of SEQ ID NO:21; amino acid residues 92 (Thr) to 178 (Glu) of SEQ ID NO:21; amino acid residues 92 (Thr) to 283 (Lys) of SEQ ID NO:21; amino acid residues 130 (Pro) to 135 (Ser) of SEQ ID NO:21; amino acid residues 130 (Pro) to 178 (Glu) of SEQ ID NO:21; amino acid residues 130 (Pro) to 283 (Lys) of SEQ ID NO:21; amino acid residues 171 (Arg) to 178 (Glu) of SEQ ID NO:21; amino acid residues 171 (Arg) to 283 (Lys) of SEQ ID NO:21; amino acid residues 279 (Asn) to 283 (Lys) of SEQ ID NO:21.

Antigenic epitope-bearing peptides and polypeptides can contain at least four to ten amino acids, at least ten to fifteen amino acids, or about 15 to about 30 amino acids of an amino acid sequence disclosed herein. Such epitope-bearing peptides and polypeptides can be produced by fragmenting an IL-20, IL-20RA or IL-20RB polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol* 10, Manson (ed.), pages 105-116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

For any IL-20, IL-20RA or IL-20RB polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise IL-20, IL-20RA and IL-20RB variants based upon the nucleotide and amino acid sequences described herein.

5. Production of IL-20, IL-20RA and IL-20RB Polypeptides

The polypeptides of the present invention, including full-length polypeptides; soluble monomeric, homodimeric, heterodimeric and multimeric receptors; full-length receptors; receptor fragments (e.g. ligand-binding fragments and antigenic epitopes), functional fragments, and fusion proteins, can be produced in recombinant host cells following conventional techniques. To express an IL-20, IL-20RA or IL-20RB gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, a IL-20RA expression vector may comprise a IL-20RA gene and a secretory sequence derived from any secreted gene.

The IL-20, IL-20RA and IL-20RB proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from mammalian viral sources, for example, adenovirus, bovine papilloma virus, simian virus, or the like, in which the regulatory signals are associated with a particular gene which has a high level of expression. Suitable transcriptional and translational regulatory sequences also can be obtained from mammalian genes, for example, actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)).

Alternatively, a prokaryotic promoter, such as the bacteriophage T3 RNA polymerase promoter, can be used to control IL-20RA gene expression in mammalian cells if the prokaryotic promoter is regulated by a eukaryotic promoter (Zhou et al., *Mol. Cell. Biol* 10:4529 (1990), and Kaufman et al., *Nucl Acids Res.* 19:4485 (1991)).

In certain embodiments, a DNA sequence encoding IL-20 or an IL-20RA or IL-20RB soluble receptor polypeptide, or a fragment of an IL-20, IL-20RA or IL-20RB polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. Multiple components of a soluble receptor complex can be co-transfected on individual expression vectors or be contained in a single expression vector. Such techniques of expressing multiple components of protein complexes are well known in the art.

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase (DHFR), which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

IL-20, IL-20RA or IL-20RB polypeptides can also be produced by cultured mammalian cells using a viral delivery system. Exemplary viruses for this purpose include adenovirus, retroviruses, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4.44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol* 15:145 (1994)).

IL-20, IL-20RA or IL-20RB can also be expressed in other higher eukaryotic cells, such as avian, fungal, insect, yeast, or plant cells. The baculovirus system provides an efficient means to introduce cloned genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed polypeptide, for example, a Glu-Glu epitope tag (Grussenmeyer et al., *Proc. Nat'l Acad. Sci.* 82:7952 (1985)). Using a technique known in the art, a transfer vector containing a gene is transformed into *E. coli*, and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed which replace the native IL-20RA secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2-5× $10^5$ cells to a density of 1-2×$10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147-168 (The Humana Press, Inc. 1991), by Patel et al., "The baculovirus expression system," in *DNA Cloning 2: Expression Systems, 2nd Edition*, Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae, Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp 17, YEp vectors such as YEp 13 and YCp vectors, such as YCp 19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells can be deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67-88 (CRC Press, 1993).

Alternatively, IL-20, IL-20RA or IL-20RB genes can be expressed in prokaryotic host cells. Suitable promoters that can be used to express IL-20, IL-20RA or IL-20RB polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al. (1995).

Suitable prokaryotic hosts include *E. coli* and *Bacillus subtilus*. Suitable strains of *E. coli* include BL21(DE3), BL21 (DE3)pLysS, BL21(DE3)pLysE, DH1, DH4I, DH5, DH5I, DH51F', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, M1120, and B170 (see, for example, Hardy, "*Bacillus* Cloning Methods," in *DNA Cloning: A Practical Approach*, Glover (ed.) (IRL Press 1985)).

When expressing a IL-20, IL-20RA or IL-20RB polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology Volume* 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol* 287: 34 (1997), Muir et al, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NO:2, SEQ ID NO:14 or SEQ ID NO:21. As an illustration, polypeptides can comprise at least six, at least nine, or at least 15 contiguous amino acid residues of SEQ ID NO:2, SEQ ID NO:14 or SEQ ID NO:21. Within certain embodiments of the invention, the polypeptides comprise 20, 30, 40, 50, 100, or more contiguous residues of these amino acid sequences. Nucleic acid molecules encoding such peptides and polypeptides are useful as polymerase chain reaction primers and probes.

Moreover, IL-20, IL-20RA and IL-20RB polypeptides and fragments thereof can be expressed as monomers, homodimers, heterodimers, or multimers within higher eukaryotic cells. Such cells can be used to produce IL-20, or IL-20RA and IL-20RB monomeric, homodimeric, heterodimeric and multimeric receptor polypeptides that comprise either at least one IL-20RA polypeptide ("IL-20RA-comprising receptors" or "IL-20RA-comprising receptor polypeptides"), or at least one IL-20RB polypeptide ("IL-20RB-comprising receptors" or "IL-20RB-comprising receptor polypeptides"); or can be used as assay cells in screening systems. Within one aspect of the present invention, a polypeptide of the present invention comprising either the IL-20RA or IL-20RB extracellular domain or both the IL-20RA and IL-20RB extracellular domains is produced by a cultured cell, and the cell is used to screen for ligands for the receptor, including the natural ligand, IL-20, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems. Each component of the monomeric, homodimeric, heterodimeric and multimeric receptor complex can be expressed in the same cell. Moreover, the components of the monomeric, homodimeric, heterodimeric and multimeric receptor complex can also be fused to a transmembrane domain or other membrane fusion moiety to allow complex assembly and screening of transfectants as described above.

To assay the IL-20 antagonist polypeptides and antibodies of the present invention, mammalian cells suitable for use in expressing IL-20 or IL-20 receptors (e.g., cells expressing IL-20RA, IL-20RB, or IL-20RA/IL-20RB) and transducing a receptor-mediated signal include cells that express other receptor subunits that may form a functional complex with IL-20RA or IL-20RB. These subunits may include those of the interferon receptor family or of other class II or class I cytokine receptors, e.g., CRF2-4 (Genbank Accession No. Z17227), IL-10R (Genbank Accession Nos. U00672 and NM_001558), IL-20RA (commonly owned U.S. Pat. No. 5,965,704), zcytor7 (IL-20RA) (commonly owned U.S. Pat. No. 5,945,511), IL-20RA/IL-20RB (WIPO Publication No. WO 01/46232), and IL-9R. It is also preferred to use a cell from the same species as the receptor to be expressed. Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines and BaF3 (Palacios and Steinmetz, *Cell* 41: 727-734, (1985)) which is an IL-3 dependent murine pre-B cell line. Other cell lines include BHK, COS-1 and CHO cells. Suitable host cells can be engineered to produce the necessary receptor subunits or other cellular component needed for the desired cellular response. This approach is advantageous because cell lines can be engineered to express receptor subunits from any species, thereby overcoming potential limitations arising from species specificity. Species orthologs of the human receptor cDNA can be cloned and used within cell lines from the same species, such as a mouse cDNA in the BaF3 cell line. Cell lines that are dependent upon one hematopoietic growth factor, such as GM-CSF or IL-3, can thus be engineered to become dependent upon another cytokine that acts through the IL-20RA receptor, such as IL-20.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65: 55-63, (1983)). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE. See, e.g., Shaw et al., *Cell* 56:563-572, (1989). A preferred such reporter gene is a luciferase gene (de Wet et al., *Mol. Cell. Biol* 7:725, (1987)). Expression of the luciferase gene is detected by luminescence using methods known in the art (e.g., Baumgartner et al., *J. Biol. Chem.* 269:29094-29101, (1994); Schenborn and Goiffin, *Promega Notes* 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

Several IL-20 responsive cell lines are known in the art or can be constructed, for example, the Baf3/cytoR11/DIRS1 or Baf3/cytoR7/DIRS1 (WIPO Publication No. WO 02/072607). Moreover several IL-20 responsive cell lines are known (Dumontier et al., J. Immunol. 164:1814-1819, 2000; Dumoutier, L. et al., Proc. Nat'l. Acad. Sci. 97:10144-10149, 2000; Xie M H et al., J. Biol. Chem. 275: 31335-31339, 2000; Kotenko S V et al., J. Biol. Chem. 276:2725-2732, 2001), as well as those that express the IL-20 receptor subunit IL-20RA and IL-20RB. For example, the following cells are responsive to IL-20: intestinal epithelial cells HT-29 (Dumoutier et al., J. Immunol. 167: 3545-3549, 2001) and Colo205, lung cancer cell line A549 and endothelial cell HUVEC (human umbilical vein endothelial cell) (Ramesh et al., Cancer Research 63: 5105-5113), and keratinocyte cell line HaCaT (Blumberg et al., Cell 104: 9-19). These cells can be used in assays to assess the functionality of anti-IL-20RA or IL-20RB mAb as an IL-20 antagonist or anti-inflammatory factor.

6. Production of IL-20RA and IL-20RB Fusion Proteins and Conjugates

One general class of IL-20RA and IL-20RB analogs are variants having an amino acid sequence that is a mutation of the amino acid sequence disclosed herein. Another general class of IL-20RA and IL-20RB analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108: 420 (1996)). Since the variable domains of anti-idiotype IL-20RA and IL-20RB antibodies mimic IL-20RA and IL-20RB, these domains can provide IL-20RA and IL-20RB binding activity. Methods of producing anti-idiotypic catalytic antibodies are known to those of skill in the art (see, for example, Joron et al., *Ann. NY Acad. Sci.* 672:216 (1992), Friboulet et al., *Appl. Biochem. Biotechnol.* 47:229 (1994), and Avalle et al., *Ann. NY Acad. Sci.* 864:118 (1998)).

Another approach to identifying IL-20RA and IL-20RB analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

IL-20RA and IL-20RB polypeptides have both in vivo and in vitro uses. As an illustration, a soluble form of IL-20RA or IL-20RB can be added to cell culture medium to inhibit the effects of IL-20 produced by the cultured cells.

Fusion proteins of IL-20RA and IL-20RB can be used to express IL-20RA and IL-20RB in a recombinant host, and to isolate the produced IL-20RA or IL-20RB. As described below, particular IL-20RA or IL-20RB fusion proteins also have uses in diagnosis and therapy. One type of fusion protein comprises a peptide that guides, for example, a IL-20RA polypeptide from a recombinant host cell. To direct a IL-20RA polypeptide into the secretory pathway of a eukaryotic host cell, a secretory signal sequence (also known as a signal peptide, a leader sequence, prepro sequence or pre sequence) is provided in the IL-20RA expression vector. While the secretory signal sequence may be derived from IL-20RA, a suitable signal sequence may also be derived from another secreted protein or synthesized de novo. The secretory signal sequence is operably linked to a IL-20RA-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of IL-20RA or IL-20RB or another protein produced by mammalian cells (e.g., tissue-type plasminogen activator signal sequence, as described, for example, in U.S. Pat. No. 5,641,655) is useful for expression of IL-20RA or IL-20RB in recombinant mammalian hosts, a yeast signal sequence is preferred for expression in yeast cells. Examples of suitable yeast signal sequences are those derived from yeast mating phermone α-factor (encoded by the MFa1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach, 2nd* Edition, Glover and Hames (eds.), pages 123-167 (Oxford University Press 1995).

IL-20RA or IL-20RB soluble receptor polypeptides can be prepared by expressing a truncated DNA encoding the extracellular domain, for example, a polypeptide which contains SEQ ID NO:14 or 21, or the corresponding region of a non-human receptor. It is preferred that the extracellular domain polypeptides be prepared in a form substantially free of transmembrane and intracellular polypeptide segments. To direct the export of the receptor domain from the host cell, the receptor DNA is linked to a second DNA segment encoding a secretory peptide, such as a t-PA secretory peptide. To facilitate purification of the secreted receptor domain, a C-terminal extension, such as a poly-histidine tag, substance P, Flag™ peptide (Hopp et al., *Biotechnology* 6:1204-1210, (1988); available from Eastman Kodak Co., New Haven, Conn.) or another polypeptide or protein for which an antibody or other specific binding agent is available, can be fused to the receptor polypeptide. Moreover, IL-20RA antigenic epitopes from the extracellular cytokine binding domains are a also prepared as described above.

In an alternative approach, a receptor extracellular domain of IL-20RA, IL-20RB or other class I or II cytokine receptor component can be expressed as a fusion with immunoglobulin heavy chain constant regions, typically an Fc fragment, which contains two constant region domains and a hinge region but lacks the variable region (See, Sledziewski, A Z et al., U.S. Pat. Nos. 6,018,026 and 5,750,375). The soluble IL-20RA or IL-20RB polypeptides of the present invention include such fusions. Such fusions are typically secreted as multimeric molecules wherein the Fc portions are disulfide bonded to each other and two receptor polypeptides are arrayed in closed proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. For Example, to purify ligand, a IL-20RA-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. The chimeras may be used in vivo to regulate inflammatory responses including acute phase responses such as serum amyloid A (SAA), C-reactive protein (CRP), and the like. Chimeras with high binding affinity are administered parenterally (e.g., by intramuscular, subcutaneous or intravenous injection). Circulating molecules bind ligand and are cleared from circulation by normal physiological processes. For use in assays, the chimeras are bound to a support via the $F_c$ region and used in an ELISA format.

To assist in isolating anti-IL-20, anti-IL-20RA or anti-IL-20RB and binding partners of the present invention, an assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, J. Immunol. Methods 145:229-40, 1991 and Cunningham and Wells, J. Mol. Biol. 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, ligand/receptor binding can be analyzed using SELDI™ technology (Ciphergen, Inc., Palo Alto, Calif.). Moreover, BIACORE technology, described above, can be used to be used in competition experiments to determine if different momnoclonal antibodies bind the same or different epitopes on IL-20, IL-20RA and IL-20RB polypeptides, and as such, be used to aid in epitope mapping of neutralizing antibodies of the present invention that bind, or antagonize IL-20.

Ligand-binding receptor polypeptides can also be used within other assay systems known in the art. Such systems include Scatchard analysis for determination of binding affinity (see Scatchard, Ann. NY Acad. Sci. 51: 660-72, 1949) and calorimetric assays (Cunningham et al., Science 253:545-48, 1991; Cunningham et al., Science 245:821-25, 1991).

The present invention further provides a variety of other polypeptide fusions and related multimeric proteins comprising one or more polypeptide fusions. For example, a soluble IL-20RA or IL-20RB receptor can be prepared as a fusion to a dimerizing protein as disclosed in U.S. Pat. Nos. 5,155,027 and 5,567,584. Preferred dimerizing proteins in this regard include immunoglobulin constant region domains, e.g., IgGγ1, and the human κ light chain. Immunoglobulin-soluble IL-20RA or IL-20RB fusions can be expressed in genetically engineered cells to produce a variety of multimeric IL-20RA or IL-20RB receptor analogs. Auxiliary domains can be fused to soluble IL-20RA or IL-20RB receptor to target them to specific cells, tissues, or macromolecules (e.g., collagen, or cells expressing the IL-20RA and IL-20RB ligands, or IL-20). A IL-20RA or IL-20RB polypeptide can be fused to two or more moieties, such as an affinity tag for purification and a targeting domain. Polypeptide fusions can also comprise one or more cleavage sites, particularly between domains. See, Tuan et al., Connective Tissue Research 34:1-9, 1996.

In bacterial cells, it is often desirable to express a heterologous protein as a fusion protein to decrease toxicity, increase stability, and to enhance recovery of the expressed protein. For example, any of the polypeptides IL-20, IL-20RA or IL-20RB can be expressed as a fusion protein comprising a glutathione S-transferase polypeptide. Glutathione S-transferase fusion proteins are typically soluble, and easily purifiable from E. coli lysates on immobilized glutathione columns. In similar approaches, a fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in E. coli Using Plasmid Vectors and Purification of Specific Polyclonal Antibodies," in DNA Cloning 2: A Practical Approach, $2^{nd}$ Edition, Glover and Hames (Eds.), pages 15-58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., Arch. Biochem. Biophys. 329:215 (1996), Morganti et al., Biotechnol. Appl. Biochem. 23:67 (1996), and Zheng et al., Gene 186:55 (1997). Nucleic acid molecules encoding such peptide tags are available, for example, from Sigma-Aldrich Corporation (St. Louis, Mo.).

Another form of fusion protein comprises either an IL-20, an IL-20RA or a IL-20RB polypeptide and an immunoglobulin heavy chain constant region, typically an $F_c$ fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:91).

In another variation, a IL-20, IL-20RA or IL-20RB fusion protein comprises an IgG sequence, a IL-20, IL-20RA or IL-20RB moiety covalently joined to the aminoterminal end of the IgG sequence, and a signal peptide that is covalently joined to the aminoterminal of the IL-20, IL-20RA or IL-20RB moiety, and wherein the IgG sequence consists of the following elements in the following order: a hinge region, a $CH_2$ domain, and a $CH_3$ domain. Accordingly, the IgG sequence lacks a $CH_1$ domain. The IL-20, IL-20RA or IL-20RB moiety displays its respective activity, as described herein, such as the ability to bind with IL-20 (IL-20RA and IL-20RB) or its ability to bind to its respective receptor (IL-20). This general approach to producing fusion proteins that comprise both antibody and nonantibody portions has been described by LaRochelle et al., EP 742830 (WO 95/21258).

Fusion proteins comprising a IL-20, IL-20RA or IL-20RB moiety and an Fc moiety can be used, for example, as an in vitro assay tool. For example, the presence of a IL-20RA ligand (i.e. IL-20) in a biological sample can be detected using a IL-20RA-immunoglobulin fusion protein, in which the IL-20RA moiety is used to bind the ligand, and a macromolecule, such as Protein A or anti-Fc antibody, is used to bind the fusion protein to a solid support. Such systems can be used to identify agonists and antagonists that interfere with the binding of a IL-20RA ligands, e.g., IL-20, to their receptor.

Other examples of antibody fusion proteins include polypeptides that comprise an antigen-binding domain and a IL-20RA or IL-20RB fragment that contains an extracellular domain. Such molecules can be used to target particular tissues for the benefit of binding activity.

The present invention further provides a variety of other polypeptide fusions. For example, part or all of a domain(s) conferring a biological function can be swapped between any of IL-20, IL-20RA or IL-20RB with the functionally equivalent domain(s) from another member of the cytokine receptor family. Polypeptide fusions can be expressed in recombinant host cells to produce a variety of IL-20, IL-20RA or IL-20RB fusion analogs. A IL-20, IL-20RA or IL-20RB polypeptide can be fused to two or more moieties or domains, such as an affinity tag for purification and a targeting domain. Polypeptide fusions can also comprise one or more cleavage sites, particularly between domains. See, for example, Tuan et al., *Connective Tissue Research* 34:1 (1996).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

IL-20, IL-20RA or IL-20RB binding domains can be further characterized by physical analysis of structure, as determined by such techniques as nuclear magnetic resonance, crystallography, electron diffraction or photoaffinity labeling, in conjunction with mutation of putative contact site amino acids of IL-20RA ligand agonists. See, for example, de Vos et al., *Science* 255:306 (1992), Smith et al., *J. Mol. Biol* 224:899 (1992), and Wlodaver et al., *FEBS Lett.* 309:59 (1992).

The present invention also contemplates chemically modified IL-20, IL-20RA or IL-20RB compositions or conjugates, in which an IL-20, IL-20RA or IL-20RB polypeptide is linked with a polymer. Typically, the polymer is water soluble so that the conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce conjugates.

IL-20, IL-20RA or IL-20RB conjugates used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypropylene oxide/ethylene oxide copolymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A IL-20, IL-20RA or IL-20RB conjugate can also comprise a mixture of such water-soluble polymers.

One example of a IL-20, IL-20RA or IL-20RB conjugate comprises a IL-20, IL-20RA or IL-20RB moiety and a polyalkyl oxide moiety attached to the N-terminus of the IL-20, IL-20RA or IL-20RB moiety. PEG is one suitable polyalkyl oxide. As an illustration, IL-20RA can be modified with PEG, a process known as "PEGylation." PEGylation of IL-20, IL-20RA or IL-20RB can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, IL-20RA conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a IL-20, IL-20RA or IL-20RB polypeptide. An example of an activated PEG ester is PEG esterified to N-hydroxysuccinimide. As used herein, the term "acylation" includes the following types of linkages between IL-20, IL-20RA or IL-20RB and a water soluble polymer: amide, carbamate, urethane, and the like. Methods for preparing PEGylated IL-20, IL-20RA or IL-20RB by acylation will typically comprise the steps of (a) reacting a IL-20, IL-20RA or IL-20RB polypeptide with PEG (such as a reactive ester of an aldehyde derivative of PEG) under conditions whereby one or more PEG groups attach to IL-20, IL-20RA or IL-20RB, and (b) obtaining the reaction product(s). Generally, the optimal reaction conditions for acylation reactions will be determined based upon known parameters and desired results. For example, the larger the ratio of, for instance, PEG:IL-20RA, the greater the percentage of polyPEGylated IL-20RA product.

The product of PEGylation by acylation is typically a polyPEGylated IL-20, IL-20RA or IL-20RB product, wherein the lysine ε-amino groups are PEGylated via an acyl linking group. An example of a connecting linkage is an amide. Typically, the resulting IL-20, IL-20RA or IL-20RB will be at least 95% mono-, di-, or tri-pegylated, although some species with higher degrees of PEGylation may be formed depending upon the reaction conditions. PEGylated species can be separated from unconjugated IL-20, IL-20RA or IL-20RB polypeptides using standard purification methods, such as dialysis, ultrafiltration, ion exchange chromatography, affinity chromatography, and the like.

PEGylation by alkylation generally involves reacting a terminal aldehyde derivative of PEG with IL-20, IL-20RA or IL-20RB in the presence of a reducing agent. PEG groups can be attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of IL-20, IL-20RA or IL-20RB monopolymer conjugates.

Reductive alkylation to produce a substantially homogenous population of monopolymer IL-20, IL-20RA or IL-20RB conjugate molecule can comprise the steps of: (a) reacting a IL-20, IL-20RA or IL-20RB polypeptide with a reactive PEG under reductive alkylation conditions at a pH suitable to permit selective modification of the α-amino group at the amino terminus of the IL-20, IL-20RA or IL-20RB, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer IL-20, IL-20RA or IL-20RB conjugates, the reductive alkylation reaction conditions are those that permit the selective attachment of the water-soluble polymer moiety to the N-terminus of IL-20, IL-20RA or IL-20RB. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer: IL-20, IL-20RA or IL-20RB need not be as large because more reactive groups are available. Typically, the pH will fall within the range of 3 to 9, or 3 to 6. This method can be employed for making IL-20, IL-20RA or IL-20RB-comprising homodimeric, heterodimeric or multimeric soluble receptor conjugates.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to IL-20, IL-20RA or IL-20RB will generally be in the range of 1:1 to 100:1. Typically, the molar ratio of water-soluble polymer to IL-20, IL-20RA or IL-20RB will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol Ther.* 59:636 (1996), Monkarsh et al., *Anal Biochem.* 247:434 (1997)). This method can be employed for making IL-20RA or IL-20RB-comprising homodimeric, heterodimeric or multimeric soluble receptor conjugates.

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

7. Isolation of IL-20, IL-20RA and IL-20RB Polypeptides

The polypeptides of the present invention can be purified to at least about 80% purity, to at least about 90% purity, to at least about 95% purity, or greater than 95%, such as 96%, 97%, 98%, or greater than 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

Fractionation and/or conventional purification methods can be used to obtain preparations of synthetic or recombinant and fusion IL-20, IL-20RA or IL-20RB purified from recombinant host cells, or the same purified from natural sources (e.g., human tissue sources). In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in isolation and purification of the polypeptides of the present invention can be devised by those of skill in the art. For example, anti-IL-20, IL-20RA and IL-20RB antibodies, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification. Moreover, the ligand-binding properties of either the IL-20RA or IL-20RB extracellular domain can be exploited for purification, for example, of IL-20RA-comprising soluble receptors; for example, by using affinity chromatography wherein IL-20 ligand is bound to a column and the IL-20RA-comprising receptor is bound and subsequently eluted using standard chromatography methods.

The polypeptides of the present invention or fragments thereof may also be prepared through chemical synthesis, as described above. The polypeptides may be monomers or multimers; glycosylated or non-glycosylated; PEGylated or non-PEGylated; and may or may not include an initial methionine amino acid residue.

8. Production of Antibodies to IL-20, IL-20RA and IL-20RB Proteins

Antibodies to the polypeptides of the present invention can be obtained, for example, using the product of a IL-20, IL-20RA or IL-20RB expression vector or any of these polypeptides isolated from a natural source as an antigen. Particularly useful anti-IL-20 antibodies "bind specifically" with IL-20; particularly useful anti-IL-20RA antibodies "bind specifically" with IL-20RA; while particularly useful anti-IL-20RB antibodies "bind specifically" with IL-20RB. Antibodies are considered to be specifically binding if the antibodies exhibit at least one of the following two properties: (1) antibodies bind to their specific target (i.e. anti-IL-20 binds to IL-20) with a threshold level of binding activity, and (2) antibodies do not significantly cross-react with polypeptides related to their specific target (i.e. anti-IL-20 does not bind to IL-22).

With regard to the first characteristic, antibodies specifically bind if they bind to a polypeptide of the present invention, or peptide or epitope thereof with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect IL-20RA, but not presently known polypeptides using a standard Western blot analysis. Examples of known related polypeptides include known cytokine receptors.

Anti-IL-20 antibodies can be produced using antigenic IL-20 epitope-bearing peptides and polypeptides. Antigenic epitope-bearing peptides and polypeptides of the present invention contain a sequence of at least nine, or between 15 to about 30 amino acids contained within SEQ ID NO:2 or 3 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with IL-20. Anti-IL-20RA antibodies can be produced using antigenic IL-20RA epitope-bearing peptides and polypeptides. Antigenic epitope-bearing peptides and polypeptides of the present invention contain a sequence of at least nine, or between 15 to about 30 amino acids contained within SEQ ID NO:14 or 15 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with IL-20. Anti-IL-20RB antibodies can be produced using antigenic IL-20RB epitope-bearing peptides and polypeptides. Antigenic epitope-bearing peptides and polypeptides of the present invention contain a sequence of at least nine, or between 15 to about 30 amino acids contained within SEQ ID NO:21 or 23 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with IL-20RB. It is desirable that the amino acid sequence of the epitope-bearing peptide is selected to provide substantial solubility in aqueous solvents (i.e., the sequence includes relatively hydrophilic residues, while hydrophobic residues are typically avoided). Moreover, amino acid sequences containing proline residues may be also be desirable for antibody production.

As an illustration, potential antigenic sites in IL-20, IL-20RA and IL-20RB were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549-586 (Plenum Press 1990), and Garnier-Robson, Garnier et al., *J. Mol. Biol* 120: 97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index."

Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that the following amino acid sequences of SEQ ID NO:2 would provide suitable antigenic peptides: Hopp/Woods hydrophilicity profiles can be used to determine regions that have the most antigenic potential within SEQ ID NO:2 (Hopp et al., Proc. Natl. Acad. Sci. 78:3824-3828, 1981; Hopp, J. Immun. Meth. 88:1-18, 1986 and Triquier et al., Protein Engineering 11:153-169, 1998). The profile is based on a sliding six-residue window. Buried G, S, and T residues and exposed H, Y, and W residues were ignored. Moreover, IL-20 antigenic epitopes within SEQ ID NO:2 as predicted by a Jameson-Wolf plot, e.g., using DNASTAR Protean program (DNASTAR, Inc., Madison, Wis.) serve as preferred antigenic epitopes, and can be determined by one of skill in the art. For Example, neutralizing antibodies to IL-20 include antibodies, such as neutralizing monoclonal antibodies that can bind IL-20 antigenic epitopes. Accordingly, antigenic epitope-bearing peptides and polypeptides of IL-20 are useful to raise antibodies that bind with the IL-20 polypeptides described herein, as well as to identify and screen anti-IL-20 monoclonal antibodies that are neutralizing, and that may antagonize, reduce, inhibit or block the activity of IL-20. Such neutralizing monoclonal antibodies of the present invention can bind to an IL-20 antigenic epitope. Such epitopes within SEQ ID NO:8 as predicted by a Jameson-Wolf plot, e.g., using DNASTAR Protean program (DNASTAR, Inc., Madison, Wis.) serve as preferred antigenic epitopes, and can be determined by one of skill in the art. Such antigenic epitopes include: amino acid residues 42 (Ile) to 102 (Asp) of SEQ ID NO:8; amino acid residues 42 (Ile) to 60 (Ile) of SEQ ID NO:8; amino acid residues 42 (Ile) to 69 (Glu) of SEQ ID NO:8; amino acid residues 42 (Ile) to 81 (Cys) of SEQ ID NO:8; amino acid residues 42 (Ile) to 96 (Lys) of SEQ ID NO:8; amino acid residues 42 (Ile) to 102 (Asp) of SEQ ID NO:8; amino acid residues 60 (Ile) to 69 (Glu) of SEQ ID NO:8; amino acid residues 60 (Ile) to 81 (Cys) of SEQ ID NO:8; amino acid residues 60 (Ile) to 96 (Lys) of SEQ ID NO:8; amino acid residues 60 (Ile) to 102 (Asp) of SEQ ID NO:8; amino acid residues 69 (Glu) to 81 (Cys) of SEQ ID NO:8; amino acid residues 69 (Glu) to 96 (Lys) of SEQ ID NO:8; amino acid residues 69 (Glu) to 102 (Asp) of SEQ ID NO:8; amino acid residues 81 (Cys) to 96 (Lys) of SEQ ID NO:8; amino acid residues 81 (Cys) to 102 (Asp) of SEQ ID NO:8; and amino acid residues 96 (Lys) to 102 (Asp) of SEQ ID NO:8.

The results of this analysis indicated that the following amino acid sequences of SEQ ID NO:14 would provide suitable antigenic peptides: amino acid residues 1 (Met) to 9 (Leu) of SEQ ID NO:14; amino acid residues 1 (Met) to 36 (Gly) of SEQ ID NO:14; amino acid residues 1 (Met) to 41 (Ala) of SEQ ID NO:14; amino acid residues 1 (Met) to 58 (Pro) of SEQ ID NO:14; amino acid residues 1 (Met) to 63 (Gln) of SEQ ID NO:14; amino acid residues 1 (Met) to 80 (Lys) of SEQ ID NO:14; amino acid residues 1 (Met) to 94 (Tyr) of SEQ ID NO:14; amino acid residues 1 (Met) to 104 (Tyr) of SEQ ID NO:14; amino acid residues 1 (Met) to 120 (Cys) of SEQ ID NO:14; amino acid residues 1 (Met) to 128 (Arg) of SEQ ID NO:14; amino acid residues 1 (Met) to 161 (Trp) of SEQ ID NO:14; amino acid residues 1 (Met) to 169 (Pro) of SEQ ID NO:14; amino acid residues 1 (Met) to 187 (Asn) of SEQ ID NO:14; amino acid residues 1 (Met) to 194 (Trp) of SEQ ID NO:14; amino acid residues 1 (Met) to 224 (Gly) of SEQ ID NO:14; amino acid residues 1 (Met) to 233 (Glu) of SEQ ID NO:14; amino acid residues 1 (Met) to 316 (Ile) of SEQ ID NO:14; amino acid residues 1 (Met) to 323 (Ile) of SEQ ID NO:14; amino acid residues 1 (Met) to 335 (Asp) of SEQ ID NO:14; amino acid residues 1 (Met) to 340 (Asn) of SEQ ID NO:14; amino acid residues 1 (Met) to 354 (Glu) of SEQ ID NO:14; amino acid residues 1 (Met) to 371 (Cys) of SEQ ID NO:14; amino acid residues 1 (Met) to 381 (Ser) of SEQ ID NO:14; amino acid residues 1 (Met) to 384 (Gln) of SEQ ID NO:14; amino acid residues 1 (Met) to 397 (Thr) of SEQ ID NO:14; amino acid residues 1 (Met) to 412 (Ala) of SEQ ID NO:14; amino acid residues 1 (Met) to 418 (Glu) of SEQ ID NO:14; amino acid residues 1 (Met) to 462 (Gln) of SEQ ID NO:14; amino acid residues 1 (Met) to 476 (Ser) of SEQ ID NO:14; amino acid residues 1 (Met) to 483 (Asp) of SEQ ID NO:14; amino acid residues 1 (Met) to 486 (Thr) of SEQ ID NO:14; amino acid residues 1 (Met) to 496 (Ser) of SEQ ID NO:14; amino acid residues 1 (Met) to 511 (Gly) of SEQ ID NO:14; amino acid residues 1 (Met) to 523 (Glu) of SEQ ID NO:14; amino acid residues 1 (Met) to 536 (Thr) of SEQ ID NO:14; amino acid residues 36 (Gly) to 63 (Gln) of SEQ ID NO:14; amino acid residues 36 (Gly) to 94 (tyr) of SEQ ID NO:14; amino acid residues 36 (Gly) to 128 (Arg) of SEQ ID NO:14; amino acid residues 36 (Gly) to 169 (Pro) of SEQ ID NO:14; amino acid residues 36 (Gly) to 194 (Trp) of SEQ ID NO:14; amino acid residues 36 (Gly) to 233 (Glu) of SEQ ID NO:14; amino acid residues 36 (Gly) to 323 (Ser) of SEQ ID NO:14; amino acid residues 36 (Gly) to 340 (Asn) of SEQ ID NO:14; amino acid residues 36 (Gly) to 354 (Glu) of SEQ ID NO:14; amino acid residues 36 (Gly) to 381 (Ser) of SEQ ID NO:14; amino acid residues 36 (Gly) to 397 (Thr) of SEQ ID NO:14; amino acid residues 36 (Gly) to 418 (Glu) of SEQ ID NO:14; amino acid residues 36 (Gly) to 476 (Ser) of SEQ ID NO:14; amino acid residues 36 (Gly) to 486 (Thr) of SEQ ID NO:14; amino acid residues 36 (Gly) to 511 (Gly) of SEQ ID NO:14; amino acid residues 36 (Gly) to 536 (Thr) of SEQ ID NO:14; amino acid residues 58 (Pro) to 63 (Gln) of SEQ ID NO:14; amino acid residues 58 (Pro) to 94 (tyr) of SEQ ID NO:14; amino acid residues 58 (Pro) to 128 (Arg) of SEQ ID NO:14; amino acid residues 58 (Pro) to 169 (Pro) of SEQ ID NO:14; amino acid residues 58 (Pro) to 194 (Trp) of SEQ ID NO:14; amino acid residues 58 (Pro) to 233 (Glu) of SEQ ID NO:14; amino acid residues 58 (Pro) to 323 (Ser) of SEQ ID NO:14; amino acid residues 58 (Pro) to 340 (Asn) of SEQ ID NO:14; amino acid residues 58 (Pro) to 354 (Glu) of SEQ ID NO:14; amino acid residues 58 (Pro) to 381 (Ser) of SEQ ID NO:14; amino acid residues 58 (Pro) to 397 (Thr) of SEQ ID NO:14; amino acid residues 58 (Pro) to 418 (Glu) of SEQ ID NO:14; amino acid residues 58 (Pro) to 476 (Ser) of SEQ ID NO:14; amino acid residues 58 (Pro) to 486 (Thr) of SEQ ID NO:14; amino acid residues 58 (Pro) to 511 (Gly) of SEQ ID NO:14; amino acid residues 58 (Pro) to 536 (Thr) of SEQ ID NO:14; amino acid residues 80 (Lys) to 94 (tyr) of SEQ ID NO:14; amino acid residues 80 (Lys) to 128 (Arg) of SEQ ID NO:14; amino acid residues 80 (Lys) to 169 (Pro) of SEQ ID NO:14; amino acid residues 80 (Lys) to 194 (Trp) of SEQ ID NO:14; amino acid residues 80 (Lys) to 233 (Glu) of SEQ ID NO:14; amino acid residues 80 (Lys) to 323 (Ser) of SEQ ID NO:14; amino acid residues 80 (Lys) to 340 (Asn) of SEQ ID NO:14; amino acid residues 80 (Lys) to 354 (Glu) of SEQ ID NO:14; amino acid residues 80 (Lys) to 381 (Ser) of SEQ ID NO:14; amino acid residues 80 (Lys) to 397 (Thr) of SEQ ID NO:14; amino acid residues 80 (Lys) to 418 (Glu) of SEQ ID NO:14; amino acid residues 80 (Lys) to 476 (Ser) of SEQ ID NO:14; amino acid residues 80 (Lys) to 486 (Thr) of SEQ ID NO:14; amino acid residues 80 (Lys) to 511

(Gly) of SEQ ID NO:14; amino acid residues 80 (Lys) to 536 (Thr) of SEQ ID NO:14; amino acid residues 120 (Cys) to 128 (Arg) of SEQ ID NO:14; amino acid residues 120 (Cys) to 169 (Pro) of SEQ ID NO:14; amino acid residues 120 (Cys) to 194 (Trp) of SEQ ID NO:14; amino acid residues 120 (Cys) to 233 (Glu) of SEQ ID NO:14; amino acid residues 120 (Cys) to 323 (Ser) of SEQ ID NO:14; amino acid residues 120 (Cys) to 340 (Asn) of SEQ ID NO:14; amino acid residues 120 (Cys) to 354 (Glu) of SEQ ID NO:14; amino acid residues 120 (Cys) to 381 (Ser) of SEQ ID NO:14; amino acid residues 120 (Cys) to 397 (Thr) of SEQ ID NO:14; amino acid residues 120 (Cys) to 418 (Glu) of SEQ ID NO:14; amino acid residues 120 (Cys) to 476 (Ser) of SEQ ID NO:14; amino acid residues 120 (Cys) to 486 (Thr) of SEQ ID NO:14; amino acid residues 120 (Cys) to 511 (Gly) of SEQ ID NO:14; amino acid residues 120 (Cys) to 536 (Thr) of SEQ ID NO:14; amino acid residues 161 (Trp) to 169 (Pro) of SEQ ID NO:14; amino acid residues 161 (Trp) to 194 (Trp) of SEQ ID NO:14; amino acid residues 161 (Trp) to 233 (Glu) of SEQ ID NO:14; amino acid residues 161 (Trp) to 323 (Ser) of SEQ ID NO:14; amino acid residues 161 (Trp) to 340 (Asn) of SEQ ID NO:14; amino acid residues 161 (Trp) to 354 (Glu) of SEQ ID NO:14; amino acid residues 161 (Trp) to 381 (Ser) of SEQ ID NO:14; amino acid residues 161 (Trp) to 397 (Thr) of SEQ ID NO:14; amino acid residues 161 (Trp) to 418 (Glu) of SEQ ID NO:14; amino acid residues 161 (Trp) to 476 (Ser) of SEQ ID NO:14; amino acid residues 161 (Trp) to 486 (Thr) of SEQ ID NO:14; amino acid residues 161 (Trp) to 511 (Gly) of SEQ ID NO:14; amino acid residues 161 (Trp) to 536 (Thr) of SEQ ID NO:14; amino acid residues 187 (Asn) to 194 (Trp) of SEQ ID NO:14; amino acid residues 187 (Asn) to 233 (Glu) of SEQ ID NO:14; amino acid residues 187 (Asn) to 323 (Ser) of SEQ ID NO:14; amino acid residues 187 (Asn) to 340 (Asn) of SEQ ID NO:14; amino acid residues 187 (Asn) to 354 (Glu) of SEQ ID NO:14; amino acid residues 187 (Asn) to 381 (Ser) of SEQ ID NO:14; amino acid residues 187 (Asn) to 397 (Thr) of SEQ ID NO:14; amino acid residues 187 (Asn) to 418 (Glu) of SEQ ID NO:14; amino acid residues 187 (Asn) to 476 (Ser) of SEQ ID NO:14; amino acid residues 187 (Asn) to 486 (Thr) of SEQ ID NO:14; amino acid residues 187 (Asn) to 511 (Gly) of SEQ ID NO:14; amino acid residues 187 (Asn) to 536 (Thr) of SEQ ID NO:14; amino acid residues 224 (Gly) to 233 (Glu) of SEQ ID NO:14; amino acid residues 224 (Gly) to 323 (Ser) of SEQ ID NO:14; amino acid residues 224 (Gly) to 340 (Asn) of SEQ ID NO:14; amino acid residues 224 (Gly) to 354 (Glu) of SEQ ID NO:14; amino acid residues 224 (Gly) to 381 (Ser) of SEQ ID NO:14; amino acid residues 224 (Gly) to 397 (Thr) of SEQ ID NO:14; amino acid residues 224 (Gly) to 418 (Glu) of SEQ ID NO:14; amino acid residues 224 (Gly) to 476 (Ser) of SEQ ID NO:14; amino acid residues 224 (Gly) to 486 (Thr) of SEQ ID NO:14; amino acid residues 224 (Gly) to 511 (Gly) of SEQ ID NO:14; amino acid residues 224 (Gly) to 536 (Thr) of SEQ ID NO:14; amino acid residues 316 (Ile) to 323 (Ser) of SEQ ID NO:14; amino acid residues 316 (Ile) to 340 (Asn) of SEQ ID NO:14; amino acid residues 316 (Ile) to 354 (Glu) of SEQ ID NO:14; amino acid residues 316 (Ile) to 381 (Ser) of SEQ ID NO:14; amino acid residues 316 (Ile) to 397 (Thr) of SEQ ID NO:14; amino acid residues 316 (Ile) to 418 (Glu) of SEQ ID NO:14; amino acid residues 316 (Ile) to 476 (Ser) of SEQ ID NO:14; amino acid residues 316 (Ile) to 486 (Thr) of SEQ ID NO:14; amino acid residues 316 (Ile) to 511 (Gly) of SEQ ID NO:14; amino acid residues 316 (Ile) to 536 (Thr) of SEQ ID NO:14; amino acid residues 335 (Asp) to 340 (Asn) of SEQ ID NO:14; amino acid residues 335 (Asp) to 354 (Glu) of SEQ ID NO:14; amino acid residues 335 (Asp) to 381 (Ser) of SEQ ID NO:14; amino acid residues 335 (Asp) to 397 (Thr) of SEQ ID NO:14; amino acid residues 335 (Asp) to 418 (Glu) of SEQ ID NO:14; amino acid residues 335 (Asp) to 476 (Ser) of SEQ ID NO:14; amino acid residues 335 (Asp) to 486 (Thr) of SEQ ID NO:14; amino acid residues 335 (Asp) to 511 (Gly) of SEQ ID NO:14; amino acid residues 335 (Asp) to 536 (Thr) of SEQ ID NO:14; amino acid residues 371 (Cys) to 381 (Ser) of SEQ ID NO:14; amino acid residues 371 (Cys) to 397 (Thr) of SEQ ID NO:14; amino acid residues 371 (Cys) to 418 (Glu) of SEQ ID NO:14; amino acid residues 371 (Cys) to 476 (Ser) of SEQ ID NO:14; amino acid residues 371 (Cys) to 486 (Thr) of SEQ ID NO:14; amino acid residues 371 (Cys) to 511 (Gly) of SEQ ID NO:14; amino acid residues 371 (Cys) to 536 (Thr) of SEQ ID NO:14; amino acid residues 384 (Gln) to 397 (Thr) of SEQ ID NO:14; amino acid residues 384 (Gln) to 418 (Glu) of SEQ ID NO:14; amino acid residues 384 (Gln) to 476 (Ser) of SEQ ID NO:14; amino acid residues 384 (Gln) to 486 (Thr) of SEQ ID NO:14; amino acid residues 384 (Gln) to 511 (Gly) of SEQ ID NO:14; amino acid residues 384 (Gln) to 536 (Thr) of SEQ ID NO:14; amino acid residues 412 (Ala) to 418 (Glu) of SEQ ID NO:14; amino acid residues 412 (Ala) to 476 (Ser) of SEQ ID NO:14; amino acid residues 412 (Ala) to 486 (Thr) of SEQ ID NO:14; amino acid residues 412 (Ala) to 511 (Gly) of SEQ ID NO:14; amino acid residues 412 (Ala) to 536 (Thr) of SEQ ID NO:14; amino acid residues 462 (Gln) to 476 (Ser) of SEQ ID NO:14; amino acid residues 462 (Gln) to 486 (Thr) of SEQ ID NO:14; amino acid residues 462 (Gln) to 511 (Gly) of SEQ ID NO:14; amino acid residues 462 (Gln) to 536 (Thr) of SEQ ID NO:14; amino acid residues 483 (Asp) to 486 (Thr) of SEQ ID NO:14; amino acid residues 483 (Asp) to 511 (Gly) of SEQ ID NO:14; amino acid residues 483 (Asp) to 536 (Thr) of SEQ ID NO:14; amino acid residues 496 (Ser) to 511 (Gly) of SEQ ID NO:14; amino acid residues 496 (Ser) to 536 (Thr) of SEQ ID NO:14; amino acid residues 523 (Glu) to 536 (Thr) of SEQ ID NO:14.

The results of this analysis indicated that the following amino acid sequences of SEQ ID NO:14 would provide suitable antigenic peptides: L-20RB antigenic epitopes within SEQ ID NO:21 include: amino acid residues 70 (Tyr) to 74 (Tyr) of SEQ ID NO:21; amino acid residues 70 (Tyr) to 101 (Asp) of SEQ ID NO:21; amino acid residues 70 (Tyr) to 135 (Ser) of SEQ ID NO:21; amino acid residues 70 (Tyr) to 178 (Glu) of SEQ ID NO:21; amino acid residues 70 (Tyr) to 283 (Lys) of SEQ ID NO:21; amino acid residues 92 (Thr) to 101 (Asp) of SEQ ID NO:21; amino acid residues 92 (Thr) to 135 (Ser) of SEQ ID NO:21; amino acid residues 92 (Thr) to 178 (Glu) of SEQ ID NO:21; amino acid residues 92 (Thr) to 283 (Lys) of SEQ ID NO:21; amino acid residues 130 (Pro) to 135 (Ser) of SEQ ID NO:21; amino acid residues 130 (Pro) to 178 (Glu) of SEQ ID NO:21; amino acid residues 130 (Pro) to 283 (Lys) of SEQ ID NO:21; amino acid residues 171 (Arg) to 178 (Glu) of SEQ ID NO:21; amino acid residues 171 (Arg) to 283 (Lys) of SEQ ID NO:21; amino acid residues 279 (Asn) to 283 (Lys) of SEQ ID NO:21. Moreover, suitable antigens also include the IL-20RA or IL-20RB polypeptides comprising a IL-20RA or IL-20RB cytokine binding, or extracellular domain disclosed above in combination with another class I or II cytokine extracellular domain, such as those that form soluble IL-20RA and/or IL-20RB heterodimeric or multimeric polypeptides.

Polyclonal antibodies to recombinant polypeptides of the present invention or to those same polypeptides isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995). The immunogenicity of a polypeptide of the present invention can be increased through the use of an adjuvant, such as alum (aluminum hydroxide) or Freund's complete or incomplete adjuvant. Polypeptides useful for immunization also include fusion polypeptides, such as fusions of IL-20RA or IL-20RB or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al, *Int. J. Cancer* 46:310 (1990).

Alternatively, monoclonal anti-IL-20, IL-20RA or IL-20RB antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1-2.6.7 (John Wiley & Sons 1991) ["Coligan"], Picksley et al., "Production of monoclonal antibodies against proteins expressed in *E. coli*," in *DNA Cloning 2: Expression Systems*, 2nd Edition, Glover et al. (eds.), page 93 (Oxford University Press 1995)).

Briefly, monoclonal antibodies can be obtained by injecting mice with a composition comprising a IL-20, IL-20RA or IL-20RB gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-IL-20, anti-IL-20RA or anti-IL-20RB antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)).

For particular uses, it may be desirable to prepare fragments of any of the anti-IL-20, anti-IL-20RA or anti-IL-20RB antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11: 1271 (1993), and Sandhu, supra).

As an illustration, a scFV can be obtained by exposing lymphocytes to a polypeptide of the present invention in vitro, and selecting antibody display libraries in phage or similar vectors (for instance, through use of immobilized or labeled IL-20, IL-20RA or IL-20RB protein or peptide). Genes encoding polypeptides having potential IL-20, IL-20RA or IL-20RB polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the IL-20, IL-20RA and IL-20RB sequences disclosed herein to identify proteins which bind to IL-20.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-IL-20, anti-IL-20RA or anti-IL-20RB antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering Principles and Practice*, Cleland et al. (eds.), pages 399-434 (John Wiley & Sons, Inc. 1996), and by Queen et al., U.S. Pat. No. 5,693,762 (1997).

Polyclonal anti-idiotype antibodies can be prepared by immunizing animals with anti-IL-20, anti-IL-20RA or anti-IL-20RB antibodies or antibody fragments, using standard techniques. See, for example, Green et al., "Production of Polyclonal Antisera," in *Methods In Molecular Biology: Immunochemical Protocols*, Manson (ed.), pages 1-12 (Humana Press 1992). Also, see Coligan at pages 2.4.1-2.4.7. Alternatively, monoclonal anti-idiotype antibodies can be prepared using anti-IL-20, anti-IL-20RA or anti-IL-20RB antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

An anti-IL-20, anti-IL-20RA or anti-IL-20RB antibody can be conjugated with a detectable label to form an anti-IL-20, anti-IL-20RA or anti-IL-20RB immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-IL-20, anti-IL-20RA or anti-IL-20RB immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-IL-20, anti-IL-20RA or anti-IL-20RB immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-IL-20, anti-IL-20RA or anti-IL-20RB immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-IL-20, anti-IL-20RA or anti-IL-20RB immunoconjugates can be detectably labeled by linking an anti-IL-20, anti-IL-20RA or anti-IL-20RB antibody component to an enzyme. When the antibody-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-IL-20, anti-IL-20RA or anti-IL-20RB antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al., *Cancer Res.* 50:1330 (1990), and Coligan, supra.

Moreover, the convenience and versatility of immunochemical detection can be enhanced by using anti-IL-20, anti-IL-20RA or anti-IL-20RB antibodies that have been conjugated with avidin, streptavidin, and biotin (see, for example, Wilchek et al. (eds.), "Avidin-Biotin Technology," *Methods In Enzymology*, Vol 184 (Academic Press 1990), and Bayer et al., "Immunochemical Applications of Avidin-Biotin Technology," in *Methods In Molecular Biology, Vol* 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay* (Academic Press, Inc. 1996).

The present invention also contemplates kits for performing an immunological diagnostic assay for IL-20, IL-20RA or IL-20RB gene expression. Such kits comprise at least one container comprising an anti-IL-20, anti-IL-20RA or anti-IL-20RB antibody, or antibody fragment. A kit may also comprise a second container comprising one or more reagents capable of indicating the presence of IL-20, IL-20RA or IL-20RB antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that IL-20, IL-20RA or IL-20RB antibodies or antibody fragments are used to detect the corresponding protein. For example, written instructions may state that the enclosed antibody or antibody fragment can be used to detect IL-20, IL-20RA or IL-20RB. The written material can be applied directly to a container, or the written material can be provided in the form of a packaging insert.

9. Use of Anti-IL-20, Anti-IL-20RA or Anti-IL-20RB Antibodies to Antagonize IL-20RA and IL-20RB Binding to IL-20

Alternative techniques for generating or selecting antibodies useful herein include in vitro exposure of lymphocytes to soluble IL-20RA or IL-20RB receptor polypeptides or fragments thereof, such as antigenic epitopes, and selection of antibody display libraries in phage or similar vectors (for instance, through use of immobilized or labeled soluble IL-20RA or IL-20RB receptor polypeptides or fragments thereof, such as antigenic epitopes). Genes encoding polypeptides having potential binding domains such as soluble IL-20RA or IL-20RB receptor polypeptides or fragments thereof, such as antigenic epitopes can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides that interact with a known target that can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the soluble IL-20RA and/or IL-20RB receptor polypeptides or fragments thereof, such as antigenic epitope polypeptide sequences disclosed herein to identify proteins which bind to IL-20RA or IL-20RB-comprising receptor polypeptides. These "binding polypeptides," which interact with soluble IL-20RA and/or IL-20RB-comprising receptor polypeptides, can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between IL-20 ligand and receptor, or viral binding to a receptor. The binding polypeptides can also be used for diagnostic assays for determining circulating levels of soluble IL-20RA and/or IL-20RB-comprising receptor polypeptides; for detecting or quantitating soluble or non-soluble IL-20RA-comprising receptors as marker of underlying pathology or disease. These binding polypeptides can also act as "antagonists" to block soluble or membrane-bound IL-20RA or IL-20RB monomeric receptor or IL-20RA/IL-20RB homodimeric, heterodimeric or multimeric polypeptide binding (e.g. to ligand) and signal transduction in vitro and in vivo. Again, these binding polypeptides serve as anti-IL-20RA or anti-IL-20RB monomeric receptor or anti-IL-20RA and/or anti-IL-20RB homodimeric, heterodimeric or multimeric polypeptides and are useful for inhibiting IL-20 activity, as well as receptor activity or protein-binding. Antibodies raised to the natural receptor complexes of the present invention, and IL-20, IL-20RA and IL-20RB-epitope-binding antibodies, and anti-IL-20, IL-20RA or IL-20RB neutralizing monoclonal antibodies may be preferred embodiments, as they may act more specifically and can inhibit IL-20. Moreover, the antagonistic and binding activity of the antibodies of the present invention can be assayed in an IL-20 proliferation, signal trap, luciferase or binding assays in the presence of IL-20, and IL-20RA and/or IL-20RB-comprising soluble receptors, and other biological or biochemical assays described herein.

Antibodies to soluble IL-20RA, IL-20RB and IL-20RB/IL-20RB receptor polypeptides or fragments thereof, such as antigenic epitopes may be used for inhibiting the inflammatory effects of IL-20 in vivo, for therapeutic use against psoriasis, endotoxemia, arthritis, asthma, IBD, colitis, psoriatic arthritis, rheumatoid arthritis or other IL-20-induced inflammatory conditions; tagging cells that express IL-20RA, IL-20RB and IL-20RB/IL-20RB receptors; for isolating soluble IL-20RA and/or IL-20RB-comprising receptor polypeptides by affinity purification; for diagnostic assays for determining circulating levels of soluble IL-20RA and/or IL-20RB-comprising receptor polypeptides; for detecting or quantitating soluble IL-20RA and/or IL-20RB-comprising receptors as marker of underlying pathology or disease; in analytical methods employing FACS; for screening expression libraries; for generating anti-idiotypic antibodies that can act as IL-20 agonists; and as neutralizing antibodies or as antagonists to block IL-20RA and/or IL-20RB receptor function, or to block IL-20 activity in vitro and in vivo. Suitable direct tags or labels include radionuclides, enzymes, substrates, cofactors, biotin, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to soluble IL-20RA and/or IL-20RB-comprising receptor polypeptides, or fragments thereof may be used in vitro to detect denatured or non-denatured IL-20RA and/or IL-20RB-comprising receptor polypeptides or fragments thereof in assays, for example, Western Blots or other assays known in the art.

Antibodies to soluble IL-20RA and/or IL-20RB receptor or soluble IL-20RA or IL-20RB homodimeric, heterodimeric or multimeric receptor polypeptides are useful for tagging cells that express the corresponding receptors and assaying their expression levels, for affinity purification, within diagnostic assays for determining circulating levels of receptor polypeptides, analytical methods employing fluorescence-activated cell sorting. Moreover, divalent antibodies, and anti-idiotypic antibodies may be used as agonists to mimic the effect of IL-20.

Antibodies herein can also be directly or indirectly conjugated to drugs, toxins, radionuclides and the like, and these conjugates used for in vivo diagnostic or therapeutic applications. For instance, antibodies or binding polypeptides which recognize soluble IL-20RA and/or IL-20RB receptor or soluble IL-20RA or IL-20RB homodimeric, heterodimeric or multimeric receptor polypeptides can be used to identify or treat tissues or organs that express a corresponding anti-complementary molecule (for example, a IL-20RA-comprising soluble or membrane-bound receptor). More specifically, antibodies to soluble IL-20RA and/or IL-20RB-comprising receptor polypeptides, or bioactive fragments or portions thereof, can be coupled to detectable or cytotoxic molecules and delivered to a mammal having cells, tissues or organs that express the IL-20RA, IL-20RB or IL-20RA/IL-20RB-comprising receptor such as IL-20RA and/or IL-20RB-expressing cancers.

Suitable detectable molecules may be directly or indirectly attached to polypeptides that bind IL-20RA and/or IL-20RB-comprising receptor polypeptides, such as "binding polypeptides," (including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, IL-20, IL-20RA or IL-20RB binding polypeptide-cytokine or antibody-cytokine fusion proteins can be used for enhancing in vivo killing of target tissues (for example, spleen, pancreatic, blood, lymphoid, colon, and bone marrow cancers), if the binding polypeptide-cytokine or anti-IL-20, IL-20RA or IL-20RB receptor antibody targets the hyperproliferative cell (See, generally, Hornick et al., Blood 89:4437-47, 1997). The described fusion proteins enable targeting of a cytokine to a desired site of action, thereby providing an elevated local concentration of cytokine. Suitable anti-IL-20, anti-IL-20RA or anti-IL-20RB monomer, homodimer, heterodimer or multimer antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, IL-20, IL-20RA or IL-20RB receptor binding polypeptides or antibody fusion proteins described herein can be used for enhancing in vivo killing of target tissues by directly stimulating a IL-20, IL-20RA or IL-20RB receptor-modulated apoptotic pathway, resulting in cell death of hyperproliferative cells expressing IL-20 receptors.

10. Therapeutic Uses of Polypeptides Having IL-20, IL-20RA or IL-20RB Activity or Antibodies Thereto Amino acid sequences having soluble IL-20RA and/or IL-20RB activity can be used to modulate the immune system by binding IL-20, and thus, preventing the binding of IL-20 with endogenous IL-20RA/IL-20RB. IL-20 antagonists, such as anti-IL-20, anti-IL-20RA and anti-IL-20RB antibodies, can also be used to modulate the immune system by inhibiting the binding of IL-20 with the endogenous receptor. Accordingly, the present invention includes the use of proteins, polypeptides, and peptides having anti-IL-20 activity (such as soluble IL-20RA, IL-20RB or IL-20RA/IL-20RB polypeptides, polypeptide fragments, analogs and fusion proteins) to a subject which lacks an adequate amount of this polypeptide, or which produces an excess of IL-20. IL-20RA and IL-20RB antagonists (e.g., anti-IL-20RA and IL-20RB antibodies) can be also used to treat a subject which produces an excess of either IL-20 or IL-20RA and/or IL-20RB. Suitable subjects include mammals, such as humans. Such polypeptides and antibodies are useful in antagonizing IL-20, in the treatment of psoriasis, psoriatic arthritis, arthritis, endotoxemia, inflammatory bowel disease (IBD), colitis, and other inflammatory conditions disclosed herein.

Two lines of evidence indicate that a role IL-20 and its receptor are involved in psoriasis. This multigenic skin disease is characterized by increased keratinocyte proliferation, altered keratinocyte differentiation, and infiltration of immune cells into the skin. The first line of evidence for a role of IL-20 in psoriasis is that the observed hyperkeratosis and thickened epidermis in the transgenic mice that resemble human psoriatic abnormalities. Decreased numbers of tonofilaments, thought to be related to defective keratinization, are a striking feature of human psoriasis. Intramitochondrial inclusions have been found in both chemically induced and naturally occurring hyperplastic skin conditions in mice. The cause of the inclusions and their effects on mitochondrial function, if any, are unknown. We conclude that IL-20 transgenic mice exhibit many of the characteristics observed in human psoriasis.

A second line of evidence that implicates the IL-20 receptor in psoriasis is that both IL-20RA and IL-20RB mRNA are markedly upregulated in human psoriatic skin compared to normal skin. Both IL-20 receptor subunits are expressed in keratinocytes throughout the epidermis and are also expressed in a subset of immune and endothelial cells. We propose that increased expression of an activated IL-20 receptor may alter the interactions between endothelial cells, immune cells and keratinocytes, leading to dysregulation of keratinocyte proliferation and differentiation.

Moreover, IL-20 stimulates signal transduction in the human keratinocyte HaCaT cell line, supporting a direct action of this novel ligand in skin. In addition, IL-1β, EGF and TNF-α, proteins known to be active in keratinocytes and to be involved with proliferative and pro-inflammatory signals in skin, enhance the response to IL-20. In both HaCaT and BHK cells expressing the IL-20 receptor, IL-20 signals through STAT3.

As indicated in the discussion above and the examples below, IL-20 is involved in the pathology of psoriasis. The present invention is in particular a method for treating psoriasis by administering antagonists to IL-20. The antagonists to IL-20 can either be a soluble receptor that binds to IL-20, such a soluble IL-20RA, IL-20RB or IL-20RA/IL-20RB, or antibodies, single chain antibodies or fragments of antibodies that bind to either IL-20 or either a subunit such as IL-20RA or IL-20RB or the IL-20 receptor as a whole. The antagonists will thus prevent activation of the IL-20 receptor.

Psoriasis is one of the most common dermatologic diseases, affecting up to 1 to 2 percent of the world's population. It is a chronic inflammatory skin disorder characterized by erythematous, sharply demarcated papules and rounded plaques, covered by silvery micaceous scale. The skin lesions of psoriasis are variably pruritic. Traumatized areas often develop lesions of psoriasis. Additionally, other external factors may exacerbate psoriasis including infections, stress, and medications, e.g. lithium, beta blockers, and anti-malarials.

The most common variety of psoriasis is called plaque type. Patients with plaque-type psoriasis will have stable, slowly growing plaques, which remain basically unchanged for long periods of time. The most common areas for plaque psoriasis to occur are the elbows knees, gluteal cleft, and the scalp. Involvement tends to be symmetrical. Inverse psoriasis affects the intertriginous regions including the axilla, groin, submammary region, and navel, and it also tends to affect the scalp, palms, and soles. The individual lesions are sharply demarcated plaques but may be moist due to their location. Plaque-type psoriasis generally develops slowly and runs an indolent course. It rarely spontaneously remits.

Eruptive psoriasis (guttate psoriasis) is most common in children and young adults. It develops acutely in individuals without psoriasis or in those with chronic plaque psoriasis. Patients present with many small erythematous, scaling papules, frequently after upper respiratory tract infection with beta-hemolytic streptococci. Patients with psoriasis may also develop pustular lesions. These may be localized to the palms and soles or may be generalized and associated with fever, malaise, diarrhea, and arthralgias.

About half of all patients with psoriasis have fingernail involvement, appearing as punctate pitting, nail thickening or subungual hyperkeratosis. About 5 to 10 percent of patients with psoriasis have associated joint complaints, and these are most often found in patients with fingernail involvement. Although some have the coincident occurrence of classic rheumatoid arthritis, many have joint disease that falls into one of five type associated with psoriasis: (1) disease limited to a single or a few small joints (70 percent of cases); (2) a seronegative rheumatoid arthritis-like disease; (3) involvement of the distal interphalangeal joints; (4) severe destructive arthritis with the development of "arthritis mutilans"; and (5) disease limited to the spine.

Psoriasis can be treated by administering antagonists to IL-20. The preferred antagonists are either a soluble receptor to IL-20 or antibodies, antibody fragments or single chain antibodies that bind to IL-20, IL-20RA or IL-20RB. Such antagonists can be administered alone or in combination with other established therapies such as lubricants, keratolytics, topical corticosteroids, topical vitamin D derivatives, anthralin, systemic antimetabolites such as methotrexate, psoralen-ultraviolet-light therapy (PUWA), etretinate, isotretinoin, cyclosporine, and the topical vitamin D3 derivative calcipotriol. Moreover, such antagonists can be administered to individual subcutaneously, intravenously, or transdermally using a cream or transdermal patch that contains the antagonist. If administered subcutaneously, the antagonist can be injected into one or more psoriatic plaques. If administered transdermally, the antagonists can be administered directly on the plaques using a cream, ointment, salve, or solution containing the antagonist.

Antagonists to IL-20 can be administered to a person who has asthma, bronchitis or cystic fibrosis or other inflammatory lung disease to treat the disease. The antagonists can be administered by any suitable method including intravenous, subcutaneous, bronchial lavage, and the use of inhalant containing the antagonist. Particular embodiments of the present invention are directed toward use of soluble IL-20RA and/or IL-20RB and anti-IL-20, anti-IL-20RA or anti-IL-20RB antibodies as antagonists in inflammatory and immune diseases or conditions such as psoriasis, psoriatic arthritis, rheumatoid arthritis, inflammatory bowel disease (IBD), Crohn's Disease, diverticulosis, asthma, pancreatitis, type I diabetes (IDDM), pancreatic cancer, pancreatitis, Graves Disease, colon and intestinal cancer, autoimmune disease, sepsis, organ or bone marrow transplant; inflammation due to endotoxemia, trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or other instances where inhibition of IL-20 cytokines is desired.

Moreover, antibodies or binding polypeptides that bind IL-20, IL-20RA or IL-20RB polypeptides described herein, are useful to:

1) Antagonize or block signaling via IL-20 receptors in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

2) Antagonize or block signaling via IL-20 receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes). Alternatively antibodies, such as monoclonal antibodies (MAb) to an y of IL-20, IL-20RA, or IL-20RB-comprising receptors, can also be used as an antagonist to deplete unwanted immune cells to treat autoimmune disease. Asthma, allergy and other atopic disease may be treated with an MAb against, for example, IL-20, to inhibit the immune response or to deplete offending cells. Blocking or inhibiting signaling via IL-20, IL-20RA or IL-20RB, using the polypeptides and antibodies of the present invention, may also benefit diseases of the pancreas, kidney, pituitary and neuronal cells. IDDM, NIDDM, pancreatitis, and pancreatic carcinoma may benefit. Polypeptides of the present invention may serve as a target for MAb therapy of cancer where an antagonizing MAb inhibits cancer growth and targets immune-mediated killing. (Holliger P, and Hoogenboom, H: Nature Biotech. 16: 1015-1016, 1998). Mabs to soluble IL-20RA may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

3) Agonize or initiate signaling via IL-20 receptors in the treatment of autoimmune diseases such as IDDM, MS, SLE, myasthenia gravis, rheumatoid arthritis, and IBD. Anti-IL-20, anti-IL-20RA or anti-IL-20RB neutralizing and monoclonal antibodies may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., J. Immunol. 160:4841-4849, 1998).

The soluble polypeptides described herein can be used to neutralize/block IL-20 or IL-20 activity, either singly or together, in the treatment of autoimmune disease, atopic disease, NIDDM, pancreatitis and kidney dysfunction as described above. A soluble form of IL-20RA, IL-20RB and/or IL-20RA/IL-20RB may be used to promote an antibody response mediated by Th cells and/or to promote the production of IL-4 or other cytokines by lymphocytes or other immune cells.

The soluble IL-20RA, IL-20RB and/or IL-20RA/IL-20RB-comprising receptors of the present invention are useful as antagonists of IL-20 cytokine. Such antagonistic effects can be achieved by direct neutralization or binding of IL-20. In addition to antagonistic uses, the soluble receptors of the present invention can bind IL-20 and act as carrier proteins for IL-20, in order to transport the Ligand to different tissues, organs, and cells within the body. As such, the soluble receptors of the present invention can be fused or coupled to molecules, polypeptides or chemical moieties that direct the soluble-receptor-Ligand complex to a specific site, such as a tissue, specific immune cell, or tumor. For example, in acute infection or some cancers, benefit may result from induction of inflammation and local acute phase response proteins by the action of IL-20. Thus, the soluble receptors of the present invention can be used to specifically direct the action of IL-20. See, Cosman, D. Cytokine 5: 95-106, 1993; and Fernandez-Botran, R. Exp. Opin. Invest. Drugs 9:497-513, 2000.

Moreover, the soluble receptors of the present invention can be used to stabilize IL-20, to increase the bioavailability, therapeutic longevity, and/or efficacy of the Ligand by stabilizing the Ligand from degradation or clearance, or by targeting the ligand to a site of action within the body. For example the naturally occurring IL-6/soluble IL-6R complex stabilizes IL-6 and can signal through the gp130 receptor. See, Cosman, D. supra., and Fernandez-Botran, R. supra. Furthermore the complexes may have distinct pharmacokinetic properties such as affecting half-life, dose/response and organ or tissue specificity. IL-20RA/IL-20 or IL-20RB/IL-20 complexes thus may have agonist activity to enhance an immune response or stimulate mesangial cells or to stimulate hepatic cells. Alternatively only tissues expressing a signaling subunit the heterodimerizes with the complex may be affected analogous to the response to IL6/IL6R complexes (Hirota H. et al., Proc. Nat'l. Acad. Sci. 92:4862-4866, 1995; Hirano, T. in Thomason, A. (Ed.) "The Cytokine Handbook", $3^{rd}$ Ed., p. 208-209). Soluble receptor/cytokine complexes for IL12 and CNTF display similar activities.

Moreover Inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., psoriasis, arthritis, rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that anti-inflammatory proteins, such as IL-20, IL-20RA and IL-20RB, and anti-IL-20, anti-IL-20RA and anti-IL-20RB antibodies, could have crucial therapeutic potential for a vast number of human and animal diseases, from asthma and allergy to autoimmunity and septic shock.

1. Arthritis

Arthritis, including osteoarthritis, rheumatoid arthritis, arthritic joints as a result of injury, and the like, are common inflammatory conditions which would benefit from the therapeutic use of anti-inflammatory proteins, such as those polypeptides of the present invention. For Example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, Expert. Opin. Biol. Ther. 2(2): 135-149, 2002). One of those mediators could be IL-20, and as such a molecule that binds or inhibits IL-20 activity, such as IL-20RA or IL-20RB polypeptides, or anti-IL-20 antibodies or binding partners, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, Curr. Opin. Rheum. 3:407-20, 1999; Williams et al., Immunol. 89:9784-788, 1992; Myers et al., Life Sci. 61:1861-78, 1997; and Wang et al., Immunol. 92:8955-959, 1995).

2. Endotoxemia

Endotoxemia is a severe condition commonly resulting from infectious agents such as bacteria and other infectious disease agents, sepsis, toxic shock syndrome, or in immuno-compromised patients subjected to opportunistic infections, and the like. Therapeutically useful of anti-inflammatory proteins, such as polypeptides and antibodies of the present invention, could aid in preventing and treating endotoxemia in humans and animals. IL-20, IL-20RA or IL-20RB polypeptides, anti-IL-20, anti-IL-20RA or anti-IL-20RB antibodies, could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., Lancet 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. Cell 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., Science 229:869, 1985). It is well established that 1 ug injection of E. Coli LPS into a C57B1/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., Science 229:869, 1985). The potential immunointervention strategies for the prevention and/or treatment of septic shock include anti-TNF mAb, IL-1 receptor antagonist, LIF, IL-10, and G-CSF.

3. Inflammatory Bowel Disease (IBD)

In the United States approximately 500,000 people suffer from Inflammatory Bowel Disease (IBD) which can affect either colon and rectum (Ulcerative colitis) or both, small and large intestine (Crohn's Disease). The pathogenesis of these diseases is unclear, but they involve chronic inflammation of the affected tissues. IL-20, IL-20RA or IL-20RB polypeptides, anti-IL-20, anti-IL-20RA or anti-IL-20RB antibodies or binding partners, could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (e.g. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. Intern. Rev. Immunol. 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. IL-20, IL-20RA or IL-20RB polypeptides, anti-IL-20, anti-IL-20RA or anti-IL-20RB antibodies or binding partners, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

IL-20 is a novel IL-10 homologue that was shown to cause neonatal lethality with skin abnormalities including aberrant epidermal differentiation in IL-20 transgenic mice (Blumberg H et al., Cell 104:9-19, 2001) IL-20 receptor is dramatically upregulated in psoriatic skin. Moreover, over expression of IL-20 was shown in human psoriatic lesions, suggesting that IL-20 is involved in human psoriasis. Moreover, as described herein, over expression of IL-20 in transgenic mice showed epidermal thickening and immune cell involvement indicative of a psoriatic phenotype. As such, antagonists to IL-20 activity, such as IL-20RA, IL-20RB and/or IL-20RA/IL-20RB soluble receptors and antibodies thereto including the anti-human-IL-20, anti-human-IL-20RA and anti-human-IL-20RB monoclonal and neutralizing antibodies of the present invention, are useful in therapeutic treatment of inflammatory diseases, particularly as antagonists to IL-20 in the treatment of psoriasis. Moreover, antagonists to IL-20 activity, such as IL-20RA, IL-20RB and/or IL-20RA/IL-20RB soluble receptors and antibodies thereto including the anti-human-IL-20, anti-human-IL-20RA and anti-human-IL-20RB monoclonal and neutralizing antibodies of the present invention, are useful in therapeutic treatment of other inflammatory diseases for example as antagonists to IL-20 in the treatment of atopic dermatitis, IBD, colitis, Endotoxemia, arthritis, rheumatoid arthritis, and psoriatic arthritis adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease.

Moreover, the soluble receptors and antibodies of the present invention can be used in the prevention and therapy against weight loss associated with a number of inflammatory diseases described herein, as well as for cancer (e.g., chemotherapy and cachexia), and infectious diseases. For example, severe weight loss is a key marker associated with models for septicemia, MS, RA, and tumor models. In addition, weight loss is a key parameter for many human diseases including cancer, infectious disease and inflammatory disease. Weight loss was shown in mice injected with IL-22Adenovirus described herein. Anti-IL-20 antibodies and IL-20 antagonists such as the soluble receptors and antibodies of the present invention, can be tested for their ability to prevent and treat weight loss in mice injected with IL-20 adenoviruses described herein. Methods of determining a prophylactic or therapeutic regimen for such IL-20 antagonists is known in the art and can be determined using the methods described herein.

The soluble receptors and antibodies of the present invention may also be used within diagnostic systems for the detection of circulating levels of IL-20, and in the detection of IL-20 associated with acute phase inflammatory response. Within a related embodiment, antibodies or other agents that specifically bind to the polypeptides and soluble receptors of the present invention can be used to detect circulating receptor polypeptides; conversely, IL-20RA, IL-20RB or IL-20RA/IL-20RB soluble receptors themselves can be used to detect circulating or locally-acting IL-20 polypeptides. Elevated or depressed levels of ligand or receptor polypeptides may be indicative of pathological conditions, including inflammation or cancer. IL-20 is known to induce associated acute phase inflammatory response. Moreover, detection of acute phase proteins or molecules such as IL-20 can be indicative of a chronic inflammatory condition in certain disease states (e.g., psoriasis, rheumatoid arthritis, colitis, IBD). Detection of such conditions serves to aid in disease diagnosis as well as help a physician in choosing proper therapy.

In utero administration of neutralizing anti-IL-20 antibodies can be used to show efficacy in vivo in disease models by reducing or eliminating the skin phenotype found in IL-20 transgenic pups which over express IL-20. There are precedents in the art for in utero treatment with neutralizing monoclonal antibodies (mAbs). In one case, the development of the B-1 subset of B cells was dramatically affected by treating pregnant female mice with a mAb specific for the B cell-specific molecule, CD19 (e.g., Krop I. Et al., Eur. J. Immunol. 26(1):238-42, 1996). Krop et al. injected timed pregnant mice intraperitoneally with 500 ug of rat anti-mouse CD19 mAb (or a rat isotype-matched control Ab) in PBS beginning on day 9 of gestation, with subsequent injections every other day until birth. Pups were also injected once with 500 ug of these antibodies at 10 days of age. In another case, Tanaka et al., found that in utero treatment with monoclonal antibody to IL-2 receptor beta-chain completely abrogates development of Thy-1+dendritic epidermal cells. The two distinct subunits of the IL-2 receptor, i.e. the alpha-chain (IL-2R alpha) and the beta-chain (IL-2R beta), are expressed in an almost mutually exclusive fashion throughout fetal thymus ontogeny. Blocking IL-2R beta, a signal transducing component of IL-2R, by administering a neutralizing mAb to IL-2R beta, resulted in the complete and selective disappearance of Thy-1+skin dendritic epidermal cells. Development of any other T cell subsets was uncompromised. This indicated that IL-2 plays a crucial role in the development of fetal V gamma 5+ cells and their descendants (see, Tanaka, T. et al., Int Immunol. 4(4): 487-9, 1992). In addition, Schattemann G C et al., showed that PDGF-A is required for normal murine cardiovascular development using an in utero system. Several lines of evidence suggest that platelet-derived growth factor A chain (PDGF-A) is required for normal embryonic cardiovascular development. Introduction of anti-PDGF-A neutralizing antibodies into mouse deciduas in utero resulted in the selective disruption of PDGF-A ligand-receptor interactions in vivo for a period of 18-24 hr and allowed assessment of whether PDGF-A is required for cardiovascular development and when it is required (see, Schattemann G C et al., Dev. Biol. 176(1):133-42, 1996). These results, as well as others described in the art, provide evidence that neutralizing mAbs can elicit strong effects in utero. Similarly, data showing the efficacy of neutralizing IL-20 with monoclonal antibodies in vivo in disease models to reduce or eliminate the skin phenotype found in IL-20 transgenic pups which over express IL-20 respectively can be shown. These transgenic mice are born with a "shiny" skin appearance, due at least in part to a thickening of the epidermis as described herein. The IL-20 TG pups expressing fairly low levels of the transgenic cytokine can recover and do survive to breed.

In addition to other disease models described herein, the activity of anti-IL-20, anti-IL-20RA and anti-IL-20RB antibodies on inflammatory tissue derived from human psoriatic lesions can be measured in vivo using a severe combined immune deficient (SCID) mouse model. Several mouse models have been developed in which human cells are implanted into immunodeficient mice (collectively referred to as xenograft models); see, for example, Cattan A R, Douglas E, Leuk. Res. 18:513-22, 1994 and Flavell, D J, Hematological Oncology 14:67-82, 1996. As an in vivo xenograft model for psoriasis, human psoriatic skin tissue is implanted into the SCID mouse model, and challenged with an appropriate antagonist. Anti-IL-20, anti-IL-20RA and anti-IL-20RB antibodies that block the activity of IL-20 are preferred antagonists, however, soluble IL-20RA, as well as other IL-20 blocking antagonists can be used in this model. Similarly, tissues or cells derived from human colitis, IBD, arthritis, or other inflammatory lesions can be used in the SCID model to assess the anti-inflammatory properties of the IL-20 antagonists described herein.

Therapies designed to abolish, retard, or reduce inflammation using anti-IL-20, anti-IL-20RA and anti-IL-20RB antibodies antibodies or its derivatives, agonists, conjugates or variants can be tested by administration of these antibodies or soluble IL-20RA, IL-20RB or IL-20RA/IL-20RB compounds to SCID mice bearing human inflammatory tissue (e.g., psoriatic lesions and the like). Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler, M. et al. Lab Invest 81:1253, 2001; Zollner, T. M. et al. J. Clin. Invest. 109:671, 2002; Yamanaka, N. et al. Microbiol. Immunol. 45:507, 2001; Raychaudhuri, S. P. et al. Br. J. Dermatol. 144:931, 2001; Boehncke, W. H et al. Arch. Dermatol. Res. 291:104, 1999; Boehncke, W. H et al. J. Invest. Dermatol. 116:596, 2001; Nickoloff, B. J. et al. Am. J. Pathol. 146:580, 1995; Boehncke, W. H et al. J. Cutan. Pathol. 24:1, 1997; Sugai, J., M. et al. J. Dermatol. Sci. 17:85, 1998; and Villadsen L. S. et al. J. Clin. Invest. 112:1571, 2003. Inflammation may also be monitored over time using well-known methods such as flow cytometry (or PCR) to quantitate the number of inflammatory or lesional cells present in a sample, score (weight loss, diarrhea, rectal bleeding, colon length) for IBD, paw disease score and inflammation score for CIA RA model. For example, therapeutic strategies appropriate for testing in such a model include direct treatment using anti-IL-20, anti-IL-20RA and anti-IL-20RB antibodies, other IL-20 antagonists, or related conjugates or antagonists based on the disrupting interaction of anti-IL-20, anti-IL-20RA or anti-IL-20RB antibodies with IL-20, or for cell-based therapies utilizing anti-IL-20, anti-IL-20RA and anti-IL-20RB antibodies or its derivatives, agonists, conjugates or variants.

Moreover, psoriasis is a chronic inflammatory skin disease that is associated with hyperplastic epidermal keratinocytes and infiltrating mononuclear cells, including CD4+ memory T cells, neutrophils and macrophages (Christophers, Int. Arch. Allergy Immunol., 110:199, 1996). It is currently believed that environmental antigens play a significant role in initiating and contributing to the pathology of the disease. However, it is the loss of tolerance to self-antigens that is thought to mediate the pathology of psoriasis. Dendritic cells and CD4$^+$ T cells are thought to play an important role in antigen presentation and recognition that mediate the immune response leading to the pathology. We have recently developed a model of psoriasis based on the CD4+ CD45RB transfer model (Davenport et al., Internat. Immunopharmacol., 2:653-672). Anti-IL-20, anti-IL-20RA or anti-IL-20RB, or soluble IL-20RA, IL-20RB or IL-20RA/IL-20RB, are administered to the mice. Inhibition of disease scores (skin lesions, inflammatory cytokines) indicates the effectiveness of IL-20 antagonists in psoriasis, e.g., anti-IL-20, anti-IL-20RA or anti-IL-20RB antibodies or IL-20RA, IL-20RB or IL-20RA/IL-20RB soluble receptors, or other antagonists such as antibodies against IL-20 or their receptors.

For pharmaceutical use, the soluble polypeptides and antibodies of the present invention are formulated for parenteral, particularly intravenous or subcutaneous, delivery according to conventional methods. Intravenous administration will be by bolus injection, controlled release, e.g., using mini-pumps or other appropriate technology, or by infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. When utilizing such a combination therapy, the cytokines may be combined in a single formulation or may be administered in separate formulations. Methods of formulation are well known in the art and are disclosed, for example, in Remington's Pharmaceutical Sciences, Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of soluble IL-20RA, IL-20RB or IL-20RA/IL-20RB or anti-IL-20, anti-IL-20RA or anti-IL-20RB antibodies of the present invention is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. The soluble IL-20RA, IL-20RB or IL-20RA/IL-20RB or anti-IL-20, anti-IL-20RA or anti-IL-20RB antibodies of the present invention can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5-15 lg/kg; IL-3, 1-5 lg/kg; and G-CSF, 1-25 lg/kg. Combination therapy with EPO, for example, is indicated in anemic patients with low EPO levels.

Generally, the dosage of administered soluble IL-20RA, IL-20RB or IL-20RA/IL-20RB or anti-IL-20, anti-IL-20RA or anti-IL-20RB antibodies will vary depending upon such factors as the patient's age, weight, height, sex, general medical condition and previous medical history. Typically, it is desirable to provide the recipient with a dosage of soluble IL-20RA, IL-20RB or IL-20RA/IL-20RB or anti-IL-20, anti-IL-20RA or anti-IL-20RB antibodies which is in the range of from about 1 pg/kg to 10 mg/kg (amount of agent/body weight of patient), although a lower or higher dosage also may be administered as circumstances dictate.

Administration of soluble IL-20RA, IL-20RB or IL-20RA/IL-20RB or anti-IL-20, anti-IL-20RA or anti-IL-20RB antibodies to a subject can be intravenous, intra-arterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising IL-20RA can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer a polypeptide of the present invention.

A pharmaceutical composition comprising a soluble IL-20RA, IL-20RB or IL-20RA/IL-20RB or anti-IL-20, anti-IL-20RA or anti-IL-20RB antibody can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, soluble IL-20RA, IL-20RB or IL-20RA/IL-20RB or anti-IL-20, anti-IL-20RA or anti-IL-20RB antibody molecules and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

A pharmaceutical composition comprising the polypeptides of the present invention can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol Pharm. Bull* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Polypeptides and antibodies can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol* 2:548 (1998)). Polyethylene glycol (PEG)-coated nanospheres can also provide carriers for intravenous administration of therapeutic proteins (see, for example, Gref et al., *Pharm. Biotechnol* 10:167 (1997)).

Other dosage forms can be devised by those skilled in the art, as shown, for example, by Ansel and Popovich, *Pharmaceutical Dosage Forms and Drug Delivery Systems*, $5^{th}$ Edition (Lea & Febiger 1990), Gennaro (ed.), *Remington's Pharmaceutical Sciences*, $19^{th}$ Edition (Mack Publishing Company 1995), and by Ranade and Hollinger, *Drug Delivery Systems* (CRC Press 1996).

As an illustration, pharmaceutical compositions may be supplied as a kit comprising a container that comprises a polypeptide with a IL-20RA or IL-20RB extracellular domain, e.g., IL-20RA or IL-20RB monomeric, homodimeric, heterodimeric or multimeric soluble receptors, or a IL-20 or IL-20RA or IL-20RB antagonist (e.g., an antibody or antibody fragment that binds a IL-20RA, IL-20RB or IL-20RA/IL-20RB polypeptide, or neutralizing anti-IL-20, anti-IL-20RA or anti-IL-20RB antibody). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the IL-20RA, IL-20RB or IL-20RA/IL-20RB composition is contraindicated in patients with known hypersensitivity to IL-20RA, IL-20RB or IL-20RA/IL-20RB.

A pharmaceutical composition comprising anti-IL-20, anti-IL-20RA or anti-IL-20RB antibodies or binding partners (or anti-IL-20, anti-IL-20RA or anti-IL-20RB antibody fragments, antibody fusions, humanized antibodies and the like), or IL-20RA, IL-20RB or IL-20RA/IL-20RB soluble receptor, can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., Pharm. Biotechnol. 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Anti-IL-20, anti-IL-20RA or anti-IL-20RB neutralizing antibodies and binding partners with IL-20 binding activity, or IL-20RA, IL-20RB or IL-20RA/IL-20RB soluble receptor, can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, Bioconjugate Chem. 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., Science 281:1161 (1998); Putney and Burke, Nature Biotechnology 16:153 (1998); Putney, Curr. Opin. Chem. Biol. 2:548 (1998)). Polyethylene glycol (PEG)-coated nanospheres can also provide carriers for intravenous administration of therapeutic proteins (see, for example, Gref et al., Pharm. Biotechnol. 10:167 (1997)).

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

The present invention contemplates compositions of soluble IL-20RA, IL-20RB or IL-20RA/IL-20RB or anti-IL-20, anti-IL-20RA or anti-IL-20RB, and methods and therapeutic uses comprising an such antibodies, peptides or polypeptides described herein. Such compositions can further comprise a carrier. The carrier can be a conventional organic or inorganic carrier. Examples of carriers include water, buffer solution, alcohol, propylene glycol, macrogol, sesame oil, corn oil, and the like.

11. Production of Transgenic Mice

Over expression of IL-20 was shown in human psoriatic lesions, suggesting that IL-20 is involved in human psoriasis. Moreover, as described herein, over expression of IL-20 in transgenic mice showed epidermal thickening and immune cell involvement indicative of a psoriatic phenotype. As such, antagonists to IL-20 activity, such as the anti-human-IL-20, anti-human-IL-20RA and anti-human-IL-20RB neutralizing and monoclonal antibodies of the present invention, as well as soluble IL-20RA, IL-20RB or IL-20RA/IL-20RB receptors, are useful in therapeutic treatment of inflammatory diseases, particularly as antagonists to IL-20 in the treatment of psoriasis. Moreover, antagonists to IL-20 activity, such as the anti-human-IL-20, anti-human-IL-20RA and anti-human-IL-20RB neutralizing and monoclonal antibodies of the present invention, as well as soluble IL-20RA, IL-20RB and IL-20RA/IL-20RB receptors, are useful in therapeutic treatment of other inflammatory diseases for example as antagonists to IL-20 in the treatment of atopic dermatitis, IBD, colitis, Endotoxemia, arthritis, rheumatoid arthritis, and psoriatic arthritis adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease, and the like.

Within one aspect, the present invention provides a method of producing an antibody to a polypeptide comprising: inoculating an animal with a polypeptide selected from the group consisting of: (a) a polypeptide consisting of the amino acid sequence of SEQ ID NO:3 from amino acid number 1 (Pro), to amino acid number 6 (Asp); (b) a polypeptide consisting of the amino acid sequence of SEQ ID NO:3 from amino acid number 26 (Ser), to amino acid number 32 (Pro); (c) a polypeptide consisting of the amino acid sequence of SEQ ID NO:3 from amino acid number 41 (Lys), to amino acid number 47 (Asp); (d) a polypeptide consisting of the amino acid sequence of SEQ ID NO:2 from amino acid number 49 (Val), to amino acid number 62 (Cys); (e) a polypeptide consisting of the amino acid sequence of SEQ ID NO:3 from amino acid number 41 (Lys) to amino acid number 62 (Cys); (f) a polypeptide consisting of the amino acid sequence of SEQ ID NO:3 from amino acid number 84 (Ala) to amino acid number 97 (Ser); (g) a polypeptide consisting of the amino acid sequence of SEQ ID NO:3 from amino acid number 103 (Thr) to amino acid number 108 (Asp); (h) a polypeptide consisting of the amino acid sequence of SEQ ID NO:3 from amino acid number 130 (Arg) to amino acid number 135 (His); (i) a polypeptide consisting of the amino acid sequence of SEQ ID NO:3 from amino acid number 164 (Gly) to amino acid number 166 (Lys); (j) a polypeptide consisting of the amino acid sequence of SEQ ID NO:3 from amino acid number 175 (Tyr), to amino acid number 179 (Glu); (k) a polypeptide consisting of the amino acid sequence of SEQ ID NO:3 from amino acid number 193 (Lys) to amino acid number 196 (Ala); (l) a polypeptide consisting of the amino acid sequence of SEQ ID NO:3 from amino acid number 203 (Lys) to amino acid number 209 (Thr); and (m) a polypeptide consisting of the amino acid sequence of SEQ ID NO:3; and (n) a polypeptide consisting of the amino acid sequence of SEQ ID NO:4; and wherein the polypeptide elicits an immune response in the animal to produce the antibody; and isolating the antibody from the animal; and wherein the antibody specifically binds to an IL-20RA polypeptide (SEQ ID NO:2 or SEQ ID NO:3); and inhibits the pro-inflammatory activity of IL-20 (SEQ ID NO:8) or IL-22 (SEQ ID NO:6).

Within one embodiment is provided the method as described above, wherein the antibody produced by the method inhibits the pro-inflammatory activity of IL-20.

Within a second aspect, the present invention provides an antibody produced by the method as disclosed above, which binds to a polypeptide of SEQ ID NO:2, SEQ ID NO:3, SEQ ID NO:14, SEQ ID NO:15, SEQ ID NO:21, or SEQ ID NO:23. Within one embodiment is provided the antibody as described above, wherein the antibody is selected from the group consisting of: (a) a polyclonal antibody, (b) a murine monoclonal antibody, (c) a humanized antibody derived from (b), (d) an antibody fragment, and (e) a human monoclonal antibody.

Within a third aspect, the present invention provides an antibody or antibody fragment that binds to a polypeptide comprising a sequence of amino acid residues as shown in SEQ ID NO:2, SEQ ID NO:3, SEQ ID NO:14, SEQ ID NO:15, SEQ ID NO:21, or SEQ ID NO:23; and inhibits the pro-inflammatory activity of IL-20. Within one embodiment is provided the antibody as described above, wherein the antibody further comprises a radionuclide, enzyme, substrate, cofactor, fluorescent marker, chemiluminescent marker, peptide tag, magnetic particle, drug, or toxin.

Within another aspect, the present invention provides a method for inhibiting IL-20-induced proliferation or differentiation of hematopoietic cells and hematopoietic cell progenitors comprising culturing bone marrow or peripheral blood cells with a composition comprising an amount of an antibody as disclosed above sufficient to reduce proliferation or differentiation of the hematopoietic cells in the bone marrow or peripheral blood cells as compared to bone marrow or peripheral blood cells cultured in the absence of soluble cytokine receptor. Within one embodiment is provided the method as described above, wherein the hematopoietic cells and hematopoietic progenitor cells are lymphoid cells.

Within another embodiment is provided the method as described above, wherein the lymphoid cells are macrophages or T cells.

Within another aspect, the present invention provides a method of reducing IL-20-induced inflammation comprising administering to a mammal with inflammation an amount of a composition of an antibody as disclosed above sufficient to reduce inflammation.

Within another aspect, the present invention provides a method of suppressing an inflammatory response in a mammal with inflammation comprising: (1) determining a level of serum amyloid A protein; (2) administering a composition comprising an antibody as disclosed above in an acceptable pharmaceutical vehicle; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Within one embodiment is provided the antibody as described above, wherein the antibody further comprises a radionuclide, enzyme, substrate, cofactor, fluorescent marker, chemiluminescent marker, peptide tag, magnetic particle, drug, or toxin.

Within another aspect, the present invention provides a method for inhibiting IL-20-induced proliferation or differentiation of hematopoietic cells and hematopoietic cell progenitors comprising culturing bone marrow or peripheral blood cells with a composition comprising an amount of an antibody as disclosed above sufficient to reduce proliferation or differentiation of the hematopoietic cells in the bone marrow or peripheral blood cells as compared to bone marrow or peripheral blood cells cultured in the absence of soluble cytokine receptor. Within one embodiment is provided the method as described above, wherein the hematopoietic cells and hematopoietic progenitor cells are lymphoid cells.

Within another embodiment is provided the method as described above, wherein the lymphoid cells are macrophages or T cells.

Within another aspect, the present invention provides a method of reducing IL-20-induced inflammation comprising administering to a mammal with inflammation an amount of a composition of a an antibody as disclosed above sufficient to reduce inflammation.

Within another aspect, the present invention provides a method of suppressing an inflammatory response in a mammal with inflammation comprising: (1) determining a level of serum amyloid A protein; (2) administering a composition comprising an antibody as disclosed above in an acceptable pharmaceutical vehicle; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response. Within another aspect, the present invention provides a method of treating a mammal afflicted with an inflammatory disease in which IL-20 plays a role, comprising: administering an antagonist of IL-20 to the mammal such that the inflammation is reduced, wherein the antagonist is selected from the group consisting of an antibody or binding polypeptide that specifically binds a polypeptide or polypeptide fragment of IL-20, IL-20RA or IL-20RB or is a polypeptide or polypeptide fragment of IL-20, IL-20RA or IL-20RB; and wherein the inflammatory activity of IL-20 is reduced. Within one embodiment is provided the method as described above, wherein the disease is a chronic inflammatory disease.

Within another embodiment is provided the method as described above, wherein the disease is a chronic inflammatory disease selected from the group consisting of: inflammatory bowel disease; ulcerative colitis; Crohn's disease; arthritis; and psoriasis.

Within another embodiment is provided the method as described above, wherein the disease is an acute inflammatory disease. Within another embodiment is provided the method as described above, wherein the disease is an acute inflammatory disease selected from the group consisting of: endotoxemia; septicemia; toxic shock syndrome; and infectious disease.

Within another embodiment is provided the method as described above, wherein the antibody further comprises a radionuclide, enzyme, substrate, cofactor, fluorescent marker, chemiluminescent marker, peptide tag, magnetic particle, drug, or toxin.

Within another aspect, the present invention provides an antibody comprising a monoclonal antibody that that binds to an epitope of human IL-20 (SEQ ID NO:2), wherein the epitope comprises a polypeptide having an amino acid sequence selected from the group consisting of: amino acid residues 42 (Ile) to 102 (Asp) of SEQ ID NO:2; amino acid residues 42 (Ile) to 60 (Ile) of SEQ ID NO:2; amino acid residues 42 (Ile) to 69 (Glu) of SEQ ID NO:2; amino acid residues 42 (Ile) to 81 (Cys) of SEQ ID NO:2; amino acid residues 42 (Ile) to 96 (Lys) of SEQ ID NO:2; amino acid residues 42 (Ile) to 102 (Asp) of SEQ ID NO:2; amino acid residues 60 (Ile) to 69 (Glu) of SEQ ID NO:2; amino acid residues 60 (Ile) to 81 (Cys) of SEQ ID NO:2; amino acid residues 60 (Ile) to 96 (Lys) of SEQ ID NO:2; amino acid residues 60 (Ile) to 102 (Asp) of SEQ ID NO:2; amino acid residues 69 (Glu) to 81 (Cys) of SEQ ID NO:2; amino acid residues 69 (Glu) to 96 (Lys) of SEQ ID NO:2; amino acid residues 69 (Glu) to 102 (Asp) of SEQ ID NO:2; amino acid residues 81 (Cys) to 96 (Lys) of SEQ ID NO:2; amino acid residues 81 (Cys) to 102 (Asp) of SEQ ID NO:2; amino acid residues 96 (Lys) to 102 (Asp) of SEQ ID NO:2, and wherein the antibody reduces or neutralizes the pro-inflammatory activity of human IL-20 (SEQ ID NO:2). Within one embodiment is provided the antibody as described above, wherein the antibody further comprises a radionuclide, enzyme, substrate, cofactor, fluorescent marker, chemiluminescent marker, peptide tag, magnetic particle, drug, or toxin.

Within another embodiment is provided the antibody as described above, wherein the antibody is selected from the group consisting of: (a) a murine monoclonal antibody, (b) a humanized antibody derived from (a), (c) an antibody fragment, and (d) a human monoclonal antibody.

Within another aspect, the present invention provides an antibody comprising a monoclonal antibody that that binds to an epitope of human IL-20RA (SEQ ID NO:14), wherein the epitope comprises a polypeptide having an amino acid sequence selected from the group consisting of: amino acid residues 1 (Met) to 9 (Leu) of SEQ ID NO:14; amino acid residues 1 (Met) to 36 (Gly) of SEQ ID NO:14; amino acid residues 1 (Met) to 41 (Ala) of SEQ ID NO:14; amino acid residues 1 (Met) to 58 (Pro) of SEQ ID NO:14; amino acid residues 1 (Met) to 63 (Gln) of SEQ ID NO:14; amino acid residues 1 (Met) to 80 (Lys) of SEQ ID NO:14; amino acid residues 1 (Met) to 94 (Tyr) of SEQ ID NO:14; amino acid residues 1 (Met) to 104 (Tyr) of SEQ ID NO:14; amino acid residues 1 (Met) to 120 (Cys) of SEQ ID NO:14; amino acid residues 1 (Met) to 128 (Arg) of SEQ ID NO:14; amino acid residues 1 (Met) to 161 (Trp) of SEQ ID NO:14; amino acid residues 1 (Met) to 169 (Pro) of SEQ ID NO:14; amino acid
residues 1 (Met) to 187 (Asn) of SEQ ID NO:14; amino acid
residues 1 (Met) to 194 (Trp) of SEQ ID NO:14; amino acid
residues 1 (Met) to 224 (Gly) of SEQ ID NO:14; amino acid
residues 1 (Met) to 233 (Glu) of SEQ ID NO:14; amino acid
residues 1 (Met) to 316 (Ile) of SEQ ID NO:14; amino acid
residues 1 (Met) to 323 (Ile) of SEQ ID NO:14; amino acid
residues 1 (Met) to 335 (Asp) of SEQ ID NO:14; amino acid
residues 1 (Met) to 340 (Asn) of SEQ ID NO:14; amino acid
residues 1 (Met) to 354 (Glu) of SEQ ID NO:14; amino acid
residues 1 (Met) to 371 (Cys) of SEQ ID NO:14; amino acid
residues 1 (Met) to 381 (Ser) of SEQ ID NO:14; amino acid
residues 1 (Met) to 384 (Gln) of SEQ ID NO:14; amino acid
residues 1 (Met) to 397 (Thr) of SEQ ID NO:14; amino acid
residues 1 (Met) to 412 (Ala) of SEQ ID NO:14; amino acid
residues 1 (Met) to 418 (Glu) of SEQ ID NO:14; amino acid
residues 1 (Met) to 462 (Gln) of SEQ ID NO:14; amino acid
residues 1 (Met) to 476 (Ser) of SEQ ID NO:14; amino acid
residues 1 (Met) to 483 (Asp) of SEQ ID NO:14; amino acid
residues 1 (Met) to 486 (Thr) of SEQ ID NO:14; amino acid
residues 1 (Met) to 496 (Ser) of SEQ ID NO:14; amino acid
residues 1 (Met) to 511 (Gly) of SEQ ID NO:14; amino acid
residues 1 (Met) to 523 (Glu) of SEQ ID NO:14; amino acid
residues 1 (Met) to 536 (Thr) of SEQ ID NO:14; amino acid
residues 36 (Gly) to 63 (Gln) of SEQ ID NO:14; amino acid
residues 36 (Gly) to 94 (tyr) of SEQ ID NO:14; amino acid
residues 36 (Gly) to 128 (Arg) of SEQ ID NO:14; amino acid
residues 36 (Gly) to 169 (Pro) of SEQ ID NO:14; amino acid
residues 36 (Gly) to 194 (Trp) of SEQ ID NO:14; amino acid
residues 36 (Gly) to 233 (Glu) of SEQ ID NO:14; amino acid
residues 36 (Gly) to 323 (Ser) of SEQ ID NO:14; amino acid
residues 36 (Gly) to 340 (Asn) of SEQ ID NO:14; amino acid
residues 36 (Gly) to 354 (Glu) of SEQ ID NO:14; amino acid
residues 36 (Gly) to 381 (Ser) of SEQ ID NO:14; amino acid
residues 36 (Gly) to 397 (Thr) of SEQ ID NO:14; amino acid
residues 36 (Gly) to 418 (Glu) of SEQ ID NO:14; amino acid
residues 36 (Gly) to 476 (Ser) of SEQ ID NO:14; amino acid
residues 36 (Gly) to 486 (Thr) of SEQ ID NO:14; amino acid
residues 36 (Gly) to 511 (Gly) of SEQ ID NO:14; amino acid
residues 36 (Gly) to 536 (Thr) of SEQ ID NO:14; amino acid
residues 58 (Pro) to 63 (Gln) of SEQ ID NO:14; amino acid
residues 58 (Pro) to 94 (tyr) of SEQ ID NO:14; amino acid
residues 58 (Pro) to 128 (Arg) of SEQ ID NO:14; amino acid
residues 58 (Pro) to 169 (Pro) of SEQ ID NO:14; amino acid
residues 58 (Pro) to 194 (Trp) of SEQ ID NO:14; amino acid
residues 58 (Pro) to 233 (Glu) of SEQ ID NO:14; amino acid
residues 58 (Pro) to 323 (Ser) of SEQ ID NO:14; amino acid
residues 58 (Pro) to 340 (Asn) of SEQ ID NO:14; amino acid
residues 58 (Pro) to 354 (Glu) of SEQ ID NO:14; amino acid
residues 58 (Pro) to 381 (Ser) of SEQ ID NO:14; amino acid
residues 58 (Pro) to 397 (Thr) of SEQ ID NO:14; amino acid
residues 58 (Pro) to 418 (Glu) of SEQ ID NO:14; amino acid
residues 58 (Pro) to 476 (Ser) of SEQ ID NO:14; amino acid
residues 58 (Pro) to 486 (Thr) of SEQ ID NO:14; amino acid
residues 58 (Pro) to 511 (Gly) of SEQ ID NO:14; amino acid
residues 58 (Pro) to 536 (Thr) of SEQ ID NO:14; amino acid
residues 80 (Lys) to 94 (tyr) of SEQ ID NO:14; amino acid
residues 80 (Lys) to 128 (Arg) of SEQ ID NO:14; amino acid
residues 80 (Lys) to 169 (Pro) of SEQ ID NO:14; amino acid
residues 80 (Lys) to 194 (Trp) of SEQ ID NO:14; amino acid
residues 80 (Lys) to 233 (Glu) of SEQ ID NO:14; amino acid
residues 80 (Lys) to 323 (Ser) of SEQ ID NO:14; amino acid
residues 80 (Lys) to 340 (Asn) of SEQ ID NO:14; amino acid
residues 80 (Lys) to 354 (Glu) of SEQ ID NO:14; amino acid
residues 80 (Lys) to 381 (Ser) of SEQ ID NO:14; amino acid
residues 80 (Lys) to 397 (Thr) of SEQ ID NO:14; amino acid
residues 80 (Lys) to 418 (Glu) of SEQ ID NO:14; amino acid
residues 80 (Lys) to 476 (Ser) of SEQ ID NO:14; amino acid
residues 80 (Lys) to 486 (Thr) of SEQ ID NO:14; amino acid
residues 80 (Lys) to 511 (Gly) of SEQ ID NO:14; amino acid
residues 80 (Lys) to 536 (Thr) of SEQ ID NO:14; amino acid
residues 120 (Cys) to 128 (Arg) of SEQ ID NO:14; amino acid residues 120 (Cys) to 169 (Pro) of SEQ ID NO:14; amino acid residues 120 (Cys) to 194 (Trp) of SEQ ID NO:14; amino acid residues 120 (Cys) to 233 (Glu) of SEQ ID NO:14; amino acid residues 120 (Cys) to 323 (Ser) of SEQ ID NO:14; amino acid residues 120 (Cys) to 340 (Asn) of SEQ ID NO:14; amino acid residues 120 (Cys) to 354 (Glu) of SEQ ID NO:14; amino acid residues 120 (Cys) to 381 (Ser) of SEQ ID NO:14; amino acid residues 120 (Cys) to 397 (Thr) of SEQ ID NO:14; amino acid residues 120 (Cys) to 418 (Glu) of SEQ ID NO:14; amino acid residues 120 (Cys) to 476 (Ser) of SEQ ID NO:14; amino acid residues 120 (Cys) to 486 (Thr) of SEQ ID NO:14; amino acid residues 120 (Cys) to 511 (Gly) of SEQ ID NO:14; amino acid residues 120 (Cys) to 536 (Thr) of SEQ ID NO:14; amino acid residues 161 (Trp) to 169 (Pro) of SEQ ID NO:14; amino acid residues 161 (Trp) to 194 (Trp) of SEQ ID NO:14; amino acid residues 161 (Trp) to 233 (Glu) of SEQ ID NO:14; amino acid residues 161 (Trp) to 323 (Ser) of SEQ ID NO:14; amino acid residues 161 (Trp) to 340 (Asn) of SEQ ID NO:14; amino acid residues 161 (Trp) to 354 (Glu) of SEQ ID NO:14; amino acid residues 161 (Trp) to 381 (Ser) of SEQ ID NO:14; amino acid residues 161 (Trp) to 397 (Thr) of SEQ ID NO:14; amino acid residues 161 (Trp) to 418 (Glu) of SEQ ID NO:14; amino acid residues 161 (Trp) to 476 (Ser) of SEQ ID NO:14; amino acid residues 161 (Trp) to 486 (Thr) of SEQ ID NO:14; amino acid residues 161 (Trp) to 511 (Gly) of SEQ ID NO:14; amino acid residues 161 (Trp) to 536 (Thr) of SEQ ID NO:14; amino acid residues 187 (Asn) to 194 (Trp) of SEQ ID NO:14; amino acid residues 187 (Asn) to 233 (Glu) of SEQ ID NO:14; amino acid residues 187 (Asn) to 323 (Ser) of SEQ ID NO:14; amino acid residues 187 (Asn) to 340 (Asn) of SEQ ID NO:14; amino acid residues 187 (Asn) to 354 (Glu) of SEQ ID NO:14; amino acid residues 187 (Asn) to 381 (Ser) of SEQ ID NO:14; amino acid residues 187 (Asn) to 397 (Thr) of SEQ ID NO:14; amino acid residues 187 (Asn) to 418 (Glu) of SEQ ID NO:14; amino acid residues 187 (Asn) to 476 (Ser) of SEQ ID NO:14; amino acid residues 187 (Asn) to 486 (Thr) of SEQ ID NO:14; amino acid residues 187 (Asn) to 511 (Gly) of SEQ ID NO:14; amino acid residues 187 (Asn) to 536 (Thr) of SEQ ID NO:14; amino acid residues 224 (Gly) to 233 (Glu) of SEQ ID NO:14; amino acid residues 224 (Gly) to 323 (Ser) of SEQ ID NO:14; amino acid residues 224 (Gly) to 340 (Asn) of SEQ ID NO:14; amino acid residues 224 (Gly) to 354 (Glu) of SEQ ID NO:14; amino acid residues 224 (Gly) to 381 (Ser) of SEQ ID NO:14; amino acid residues 224 (Gly) to 397 (Thr) of SEQ ID NO:14; amino acid residues 224 (Gly) to 418 (Glu) of SEQ ID NO:14; amino acid residues 224 (Gly) to 476 (Ser) of SEQ ID NO:14; amino acid residues 224 (Gly) to 486 (Thr) of SEQ ID NO:14; amino acid residues 224 (Gly) to 511 (Gly) of SEQ ID NO:14; amino acid residues 224 (Gly) to 536 (Thr) of SEQ ID NO:14; amino acid residues 316 (Ile) to 323 (Ser) of SEQ ID NO:14; amino acid residues 316 (Ile) to 340 (Asn) of SEQ ID NO:14; amino acid residues 316 (Ile) to 354 (Glu) of SEQ ID NO:14; amino acid residues 316 (Ile) to 381 (Ser) of SEQ ID NO:14; amino acid residues 316 (Ile) to 397 (Thr) of SEQ ID NO:14; amino acid residues 316 (Ile) to 418 (Glu) of SEQ ID NO:14; amino acid residues 316 (Ile) to 476 (Ser) of SEQ ID NO:14; amino acid residues 316 (Ile) to 486 (Thr) of SEQ ID NO:14; amino acid residues 316 (Ile) to 511 (Gly) of SEQ ID NO:14; amino acid residues 316 (Ile) to 536 (Thr) of SEQ ID NO:14; amino acid residues 335 (Asp) to 340 (Asn) of SEQ ID NO:14; amino acid residues 335 (Asp) to 354 (Glu)

of SEQ ID NO:14; amino acid residues 335 (Asp) to 381 (Ser) of SEQ ID NO:14; amino acid residues 335 (Asp) to 397 (Thr) of SEQ ID NO:14; amino acid residues 335 (Asp) to 418 (Glu) of SEQ ID NO:14; amino acid residues 335 (Asp) to 476 (Ser) of SEQ ID NO:14; amino acid residues 335 (Asp) to 486 (Thr) of SEQ ID NO:14; amino acid residues 335 (Asp) to 511 (Gly) of SEQ ID NO:14; amino acid residues 335 (Asp) to 536 (Thr) of SEQ ID NO:14; amino acid residues 371 (Cys) to 381 (Ser) of SEQ ID NO:14; amino acid residues 371 (Cys) to 397 (Thr) of SEQ ID NO:14; amino acid residues 371 (Cys) to 418 (Glu) of SEQ ID NO:14; amino acid residues 371 (Cys) to 476 (Ser) of SEQ ID NO:14; amino acid residues 371 (Cys) to 486 (Thr) of SEQ ID NO:14; amino acid residues 371 (Cys) to 511 (Gly) of SEQ ID NO:14; amino acid residues 371 (Cys) to 536 (Thr) of SEQ ID NO:14; amino acid residues 384 (Gln) to 397 (Thr) of SEQ ID NO:14; amino acid residues 384 (Gln) to 418 (Glu) of SEQ ID NO:14; amino acid residues 384 (Gln) to 476 (Ser) of SEQ ID NO:14; amino acid residues 384 (Gln) to 486 (Thr) of SEQ ID NO:14; amino acid residues 384 (Gln) to 511 (Gly) of SEQ ID NO:14; amino acid residues 384 (Gln) to 536 (Thr) of SEQ ID NO:14; amino acid residues 412 (Ala) to 418 (Glu) of SEQ ID NO:14; amino acid residues 412 (Ala) to 476 (Ser) of SEQ ID NO:14; amino acid residues 412 (Ala) to 486 (Thr) of SEQ ID NO:14; amino acid residues 412 (Ala) to 511 (Gly) of SEQ ID NO:14; amino acid residues 412 (Ala) to 536 (Thr) of SEQ ID NO:14; amino acid residues 462 (Gln) to 476 (Ser) of SEQ ID NO:14; amino acid residues 462 (Gln) to 486 (Thr) of SEQ ID NO:14; amino acid residues 462 (Gln) to 511 (Gly) of SEQ ID NO:14; amino acid residues 462 (Gln) to 536 (Thr) of SEQ ID NO:14; amino acid residues 483 (Asp) to 486 (Thr) of SEQ ID NO:14; amino acid residues 483 (Asp) to 511 (Gly) of SEQ ID NO:14; amino acid residues 483 (Asp) to 536 (Thr) of SEQ ID NO:14; amino acid residues 496 (Ser) to 511 (Gly) of SEQ ID NO:14; amino acid residues 496 (Ser) to 536 (Thr) of SEQ ID NO:14; amino acid residues 523 (Glu) to 536 (Thr) of SEQ ID NO:14, and wherein the antibody reduces or neutralizes the pro-inflammatory activity of human IL-20 (SEQ ID NO:2). Within one embodiment is provided the antibody as described above, wherein the antibody further comprises a radionuclide, enzyme, substrate, cofactor, fluorescent marker, chemiluminescent marker, peptide tag, magnetic particle, drug, or toxin.

Within another embodiment is provided the antibody as described above, wherein the antibody is selected from the group consisting of: (a) a murine monoclonal antibody, (b) a humanized antibody derived from (a), (c) an antibody fragment, and (d) a human monoclonal antibody.

Within another aspect, the present invention provides an antibody comprising a monoclonal antibody that that binds to an epitope of human IL-20RB (SEQ ID NO:21), wherein the epitope comprises a polypeptide having an amino acid sequence selected from the group consisting of: amino acid residues 70 (Tyr) to 74 (Tyr) of SEQ ID NO:21; amino acid residues 70 (Tyr) to 101 (Asp) of SEQ ID NO:21; amino acid residues 70 (Tyr) to 135 (Ser) of SEQ ID NO:21; amino acid residues 70 (Tyr) to 178 (Glu) of SEQ ID NO:21; amino acid residues 70 (Tyr) to 283 (Lys) of SEQ ID NO:21; amino acid residues 92 (Thr) to 101 (Asp) of SEQ ID NO:21; amino acid residues 92 (Thr) to 135 (Ser) of SEQ ID NO:21; amino acid residues 92 (Thr) to 178 (Glu) of SEQ ID NO:21; amino acid residues 92 (Thr) to 283 (Lys) of SEQ ID NO:21; amino acid residues 130 (Pro) to 135 (Ser) of SEQ ID NO:21; amino acid residues 130 (Pro) to 178 (Glu) of SEQ ID NO:21; amino acid residues 130 (Pro) to 283 (Lys) of SEQ ID NO:21; amino acid residues 171 (Arg) to 178 (Glu) of SEQ ID NO:21; amino acid residues 171 (Arg) to 283 (Lys) of SEQ ID NO:21; amino acid residues 279 (Asn) to 283 (Lys) of SEQ ID NO:21, and wherein the antibody reduces or neutralizes the pro-inflammatory activity of human IL-20 (SEQ ID NO:2). Within one embodiment is provided the antibody as described above, wherein the antibody further comprises a radionuclide, enzyme, substrate, cofactor, fluorescent marker, chemiluminescent marker, peptide tag, magnetic particle, drug, or toxin.

Within another embodiment is provided the antibody as described above, wherein the antibody is selected from the group consisting of: (a) a murine monoclonal antibody, (b) a humanized antibody derived from (a), (c) an antibody fragment, and (d) a human monoclonal antibody.

Within another aspect, the present invention provides a method of treating a pathological condition in a subject associated with IL-20 activity comprising administering an effective amount of the antibody as disclosed above thereby treating said pathological condition. Within one embodiment is provided the method as described above, wherein said pathological condition is a chronic inflammatory condition.

Within another embodiment is provided the method as described above, wherein said chronic inflammatory condition is selected from the group consisting of: inflammatory bowel disease; ulcerative colitis; Crohn's disease; arthritis; and psoriasis. Within another embodiment is provided the method as described above, wherein said pathological condition is an acute inflammatory condition.

Within another embodiment is provided the method as described above, wherein said acute inflammatory condition is selected from the group consisting of: endotoxemia; septicemia; toxic shock syndrome; and infectious disease.

The invention is further illustrated by the following non-limiting examples.

EXAMPLES

Example 1

Cloning of IL-20

Cloning of Human IL-20

The full length sequence of IL-20×1 (the longer form—SEQ ID NO:1) and IL-20×2 (the shorter form—SEQ ID NO:4) was elucidated by using 3' RACE® and submitting two fragments generated to sequencing (SEQ ID NO:30 and SEQ ID NO:31), then artificially splicing together by computer the est sequence shown in SEQ ID NO:32 with the overlapping sequence from the two 3' race fragments.

An oligo, zc15907 (SEQ ID NO: 33), was designed to the area just upstream (5') of the putative methionine for IL-20. Further downstream, another oligo, zc15906 (SEQ ID NO: 34), was designed to the area just upstream of the signal sequence cleavage site. These oligos were used in 3' RACE reactions on human trachea marathon cDNA. ZC15907 was used in the primary 3' race reaction and zc15906 was used in the nested 3' race reaction. The MARATHON cDNA was made using the Marathon cDNA Amplification Kit (Clontech, Palo Alto, Calif.) according to the manufacturer's instructions, starting with human trachea mRNA purchased from Clontech.

The PCR reactions were run according to the manufacturer's instructions in the Marathon cDNA Amplification Kit with some modification in the thermal cycling parameters. The cycling parameters used in the primary PCR reaction were:

94 C 1 min 30 sec 1×
94 C 15 sec 68 C 1 min 30×
72 C 7 min 1×

The cycling parameters used in the nested PCR reaction were: 94 C 1 min 30 sec 1×, 94 C 15 sec 68 C 1 min 20 seq. 30× 72 C 7 min 1×.

The resulting products were run out on a 1.2% agarose gel (Gibco agarose) and two main bands were seen, approximately 80 bp apart. The bands were cut out and gel purified using QIAEX™ resin (Qiagen) according to the manufacturer's instructions. These fragments were then subjected to sequencing, allowing the full length sequence of IL-20 to be discerned.

Cloning of Murine IL-20

PCR primers 5' MARATHON RACE™ (Clontech, Palo Alto, Calif.) primer set SEQ ID NO: 35 attached to MARATHON™ API adapter, nested with SEQ ID NO:36 attached to AP2 MARATHON™ adapter, with 3' MARATHON RACE™ primer set SEQ ID NO: 37 attached to MARATHON RACE™ API adapter, nested with SEQ ID NO:38 attached to MARATHON RACE™ AP2 adapter and 5' and 3' race was performed on mouse skin MARATHON RACE™ cDNA. Several fragments were from these reactions were gel purified and sequenced, allowing the elucidation of the full length coding sequence of the mouse IL-20, plus some 5' and 3' UTR sequence. Two murine IL-20 variants were discovered, namely SEQ ID NOs: 39 and 40 and SEQ ID NOs: 41 and 42. The clones were amplified by PCR using primers SEQ ID NOs:43 and 44.

Example 2

Cloning of IL-20RA

Cloning of Human IL-20RA

Expressed sequence tag (EST) 277139 (SEQ ID NO:45) was identified. The cDNA clone (ID No. 50416) was obtained from the IMAGE consortium Lawrence Livermore National Laboratory through Genome Systems, Inc. The cDNA was supplied as an agar stab containing *E. coli* transfected with a plasmid having the cDNA of interest. The *E. coli* was streaked on an agar plate. The plasmid was designated pSL7139. The cDNA insert in plasmid pSL7139 was sequenced. The insert was determined to be 1231 bp in length, but was not a full length sequence.

A human testis cDNA template was made using a MARATHON™ cDNA Amplification Kit (Clontech Laboratories, Inc., Palo Alto, Calif.) according to the supplier's instructions. A 5' RACE reaction was used to obtain a full-length cDNA. The RACE reaction was carried out in two reactions employing two sets of primers. Reaction I (outer nest), using primers ZC11,107 (SEQ ID NO:46) and AP-1 (SEQ ID NO: 47) (Clontech Laboratories) was run for 35 cycles at 98° C. for 20 seconds, 45° C. for 20 seconds; 68° for 4 minutes and a final extension time of 10 minutes at 68° C. One μl of a 1:100 dilution of the reaction product was used as a template in reaction II (inner nest). Primers were ZC11,108 (SEQ ID NO:48) and AP-2 (SEQ ID NO:49) (Clontech Laboratories). The reaction was run at 98° C. for 30 seconds, and 30 cycles each cycle being comprised of 98° C. for 28 seconds; 43° C. for 20 seconds; and 68° C. for 3.5 minutes with a final extension at 68° C. for 10 minutes.

The product of the inner nest RACE reaction was subcloned using a PCR-SCRIPT™ kit (Stratagene Cloning Systems, La Jolla, Calif.) to prepare the plasmid pSLR7-1. Sequence analysis of this plasmid indicated that the 5' RACE-generated sequence extended the sequence of pSL7139 by 555 bp.

Full-length cDNA was obtained by screening a λZAP® II human testis cDNA library using a probe that was generated by PCR primers ZC11,526 (SEQ ID NO:50) and ZC11,108 (SEQ ID NO:48) and pSLR7-1 as template and then re-amplified. The resulting probe was purified through recovery from low-melt agarose gel electrophoresis and was labeled with $^{32}$P-xxxxx-dCTP using a MEGAPRIME™ labeling kit (Amersham Corp., Arlington, Heights, Ill.). The labeled probe was purified on a push column (NUCTRAP® probe purification column; Stratagene Cloning Systems).

The first strand cDNA reaction contained 15 μl of human testis twice poly d(T)-selected poly (A)$^+$ mRNA (Clontech Laboratories) at a concentration of 1.0 μg/μl, and 3 μl of 20 pmole/μl first strand primer ZC6091 (SEQ ID NO:51) containing an Xho I restriction site. The mixture was heated at 70° C. for 4 minutes and cooled by chilling on ice. First stand cDNA synthesis was initiated by the addition of 12 μl of first strand buffer (5× SUPERSCRIPT™ buffer; Life Technologies, Gaithersburgh, Md.), 6 μl of 100 mM dithiothreitol, 3 μl of deoxynucleotide triphosphate solution containing 10 mM each of dTTP, dATP, dGTP, and 5-methyl-dCTP (Pharmacia LKB Biotechnology, Piscataway, N.J.) to the RNA-primer mixture. The reaction mixture was incubated at 37° C. for 2 minutes, followed by the addition of 15 μl of 200 U/μl Rnase H$^-$ reverse transcriptase (SUPERSCRIPT II$^{<<}$; Life Technologies). The efficiency of the first strand synthesis was analyzed in a parallel reaction by the addition of 5 μCi of $^{32}$P-xxxxxdCTP to 5 μl aliquot from one of the reaction mixtures to label the reaction for analysis. The reactions were incubated at 37° C. for 10 minutes, 45° C. for 1 hour, then incubated at 50° C. for 10 minutes. Unincorporated $^{32}$P-xxxxxdCTP in the labeled reaction and the unincorporated nucleotides and primers in the unlabeled first strand reactions were removed by chromatography on a 400 pore size gel filtration column (Clontech Laboratories). The length of labeled first strand cDNA was determined by agarose gel electrophoresis.

The second strand reaction contained 120 μl of the unlabeled first strand cDNA, 36 μl of 5× polymerase I buffer (125 mM Tris: HCl, pH 7.5, 500 mM KCl, 25 mM MgCl$_2$, 50 mM (NH$_4$)$_2$SO$_4$)), 2.4 μl of 100 mM dithiothreitol, 3.6 μl of a solution containing 10 mM of each deoxynucleotide triphosphate, 6 μl of 5 mM β-NAD, 3.6 μl of 3 U/μl *E. coli* DNA ligase (New England Biolabs), 9 μl of 10 U/μl *E. coli* DNA polymerase I (New England Biolabs), and 1.8 μl of 2 U/μl RNase H (life Technologies). A 10 μl aliquot from one of the second strand synthesis reactions was labeled by the addition of 10 μCi $^{32}$P-xxxxxdCTP to monitor the efficiency of second strand synthesis. The reactions were incubated at 16° C. for two hours, followed by the addition of 15 μl T4 DNA polymerase (10 U/μl, Boerhinger Mannheim, Indianapolis, Ind.) and incubated for an additional 5 minutes at 16° C. Unincorporated $^{32}$P-xxxxxdCTP in the labeled reaction was removed by chromatography through a 400 pore size gel filtration (Clontech Laboratories) before analysis by agarose gel electrophoresis. The unlabeled second strand reaction was terminated by the addition of 20 μl 0.5 M EDTA and extraction with phenol/chloroform and chloroform followed by ethanol precipitation in the presence of 2.5 M ammonium acetate and 4 μg of glycogen carrier. The yield of cDNA was estimated to be approximately 3 μg from starting mRNA template of 15 μg.

Eco RI adapters were ligated onto the 5' ends of the cDNA described above to enable cloning into an expression vector. A 10 μl aliquot of cDNA (approximately 1.5 μg) and 5 μl of 65 pmole/μl of Eco RI adapter (Pharmacia LKB Biotechnology Inc.) were mixed with 2 μl 10× ligase buffer (660 mM Tris-HCl pH 7.5, 100 mM MgCl$_2$), 2 μl of 10 mM ATP and 1 μl of 15 U/μl T4 DNA ligase (Promega Corp., Madison, Wis.). The reaction was incubated 2 hours at 5° C., two hours at 7.5° C., 2 hours at 10° C., and 10 hours at 12.5° C. The reaction was terminated by incubation at 70° C. for 20 minutes.

To facilitate the directional cloning of the cDNA into an expression vector, the cDNA was digested with Xho I, resulting in a cDNA having a 5' Eco RI cohesive end and a 3' Xho cohesive end. The Xho I restriction site at the 3' end of the cDNA had been previously introduced using the ZC6091 primer (SEQ ID NO: 51). Restriction enzyme digestion was carried out in a reaction mixture containing 20 μl of cDNA as described above, 10 μl of 10× H Buffer Xho I (Boehringer Mannheim), 69 μl $H_2O$, and 1.0 μl of 40 U/μl Xho I (Boehringer Mannheim). Digestion was carried out at 37° C. for 40 minutes. The reaction was terminated by incubation at 70° C. for 10 minutes and chromatography through a 400 pore size gel filtration column (Clontech Laboratories).

The cDNA was ethanol precipitated, washed with 70% ethanol, air dried and resuspended in 14 μl water, 2 μl of ligase buffer (Promega Corp., Madison, Wis.), 2 μl T4 polynucleotide kinase (10 U/μl, Life Technologies). Following incubation at 37° C. for 30 minutes, the cDNA was heated to 65° C. for 5 minutes, cooled on ice, and electrophoresed on a 0.8% low melt agarose gel. The contaminating adapters and cDNA below 0.6 kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) and 35 μl 10× β-agarose I buffer (New England Biolabs) were added to the tube, and the agarose was melted by heating to 65° C. for 15 minutes. Following equilibration of the sample to 45° C., 3 μl of 1 U/μl β-agarose I (New England Biolabs) was added, and the mixture was incubated for 60 minutes at 45° C. to digest the agarose. After incubation, 40 μl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 10 μl water.

The resulting cDNA was cloned into the lambda phage vector λZap<<II (Stratagene Cloning Systems) that was pre-digested with Eco RI and Xho I and dephosphorylated. Ligation of the cDNA to the λZap<<II vector was carried out in a reaction mixture containing 1.0 μl of prepared vector, 1.0 μl of human testis cDNA, 1.0 μl 10× Ligase Buffer (Promega Corp.), 1.0 μl of 10 mM ATP, 5 μl water, and 1.0 μl of T4 DNA Ligase at 15 units/ml (Promega Corp.). The ligation mixture was incubated at 5'-15° C. overnight in a temperature gradient. After incubation, the ligation mixture was packaged into phage using an in vitro packaging extract (Gigapack<<III Gold packaging extract; Stratagene Cloning Systems), and the resulting library was titered according to the manufacturer's specifications.

The human testis λZAP<<II library was used to infect *E. coli* host cells (XL1-Blue MRF' strain (Stratagene Cloning Systems), and $1.5 \times 10^6$ plaque forming units (pfu) were plated onto 150-mm NZY plates at a density of about 50,000 pfu/plate. The inoculated plates were incubated overnight at 37° C. Filter plaque lifts were made using nylon membranes (Hybond™-N; Amersham Corp., Arlington Heights, Ill.), according to the procedures provided by the manufacturer. The filters were processed by denaturation in solution containing 1.5 M NaCl and 0.5 M NaOH for 6 minutes at room temperature. The filters were blotted briefly on filter paper to remove excess denaturation solution, followed by neutralization for 6 minutes in 1 M Tris-HCl, pH 7.5, and 1.5 M NaCl.

Phage DNA was fixed onto the filters with 1,200 μJoules of UV energy in a UV Crosslinker (Stratalinker<<; Stratagene Cloning Systems). After fixing, the filters were first pre-washed in an aqueous solution containing 0.25× standard sodium citrate (SSC), 0.25% sodium dodecyl sulfate (SDS) and 1 mM EDTA to remove cellular debris and then prehybridized in hybridization solution (5×SSC, 5×Denhardt's solution, 0.2% SDS and 1 mM DTA). Heat-denatured, sheared salmon sperm DNA at a final concentration of 100 μg/ml was added. The filters were prehybridized at 65° C. overnight.

A probe was prepared as a PCR product by using oligonucleotide primers designed to amplify the human IL-20RA coding region. A PCR reaction mixture was prepared containing 2 μl of ZC11526 (SEQ ID NO:50) 2 μl of ZC11,108 (SEQ ID NO:48), 1 μl of an overnight bacterial culture of pSLR7-1, 1 μl of 10 mM dNTP, 10 μl of 10× KlenTaq buffer (Clontech Laboratories), 82 μl water, and 2 μl KlenTaq DNA polymerase (Clontech laboratories). The PCR reaction was run as follows: 94° C. for 1 minute; 30 cycles of 95° C. for 20 seconds, 43° C. for 20 seconds, 68° C. for 1 minute; then held at 68° C. for 10 minutes. The PCR product was re-amplified and gel purified on a 0.8% low melt agarose gel.

Fifty nanograms PCR product was radiolabeled with $^{32}P$-xxxxx-dCTP by random priming using the MEGAPRIME<<DNA Labeling System (Amersham), according to the manufacturer's specifications. The prehybridization solution was replaced with fresh hybridization solution containing $1.4 \times 10^6$ cpm/ml labeled probe and allowed to hybridize for 64 hours at 60° C. After hybridization, the hybridization solution was removed and the filters were rinsed in a wash solution containing 0.25×SSC, 0.25% SDS and 1 mM EDTA at 65° C. The filters were placed on autoradiograph film and exposed at −70° C. with intensifying screens for 72 hours.

Examination of the autoradiographs revealed multiple regions that hybridized with labeled probe. Agar plugs were picked from 12 regions for purification. Each agar plug was soaked 2 hours in 0.5 ml of SM solution containing 25 ml 4M NaCl, 10 ml 1M $MgSO_4$, 25 ml 2M Tris HCl, 5 ml 2% gelatin and 935 ml $H_2O$ and 10% (v/v) chloroform (Sambrook et al. *Molecular Cloning: A Laboratory Manual.*, $2^{nd}$ ed., Cold Spring Harbor Laboratory Press, Cold Spring Harbor, N.Y., 1989). After incubation, the phages from each plug were diluted 1:1000 in SM. Aliquots of 50 μl were plated on 100 mm plates containing 300 μl of *E. coli* XL-1 Blue MRF' cells. The plates were incubated overnight at 37° C., and filter lifts were prepared, prehybridized overnight, hybridized overnight with a hybridization solution containing $1.1 \times 10^6$ cpm/ml labeled probe, washed and autoradiographed. Examination of the resulting autoradiographs revealed 10 positive signals. The positive plaques were subjected to an additional round of purification.

The plasmids were excised using an ExASSIST/SOLR<<system (Stratagene Cloning Systems), according to the manufacturer's specifications. These plasmid inserts were amplified by PCR for size determination. A clone, designated pSLR7-2 was sequenced and determined to have an insert of 3,532 bp in size.

Cloning of Murine IL-20RA

A cross-species hybridization probe was generated which contained the full-length cDNA fragment encoding human IL-20RA. A Southern blot of mouse genomic DNA and Northern blots of mouse RNA were performed to demonstrate that the human IL-20RA cDNA could specifically hybridize to mouse sequences. The Northern blot results indicated that mouse IL-20RA RNA was present in mouse embryo day 15 and 17 as well as heart, brain, lung, liver, kidney, testes, spleen, thymus, liver, stomach, and small intestine.

The human IL-20RA full length DNA hybridization probe was used to screen a mouse genomic library. The library, which was obtained from Clontech (Palo Alto, Calif.), was generated from an MboI partial digest of mouse genomic DNA and cloned into the BamHI site of Lambda bacteriophage EMBL3 SP6/T7. Positive bacteriophage was plaque purified and bacteriophage DNA was prepared using Promega's Wizard Lambda Preps DNA Purification System. Two genomic restriction enzyme fragments, a 5.7 kb EcoRI fragment and an 8.0 kb SacI fragment, were generated from the positive bacteriophage and subcloned into pBluescript. DNA sequence analysis revealed the presence of 3 exons from the mouse ortholog to human IL-20RA.

PCR primers from the 5' UTR (SEQ ID NO: 52) and 3' UTR (SEQ ID NO: 53) were designed to generate a full-length mouse IL-20RA sequence by PCR amplification. Mouse embryo 15 day plus 17 day cDNA was used as the template for the PCR amplification. PCR products were subcloned and sequenced for confirmation. The mouse sequences are SEQ ID NOs: 54 and 55. The mature extracellular domain is comprised of SEQ ID NO: 56.

Example 3

Cloning of Human IL-20RB

Two PCR primers were designed based on the sequence from International Patent Application No. PCT/US99/03735 filed on Mar. 8, 1999. SEQ ID NO: 57 contains the ATG (Met1) codon with an EcoRI restriction site, SEQ ID NO: 58 contains the stop codon (TAG) with an XhoI restriction site. The PCR amplification was carried out using a human keratinocyte (HaCaT) cDNA library DNA as a template and SEQ ID NO: 59 and SEQ ID NO: 58 as primers. The PCR reaction was performed as follows: incubation at 94° C. for 1 min followed by 30 cycles of 94° C. for 30 sec and 68° C. for 2 min, after additional 68° C. for 4 min, the reaction was stored at 4° C. The PCR products were run on 1% Agarose gel, and a 1 kb DNA band was observed. The PCR products were cut from the gel and the DNA was purified using a QIAquick Gel Extraction Kit (Qiagen). The purified DNA was digested with EcoRI and XhoI, and cloned into a pZP vector that was called pZP7N. A pZP plasmid is a mammalian expression vector containing an expression cassette having the mouse metallothionein-1 promoter, human tPA leader peptide, multiple restriction sites for insertion of coding sequences, a Glu-Glu tag, and a human growth hormone terminator. The plasmid also has an E. coli origin of replication, a mammalian selectable marker expression unit having an SV40 promoter, an enhancer and an origin of replication, as well as a DHFR gene, and the SV40 terminator. Several IL-20RB-pZP7N clones were sequenced. They all contain three non-conservative mutations compared with the sequence of IL-20RB in PCT/US99/03735: (sequence IL-20RB-pZP7N), 146 Pro (CCC)—Thr (ACC), 148 His (CAT)—Asp (GAT), and 171 Thr (ACG)—Arg (AGG).

To verify the three substitutions in IL-20RB-pZP7N clone, PCR amplification was carried out using three difference cDNA sources—fetal skin marathon cDNA, HaCaT cDNA library DNA, and prostate smooth muscle cDNA library DNA—as templates. The PCR products were gel purified and sequenced. The sequence of each of the three PCR products was consistent with that of the IL-20RB-pZP7N clone.

IL-20RB is SEQ ID NO: 20 and 21, and the mature extracellular domain is SEQ ID NO: 59.

Example 4

IL-20RA/RB Receptor-Ig fusion Heterotetramer

The expression vector pEZE3 was used to express the recombinant IL-20 receptor-Ig fusion protein. The plasmid pEZE3 is derived from pDC312. pDC312 was obtained through license from Immunex Corporation. The plasmids pDC312 and pEZE3 contain an EASE segment as described in WO 97/25420. The presence of the EASE segment in an expression vector can improve expression of recombinant proteins two to eight fold in stable cell pools.

The plasmid pEZE3 is a tricistronic expression vector that may be used to express up to three different proteins in mammalian cells, preferably Chinese Hamster Ovary (CHO) cells. The pEZE3 expression unit contains the cytomegalovirus (CMV) enhancer/promoter, the adenovirus tripartite leader sequence, a multiple cloning site for insertion of the coding region for the first recombinant protein, the poliovirus type 2 internal ribosome entry site, a second multiple cloning site for insertion of the coding region for the second recombinant protein, an encephalomyocarditis virus internal ribosome entry site, a coding segment for mouse dihydrofolate reductase, and the SV40 transcription terminator. In addition, pEZE3 contains an E. coli origin of replication and the bacterial beta lactamase gene.

The IL-20 receptor-Ig fusion protein is a disulfide linked heterotetramer consisting of two chains of the extracellular domain of the human IL-20RB fused to the wild type human immunoglobulin kappa light chain constant region and two chains of the human IL-20RA protein extracellular domain fused to a mutated human immunoglobulin gamma 1 constant region. The human immunoglobulin gamma 1 constant region contains amino acid substitutions to reduce FcγRI binding and C1q complement fixation.

The human IL-20RB extracellular domain human immunoglobulin kappa light chain constant region fusion construct was generated by overlap PCR. The IL-20RB coding segment consists of amino acids 1 to 230 of SEQ ID NO:20. The template used for the PCR amplification of the IL-20R segment was generated IL-20RB human kappa light chain constant region expression construct as described below. Oligonucleotide primers SEQ ID NO: 60 and SEQ ID NO: 61 were used to amplify the IL-20RB segment. The entire wild type human immunoglobulin kappa light chain constant region was used. The template used for the PCR amplification of the wild type human immunoglobulin kappa light chain constant region segment was generated IL-20RB human kappa light chain constant region expression construct as described in Example 12. Oligonucleotide primers SEQ ID NO: 62 and SEQ ID NO: 63 were used to amplify the wild type human immunoglobulin kappa light chain constant region. The two protein coding domains were linked by overlap PCR using oligonucleotides SEQ ID NO: 60 and SEQ ID NO: 63. A (Gly$_4$Ser)$_3$ (SEQ ID NO: 64) peptide linker was inserted between the two protein domains. The (Gly$_4$Ser)$_3$ peptide linker was encoded on the PCR primers SEQ ID NO: 61 and SEQ ID NO:62. The resultant IL-20RB extracellular domain/kappa light chain constant region fusion construct is shown by SEQ ID NOs: 65 and 66. The predicted mature polypeptide, minus the signal sequence, is SEQ ID NO: 67. The portion of the extracellular domain of IL-20RB that was actually used was comprised of the amino acid sequence of SEQ ID NO: 26. N-terminal sequencing resulted in the predicted amino acid sequence.

The human IL-20RA extracellular domain human immunoglobulin gamma 1 heavy chain constant region fusion construct was generated by overlap PCR of four separate DNA fragments, each generated by separate PCR amplification reactions. The first fragment contained an optimized tPA (tissue plasminogen activator) signal sequence. The tPA signal sequence was amplified using oligonucleotide primers SEQ ID NO: 68 and SEQ ID NO: 69 using an in-house previously generated expression vector as the template. The second fragment contained the IL-20RA extracellular domain-coding region consisting of amino acids 30 to 243 of SEQ ID NO:14. Oligonucleotide primers SEQ ID NO: 70 and SEQ ID NO: 71 were used to amplify this IL-20RA segment using a previously generated clone of IL-20RA as the template.

The human gamma 1 heavy chain constant region was generated from 2 segments. The first segment containing the $C_H1$ domain was amplified using oligonucleotide primers SEQ ID NO: 72 and SEQ ID NO: 73 using a clone of the wild type human gamma 1 heavy chain constant region as the template. The second segment containing the remaining hinge, $C_H2$, and $C_H3$ domains of the human immunoglobulin gamma 1 heavy chain constant region was generated by PCR amplification using oligonucleotide primers SEQ ID NO: 74 and SEQ ID NO: 75. The template used for this PCR amplification was from a previously generated human gamma 1 Fc construct that contained codons for amino acid substitutions to reduce FcγRI binding and C1q complement fixation.

The four protein coding domains were linked by overlap PCR using oligonucleotides SEQ ID NO: 68 and SEQ ID NO: 75. A $(Gly_4Ser)_3$ peptide linker was inserted between the IL-20RA and CH1 protein domains. The $(Gly_4Ser)_3$ peptide linker was encoded on the PCR primers SEQ ID NO: 71 and SEQ ID NO: 72. The IL-20RA extracellular domain/domain human immunoglobulin gamma 1 heavy constant region fusion protein and DNA sequence are shown in SEQ ID NOs: 76 and 77. The predicted mature polypeptide sequence, minus the signal sequence, is SEQ ID NO: 78. The portion of extracellular domain of IL-20RA that was actually used was comprised of SEQ ID NO: 79.

The IL-20RB extracellular domain human immunoglobulin kappa light chain constant region fusion coding segment was cloned into the second MCS while the human IL-20RA extracellular domain human immunoglobulin gamma 1 heavy chain constant region fusion coding segment was cloned into the first MCS of pEZE3. The plasmid was used to transfect CHO cells. The cells were selected in medium without hypoxanthine or thymidine and the transgene was amplified using methotrexate. The presence of protein was assayed by Western blotting using anti human gamma 1 heavy chain constant region and anti human kappa light chain antibodies. N-terminal sequencing revealed that the optimized tPA leader was not completely cleaved. The observed mass indicated that the first residue of the polypeptide sequence to be pyroglutamic acid, and the N-terminal sequence appears to be pyroEEIHAELRRFRRVPCVSGG (SEQ ID NO: 80), the underlined portion being remnants of the tPA leader.

Example 5

Construction of an IL-20 Receptor Heterodimer

A vector expressing a secreted human IL-20RA/hIL-20B heterodimer was constructed. In this construct, the extracellular domain of human IL-20RA was fused to the heavy chain of IgG gamma 1 (IgGγ1), while the extracellular portion of IL-20RB was fused to human kappa light chain (human κ light chain).

Construction of IgG Gamma 1 and Human κ Light Fusion Vectors

The heavy chain of IgGγ1 was cloned into the Zem229R mammalian expression vector (ATCC deposit No. 69447) such that any extracellular portion of a receptor having a 5' EcoRI and 3' NheI site can be cloned in, resulting in an N-terminal extracellular domain-C-terminal IgGγ1 fusion. The IgGγ1 fragment used in this construct was made by using PCR to isolate the IgGγ1 sequence from a Clontech hFetal Liver cDNA library as template. A PCR reaction using oligos (SEQ ID NO: 61) ZC11,450 and (SEQ ID NO: 62) ZC11,443 was run as follows: 40 cycles of 94° C. for 60 sec., 53° C. for 60 sec., and 72° C. for 120 sec.; and 72° C. for 7 min. PCR products were separated by agarose gel electrophoresis and purified using a QiaQuick™ (Qiagen) gel extraction kit. The isolated, 990 bp, DNA fragment was digested with MluI and EcoRI (Boerhinger-Mannheim), ethanol precipitated and ligated with oligos (SEQ ID NO: 63) ZC11,440 and (SEQ ID NO: 68) ZC11,441, which comprise an MluI/EcoRI linker, into Zem229R previously digested with MluI and EcoRI using standard molecular biology techniques disclosed herein. This generic cloning vector was called Vector#76 hIgGgamma1 w/Ch1 #786 Zem229R (Vector #76). The polynucleotide sequence of the extracellular domain of hIL-20RA fused to the heavy chain of IgG gamma 1 is show in SEQ ID NO: 69 and the corresponding polypeptide sequence shown in SEQ ID NO: 70, the mature sequence of which is SEQ ID NO: 81.

The human κ light chain was cloned in the Zem228R mammalian expression vector (ATCC deposit No. 69446) such that any extracellular portion of a receptor having a 5' EcoRI site and a 3' KpnI site can be cloned in, resulting in an N-terminal extracellular domain-C-terminal human κ light chain fusion. The human κ light chain fragment used in this construct was made by using PCR to isolate the human κ light chain sequence from the same Clontech hFetal Liver cDNA library used above. A PCR reaction using oligos (SEQ ID NO: 71) ZC11,501 and (SEQ ID NO: 72) ZC11,451 was run under condition described above. PCR products were separated by agarose gel electrophoresis and purified using a QiaQuick™ (Qiagen) gel extraction kit. The isolated, 315 bp, DNA fragment was digested with MluI and EcoRI (Boerhinger-Mannheim), ethanol precipitated and ligated with the MluI/EcoRI linker described above, into Zem228R previously digested with MluI and EcoRI using standard molecular biology techniques disclosed herein. This generic cloning vector was called Vector #77 hκlight #774 Zem228R (Vector #77). The polynucleotide sequence of the extracellular portion of IL-20RB fused to human kappa light chain is shown in SEQ ID NO: 73 and the corresponding polypeptide sequence shown in SEQ ID NO: 74, the mature sequence of which is SEQ ID NO: 82.

Insertion of IL-20RA and IL-20RB Extracellular Domains into Fusion Vector Constructs Using the construction vectors above, a construct having human IL-20RA fused to IgGγ1 was made. This construction was done by PCRing human IL-20RA receptor from hIL-20RA/IgG Vector #102 with oligos (SEQ ID NO: 75) ZC12,909 and (SEQ ID NO: 83) ZC26,564 under conditions described as follows: 30 cycles of 94° C. for 60 sec., 57° C. for 60 sec., and 72° C. for 120 sec.; and 72° C. for 7 min. The resulting PCR product was digested with EcoRI and NheI, gel purified, as described herein, and ligated into a previously EcoRI and NheI digested and band-purified Vector #76 (above). The resulting vector was sequenced to confirm that the human IL-20Rα/IgG gamma 1 fusion (hIL-20RA/Ch1 IgG) was correct. The hIL-20RA/Ch1 IgG gamma 1 #1825 Zem229R vector was called vector #195.

A separate construct having IL-20RB fused to κ light was also constructed. The IL-20RB/human κ light chain construction was performed as above by PCRing from DR1/7N-4 with oligos (SEQ ID NO: 84) ZC26,602 and (SEQ ID NO: 85) ZC26,599, digesting the resulting band with EcoRI and KpnI and then ligating this product into a previously EcoRI and KpnI digested and band-purified Vec#77 (above). The resulting vector was sequenced to confirm that the IL-20RB/human κ light chain fusion (IL-20RB/κlight) was correct. This IL-20RB//κlight #1833 Zem228R vector was called Vector #194.

Co-Expression of the Human IL-20RA and Human IL-20RB Receptors

Approximately 16 μg of each of vectors #194 and #195, above, were co-transfected into BHK-570 cells (ATCC No. CRL-10314) using LipofectaminePlus™ reagent (Gibco/BRL), as per manufacturer's instructions. The transfected cells were selected for 10 days in DMEM+5% FBS (Gibco/BRL) containing 1 μM of methotrexate (MTX) (Sigma, St. Louis, Mo.) and 0.5 mg/ml G418 (Gibco/BRL) for 10 days. The resulting pool of transfectants was selected again in 10 μM MTX and 0.5 mg/ml G418 for 10 days.

The resulting pool of doubly selected cells was used to generate protein. Three factories (Nunc, Denmark) of this pool were used to generate 8 L of serum free conditioned medium. This conditioned media was passed over a 1 ml protein-A column and eluted in (10) 750 microliter fractions. 4 of these fractions found to have the highest concentration were pooled and dialyzed (10 kD MW cutoff) against PBS. Finally, the dialyzed material was analyzed by BCA (Pierce) and found to have a concentration of 317 μg/ml. A total of 951 μg was obtained from this 8 L purification.

Example 6

Binding of IL-20 to the IL-20RB/IL-20RA Heterodimer

A cell-based binding assay was used to verify IL-20 binds to IL-20RA-IL-20RB heterodimer. Expression vectors containing known and orphan Class II cytokine receptors (including IL-20RA and IL-20RB) were transiently transfected into COS cells in various combinations, which were then assayed for their ability to bind biotin-labeled IL-20 protein. The results show IL-20RB-IL-20RA heterodimer is a receptor for IL-20. The procedure used is described below.

The COS cell transfection was performed in a 12-well tissue culture plate as follows: 0.5 μg DNA was mixed with medium containing 5 μl lipofectamine in 92 μl serum free Dulbecco's modified Eagle's medium (DMEM) (55 mg sodium pyruvate, 146 mg L-glutamine, 5 mg transferrin, 2.5 mg insulin, 1 μg selenium and 5 mg fetuin in 500 ml DMEM), incubated at room temperature for 30 minutes and then added to 400 μl serum free DMEM media. This 500 μl mixture was then added to $1.5 \times 10^5$ COS cells/well and incubated for 5 hours at 37° C. 500 μl 20% fetal bovine serum (FBS) DMEM media was added and incubated overnight.

The assay, a modification of the "secretion trap" (Davis, S., et al., *Cell* 87: 1161-1169 (1996), was performed as follows: cells were rinsed with PBS/1% bovine serum albumin (BSA) and blocked for 1 hour with TNB (0.1 M Tris-HCl, 0.15 M NaCl and 0.5% Blocking Reagent (NEN Renaissance TSA-Direct Kit Cat#NEL701) in water). This was followed by a one-hour incubation with 3 μg/ml biotinylated IL-20 protein in TNB. Cells were washed with PBS/1% BSA and incubated for another hour with 1:300 diluted streptavidin-HRP (NEN kit) in TNB. Following another wash, cells were fixed for 15 minutes with 1.8% Formaldehyde in phosphate-buffered saline (PBS). Cells were then washed with TNT (0.1 M Tris-HCL, 0.15 M NaCl, and 0.05% Tween-20 in water). Positive binding signals were detected following a five-minute incubation with fluorescein tyramide reagent diluted 1:50 in dilution buffer (NEN kit). Cells were washed with TNT, preserved with Vectashield Mounting Media (Vector Labs) diluted 1:5 in TNT, and visualized using an FITC filter on an inverted fluorescent microscope.

Example 7

IL-20RA/RB Receptor-Ig Fusion Heterotetramer

The expression vector pEZE3 was used to express the recombinant IL-20 receptor-Ig fusion protein. The plasmid pEZE3 is derived from pDC312. pDC312 was obtained through license from Immunex Corporation. The plasmids pDC312 and pEZE3 contain an EASE segment as described in WO 97/25420. The presence of the EASE segment in an expression vector can improve expression of recombinant proteins two to eight fold in stable cell pools.

The plasmid pEZE3 is a tricistronic expression vector that may be used to express up to three different proteins in mammalian cells, preferably Chinese Hamster Ovary (CHO) cells. The pEZE3 expression unit contains the cytomegalovirus (CMV) enhancer/promoter, the adenovirus tripartite leader sequence, a multiple cloning site for insertion of the coding region for the first recombinant protein, the poliovirus type 2 internal ribosome entry site, a second multiple cloning site for insertion of the coding region for the second recombinant protein, an encephalomyocarditis virus internal ribosome entry site, a coding segment for mouse dihydrofolate reductase, and the SV40 transcription terminator. In addition, pEZE3 contains an *E. coli* origin of replication and the bacterial beta lactamase gene.

The IL-20 receptor-Ig fusion protein is a disulfide linked heterotetramer consisting of two chains of the extracellular domain of the human IL-20RB fused to the wild type human immunoglobulin kappa light chain constant region and two chains of the human IL-20RA protein extracellular domain fused to a mutated human immunoglobulin gamma 1 constant region. The human immunoglobulin gamma 1 constant region contains amino acid substitutions to reduce FcγRI binding and C1q complement fixation.

The human IL-20RB extracellular domain human immunoglobulin kappa light chain constant region fusion construct was generated by overlap PCR. The IL-20RB coding segment consists of amino acids 1 to 230 of SEQ ID NO:20. The template used for the PCR amplification of the IL-20R segment was generated IL-20RB human kappa light chain constant region expression construct as described herein. Oligonucleotide primers SEQ ID NO: 60 and SEQ ID NO: 61 were used to amplify the IL-20RB segment. The entire wild type human immunoglobulin kappa light chain constant region was used. The template used for the PCR amplification of the wild type human immunoglobulin kappa light chain constant region segment was generated IL-20RB human kappa light chain constant region expression construct as described in Example 12. Oligonucleotide primers SEQ ID NO: 62 and SEQ ID NO: 63 were used to amplify the wild type human immunoglobulin kappa light chain constant region. The two protein coding domains were linked by overlap PCR using oligonucleotides SEQ ID NO: 60 and SEQ ID NO: 63. A (Gly$_4$Ser)$_3$ (SEQ ID NO: 64) peptide linker was inserted between the two protein domains. The (Gly$_4$Ser)$_3$ peptide linker was encoded on the PCR primers SEQ ID NO: 61 and SEQ ID NO:62. The resultant IL-20RB extracellular domain/ kappa light chain constant region fusion construct is shown by SEQ ID NOs: 65 and 66. The predicted mature polypeptide, minus the signal sequence, is SEQ ID NO: 67. The portion of the extracellular domain of IL-20RB that was actually used was comprised of the amino acid sequence of SEQ ID NO: 86. N-terminal sequencing resulted in the predicted amino acid sequence.

The human IL-20RA extracellular domain human immunoglobulin gamma 1 heavy chain constant region fusion construct was generated by overlap PCR of four separate DNA fragments, each generated by separate PCR amplification reactions. The first fragment contained an optimized tPA (tissue plasminogen activator) signal sequence. The tPA signal sequence was amplified using oligonucleotide primers SEQ ID NO: 68 and SEQ ID NO: 69 using an in-house previously generated expression vector as the template. The second fragment contained the IL-20RA extracellular domain-coding region consisting of amino acids 30 to 243 of SEQ ID NO: 14. Oligonucleotide primers SEQ ID NO: 70 and SEQ ID NO: 71 were used to amplify this IL-20RA segment using a previously generated clone of IL-20RA as the template.

The human gamma 1 heavy chain constant region was generated from 2 segments. The first segment containing the C$_H$1 domain was amplified using oligonucleotide primers SEQ ID NO: 72 and SEQ ID NO: 73 using a clone of the wild type human gamma 1 heavy chain constant region as the template. The second segment containing the remaining hinge, C$_H$2, and C$_H$3 domains of the human immunoglobulin gamma 1 heavy chain constant region was generated by PCR amplification using oligonucleotide primers SEQ ID NO: 74 and SEQ ID NO: 75. The template used for this PCR amplification was from a previously generated human gamma 1 Fc construct that contained codons for amino acid substitutions to reduce FcγRI binding and C1q complement fixation as described herein.

The four protein coding domains were linked by overlap PCR using oligonucleotides SEQ ID NO: 68 and SEQ ID NO: 75. A (Gly$_4$Ser)$_3$ peptide linker was inserted between the IL-20RA and CH1 protein domains. The (Gly$_4$Ser)$_3$ peptide linker was encoded on the PCR primers SEQ ID NO: 72 and SEQ ID NO: 71. The IL-20RA extracellular domain/domain human immunoglobulin gamma 1 heavy constant region fusion protein and DNA sequence are shown in SEQ ID NOs: 76 and 77. The predicted mature polypeptide sequence, minus the signal sequence, is SEQ ID NO: 78. The portion of extracellular domain of IL-20RA that was actually used was comprised of SEQ ID NO: 79.

The IL-20RB extracellular domain human immunoglobulin kappa light chain constant region fusion coding segment was cloned into the second MCS while the human IL-20RA extracellular domain human immunoglobulin gamma 1 heavy chain constant region fusion coding segment was cloned into the first MCS of pEZE3. The plasmid was used to transfect CHO cells. The cells were selected in medium without hypoxanthine or thymidine and the transgene was amplified using methotrexate. The presence of protein was assayed by Western blotting using anti human gamma 1 heavy chain constant region and anti human kappa light chain antibodies. N-terminal sequencing revealed that the optimized tPA leader was not completely cleaved. The observed mass indicated that the first residue of the polypeptide sequence to be pyroglutamic acid, and the N-terminal sequence appears to be pyroEEIHAELRRFRRVPCVSGG (SEQ ID NO: 80), the underlined portion being remnants of the tPA leader.

Example 8

Purification of Baculovirus Expressed IL-20RB-TbX-Fc4 Fusion Protein and Recovery of the pDIRS1 Fragment Purification of IL-20RB-TbX-Fc4 Polypeptide from Baculovirus Insect Cell Conditioned Media Unless otherwise noted, all operations were carried out at 4° C., and all liquid chromatography procedures were done via an Applied Biosystems BioCad workstation (Framingham, Mass.). IL-20RB-TbX-Fc4 fusion polypeptide was directly captured from the conditioned media via a conjugated Protein A resin available from Applied Biosystems. The centrifuged and sterile filtered condition media was adjusted to 0.02% w/v sodium azide and chilled to 4° C., then directly loaded onto an appropriate sized and PBS (Gibco/BRL) equilibrated POROS 50 A column, according to the manufacture's specifications. Captured protein was then eluted from the column with a step gradient of 0.1M glycine pH 3.0. Collected fractions were immediately pH neutralized via a predetermined volume of 2M tris pH 8.0 added to the collection tubes, and the fractions of interest were determined via SDS PAGE (Invitrogen, Carlsbad, Calif.) silver staining analysis (Geno Tech. Inc., St. Louis, Mo.). The pooled fractions were sterile filtered and the protein concentration was estimated by an UV absorbance reading of 280 nm. The final material was stored at −80° C. until further processing was initiated.

In order to remove any high molecular weight aggregates or smaller polypeptide contaminants, a size exclusion chromatography was performed on the Protein A captured material. The protein A captured pool was thawed, concentrated against a YM30 30 kD MWCO stirred cell concentrator membrane (Millipore, Bedford, Mass.) to a nominal volume, then loaded onto an appropriately sized Pharmacia sephacryl 200 size exclusion column (Piscataway, N.J.), according to the manufacture's specifications. Fractions of interest were determined via SDS PAGE analysis, pooled, and sterile filtered. The protein concentration was determined via BCA analysis (Pierce, Rockford, Ill.).

Thrombin Activated Enzymatic Digest of the pDIRS-TbX-Fc4 Polypeptide

To separate IL-20RB from the Fc4 portion of the full-length molecule, thrombin was used to promote a sequence specific cleavage at the engineered thrombin cleavage site linker between IL-20RB and Fc4 domains. In addition, the full-length polypeptide was immobilized on a protein A resin prior to the thrombin-activated cleavage to provide purification of IL-20RB from the Fc4. A known amount of the purified full-length polypeptide was added to an appropriate slurry volume of PBS pH 7.2 washed and equilibrated POROS 50 A resin, and allowed to batch absorb overnight with proper mixing. The batch absorption vial was warmed to room temperature, then a predetermined amount (1:100 w/w, enzyme to target) of rhthrombin (ZymoGenetics, Inc) was added to the reaction. The enzymatic process was continued for the predetermined time of 10 minutes at room temperature with proper mixing, and then the slurry was collected into a glass gravity column (Bio-Rad, Hercules, Calif.).

Purification of the Thrombin Liberated IL-20RB Polypeptide Fragment

In order to separate IL-20RB from the thrombin, an ABA resin was used to selectively bind the thrombin out of solution. The eluate and three column volume washes from the post enzymatic reaction slurry were collected on ice, then equilibrated to 0.5 M NaCl & 20 mM tris pH 8.0. An appropriately sized Tosohass TSK-GEL ABA-5PW Guardgel gravity column (Montgomeryville, Pa.) was washed and equilibrated in 0.5 M NaCl & 20 mM tris pH 8.0, according to the manufacture's specifications. Application of the buffer adjusted post enzymatic fractions were applied slowly over the ABA column, and that column's eluates and washes were also collected on ice.

To provide a final separation of IL-20RB from any high molecular weight aggregates or smaller polypeptide contaminants, a size exclusion chromatography was performed. This method also provided a buffer exchange in to the formulation buffer of choice. The collected fractions were pooled then concentrated against a Millipore 5 kD MWCO centrifugal concentrator to a nominal volume. The concentrate was then applied to a PBS pH 7.2 equilibrated Pharmacia superdex 75 size exclusion column. Fractions of interest were determined via SDS PAGE analysis, pooled, sterile filtered, vialed and stored under proper established conditions.

Characterization of IL-20RB

The final product was characterized by the following methods: SDS PAGE analyses (including coomassie stain and Western analysis), BCA, AAA, and N-terminal sequencing. SDS PAGE analyses showed a doublet band with a gel migration of an approximately 25 kD polypeptide. Both AAA and n-terminal sequencing provided evidence of a sample of high purity and a single N-terminus.

Example 9

Up-regulation of Inflammatory Cytokines by IL-20

Cell Treatment

The human keratinocyte cell line, HaCaT was grown at 37° C. to several days post-confluence in T-75 tissue culture flasks. At this point, normal growth media (DMEM+10% FBS) was removed and replaced with serum-free media. Cells were then incubated for two days at 37° C. DMEM was then removed and four flasks of cells per treatment were treated with one of each of the following conditions for four hours at 37° C.: recombinant human (rh) IL-1 alpha at 5 ng/mL, rh IL-1 alpha at 20 ng/mL, rh IL-1 alpha at 5 ng/mL+IL-20 at 1 µg/mL, IL-20 at 1 µg/mL, or rh IL-10 at 10 ng/mL.

RNA Isolation

Following cytokine treatment, media was removed and cells were lysed using a guanidium thiocyanate solution. Total RNA was isolated from the cell lysate by an overnight spin on a cesium chloride gradient. The following day, the RNA pellet was resuspended in a TE/SDS solution and ethanol precipitated. RNA was then quantitated using a spectrophotometer, followed by a DNase treatment as per Section V.B. of Clontech's Atlas™ cDNA Expression Arrays User Manual (version PT3140-1/PR9x390, published Nov. 5, 1999). Quality of RNA samples was verified by purity calculations based on spec readings, and by visualization on agarose gel. Genomic contamination of the RNA samples was ruled out by PCR analysis of the beta-actin gene.

Probe Synthesis

Clontech's protocols for polyA+ enrichment, probe synthesis and hybridization to Atlas™ arrays were followed (see above, plus Atlas™ Pure Total RNA Labeling System User Manual, PT3231-1/PR96157, published Jun. 22, 1999). Briefly, polyA+ RNA was isolated from 50 mg of total RNA using streptavidin coated magnetic beads (by Clontech, Paolo Alto, Calif.) and a magnetic particle separator. PolyA+ RNA was then labeled with $^{alpha 32}$P-dATP via RT-PCR. Clontech CDS primers specific to the 268 genes on the Atlas™ human cytokine/receptor array (Cat. #7744-1) were used in the reaction. Labeled probe was isolated using column chromatography and counted in scintillation fluid.

Array Membrane Hybridization

Atlas™ arrays were pre-hybridized with Clontech ExpressHyb plus 100 mg/mL heat denatured salmon sperm DNA for at least thirty minutes at 68° C. with continuous agitation. Membranes were then hybridized with $1.9 \times 10^6$ CPM/mL (a total of $1.14 \times 10^7$ CPM) overnight at 68° C. with continuous agitation. The following day, membranes were washed for thirty minutes×4 in 2×SSC, 1% SDS at 68° C., plus for thirty minutes×1 in 0.1×SSC, 0.5% SDS at 68° C., followed by one final room temperature wash for five minutes in 2×SSC. Array membranes were then placed in Kodak plastic pouches sealed and exposed to a phosphor imager screen overnight at room temperature. The next day, phosphor screens were scanned on a phosphor imager and analyzed using Clontech's AtlasImage™ 1.0 software.

Genes Up-Regulated by IL-20

1. Tumor necrosis factor (TNF) was up-regulated 1.9-2.4 fold by IL-20.
2. Placental growth factors 1 & 2 (PLGF) were up-regulated 1.9-2.0 fold by IL-20.
3. Coagulating factor II receptor was up-regulated 2.0-2.5 fold by IL-20.
4. Calcitonin receptor was up-regulated 2.2-2.3 fold by IL-20.
5. TNF-inducible hyaluronate-binding protein TSG-6 was up-regulated 2.1-2.2 fold by IL-20.
6. Vascular endothelial growth factor (VEGF) receptor-1 precursor, tyrosine-protein kinase receptor (FLT-1) (SFLT) was up-regulated 2.1-2.7 fold by IL-20.
7. MRP-8 (calcium binding protein in macrophages MIF-related) was up-regulated 2.9-4.1 fold by IL-20.
8. MRP-14 (calcium binding protein in macrophages MIF-related) was up-regulated 3.0-3.8 fold by IL-20.
9. Relaxin H2 was up-regulated 3.14 fold by IL-20.
10. Transforming growth factor beta (TGFβ) receptor III 300 kDa was up-regulated 2.4-3.6 fold by IL-20.

Genes Showing Synergy with IL-20+IL-1 Treatment

1. Bone morphogenic protein 2a was up-regulated 1.8 fold with IL-20 treatment alone, 2.5 fold with IL-1 treatment alone, and 8.2 fold with both IL-20 and IL-1 treatment together.
2. MRP-8 was up-regulated 2.9 fold with IL-20 treatment alone, 10.7 fold with IL-1 treatment alone and 18.0 fold with both IL-20 and IL-1 treatment together.
3. Erythroid differentiation protein (EDF) was up-regulated 1.9 fold with IL-20 treatment alone, 9.7 fold with IL-1 treatment alone and 19.0 fold with both IL-20 and IL-1 treatment together.
4. MRP-14 (calcium binding protein in macrophages, MIF related) was up-regulated 3.0 fold with IL-20 treatment alone, 12.2 fold with IL-1 treatment alone and 20.3 fold with both IL-20 and IL-1 treatment together.
5. Heparin-binding EGF-like growth factor was up-regulated 2.0 fold with IL-20 treatment alone, 14 fold with IL-1 treatment alone and 25.0 fold with both IL-20 and IL-1 treatment together.

6. Beta-thromboglobulin-like protein was up-regulated 1.5 fold with IL-20 treatment alone, 15 fold with IL-1 treatment alone and 27 fold with both IL-20 and IL-1 treatment together.
7. Brain-derived neurotrophic factor (BDNF) was up-regulated 1.7 fold with IL-20 treatment alone, 25 fold with IL-1 treatment alone and 48 fold with both IL-20 and IL-1 treatment together.
8. Monocyte chemotactic and activating factor MCAF was up-regulated 1.3 fold with IL-20 treatment alone, 32 fold with IL-1 treatment alone and 56 fold with both IL-20 and IL-1 treatment together.

Example 10

Specificity and Affinity of IL-20 for its Receptor

The specificity and affinity of IL-20 for its receptor was determined using BHK cells stably transfected with IL-20RA, IL-20RB or both receptor subunits. Binding assays using radiolabeled ligand demonstrated that IL-20 bound to BHK transfectants expressing both IL-20RA and IL-20RB but not to untransfected cells nor to transfectants expressing either receptor subunit alone. Binding of $^{125}$I-labeled IL-20 was eliminated in the presence of 100-fold excess of unlabeled IL-20 but not with 100-fold excess of the unrelated cytokine, IL-21. The binding affinity (kD) of IL-20 to the IL-20RA/IL-20RB heterodimeric receptor was determined to be approximately 1.5 nM.

Example 11

IL-20 Receptor Activation

To determine if IL-20 binding leads to receptor activation, the factor-dependent pre-B cell line BaF3 was co-transfected with IL-20RA and IL-20RB and treated with IL-20 at various concentrations. IL-20 stimulated proliferation in a dose-dependent manner and gave a detectable signal at 1.1 pM, with a half maximal response at 3.4 pM. We note that the IL-20 concentration for the half maximal proliferative response in BaF3 cells is 1000× lower than that for half maximal binding affinity in BHK cells. Possible explanations for this large difference include the use of different cell lines, different receptor expression levels and different assay outputs. IL-20 also stimulated signal transduction in the biologically relevant human keratinocyte cell line HaCaT, which naturally expresses IL-20RA and IL-20RB. Therefore, IL-20 binds and activates the heterodimeric IL-20RA/IL-20RB receptor at concentrations expected for a cytokine. While the negative controls containing untransfected BaF3.

Example 12

Expression Analysis of IL-20RA and IL-20RB

RT-PCR analysis was performed on a variety of human tissues to determine the expression pattern of IL-20RA and IL-20RB. Both receptor subunits are most highly expressed in skin and testis. The significant result is that IL-20RA and IL-20RB are both expressed in skin, where they have been shown to mediate the IL-20-induced response. Both IL-20RA and IL-20RB are also both expressed in monocytes, lung, ovary, muscle, testis, adrenal gland, heart, salivary gland and placenta. IL-20RA is also in brain, kidney, liver, colon, small intestine, stomach, thyroid, pancreas, uterus and prostate while IL-20RB is not.

Example 13

IL-20 is Upregulated in Human Psoriatic Skin Samples

RNA Samples

Normal skin samples as well as skin from psoriasis patients were obtained. The latter included involved skin from psoriasis and from adjacent uninvolved skin. RNA was isolated from human skin samples using conventional methods. The integrity and quality of RNA samples was tested on the Agilent 2100 Bioanalyzer (Agilent Technologies, Waldbronn Germany).

Primers and Probes for Quantitative RT-PCR-

Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U. E. M. et al., *Genome Research* 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by the 5' to 3' nucleolytic activity of the rTth DNA Polymerase which releases the reporter dye from the probe resulting in an increase in fluorescent emission.

The primers and probes used for real-time quantitative RT-PCR analyses of IL-20 expression were designed using the primer design software Primer Express™ (PE Applied Biosystems, Foster City, Calif.). The forward primer, ZC40541 (SEQ ID NO:87) and the reverse primer, ZC 40542 (SEQ ID NO:88) were used in a PCR reaction (below) at a 800 nM concentration to synthesize a 71 bp product. The corresponding IL-20 TaqMan® probe, ZC 40544 (SEQ ID NO:89) was synthesized and labeled by PE Applied Biosystems. The IL-20 probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems).

Real-Time Quantitative RT-PCR

Relative levels of IL-20 mRNA were determined by analyzing total RNA samples using the TAQMAN® EZ RT-PCR Core Reagents Kit (PE Applied Biosystems). Runoff IL-20 transcript was made to generate a standard curve used for quantitation. The curve consisted of 10-fold serial dilutions ranging from 1e8 to 1e3 total copies of whole message for IL-20 with each standard curve point analyzed in triplicate. The total RNA samples from skin were also analyzed in triplicate for human IL-20 transcript levels and for levels of hGUS as an endogenous control. In a total volume of 25 µl, each RNA sample was subjected to TAQMAN® EZ RT-PCR reaction (PE Applied Biosystems) containing: approximately 25 ng of total RNA in DEPC treated water (Dnase/Rnase free); appropriate primers (approximately 800 nM ZC40541 (SEQ ID NO:87) and ZC40542 (SEQ ID NO:88); appropriate probe (approximately 100 nM ZC40544 (SEQ ID NO:89); 1× TAQMAN® EZ Buffer; 3 mM Manganese acetate; 300 µM each d-CTP, d-ATP, and d-GTP and 600 µM of d-UTP; rTth DNA Polymerase (0.1 U/µl); and AMPERASE® UNG (0.01 U/µl). PCR thermal cycling conditions were as follows: an initial UNG treatment step of one cycle at 50° C. for 2 minutes; followed by a reverse transcription (RT) step of one cycle at 60° C. for 30 minutes; followed by a deactivation of UNG step of one cycle at 95° C. for 5 minutes; followed by 40 cycles of amplification at 94° C. for 20 seconds and 60° C. for 1 minute.

Relative IL-20 RNA levels were determined by using the Standard Curve Method as described by the manufacturer, PE Biosystems (User Bulletin #2: ABI Prism 7700 Sequence Detection System, Relative Quantitation of Gene Expression, Dec. 11, 1997). The hGUS measurements were used to normalize IL-20 levels. Data are shown in Table 4 below.

TABLE 4

| Skin Sample | IL-20 |
|---|---|
| Normal | 2903 |
| Uninvolved | 7233 |
| Involved | 27,695 |

IL-20 mRNA was detectable in skin samples from normal patients or from uninvolved areas. In contrast, there was upregulation for IL-20 message in involved skin from psoriasis patients. IL-20RA and IL-20RB are expressed in human normal and diseased skin. These data support a strong disease association for IL-20 to human psoriasis.

Overexpression of IL-20 was shown in human psoriatic lesions, suggesting that IL-20 is involved in human psoriasis. Moreover, as described herein, over expression of IL-20 in transgenic mice showed epidermal thickening and immune cell involvement indicative of a psoriatic phenotype. Such in vivo data further suggests that IL-20 is involved in psoriasis. As such, antagonists to IL-20 activity, such as the anti-human-IL-20, anti-human-IL-20RA and anti-human-IL-20RB monoclonal antibodies of the present invention, as well as soluble receptors and antibodies thereto, are useful therapeutically as antagonists to IL-20 in the treatment of inflammatory diseases, such as psoriasis, as well as other indications as disclosed herein.

Example 14

IL-20RA and IL-20RB mRNA are Up-Regulated in Psoriasis

In situ hybridization was used to determine whether IL-20 receptor expression is altered in psoriasis. Skin samples from four psoriasis patients and three unaffected patients were assayed with probes specific for the two-receptor subunit mRNAs. All four psoriatic skin samples had high levels of IL-20RA and IL-20RB mRNA in keratinocytes whereas normal skin samples did not have detectable levels of either receptor subunit mRNA. Positive signals in psoriatic skin were also observed in mononuclear immune cells and in endothelial cells in a subset of vessels. Therefore, both IL-20RA and IL-20RB are expressed in keratinocytes, immune cells and endothelial cells, the major cell types thought to interact in psoriasis.

Example 15

IL-20 Binding Activates STAT3 in the HaCaT Keratinocyte Cell Line

IL-20 binds cell lines transfected with both subunits of its receptor (i.e. IL-20RA and IL-20RB). However, these cell lines overexpress the IL-20 receptor relative to its normal level and their relevance to the physiological role of IL-20 is unclear. The human HaCaT keratinocyte cell line, which expresses endogenous IL-20RA and IL-20RB was used to examine IL-20 signal transduction in a biologically relevant cell type. HaCaT cells were infected with recombinant adenovirus containing a reporter construct to allow detection of intracellular signaling. The construct consists of the firefly luciferase gene driven by promoter/enhancer sequences comprised of the serum response element (SRE) and signal transducers and activators of transduction elements (STATs). This assay system detects productive ligand-receptor interactions and indicates possible downstream signal transduction components involved in receptor activation. Treatment with IL-20 alone resulted in a dose-dependent increase in luciferase activity with a half maximal response occurring at approximately 2.3 nM. Subsequent luciferase reporter assays using adenovirus vectors containing only the SRE element or only the STAT elements produced detectable reporter activation only through STATs.

To determine if other cytokines act in concert with IL-20, HaCaT cells were treated with IL-20 alone or in combination with a single submaximal dose of EGF, IL-1$\beta$, or TNF$\alpha$. In the presence of each of these three proteins, IL-20 treatment resulted in a dose-dependent increase in luciferase activity. IL-20 in combination with IL-1$\beta$ results in a half-maximal response at approximately 0.5 nM, about five-fold lower than with IL-20 alone. In addition, activation of the reporter gene is detectable at 0.1 nM IL-20, a dose that is at least tenfold lower than the IL-20 dose required alone.

BHK cells transfected with IL-20RA, IL-20RB or both receptor subunits were used to determine whether receptor pairing was required for IL-20 stimulation of STAT-luciferase. As was the case with binding assays, only cells transfected with both receptor subunits responded to IL-20 and did so with a half-maximal response of 5.7 pM. We note that the IL-20 concentration for the half-maximal response in BHK cells is 400-fold lower than that for half-maximal response in HaCaT cells. It is likely that a lower concentration of IL-20 is needed for half-maximal response in BHK cells, as compared to HaCaT cells, due to higher receptor levels in the BHK IL-20 receptor transfectants.

A nuclear translocation assay was used to identify STAT proteins involved in IL-20 action. Both HaCaT cells, with endogenous IL-20 receptors, and BHK cells transfected with IL-20RA and IL-20RB, were treated with IL-20 protein and translocation of STAT3 and STAT1 transcription factors from the cytoplasm to the nucleus was assayed by immunofluorescence.

In unstimulated HaCaT cells, STAT3 staining was predominantly in the cytosol. Treatment of HaCaT cells with IL-20 resulted in a distinct accumulation of STAT3 in the nucleus. Nuclear translocation of STAT3 in response to increasing concentrations of IL-20 occurred with a half-maximal IL-20 concentration of 7 nM. In contrast to STAT3 translocation, HaCaT cells treated with IL-20 did not show any detectable nuclear accumulation of STAT1.

BHK cells transfected with IL-20RA and IL-20RB were used to confirm that the IL-20 receptor was required for IL-20 stimulation of STAT3 nuclear translocation. In BHK cells lacking the IL-20 receptor, STAT3 remained cytosolic following treatment with IL-20. In contrast, in BHK cells transfected with the IL-20 receptor, STAT3 translocated to the nucleus in response to IL-20. Again, STAT1 remained cytosolic regardless of IL-20 treatment or IL-20 receptor expression. Thus, the IL-20 receptor is required for IL-20-mediated STAT3 activation.

Example 16

IL-20 Transgenic Phenotype

Both human and mouse IL-20 were overexpressed in transgenic mice using a variety of promoters. The liver-specific mouse albumin promoter, directing expression of human IL-20, was used initially in an attempt to achieve circulating levels of protein. Subsequent studies were conducted using the keratin 14 (K14) promoter, which primarily targets expression to the epidermis and other stratified squamous epithelia; the mouse metallothionein-1 promoter, which gives a broad expression pattern; and the E☐LCK promoter, which drives expression in cells of the lymphoid lineage. Similar results were obtained in all four cases, possibly because these promoters all give rise to circulating levels of IL-20.

In all cases, transgenic pups expressing the IL-20 transgene were smaller than non-transgenic littermates, had a shiny appearance with tight, wrinkled skin and died within the first few days after birth. Pups had milk in their stomachs indicating that they were able to suckle. These mice had swollen extremities, tail, nostril and mouth regions and had difficulty moving. In addition, the mice were frail, lacked visible adipose tissue and had delayed ear and toe development. Low expression levels in liver (less than 100 mRNA molecules/cell) were sufficient for both the neonatal lethality and skin abnormalities. Transgenic mice without a visible phenotype either did not express the transgene, did not express it at detectable levels, or were mosaic.

Histologic analysis of the skin of the IL-20 transgenic mice showed a thickened epidermis, hyperkeratosis and a compact stratum corneum compared to non-transgenic littermates. Serocellular crusts (scabs) were observed occasionally. Electron microscopic (EM) analysis of skin from transgenic mice showed intramitochondrial lipid inclusions, mottled keratohyaline granules, and relatively few tonofilaments similar to that observed in human psoriatic skin and in mouse skin disease models. In addition, many of the transgenic mice had apoptotic thymic lymphocytes. No other abnormalities were detected by histopathological analysis. These histological and EM results support and extend the observed gross skin alterations.

Example 17

Anti-Human IL-20 Polyclonal Antibodies

Polyclonal antibodies were prepared by immunizing 2 female New Zealand white rabbits with the peptide, human IL-20×1-2 (cgeeamkkyeqilshfeklepqaavvkalgeldillqw) (SEQ ID NO: 90) or the purified mature recombinant human polypeptide (SEQ ID NO:3) produced in BKH cells, human IL-20-BHK. The peptide was synthesized using an Applied Biosystems Model 431A peptide synthesizer (Applied Biosystems, Inc., Foster City, Calif.) according to manufacturer's instructions. The synthetic peptide human IL-20×1-2 was then conjugated to the carrier protein maleimide-activated keyhole limpet hemocyanin (KLH) through the terminal cysteine residue (Pierce, Rockford, Ill.). The rabbits were each given an initial intraperitoneal (ip) injection of 200 µg of the conjugated synthetic peptide human IL-20×1-2 or the purified mature recombinant polypeptide human IL-20-BHK in Complete Freund's Adjuvant followed by matched booster ip injections of 100 µg of the conjugated peptide or the mature polypeptide in Incomplete Freund's Adjuvant every three weeks. Seven to ten days after the administration of the second booster injection (3 total injections), the animals were bled and the serum was collected. The animals were then boosted and bled every three weeks.

The human IL-20×1-2 peptide-specific and human IL-20-BHK polypeptide-specific rabbit sera were characterized by ELISA using 1 µg/ml of the peptide human IL-20×1-2 or 500 ng/ml of the polypeptide human IL-20-BHK as specific antibody targets. The 4 rabbit serum samples had titer to their specific antibody targets at a dilution of 1:5 E6 (1:5,000,000).

The human IL-20×1-2 peptide-specific polyclonal antibodies were affinity purified from appropriately pooled immune rabbit serum using an EPOXY-SEPHAROSE 6B peptide column (Pharmacia LKB) that was prepared using 10 mg of the synthetic peptide human IL-20×1-2 per gram of EPOXY-SEPHAROSE 6B. The human IL-20 polypeptide-specific polyclonal antibodies were affinity purified from appropriately pooled immune rabbit serum using a CNBr-SEPHAROSE 4B protein column (Pharmacia LKB) that was prepared using 10 mg of the purified mature recombinant human polypeptide produced in *E. coli*, human IL-20-*E. coli* per gram of CNBr-SEPHAROSE. Following purification, the resulting polyclonal antibodies were dialyzed against 4 changes of 20 times the antibody volume of PBS over a time period of at least 8 hours.

Human IL-20×1-2 peptide and human IL-20 polypeptide-specific polyclonal antibodies were characterized by ELISA using 1 µg/ml of the synthetic peptide human IL-20×1-2 or 500 ng/ml of the purified recombinant polypeptides, human IL-20-BHK, human IL-20-Bv, or human IL-20-*E. coli* as antibody targets. The human IL-20×1-2 peptide-specific polyclonal antibodies exhibited lower limits of detection (LLDs) of 100 pg/ml and 500 pg/ml to its specific antigen human IL-20×1-2 and the polypeptide human IL-20-BHK, respectively. The human IL-20 polypeptide-specific polyclonal antibodies exhibited LLDs of 100 pg/ml on the antigen targets human IL-20-BHK, human IL-20-Bv, and human IL-20-*E. coli*.

The human IL-20 polypeptide-specific affinity purified polyclonal antibodies were characterized further for their ability to block the cell-proliferative activity ("neutralization assay") of purified recombinant human IL-20 on BaF3/IL-20RA/IL-20RB cells. A 100× molar excess of the human IL-20 polypeptide-specific polyclonal antibodies was sufficient to inhibit cell proliferation.

The human IL-20 polypeptide-specific affinity purified polyclonal antibodies were characterized for their utility in an ELISA for the quantitative determination of the recombinant mature polypeptides human IL-20-BHK, human IL-20-Bv, or human IL-20-*E. coli* in mouse and human serum samples. The resulting ELISA exhibited a lower limit of detection of 1 ng/ml in 100% normal mouse serum and 5 ng/ml in 100% human serum for all three forms of recombinant mature polypeptide human IL-20.

Example 18

Construction of BaF3 Cells Expressing the KZ134 Plasmid and IL-20RA and IL-20RB Subunits BaF3 cells expressing the KZ134 plasmid were constructed as described below and designated BaF3/KZ134. These cells were used as a control and further transfected with full length IL-20RB (SEQ ID NO:20) as described below. The BaF3/KZ134 cells expressing the IL-20RB were designated as BaF3/KZ134/IL-20RB. These cells were used as a control and further transfected with full length IL-20RA (SEQ ID NO:13) as described below. The BaF3/KZ134/IL-20RB cells expressing the IL-20RA were designated as BaF3/KZ134/IL-20RA/IL-20RB.

Construction of BaF3 Cells Expressing the KZ134 Plasmid
BaF3, an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol.* 6: 4133-4135, 1986), was maintained in complete media (RPMI 1640 medium (JRH Bioscience Inc., Lenexa, Kans.) supplemented with 10% heat-inactivated fetal bovine serum, 1 ng/ml murine IL-3 (mIL-3) (R & D, Minneapolis, Minn.), 2 mM L-Glutamine (Gibco BRL), 1 mM Sodium Pyruvate (Gibco BRL), and PSN antibiotics (Gibco BRL)). The KZ134 plasmid is constructed with complementary oligonucleotides ZC12,749 (gtaccttcccgtaaatccctccccttc-ccggaattacacccgcgtatttcccagaa aaggaactgtagatttctaggaat-tcaatccttggccacgcgtc) and ZC12,748 (tcgagacgcgtggccaaggat tgaattcctagaaatctacagttc-cttttctgggaaatacgcgggtgta attccgggaaggggagggatttacgggaag) that contain STAT transcription factor binding elements from 4 genes. A modified c-fos S is inducible element (m67SIE, or hSIE) (Sadowski, H. et al., *Science* 261:1739-1744, 1993), the p21 SIE1 form the p21 WAF1 gene (Chin, Y. et al., *Science* 272:719-722, 1996), the mammary gland response element of the β-casein gene (Schmitt-Ney, M. et al., *Mol. Cell. Biol.* 11:3745-3755, 1991), and a STAT inducible element of the Fcg RI gene (Seidel, H. et al., *Proc. Natl. Acad. Sci.* 92:3041-3045, 1995). These oligonucleotides contain Asp718-XhoI compatible ends and are ligated, using standard methods, into a recipient firefly luciferase reporter vector with a c-fos promoter (Poulsen, L. K. et al., *J. Biol. Chem.* 273:6229-6232, 1998) digested with the same enzymes and containing a neomycin selectable marker. The KZ134 plasmid is used to stably transfect BaF3 cells, using standard transfection and selection methods (as describe below) with 500 µg/ml neomycin, to make the BaF3/KZ134 cell line.

Construction of BaF3/KZ134 Cells Expressing the IL-20RB

The full-length cDNA sequence of IL-20RB (SEQ ID NO:20) was isolated from a cDNA library, and then cloned into an expression vector pZP7P. Prior to electroporation, IL-20RB/pZP7P was prepared and purified using a Qiagen Maxi Prep kit (Qiagen) as per manufacturer's instructions. For electroporation, BaF3/KZ134 cells were washed once in serum-free RPMI media and then resuspended in serum-free RPMI media at a cell density of $10^7$ cells/ml. One ml of resuspended BaF3/KZ134 cells was mixed with 30 µg of the IL-20RB/pZP7P plasmid DNA and transferred to separate disposable electroporation chambers (GIBCO BRL). Following a 15-minute incubation at room temperature the cells were given two serial shocks (800 lFad/300 V.; 1180 lFad/300 V.) delivered by an electroporation apparatus (CELL-PORATOR™; GIBCO BRL). After a 5-minute recovery time, the electroporated cells were transferred to 50 ml of complete media and placed in an incubator for 15-24 hours at 37° C. and 5% $CO_2$. The cells were then spun down and resuspended in 50 ml of complete media containing 500 µg/ml neomycin and 2 µg/ml puromycin in a T-162 flask to isolate the puromycin-resistant pool. Pools of the transfected BaF3/KZ134 cells, hereinafter called BaF3/KZ134/IL-20RB, were assayed for signaling capability as described below. Moreover these cells were further transfected with IL-20RA as described below. BaF3/KZ134/IL-20RA cells were also made as described above.

Construction of BaF3/KZ134/IL-20RB Cells Expressing the IL-20RA

BaF3/KZ134/IL-20RB cells expressing the full-length IL-20RA (SEQ ID NO:14) were constructed as per above, using 30 µg of a IL-20RA/pZP7Z expression vector. Following recovery, transfectants were selected using 500 µg/ml neomycin, 2 µg/ml puromycin, and 200 µg/ml zeocin to isolate the zeocin-resistant pool. Pools of the transfected BaF3/KZ134/IL-20RB cells were diluted and plated out using standard techniques. Individual clones were screened by luciferase assay described in U.S. Ser. No. 09/745,792, Example 13, which is incorporated herein in its entirety, using purified recombinant human IL-20×1-Bv as an inducer. Clones with the highest luciferase response (via STAT luciferase) and the lowest background were selected. Hereinafter the transfected cell line is called BaF3/KZ134/IL-20RA/IL-20RB.

Similarly, a BHK cell line was also constructed using the method described herein, and can be used in luciferase assay described above. The cell line is called BHK/KZ134/IL-20RA/IL-20RB.

Example 19

Screening for IL-20 Activity Using BaF3/KZ134/IL-20RA/IL-20RB Proliferation Assay Purified recombinant human IL-20×1-Bv was used to test for the presence of proliferative activity as described below. BaF3/KZ134/IL-20RA/IL-20RB cells were spun down and washed in BaF3 assay media (RPMI 1640 medium (JRH Bioscience Inc., Lenexa, Kans.) supplemented with 10% heat-inactivated fetal bovine serum, 2 mM L-Glutamine (Gibco BRL), 1 mM Sodium Pyruvate (Gibco BRL), and PSN antibiotics (Gibco BRL); without mIL-3 and neomycin, puromycin, and zeocin selection (hereinafter referred to as BaF3 assay media)). The cells were spun down and washed 3 times in BaF3 assay media to ensure the removal of the mIL-3. BaF3/KZ134/IL-20RA/IL-20RB cells were then counted and plated out in 96-well format at 5000 cells per well in 100 µl of BaF3 assay media. Serial dilutions of IL-20 ranging from 1 pM to 1 nM were added to the BaF3/KZ134/IL-20RA/IL-20RB cells in 100 µl of BaF3 assay media. Total assay volume is 200 µl per well. The assay plates were incubated at 37° C. and 5% $CO_2$ for 72 hours at which time Alamar Blue (Accumed, Chicago, Ill.) was added at 20 µl per well. Plates were again incubated at 37° C. and 5% $CO_2$ for 24 hours. Alamar Blue gives a fluourometric readout based on the number of live cells, and is thus a direct measurement of cell proliferation in comparison to a negative control (BaF3 assay media alone). Plates were read on the Fmax™ plate reader (Molecular Devices, Sunnyvale, Calif.) using the Softmax™ Pro program at wavelengths 544 nm excitation and 590 nm emission. Results confirmed the dose dependent proliferative response of the BaF3/KZ134/IL-20RA/IL-20RB cells to IL-20. The response, as measured, was approximately 30-fold over background at the high end of 1 nM down to a 2-fold over background at the low end of 1 pM. The BaF3/KZ134 parental cells, the BaF3/KZ134/IL-20RA only cells, and the BaF3/KZ134/IL-20RB only cells did not proliferate in response to IL-20, showing that IL-20 is specific for the IL-20RA/IL-20RB heterodimeric receptor. The BaF3/KZ134/IL-20RA/IL-20RB alamar blue proliferation assay can also be used to look for antagonists to IL-20, by measuring the abstinence of the cell-proliferative response of IL-20 when run in combination with antagonists ("neutralization assay").

Example 20

Anti-Human IL-20 Monoclonal Antibodies

Rat monoclonal antibodies were prepared by immunizing 4 female Sprague-Dawley Rats (Charles River Laboratories, Wilmington, Mass.), with the purified mature recombinant polypeptide (SEQ ID NO:3) produced in Baculovirus, human IL-20-Bv. The rats were each given an initial intraperitoneal (IP) injection of 25 µg of the purified recombinant polypeptide in Complete Freund's Adjuvant (Pierce, Rockford, Ill.)

followed by booster IP injections of 10 μg of the purified recombinant polypeptide in Incomplete Freund's Adjuvant every two weeks. Seven days after the administration of the second booster injection, the animals were bled and serum was collected.

The human IL-20-specific rat serum samples were characterized by ELISA using 1 ug/ml of the purified mature recombinant polypeptide human IL-20-Bv as the specific antibody target. Three rat serum samples had titer to the specific antibody target at a dilution of 1:1E6. One rat serum sample had titer to the specific antibody target at a dilution of 1:1E4.

Splenocytes were harvested from a single high-titer rat and fused to SP2/0 (mouse) myeloma cells using PEG 1500 in a single fusion procedure (4:1 fusion ratio, splenocytes to myeloma cells, "Antibodies: A Laboratory Manual., E. Harlow and D. Lane, Cold Spring Harbor Press). Following 9 days growth post-fusion, specific antibody-producing hybridoma pools were identified by radioimmunoprecipitation (RIP) using the Iodine-125 labeled recombinant polypeptide human IL-20-Bv as the specific antibody target and by ELISA using 500 ng/ml of the recombinant polypeptide human IL-20-Bv as the specific antibody target. Hybridoma pools positive in either assay protocol were analyzed further for their ability to block the cell-proliferative activity ("neutralization assay") of purified recombinant polypeptide human IL-20-Bv on Baf3/IL-20RA/IL-20RB cells.

Hybridoma pools yielding positive results by RIP only or RIP and the "neutralization assay" were cloned at least two times by limiting dilution.

Monoclonal antibodies purified from tissue culture media were characterized for their ability to block the cell-proliferative activity ("neutralization assay") of purified recombinant human IL-20 on Baf3 cells expressing both receptor sequences human IL-20RA and human IL-20RB. Three "neutralizing" monoclonal antibodies were identified in this manner.

Hybridomas expressing the neutralizing monoclonal antibodies to human IL-20 described above were deposited on Jul. 30, 2003 with the American Type Tissue Culture Collection (ATCC; P.O. Box 1549, Manassas Va. 20108) patent depositary as original deposits under the Budapest Treaty and were given the following ATCC Accession Nos: 262.4.1.2.2.1 (ATCC [PTA-5350]); 262.5.1.6.4.4 (ATCC [PTA-5351]); 262.7.1.3.2.4 (ATCC [PTA-5352]).

Example 21

Screening for IL-20 Antagonist Activity using BaF3/KZ134/IL-20RA/IL-20RB Proliferation Assay In order to determine if rat anti-human IL-20 monoclonal antibodies are capable of antagonizing purified recombinant human IL-20×1-Bv, hybridoma pools positive in the RIP assay were analyzed further for their ability to block the cell-proliferative activity ("neutralization assay") of IL-20 on BaF3/KZ134/IL-20RA/IL-20RB cells (Example 18).

Monoclonal antibodies purified from tissue culture media were characterized for their ability to block the cell-proliferative activity ("neutralization assay") of purified recombinant human IL-20×1-E. coli on BaF3/KZ134/IL-20RA/IL-20RB cells. Results are given as $EC_{50}$ and $EC_{100}$ values in Table 5 below.

TABLE 5

| Rat anti-human IL-20 Monoclonal Antibody | $EC_{50}$ | $EC_{100}$ |
| --- | --- | --- |
| 262.4.1.2.2.1 | 0.34 nM | 1 nM |
| 262.5.1.6.4.4 | 2.54 nM | 10 nM |
| 262.7.1.3.2.4 | 0.19 nM | 0.3 nM |

$EC_{50}$ (effective concentration at 50 percent)
$EC_{100}$ (effective concentration at 100 percent)

Example 22

Determining the Binding Affinity ($K_d$) for the Rat Anti-Human IL-20 Monoclonal Antibodies to IL-20

Preparation of $^{125}$I-IL-20. Radiolabeled purified recombinant human IL-20×1-E. coli was prepared with Iodo-Beads® Iodination Reagent (Pierce) according to manufacturer's instructions. Twenty μg of IL-20 was radiolabeled to specific activities of 45,000 to 137,000 counts per minute per nano gram with 95 to 100 percent of the radioactivity precipitating with 10 percent TCA. Bioactivity of each preparation of $^{125}$I-IL-20 was measured using BHK/KZ134/IL-20RA/IL-20RB cells for luciferase response (via STAT luciferase) (U.S. Ser. No. 09/745,792). There was no significant differences in bioactivities of the 1251 labeled IL-20 and unlabeled IL-20.

Binding of $^{125}$I-IL-20 to the rat anti-human IL-20 monoclonal antibodies (Example 20). BreakApart Module 96 well micro titer plates (NUNC Brand Products, Roskilde Denmark) were coated overnight at 4° C. with the rat anti-human IL-20 monoclonal antibodies at a 2 nM concentration in 100 μl per well of ELISA A (0.1M Sodium Carbonate Buffer, pH 9.6). Two nM coating concentration of antibody was optimized for assay conditions. Plates were washed two times using automated plate washer (SLT 96PW), 300 μl per well with ELISA C (0.05% Tween 20/1× Phosphate Buffered Saline). Plates were blocked for 5 minutes with 200 μl per well SuperBlock® Blocking Buffer (Pierce), repeated. Plates were washed as described above using automated plate washer. Binding was performed at 37° C. with shaking for 3.0 hours using serial dilutions of $^{125}$I-IL-20 ranging from 3.3 pM to 2 nM concentration in 100 μl per well of ELISA B (1% Bovine Serum Albumin Fraction IV/0.05% Tween 20/1× Phosphate Buffered Saline). Specific binding was determined in the presence (nonspecific binding) and absence (total binding) of unlabeled IL-20 at 2 μM concentration. Three hour time point, serial dilutions of $^{125}$I-IL-20, and 2 μM unlabeled IL-20 concentration, were all optimized for assay conditions. Binding reactions were terminated by removal of the binding medium and washing of the plates manually four times with 200 μl per well of ELISA C. Plates were then broken apart and individual wells read on a gamma counter (Packard, Meriden, Conn.) for counts per minute incorporated.

For all three rat anti-human IL-20 monoclonal antibodies, specific binding curves were generated using GraphPad Prism® (GraphPad Software Inc., San Diego, Calif.). The specific binding data was directly fitted using non-linear regression to evaluate the $K_d$ of $^{125}$I-IL-20 to each of the rat anti-hu-IL-20 monoclonal antibodies, as shown in Table 6 below.

TABLE 6

| Rat anti-human IL-20 Monoclonal Antibody | $K_d$ of $^{125}$I-IL-20 |
|---|---|
| 262.4.1.2.2.1 | 0.074 nM |
| 262.5.1.6.4.4 | 0.274 nM |
| 262.7.1.3.2.4 | 0.128 nM |

Example 23

Human IL-20RA Monoclonal Antibodies

Mouse monoclonal antibodies were prepared by immunizing 5 female Balb C mice (Charles River Laboratories, Wilmington, Mass.), with the purified recombinant protein, IL-20RA-BHK. The mice were each given an initial intraperitoneal (IP) injection of 20 µg of the purified recombinant protein in Complete Freund's Adjuvant (Pierce, Rockford, Ill.) followed by booster IP injections of 10 µg of the purified recombinant protein in Incomplete Freund's Adjuvant every two weeks. Five days after the administration of the second booster injection, the animals were bled and serum was collected.

The IL-20RA-specific mouse sera samples were characterized by ELISA using 500 ng/ml of the purified recombinant protein IL-20RA/RB Receptor-Ig Fusion heterodimer as specific antibody target. All 5 mouse serum samples had titer by ELISA to the specific antibody target at a dilution of 1:1 E6.

Splenocytes and lymph nodes were harvested from two high-titer mice and fused to the P3-X63-Ag8.653 mouse myeloma cell line in a single fusion procedure (2.3:1 fusion ratio, Hope Heart Institute Contract Antibody Development, Journal of Immunological Methods 81, 223-228). Following 9 or 10 days growth post-fusion, specific antibody-producing hybridoma pools were identified by ELISA using 1 µg/ml of the purified recombinant protein IL-20RA Receptor-Ig Fusion homodimer as the specific antibody target. IL-20RA-specific hybridoma pools were analyzed further by ELISA using 1 µg/ml of the purified recombinant protein IL-20RA/IL-20RB Receptor-Ig Fusion heterodimer and by FACS for their ability to bind to Baf3/KZ55/IL-20RA/IL-20RB cells.

Hybridoma pools yielding positive results by the ELISA and the FACS assay were analyzed for their ability to block the cell-proliferative activity ('neutralization assay') of the purified recombinant protein human IL-20-Bv on Baf3/KZ55/IL-20RA/IL-20RB cells. One 'neutralizing' hybridoma pool was identified in this manner.

Hybridoma pools yielding positive results by the ELISA and FACS assays were cloned at least two times by limiting dilution.

Monoclonal antibodies purified from tissue culture media were characterized by FACS for their ability to bind to human monocytic cell lines THP-1 ATCC#TIB-202, HL-60, and U937 and to human monocytes in blood. One positive-binding monoclonal antibody was identified and isolated.

Example 24

Human IL-20RB Polyclonal Antibodies

Anti IL-20RB polyclonal antibodies were prepared by immunizing 2 female New Zealand white rabbits with the purified mature recombinant human IL-20RB receptor-Ig fusion homodimer. The rabbits were each given an initial intraperitoneal (ip) injection of 200 µg of purified protein in Complete Freund's Adjuvant followed by booster IP injections of 100 µg peptide in Incomplete Freund's Adjuvant every three weeks. Seven to ten days after the administration of the second booster injection (3 total injections), the animals were bled and the serum was collected. The animals were then boosted and bled every three weeks.

The human IL-20RA-specific polyclonal antibodies were affinity purified from the immune rabbit serum using a CNBr-SEPHAROSE 4B protein column (Pharmacia LKB) that was prepared using 10 mg of the specific antigen thrombin-cleaved and purified recombinant human IL-20RB receptor-Ig fusion homodimer per gram of CNBr-SEPHAROSE. Following purification, the polyclonal antibodies were dialyzed with 4 changes of 20× the antibody volume of PBS over a period of at least 8 hours. Human IL-20RB-specific antibodies were characterized by ELISA using 500 ng/ml of the purified recombinant protein human IL-20RB receptor-Ig fusion heterotetramer as the antibody target. The lower limit of detection (LLD) of the rabbit anti-human IL-20RB affinity purified antibody was 500 pg/ml on its specific antigen.

The human IL-20-specific polyclonal antibodies were characterized further for their ability to block the cell-proliferative activity ("neutralization assay") of purified recombinant human IL-20-BHK on BaF3/IL-20RA/IL-20RB cells (as described herein). A 10× molar excess of the human IL-20-specific polyclonal antibodies was sufficient to inhibit cell proliferation. The human IL-20RB-specific polyclonal antibodies were also characterized further for their utility in an ELISA for the quantative determination of purified recombinant human IL-20RA/IL-20RB receptor-Ig fusion heterotetramer in SCID mouse serum samples. The resulting ELISA exhibited a lower limit of detection of 20.6 ng/ml in 100% SCID mouse serum.

Example 25

Human IL-20RB Monoclonal Antibodies

Rat monoclonal antibodies were prepared by immunizing 4 female Sprague-Dawley Rats (Charles River Laboratories, Wilmington, Mass.), with the thrombin-cleaved and purified recombinant protein, human IL-20RB Receptor-Ig Fusion homodimer. The rats were each given an initial intraperitoneal (IP) injection of 100 µg of the purified recombinant protein in Complete Freund's Adjuvant (Pierce, Rockford, Ill.) followed by booster IP injections of 50 µg of the purified recombinant protein in Incomplete Freund's Adjuvant every two weeks. Seven days after the administration of the second booster injection, the animals were bled and serum was collected.

The human IL-20RB-specific rat sera samples were characterized by ELISA and FACS using 500 ng/ml of the cleaved purified recombinant protein human IL-20RB Receptor-Ig Fusion homodimer or Baf3/KZ55/IL-20RA/IL-20RB cells as specific antibody targets. All 4 rat serum samples had titer by ELISA to the specific antibody target at a dilution of 1:1E6. Two rat serum samples had titer by FACS to the Baf3/KZ55/IL-20RA/IL-20RB cells at a dilution of 1:1 E3.

Splenocytes were harvested from a single high-titer rat and fused to SP2/0 (mouse) myeloma cells using PEG 1500 in a single fusion procedure (4:1 fusion ratio, splenocytes to myeloma cells, 'Antibodies: A Laboratory Manual', E. Harlow and D. Lane, Cold Spring Harbor Press). Following 10 days growth post-fusion, specific antibody-producing hybridoma pools were identified by ELISA using 1 µg/ml of the purified recombinant protein human IL20-RA/RB Receptor-Ig Fusion heterodimer as the specific antibody target and 1 µg/ml of an unrelated purified recombinant human Receptor- Ig Fusion protein as the non-specific target. IL-20RB-specific hybridoma pools were analyzed further by FACS for their ability to bind to Baf3/KZ55/IL-20RA/IL-20RB cells.

Hybridoma pools yielding positive results by either the ELISA or the FACS assay were analyzed for their ability to block the cell-proliferative activity ('neutralization assay') of the purified recombinant protein human IL-20-Bv on Baf3/KZ55/IL-20RA/IL-20RB cells. Seven 'neutralizing' hybridoma pools were identified in this manner.

Hybridoma pools yielding positive results by ELISA and FACS assays were cloned at least three times by limiting dilution.

Monoclonal antibodies purified from tissue culture media were characterized by FACS for their ability to bind to the human acute monocytic leukemia cell line THP-1 ATCC#TIB-202. Two positive-binding monoclonal antibodies were identified.

Example 26

IL-20 Antagonists in CD4$^+$CD45RB$^{hi}$ (CD25$^-$) Colitis and Psoriasis Model Transfer of CD4+ CD45RB$^{hi}$ or CD4+CD25− T cells into syngeneic SCID mice results in colitis in the mice. Co-transfer of regulatory T cells (CD4+CD25+ or CD4+CD45RB$^{lo}$) inhibits this colitis. After transfer of CD4+CD25− T cells into mice, if mice are additionally injected with staphylococcal enterotoxin B (SEB), mice not only develop colitis, but also psoriasis. Antibodies against IL-20, IL-20RA and/or IL-20RB, or soluble IL-20RA, IL-20RB or IL-20RA/IL-20RB receptors are administered from days 0-21 after cell transfer and symptoms for colitis and psoriasis are monitored. Inhibition of psoriatic score or colitis (histology) indicates that antibodies against IL-20, IL-20RA and/or IL-20RB, or soluble IL-20RA, IL-20RB or IL-20RA/IL-20RB receptors can inhibit these autoimmune diseases.

Study Design

Spleens and inguinal lymph nodes are isolated from B10.D2 mice. Single cell suspensions are formed and counted. Using the Miltenyi Bead system, CD25+ cells are sorted out by positive selection. Cells are stained with CD25-PE (BD Pharmingen) at 1:100 dilution and incubated for 15 minutes. Excess antibody is washed out and the cells are incubated with 10 ul anti-PE beads/10$^6$ cells for 20 minutes. The cells are washed with PBS and passed over an LS column (Miltenyi Biotech). Cells that pass through the column (CD25−) are retained for further analysis. A CD4 enrichment cocktail (Stem Cell technologies) is added (1:100) to these CD25− cells and incubated for 15 minutes. Cells are washed with PBS. A 1:10 dilution of anti-biotin tetramer is added to the cells for 15 minutes followed by a magnetic colloid (60 ul/10$^6$ cells) for 15 minutes (all from Stem Cell Technologies). Cells are passed through a negative selection column (0.5", Stem cell Technologies). Cells that pass through are the CD4+CD25− cells. Purity is analyzed using flow cytometry. 0.4×10$^6$ cells are injected i.v into naïve CB-17 SCID mice in a total volume of 200 µl. Mice are injected i.p with 10 µg SEB the following day (d1). Symptoms for psoriasis and colitis are followed from 2-5 weeks. Mice are scored for psoriasis disease under the following criteria. 0—no lesions, 1—mild lesions on the neck, 2—severe lesions on the neck and back (trunk) 3—very severe lesions on the neck, back and the belly of mice. Ear thickening is also measured as a measure of disease severity. Groups of mice are injected i.p. with PBS, 100 µg control antibody or 10-100 µg antibodies against IL-20, IL-20RA and/or IL-20RB, or soluble IL-20RA, IL-20RB or IL-20RA/IL-20RB from days 1-30 under different dosing regimen (3×/week or 2×/week).

Results and Conclusion

Inhibition of psoriatic and colitis symptoms in antibody treated mice indicates that inhibition of IL-20 function can inhibit autoimmune symptoms in this model for psoriasis and colitis.

Example 27

Screening for IL-20 Antagonist Activity in an Alamar Blue Proliferation Assay

The factor-dependent pre-B cell line BaF3 was co-transfected with IL-20RA and IL-20RB and treated with IL-20 at various concentrations. Proliferation was assessed busing and alamar blue assay. IL-20 stimulated proliferation in a dose-dependent manner at concentrations expected for a cytokine, demonstrating that IL-20 binds and activates the heterodimeric IL-20RA/IL-20RB receptor at concentrations expected for a cytokine. The negative controls containing untransfected BaF3 did not proliferate.

In order to determine if anti-IL-20RA antibodies are capable of antagonizing IL-20 activity, the assay described above is performed using either anti-il-20 antibodies, anti-IL-20RA antibodies or anti-IL-20RB antibodies as an antagonist to IL-20 activity. When IL-20 is combined with such antagonist, the response to IL-20 at all concentrations is brought down to background levels. That the presence of an antagonist that ablates or reduces the proliferative effects of IL-20 demonstrates that it is an antagonist of the IL-20 ligand. This assay can be used to test other antagonists of IL-20 activity described herein, such as soluble IL-20RA, IL-20RB or IL-20RA/IL-20RB receptor.

Example 28

Anti-IL-20 mAbs Anti-IL-20RA mAbs or Anti-IL-20RB mAbs Inhibit Disease Severity in a Mouse CIA Model The collagen-induced arthritis (CIA) model is a mouse model for rheumatoid arthritis that reflects to large extent the disease seen in humans. (Moore, *Methods Mol. Biol.* 225: 175-179, 2003: Waksman, *Scand. J. Immunol.*, 56:12-34, 2002). Mice are immunized with 2 doses of collagen emulsified in CFA at the base of the tail. This results in swelling of the paws that increases over a period of time and can be both visually scored and measured using calipers. Furthermore, serum anti-collagen antibodies correlates well with severity of disease. Based on data showing IL-20 and IL-22 induce inflammation, anti-IL-20, anti-IL-20RA and anti-IL-20RB mAbs are administered separately or in any combination thereof (i.e. anti-IL-20 mAbs in combination with anti-IL-20RA and/or anti-IL-20RB mAbs; or anti-IL-20RA mAbs in combination with anti-IL-20RB) to groups of collagen-immunized mice, and effects on disease scores are evaluated. A decrease in paw scores and paw thickness after administration of any of these mAbs suggests IL-20 promotes ongoing immune response in a model for autoimmunity and blocking IL-20's function may inhibit autoimmune disorders. Inhibition of serum TNFa and anti-collagen antibodies also suggests that blocking IL-20, IL-20RA and/or IL-20RB may be beneficial in autoimmune disease.

Thus, to determine if anti-IL-20, anti-IL-20RA and anti-IL-20RB mAbs have an effect on autoimmunity, they are tested in a mouse model for rheumatoid arthritis—collagen-induced arthritis (CIA). Specifically, DBA1J mice are given collagen injections to induce rheumatoid-like arthritis. The inoculation on Day 0 is a subcutaneous injection of a homogenate consisting of Complete Freund's Adjuvant (CFA) and Type II collagen (50-100 µl, prepared as 2 mg/ml of collagen). The injection is given near the base of the tail. On Day 21, a second inoculation is administered, the only difference being that the homogenate is prepared using Incomplete Freund's Adjuvant (IFA), instead of the CFA. Paw scores and thickness are measured daily. Groups of mice receive PBS, 20-200 ug control isotype matched monoclonal antibody or 20-200 ug anti-IL-20, anti-IL-20RA and anti-IL-20RB mAb i.p 2× or 3×/week for 1-4 weeks starting at second collagen injection. Mice are monitored daily till day 30. Mice are sacrificed on day 30, serum taken for anti-collagen antibody analysis and serum cytokine analysis (TNF-alpha).

Inhibition of paw scores, paw thickness, serum TNF-alpha and serum anti-collagen antibodies by administration of anti-IL-20, anti-IL-20RA and anti-IL-20RB mAbs suggests that blocking IL-20, IL-20RA and/or IL-20RB can inhibit an ongoing immune response in a model for autoimmunity and may inhibit autoimmune disorders.

Example 29

IL-20 is Up-Regulated in Human Atopic Dermatitis Skin Samples

RNA Samples

Normal skin samples as well as skin from atopic dermatitis patients were obtained. RNA was isolated from human skin samples using conventional methods. The integrity and quality of RNA samples was tested on the Agilent 2100 Bioanalyzer (Agilent Technologies, Waldbronn Germany).
Primers and Probes for Quantitative RT-PCR Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U. E. M. et al., *Genome Research* 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by the 5' to 3' nucleolytic activity of the rTth DNA Polymerase which releases the reporter dye from the probe resulting in an increase in fluorescent emission.

The primers and probes used for real-time quantitative RT-PCR analyses of IL-20 expression were designed using the primer design software Primer Express™ (PE Applied Biosystems, Foster City, Calif.). The forward primer, ZC40541 (SEQ ID NO:25) and the reverse primer, ZC 40542 (SEQ ID NO:26) were used in a PCR reaction (below) at a 800 nM concentration to synthesize a 71 bp product. The corresponding IL-20 TaqMan® probe, ZC 40544 (SEQ ID NO:27) was synthesized and labeled by PE Applied Biosystems. The IL-20 probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems).
Real-Time Quantitative RT-PCR Relative levels of IL-20 mRNA were determined by analyzing total RNA samples using the TAQMAN® EZ RT-PCR Core Reagents Kit (PE Applied Biosystems). Runoff IL-20 transcript was made to generate a standard curve used for quantitation. The curve consisted of 10-fold serial dilutions ranging from 1e8 to 1 e3 total copies of whole message for IL-20 with each standard curve point analyzed in triplicate. The total RNA samples from skin were also analyzed in triplicate for human IL-20 transcript levels and for levels of hGUS as an endogenous control. In a total volume of 25 µl, each RNA sample was subjected to TAQMAN® EZ RT-PCR reaction (PE Applied Biosystems) containing: approximately 25 ng of total RNA in DEPC treated water (Dnase/Rnase free); appropriate primers (approximately 800 nM ZC40541 (SEQ ID NO:25) and ZC40542 (SEQ ID NO:26); appropriate probe (approximately 100 nM ZC40544 (SEQ ID NO:27); 1× TAQMAN® EZ Buffer; 3 mM Manganese acetate; 300 µM each d-CTP, d-ATP, and d-GTP and 600 µM of d-UTP; rTth DNA Polymerase (0.1 U/µl); and AMPERASE® UNG (0.01 U/µl). PCR thermal cycling conditions were as follows: an initial UNG treatment step of one cycle at 50° C. for 2 minutes; followed by a reverse transcription (RT) step of one cycle at 60° C. for 30 minutes; followed by a deactivation of UNG step of one cycle at 95° C. for 5 minutes; followed by 40 cycles of amplification at 94° C. for 20 seconds and 60° C. for 1 minute.

Relative IL-20 RNA levels were determined by using the Standard Curve Method as described by the manufacturer, PE Biosystems (User Bulletin #2: ABI Prism 7700 Sequence Detection System, Relative Quantitation of Gene Expression, Dec. 11, 1997). The hGUS measurements were used to normalize IL-20 levels.

IL-20 mRNA was detectable at a low level (796 copies) in skin samples. In contrast, there was upregulation for IL-20 message in skins from atopic dermatitis patients (8598 copies). The receptor subunits for IL-20, including IL-20RA), IL-20RA, and IL-20RB are expressed in human normal and diseased skin. These data support a strong disease association for IL-20 to human atopic dermatitis.

Overexpression of IL-20 was shown in human atopic dermatitis skins, suggesting that IL-20 is involved in human atopic dermatitis. Moreover, as described herein, over expression of IL-20 in transgenic mice showed epidermal thickening and immune cell involvement indicative of an atopic dermatitis phenotype. Such in vivo data further suggests that IL-20 is involved in atopic dermatitis. As such, antagonists to IL-20 activity, such as the anti-human-IL-20RA monoclonal antibodies of the present invention, as well as soluble receptors and antibodies thereto, are useful therapeutically as antagonists to IL-20 in the treatment of inflammatory diseases, such as atopic dermatitis, as well as other indications as disclosed herein.

Example 30

Pharmacokinetics of an Anti-Human IL-20 Monoclonal Antibody

The test monoclonal antibody, anti-human IL-20 mAb, (clone #262.7.1.3.2.4; kd=0.133 nM) was provided in 3×3 mL aliquots at a concentration of 1.08 mg/mL (determined by UV Absorbance at 280 nM) and was stored at −80° C. until use. The vehicle was 1×PBS (50 mM NaPO4, 109 mM NaCl), pH 7.3. The mAb was thawed at room temperature before use and aliquots 1 and 2 were used as provided for the 100 µg IV and SC dosing groups, respectively. Half of aliquot 3 was diluted 1:2 in 1×PBS for the 50 µg SC dose group and the second half of aliquot 3 was diluted 1:10 in 1×PBS for the 10 µg SC dose group. Female SCID mice (n=96), were received from Charles River Labs. Animals were checked for health on arrival and group-housed (3 animals per cage). The mice were 12 weeks old with an average body weight of 22 g at the beginning of the study.
Dosing Protocol Female SCID mice (n=24/dose group) were randomly placed into four dosing groups (Table 7). Group 1 was administered the anti-human IL-20 mAb via IV injection of approximately 93 µL in a tail vein and Groups 2, 3, and 4 were administered the mAb via SC injection of approximately 93 µL in the scruff of the neck.

Sample Collection

Prior to blood collection, mice were fully anesthetized with halothane or isofluorane. Blood samples were collected via cardiac stick for all timepoints except the 168 hr timepoint (collected via eye bleed and the same animals were bled again at the 504 hr timepoint via cardiac stick). Blood was collected into serum separator tubes and allowed to clot for 15 minutes. Samples were subsequently centrifuged for 3 minutes at 14,000 rpm. Following centrifugation, aliquots of 125-150 uL were dispensed into labeled eppendorf tubes and immediately stored at −80° C. until analysis (Table 7).

TABLE 7

| Group # | Dose (ROA) | Animals | PK Timepoints |
|---|---|---|---|
| 1 | 100 µg (IV) | 3 mice/timepoint* | 0.25, 1, 4, 8, 24, 72, 168, 336 and 504 hr |
| 2 | 100 µg (SC) | 3 mice/timepoint* | 0.25, 1, 4, 8, 24, 72, 168, 336 and 504 hr |
| 3 | 50 µg (SC) | 3 mice/timepoint* | 0.25, 1, 4, 8, 24, 72, 168, 336 and 504 hr |
| 4 | 10 µg (SC) | 3 mice/timepoint* | 0.25, 1, 4, 8, 24, 72, 168, 336 and 504 hr |

*The same animals were used for the 168 and 504 hr timepoints.

Quantification of Serum Anti-huIL-20 mAb Concentrations by ELISA

An Enzyme Linked Immunosorbant Assay (ELISA) was developed and qualified to analyze mouse serum samples from animals dosed with rat anti-IL-20 mAb 267.7.1.3.2.4 during pharmacokinetic studies. This assay was designed to take advantage of a commercially available secondary antibody and calorimetric detection using TMB. The dilutions used for the standard curve were modified to improve the definition of the linear portion of the standard curve. A standard curve in the range of 100 ng/mL to 0.231 ng/mL with 2-fold dilutions allowed for quantitation of the mouse serum samples. QC samples were diluted to 1:100, 1:1000 and 1:10000 in 10% SCID mouse serum and back calculated from the standard curve.

Pharmacokinetic Analysis

Serum concentration versus time data were downloaded into WinNonlin Professional 4.0 software (Pharsight, Inc.; Cary, N.C.) for pharmacokinetic analysis. Noncompartmental analysis was used to determine pharmacokinetic parameters based on the mean data at each time point.

Results

Mean serum anti-human IL-20 mAb concentrations following administration of 100 µg IV and 100, 50, and 10 µg SC are shown in Table 8.

TABLE 8

| Time (hr) | 100 µg IV Conc (µg/mL) | 10 µg SC Conc (µg/mL) | 50 µg SC Conc (µg/mL) | 100 µg SC Conc (µg/mL) |
|---|---|---|---|---|
| 0.25 | 196 (12) | LTR | 0.101 (0.065) | 0.481 (0.485) |
| 1 | 154 (18) | 0.356 (0.146) | 1.61 (0.52) | 3.48 (1.72) |
| 4 | 118 (20) | 2.42 (0.53) | 10.4 (3.4) | 19.7 (4.7) |
| 8 | 112 (20) | 3.41 (0.30) | 18.9 (3.6) | 40.2 (6.4) |
| 24 | 103 (13) | 4.95 (0.05) | 26.3 (0.7) | 50.1 (6.2) |
| 72 | 101 (16) | 4.27 (0.79) | 21.0 (3.4) | 43.4 (2.7) |
| 168 | 45.6 (15.4) | 2.92 (0.53) | 19.6 (2.7) | 37.6 (3.4) |
| 336 | 36.4 (16.6) | 3.60 (0.31) | 23.5 (3.5) | 34.4 (5.8) |
| 504 | 28.8 (3.8) | 2.74 (0.39) | 20.5 (3.6) | 25.7 (2.1) |

LTR: less than reportable

Following IV administration, the mAb concentration versus time profile demonstrated a biexponential decline. Following SC administration, the mAb appeared to have a slow absorption phase, with absorption rate-limited elimination. The serum pharmacokinetic parameters based on the mean data at each time point are shown in Table 9.

TABLE 9

| Parameter | Units | 100 µg IV | 10 µg SC | 50 µg SC | 100 µg SC |
|---|---|---|---|---|---|
| $C_0$(IV); $C_{max}$ (SC) | µg/mL | 212 | 4.95 | 26.3 | 50.1 |
| $T_{max}$ | hr | N/A | 24 | 24 | 24 |
| $t_{1/2, \lambda z}$ | hr | 509 | ND | ND | 612 |
| $AUC_{(0-t)}$ | hr · µg/mL | 27059 | 1730 | 10845 | 18110 |
| $AUC_{(0-inf)}$ | hr · µg/mL | 48269 | ND | ND | 41561 |
| AUC (% extrapolated) | % | 43.9 | ND | ND | 56.4 |
| $V_{ss}$ (IV); $V_z/F$ (SC) | mL | 1.34 | ND | ND | 2.12 |
| Cl (IV); Cl/F (SC) | mL/hr | 0.002 | ND | ND | 0.002 |
| F (bioavailability) | % | N/A | ND | ND | 86.1 |

ND: not determinable due to lack of data in the terminal elimination phase of the concentration versus time profile Following IV administration, the mAb demonstrated a very low clearance (Cl=0.002 mL/hr) and long elimination half-life ($t_{1/2, \lambda z} \approx 21$ days). The mAb demonstrated a steady-state volume of distribution ($V_{ss}=1.3$ mL) that is less than the blood volume in a mouse ($\approx 1.7$ mL), suggesting that the mAb did not distribute substantially out of the vascular compartment. The back-calculated maximum concentration ($C_0$) was higher than expected based on the injected dose and the blood volume in the mouse. This, along with the small $V_{ss}$, suggests that the mAb may be confined, to a large extent, in the serum fraction of the blood.

Following SC administration, $C_{max}$ values increased linearly with dose. At the 100 µg SC dose, the mAb had a $t_{1/2, \lambda z}$ of approximately 25 days with clearance and an apparent volume of distribution similar to that following IV dosing. Bioavailability was 86%. At the lower two SC doses, most pharmacokinetic parameters could not be estimated due to the lack of a measurable terminal elimination phase, even though samples were taken out to 504 hours. The absorption of the mAb following SC dosing appears to reach a steady-state with elimination throughout the duration of the study.

Example 31

IL-20 Antagonists in a SCID-hu Transplant Psoriasis Model

Human psoriasis skin grafted on SCID mouse can maintain its clinical, light microscopic, and immunohistochemical psoriatic features for several weeks. This model provides a system for evaluating therapies intended to restore lesional tissue to a normal phenotype. Once the human skin is successfully grafted, antibodies against IL-20, IL-20RA, IL-20RB and/or IL-20RA/IL-20RB heterodimers, or soluble IL-20 receptors can be administered for several weeks, and the epidermal thickness can be analyzed to evaluate the effect of these antagonists on psoriasis.
Study Design Full-thickness 6-mm punch biopsies consisting of the entire epidermis and several mm of dermis are obtained healthy adult volunteers and psoriatic lesional skins. Four to six biopsies are obtained from each donor. One punch biopsy from each donor is transplanted onto the dorsal surface of recipient SCID mouse (CB-17, Taconic). The animals are maintained in a pathogen-free environment. The treatment is initiated after a successful grafting (2-3 weeks post-transplantation) as following: one biopsy for negative control (PBS or isotype mAb), one biopsy for positive control (Cyclosporin A), and 2-3 biopsies for treatment with anti-human IL-20, anti-human IL-20RA, anti-human IL-20RB or anti-human IL-20RA/IL-20RB heterodimer mAb or soluble receptors for IL-20 (intraperitoneal injection, three times a week for 2-4 weeks on a M-W-F schedule).
Quantitative Analysis Clinical observations and assessments will be made regularly throughout the experiments, and will be recorded. The severity of the psoriatic lesions is assessed for scaliness, induration, and erythema in a blinded fashion. The parameters can be scored using the three-point scale: 0=complete lack of cutaneous involvement; 1=slight involvement; 2=moderate involvement; 3=severe involvement. At the end of the dosing period each animal is euthanized and tissues are collected for histology and IHC. (1) Part of the tissue is fixed in 10% formalin and stained with hematoxylin and eosin. Epidermal area is measured as a function of changes in epidermal thickness per unit length using NIH Image software. Multiple areas from each transplant are quantified to provide a high n value and mean epidermal area. (2) number of inflammatory mononuclear cells per high-power field (0.103×0.135 mm) in the upper dermis; (3) the grade of parakeratosis is rated on an arbitrary scale from 0 to 3, where 0 is no parakeratosis, 1 is parakeratosis in less than one third of the section, 2 was parakeratosis in more than one third but less than two thirds of the section, a d 3 is parakeratosis in more than two thirds of the section. (4) The remaining of the tissue will be stained for Ki67 (marker of proliferating keratinocytes), to evaluate the number of Ki67 cycling keratinocytes-per-millimeter length of the section. The reduced severity of psoriasis as measured by epidermal thickness, indicates the neutralization of IL-20 function can be effective in this psoriasis model. To quantify the reduced severity of psoriasis, we measure epidermal thickness, the number of inflammatory cells in the upper dermis, the numbers of Ki67 cycling keratinocytes, and the grades of parakeratosis. The significantly reduced all four parameters for the treated groups compared to the control mice, indicate the potential therapeutic use of IL-20 antagonists.

Example 32

IL-20 Antagonists in an Organ Culture Psoriasis Model

Human psoriatic plaque skin can be maintained in organ culture, and the abnormal histological features of lesional skin are maintained in the absence of exogenous growth factors. Antibodies against IL-20, IL-20RA, IL-20RB and/or IL-20RA/IL-20RB heterodimers, or soluble IL-20 receptors can be administered, and the histological features of psoriatic lesional skin can be ameliorated.
Study Design Full-thickness 2-mm punch biopsies consisting of the entire epidermis and several mm of dermis are obtained from either healthy adult volunteers or from psoriatic lesional skin. Immediately upon biopsy, the tissue is immersed in culture medium consisting of Keratinocyte Basal Medium (KBM) (Clonetics Inc, Walkersville, Md.). The culture medium is supplemented with CaCl2 to bring the final Ca2+ concentration to 1.4 mM (Varani et al, 1993, 1994). The biopsies are then incubated in wells of a 96-well dish containing 200 ul of Ca2+ supplemented KBM with or without additional treatments of antibodies against IL-20, IL-20RA, IL-20RB and/or IL-20RA/IL-20RB heterodimers, or soluble IL-20 receptors. Cultures are incubated at 37° C. in an atmosphere of 95% air and 5% $CO_2$ for 8 days.
Quantitative Analysis At the end of incubation period, tissue is fixed in 10% buffered formalin and examined histologically after staining with hematoxylin and eosin. The appearance of psoriatic tissue exposed to the antibodies or soluble receptors could be more closely resembled that of normal tissues, including the following observation: the initially disorganized, irregular-shaped basal epithelial cells developed a more columnar appearance with restored polarity; epidermal rete ridges regressed, with fewer areas of epithelial cell expansion into the dermal space; and there was less overall degeneration of the upper epidermal layers. The organ culture model provides a rapid and sensitive means for determining if a particular compound has potential as an anti-hyperproliferative agent. The abnormal histological feature may be ameliorated in the presence of an IL-20 antagonist, suggesting the effectiveness of such agent in the treatment of psoriasis.

Example 33

Treatment of Pregnant IL-20 Transgenic Mice with Neutralizing Anti-IL-20 Anti-IL-20RA or Anti-IL-20RB monoclonal antibody To test the rat anti-mouse IL-20, IL-20RA or IL-20RB monoclonal antibodies (mAb) for neutralizing activity in vivo, pregnant IL-20 transgenic (Tg) a mice are injected intraperitoneally with one of the mAbs listed above. The newborn pups are then assessed for the presence or absence of the "shiny" skin phenotype that normally characterizes these strains of mice.

Specifically, male IL-20 Tg (which are generated using the keratin-14 or Eulck promoters) mice are bred to C57BL/6 females in estrus and the bred females are identified by the presence of a vaginal plug the following day. Each pregnant female is set aside in a separate cage and monitored daily. Treatment groups include at least 4 pregnant females each, to allow for a statistically significant analysis of both Tg and nonTg pups. Based on prior experience with these Tg mice, a litter usually ranges between approximately 6 to 8 pups per litter, of which between 2 to 3 are Tg+.

Seven to nine days after the mice are bred (embryonic age 7-9; e7-9), the females are injected intraperitoneally with 250-500 ug of the mAb (rat IgG2a isotype) in a volume of 200-250 ul of PBS. Short needles are used at a shallow injection angle to avoid directly injecting the uterus. The pregnant females are injected in this manner 3 days a week (Monday, Wednesday, and Friday) for 2 weeks (until birth) in order to successfully access the developing embryos. Control groups (of not less than 4 pregnant female mice each) include the following: isotype control rat IgG2a mAb, anti-human/mouse IL-20 mAb (rat IgG1 isotype), and an isotype control rat IgG1 mAb.

From days 1 through 5 after birth, the pups are closely monitored for the appearance of the shiny skin phenotype. On day 5, the pups are euthanized and a portion of the tail is collected for DNA isolation to determine the genotype (Tg or nonTg) of each pup. Skin samples are collected for histological analysis in order to assess whether the pups exhibit the thickened epidermal cell layers that usually characterize these Tg mice. Trunk blood is also collected from the pups (and an eyebleed from the dams one day after birth) to quantitate, via ELISA, the levels of mAb in the serum of each mouse. Because these mAbs are potent inhibitors of IL-20 in vivo, the Tg pups have normal skin (i.e. no epidermal thickening or "shiny" appearance).

Example 34

Evaluation of Levels of IL-20, IL-20RA and IL-20RB in Psoriatic Skin Samples Five (5) skin samples with two mice in the control group (CD4+ control CD25+) and three mice in the psoriatic group (CD4+ psoriatic/CD25−) were evaluated. Each tissue specimen was fixed in ZnTRIS and stained with a mouse anti-human IL-20 monoclonal antibody (clone 240.8.4.7.16.5), mouse anti-human IL-20RA monoclonal antibody (clone HH7.34.1F11.1G2), rat anti-human IL-20RB monoclonal antibody (clone 264.13.1.3.2.3) and rat anti-human IL-22 monoclonal antibody (clone 266.19.1.10.5.2), respectively by immunohistochemistry. No positive and negative control cells were applied in this study because the fixative used for the cells (10% NBF) was different from the tissues (ZnTRIS). The reagent negative control included mouse isotype IgG and rat isotype IgG to replace the primary antibodies. The staining intensity of each antibody in the skin samples was outlined in Table 10.

TABLE 10

| | | Monoclonal antibodies | | | | Isotype IgG | |
|---|---|---|---|---|---|---|---|
| Animal/group # | Treatment | IL-20 | IL-20RA | IL-20RB | IL-22 | Mouse | Rat |
| 301 (group 1) | CD4+ control/CD25+ | − | − | − | − | ++/b | ++/b |
| 307 (group 1) | CD4+ control/CD25+ | | | | − | ++/b | ++/b |
| 315 (group 2) | CD4+ psoriatic/CD25− | | | − | − | ++++/b | ++++/b |
| 321 (group 2) | CD4+ psoriatic/CD25− | | | | − | ++++/b | ++++/b |
| 327 (group 2) | CD4+ psoriatic/CD25− | | − | − | − | ++++/b | ++++/b |

±, +, ++, +++ & ++++: Staining intensity from weak to strong; −: No staining; b: Background staining.

Human IL-20 Monoclonal Antibody (Clone 240.8.4.7.16.5)

IL-20 was not detected in either the control or psoriatic skin samples.

Mouse Anti-Human IL-20RA Monoclonal Antibody (Clone HH7.34.1F11.1G2)

High expression of IL-20RA was observed in the psoriatic skin samples (group 2) compared to the controls (group 1). In the control group, epidermis and few scattered mononuclear cells in the dermis displayed positive staining. In the psoriatic group, the tissues were stained in the same manner but at a higher level, e.g., strong positive staining was observed in the epidermis and on large number infiltrated mononuclear cells in the dermis. The skin demonstrated psoriasis-like dermatitis and the IL-20RA staining in the epidermis was mainly located in the outer layers (stratum granulosum and stratum corneum). Stratum basale, the germinal layer of the epidermis showed no staining and stratum spinosum, the prickle layer of the epidermis showed weak and diffused staining. The antibody also showed some non-specific staining in the connective tissues. Skin samples stained with mouse isotype IgG showed negative staining.

Rat Anti-Human IL-20RB Monoclonal Antibody (Clone 264.13.1.3.2.3)

The rat anti-human IL-20RB monoclonal antibody demonstrated a similar staining as the mouse anti-human IL-20RA monoclonal antibody but with few positive mononuclear cells in the dermis. The antibody also showed non-specific staining to skeletal muscle. Skin samples stained with rat isotype IgG exhibited negative staining Rat Anti-Human IL-22 Monoclonal Antibody (Clone 266.19.1.10.5.2)

IL-22 was not detected in either the control or psoriatic skin samples.

Conclusion

IL-20RA and IL-20RB expression were observed in the epidermis in the psoriatic skin samples (CD4+ psoratic/CD25−) by immunohistochemistry and microscopically these tissues exhibited abnormally thickened epidermis and severe dermatitis. The vast majority of the IL-20RA and IL-20RB expression was found in the epidermis appeared to be in the keratinocytes above the basal and prickle cell layers mainly in the stratum granulosum characterized by intracellular granules which contributed to the process of keratinisation and in the stratum corneum consisted of flattened, fused cell remnants (keratine). In addition, IL-20RA expression was also observed on mononuclear cells in the area with dermatitis. The control tissues (CD4+/control/CD25+) demonstrated relatively low level of IL-20RA and IL-20RB expression compared with the psoriatic tissues. No IL-20 and IL-22 ligand were detected in either the control or psoriatic skin samples using the human IL-20 monoclonal antibody and the rat anti-human IL-22 monoclonal antibody. All the skin samples stained with mouse isotype IgG or rat isotype IgG showed negative staining.

Example 35

IL-20RA Expression in Skin Samples from IL-20TG/IL-20RA Knock-Out Mice

Eight (8) neonates with two (2) neonates in each genotype group: TG/O HOM, TG/O Het, 0/0 HOM and 0/0 Het from the K14 IL-20m (TG)/IL-20RA (KO) were studied. The caudal thorax from each animal was fixed in 10% neutral buffered formalin (NBF) and stained with a mouse anti-human IL-20RA monoclonal antibody (clone HH7.34.1F11.1G2) by immunohistochemistry (IL-20RA-IHC#15, ARK IHC protocol). Baf3 cells transfected with either human or murine IL-20RA/RB and human lung known with IL-20RA expression were used as positive controls. The reagent negative control included mouse isotype IgG to replace the primary antibody.

IHC Results

A. The Positive Control Cells and Tissues

Scattered mononuclear cells in the human lung demonstrated weak staining, however, the Baf3 cells transfected with murine IL-20RA/RB displayed negative staining. The Baf3 cells transfected with human IL-20RA/RB were not found on the slide, which might due to a poor sample preparation or cell loss by repeat buffer washing during IHC procedure. The wild type Baf3 cells were clear with no staining.

B. The K14 IL20m (TG)/IL-20RA (KO) Neonate Skins

Weak expression of IL-20RA was found in one out of two TG/0 Het and one out of two 0/0 Het neonate skins, e.g., epidermal cells above the basal layer in the skin showed diffused cytoplasmic staining with the monoclonal antibody. The skins from TG/0 HOM (n=2) and 0/0 HOM (n=2) neonates showed no IL-20RA expression. All the neonate skins (TG/0 HOM, TG/0 Het, 0/0 HOM and 0/0 Het) stained with mouse isotype IgG showed negative staining. The staining intensity of IL-20RA was outlined in Table 11.

TABLE 11

| Genotype | Animal number | Epidermal thickness | IL-20RA expression |
|---|---|---|---|
| TG/0 HOM | 36109 | 44.28 μm | − |
| TG/0 HOM | 36242 | 39.01 μm | − |
| TG/0 Het | 36020 | 40.90 μm | − |
| TG/0 Het | 36241 | 39.63 μm | ± |
| 0/0 HOM | 36130 | 30.05 μm | − |
| 0/0 HOM | 36176 | 29.44 μm | − |
| 0/0 Het | 36128 | 30.72 μm | − |
| 0/0 Het | 36245 | 30.05 μm | ± |

±, +, ++, +++ & ++++: Staining intensity from weak to strong; −: No staining.

Conclusion

IL-20RA expression was observed in the epidermal cells in the TG/0 Het (IL-20TG×IL-20RA KO) neonates by immunohistochemistry as described above. Physioscreen studies revealed that these neonates grossly exhibited shiny skin phenotype and microscopically exhibited abnormally thickened epidermis. Further, IL-20RA mAb staining was associated with epidermal thickening. The IHC results revealed that one out of two neonate skins in TG/0 Het and 0/0 Het showed positive staining of IL-20RA, respectively. The vast majority of the IL-20RA expressing cells in the epidermis appeared to be in the keratinocytes above the basal layer (suprabasal), but the staining was relatively weaker compared to the skin samples of TG/0 Het from the IL-20 TG×IL-20RA KO study. No IL-20RA expression was observed in the epidermis in either the TG/0 HOM or 0/0 HOM. In sum, IL-20RA mAb staining was positive in Het but not in HOM.

Example 36

IL-20RA Expression in Skin Samples from IL-20TG/IL-20RA Knock-Out Mice

Eight (8) neonates with two (2) neonates in each genotype group: TG/− HOM, TG/− Het, −/− HOM and −/− Het from the K14 IL-20m (TG)/IL-22RA (KO) were studied. The caudal thorax from each animal was fixed in 10% neutral buffered formalin (NBF) and stained with a mouse anti-human IL-20RA monoclonal antibody raised against human (clone HH7.34.1F11.1G2). Cos cells transfected with human IL-20RA and human lung known with IL-20RA expression was used as positive controls. However, cells and tissues expressing mouse IL-20RA were not available, as the control because the IL-20RA TG mice died before birth. The reagent negative control included mouse isotype IgG to replace the primary antibody.

IHC Results

A. The Positive Control Tissue (Human Lung)

Scattered mononuclear cells in the human lung demonstrated positive staining.

B. The mouse tissues (IL-20TG/IL-22RA KO Neonate Skins)

The anti-IL-20RA MAb recognized mouse IL-20RA in IHC. Expression of IL-20RA was found in IL-20TG/IL-20RA KO Het neonate skins (n=2) using IHC, e.g., epidermal cells in the skin showed diffused cytoplasmic staining with the antibody. The skins from TG/− HOM (n=2), −/− HOM (n=2) and −/− Het (n=2) neonates showed no IL-20RA expression. The TG/Het neonate skin stained with mouse isotype IgG showed negative staining.

Conclusion

IL-20RA expression was observed in the epidermal cells in the TG/− Het neonates by immunohistochemistry and previous physioscreen studies revealed that these neonates grossly exhibited shiny skin phenotype and microscopically exhibited abnormally thickened epidermis. The vast majority of the IL-20RA expressing cells in the epidermis appeared to be in the keratinocytes above the basal layer (suprabasal) and the staining was not observed in the other tissues in the section. No IL-20RA expression was observed in the epidermis in either of the TG/− HOM neonates or the non-IL-20 TG neonates (−/− HOM and −/− Het) that displayed no shiny phenotype. Further, all the skin samples stained with mouse isotype IgG showed negative staining.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated antibody, or antigen-binding fragment thereof, comprising the heavy and light chain CDR sequences, or the heavy and light chain variable region sequences, from an antibody expressed by hybridoma clone 262.5.1.6.4.4 (ATCC No. PTA-5351) or hybridoma clone 262.7.1.3.2.4 (ATCC No. PTA-5352), and wherein the antibody specifically binds to a polypeptide of SEQ ID NO:2 or SEQ ID NO:3.

2. The antibody or fragment of claim 1, wherein the antibody or fragment is a recombinant monoclonal antibody.

3. The antibody or fragment of claim 1, wherein the antibody or fragment is a humanized antibody.

4. The fragment of claim 1 which is a F(ab')2, F(ab)2, Fab', Fab, Fv, or scFv.

5. The antibody or fragment of claim 1, wherein the antibody or fragment inhibits the pro-inflammatory activity of IL-20.

6. An immunoconjugate comprising the antibody or fragment of claim 1.

7. The immunoconjugate of claim 6, wherein the immunoconjugate reduces or neutralizes the pro-inflammatory activity of the polypeptides.

8. The antibody or fragment of claim 1, wherein the antibody or fragment is conjugated with polyethylene glycol.

9. A pharmaceutical composition comprising the antibody or fragment of claim 1.

* * * * *